(12) United States Patent
Wenglowsky et al.

(10) Patent No.: US 11,046,697 B2
(45) Date of Patent: Jun. 29, 2021

(54) COMPOUNDS AND COMPOSITIONS USEFUL FOR TREATING DISORDERS RELATED TO NTRK

(71) Applicant: BLUEPRINT MEDICINES CORPORATION, Cambridge, MA (US)

(72) Inventors: Steven Mark Wenglowsky, Cambridge, MA (US); Natasja Brooijmans, Boston, MA (US); Chandrasekhar V. Miduturu, Cambridge, MA (US); Neil Bifulco, Jr., Sudbury, MA (US)

(73) Assignee: Blueprint Medicines Corporation

( * ) Notice: Subject to any disclaimer, the term of this patent is extended or adjusted under 35 U.S.C. 154(b) by 0 days.

(21) Appl. No.: 16/027,166

(22) Filed: Jul. 3, 2018

(65) Prior Publication Data

US 2019/0169194 A1   Jun. 6, 2019

Related U.S. Application Data

(62) Division of application No. 15/248,207, filed on Aug. 26, 2016, now Pat. No. 10,017,512.

(60) Provisional application No. 62/210,264, filed on Aug. 26, 2015.

(51) Int. Cl.
| | | |
|---|---|---|
| *C07D 487/04* | (2006.01) | |
| *A61P 35/04* | (2006.01) | |
| *A61K 31/519* | (2006.01) | |
| *A61P 35/02* | (2006.01) | |

(52) U.S. Cl.
CPC .......... *C07D 487/04* (2013.01); *A61K 31/519* (2013.01); *A61P 35/02* (2018.01); *A61P 35/04* (2018.01)

(58) Field of Classification Search
CPC ............................ C07D 487/04; A61K 31/519
See application file for complete search history.

(56) References Cited

U.S. PATENT DOCUMENTS

| | | |
|---|---|---|
| 6,251,911 B1 | 6/2001 | Bold et al. |
| 8,802,697 B2 | 8/2014 | Bifulco, Jr. et al. |
| 9,126,951 B2 | 9/2015 | Bifulco, Jr. et al. |
| 9,200,002 B2 | 12/2015 | Hodous et al. |
| 9,334,263 B2 | 5/2016 | Hodous et al. |
| 9,340,514 B2 | 5/2016 | Bifulco, Jr. et al. |
| 9,434,700 B2 | 9/2016 | Bifulco, Jr. et al. |
| 9,499,522 B2 | 11/2016 | DiPietro et al. |
| 9,688,680 B2 | 6/2017 | Hodous |
| 9,695,165 B2 | 7/2017 | Bifulco, Jr. et al. |
| 9,884,861 B2 | 2/2018 | Hodous et al. |
| 9,944,651 B2 | 4/2018 | Hodous et al. |
| 9,994,552 B2 | 6/2018 | DiPietro et al. |
| 9,994,575 B2 | 6/2018 | Hodous et al. |
| 10,000,490 B2 | 6/2018 | Bifulco, Jr. et al. |
| 10,000,496 B2 | 6/2018 | Hodous et al. |
| 10,017,512 B2 | 7/2018 | Wenglowsky et al. |
| 10,030,005 B2 | 7/2018 | Brubaker et al. |
| 10,035,789 B2 | 7/2018 | Brubaker et al. |
| 10,139,872 B1 | 11/2018 | Li et al. |
| 10,202,365 B2 | 2/2019 | Brooijmans et al. |
| 10,227,329 B2 | 3/2019 | Brubaker et al. |
| 2014/0045779 A1 | 2/2014 | Xu |
| 2014/0187559 A1 | 7/2014 | Miduturu |
| 2016/0102097 A1 | 4/2016 | Hodous et al. |
| 2016/0168156 A1 | 6/2016 | Kim et al. |
| 2017/0022206 A1 | 1/2017 | Hodous et al. |
| 2017/0029409 A1 | 2/2017 | DiPietro et al. |
| 2017/0066773 A1 | 3/2017 | Wenglowsky et al. |
| 2017/0066812 A1 | 3/2017 | Bifulco, Jr. et al. |
| 2017/0121312 A1 | 5/2017 | Brubaker et al. |
| 2017/0145018 A1 | 5/2017 | Wenglowsky et al. |
| 2017/0174652 A1 | 6/2017 | Bifulco, Jr. et al. |
| 2017/0204104 A1 | 7/2017 | Hodous et al. |
| 2017/0253593 A1 | 9/2017 | Bifulco, Jr. et al. |
| 2017/0267661 A1 | 9/2017 | Kim et al. |
| 2017/0298069 A1 | 10/2017 | Brooijmans et al. |
| 2018/0022731 A1 | 1/2018 | Brooijmans et al. |

(Continued)

FOREIGN PATENT DOCUMENTS

| | | |
|---|---|---|
| CN | 103965199 A | 8/2014 |
| EP | 2194058 A1 | 6/2010 |

(Continued)

OTHER PUBLICATIONS

Database Caplus (2010), Accession No. 2010:366855: Radl, S. et al. "Synthetic studies connected with the preparation of N-[3-(3-cyanopyrazolo[1,5-a]pyrimidin-5-yl)phenyl]-N-ethylacetamide, a zaleplon regioisomer" Chemical Abstracts Service [online]. Retrieved from STN on Jan. 24, 2017 (1 page).

(Continued)

*Primary Examiner* — Susanna Moore

(74) *Attorney, Agent, or Firm* — McCarter & English, LLP; Steven G. Davis; Wei Song

(57) ABSTRACT

This disclosure relates to inhibitors of NTRK that are active against wild-type NTRK and its resistant mutants, such as compounds of Formula (I):

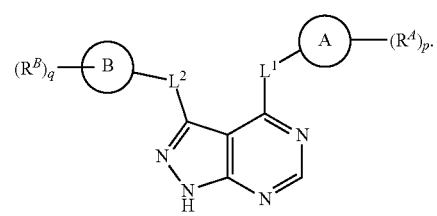

20 Claims, 61 Drawing Sheets

(56) References Cited

U.S. PATENT DOCUMENTS

| | | | |
|---|---|---|---|
| 2018/0022732 A1 | 1/2018 | Brubaker et al. | |
| 2018/0030032 A1 | 2/2018 | Brubaker et al. | |
| 2019/0185454 A1 | 6/2019 | Brubaker et al. | |
| 2019/0382410 A1 | 12/2019 | Wenglowsky et al. | |

FOREIGN PATENT DOCUMENTS

| | | | |
|---|---|---|---|
| GB | 2515785 A | 1/2015 | |
| JP | 2007-534687 A | 11/2007 | |
| JP | 2013-525481 A | 6/2013 | |
| RU | 2379308 C2 | 1/2010 | |
| WO | WO 2005/040171 A1 | 5/2005 | |
| WO | WO 2005/117909 A2 | 12/2005 | |
| WO | WO 2009/032694 A1 | 3/2009 | |
| WO | 2010/048314 A1 | 4/2010 | |
| WO | WO 2011/006074 | 1/2011 | |
| WO | WO 2011/139273 A1 | 11/2011 | |
| WO | WO 2012/034091 A1 | 3/2012 | |
| WO | WO 2012/034095 A1 | 3/2012 | |
| WO | WO 2014/036387 A2 | 3/2014 | |
| WO | WO 2014/055955 A1 | 4/2014 | |
| WO | WO 2014/071358 A2 | 5/2014 | |
| WO | WO 2014/118226 A1 | 8/2014 | |
| WO | WO 2014/130375 A1 | 8/2014 | |
| WO | WO 2014/139326 A1 | 9/2014 | |
| WO | 2015/157093 A1 | 10/2015 | |
| WO | WO 2016/133838 A1 | 8/2016 | |
| WO | WO 2018/049233 A1 | 3/2018 | |

OTHER PUBLICATIONS

Dowling, J.E. et al. (Jan. 24, 2010) "Potent and Selective Inhibitors of CK2 Kinase Identified through Structure-Guided Hybridization," *ACS Medicinal Chemistry Letters*, 3(4):278-283.

Dowling, J.E. et al. (Jul. 2013) "Structure and Property Based Design of Pyrazolo[1,5-a]pyrimidine Inhibitors of CK2 Kinase with Activity in Vivo" *ACS Medicinal Chemistry Letters*, 4(8):800-805.

Dwyer, M.P. et al. (Jan. 2011) "Discovery of pyrazolo[1,5-a]pyrimidine-based CHK1 inhibitors: A template-based approach—Part 1" *Bioorganic & Medicinal Chemistry Letters*, 21:467-470.

International Search Report and Written Opinion dated Feb. 10, 2017, in International Patent Application No. PCT/US2016/062731, filed Nov. 18, 2016, by Blueprint Medicines Corp.

International Search Report and Written Opinion dated Nov. 18, 2016, in International Patent Application No. PCT/US2016/048698, filed Aug. 25, 2016, by Blueprint Medicines Corp.

Notice of Allowance dated Mar. 9, 2018, in U.S. Appl. No. 15/248,207, filed Aug. 26, 2016, by Blueprint Medicines Corp.

Notice of Allowance dated Jun. 5, 2018, in U.S. Appl. No. 15/340,428, filed Nov. 1, 2016, by Blueprint Medicines Corp.

Notice of Allowance dated Jun. 27, 2018, in U.S. Appl. No. 15/222,523, filed Jul. 28, 2016, by Blueprint Medicines Corp.

Notice of Allowance dated Apr. 25, 2018, in U.S. Appl. No. 15/462,255, filed Mar. 17, 2017, by Blueprint Medicines Corp.

Notice of Allowance dated Feb. 13, 2018, in U.S. Appl. No. 15/660,840, filed Jul. 26, 2017, by Blueprint Medicines Corp.

Traxler, P. et al. (1997) "Use of a Pharmacore Model for the Design of EGF-R Tyrosine Kinase Inhibitors: 4-(Phenylamino)pyrazolo[3,4-d]pyrimidines" *J Med Chem*, 40(22):3601-3616.

U.S. Appl. No. 15/867,637, filed Jan. 10, 2018, by Blueprint Medicines Corp.

U.S. Appl. No. 15/973,340, filed May 7, 2018, by Blueprint Medicines Corp.

U.S. Appl. No. 15/973,378, filed May 7, 2018, by Blueprint Medicines Corp.

U.S. Appl. No. 16/002,587, filed Jun. 7, 2018, by Blueprint Medicines Corp.

STN Registry No. 1017684-07-9, 1 page, dated Apr. 28, 2008.
STN Registry No. 1017684-10-4, 1 page, dated Apr. 28, 2008.
STN Registry No. 1017684-13-7, 1 page, dated Apr. 28, 2008.
STN Registry No. 1017684-15-9, 1 page, dated Apr. 28, 2008.
STN Registry No. 1017684-17-1, 1 page, dated Apr. 28, 2008.
STN Registry No. 1224289-06-8, 1 page, dated May 17, 2010.
STN Registry No. 1224289-08-0, 1 page, dated May 17, 2010.
STN Registry No. 1265679-25-1, 1 page, dated Mar. 2, 2011.
STN Registry No. 138904-40-2, 1 page, dated Feb. 14, 1992.
STN Registry No. 138904-41-3, 1 page, dated Feb. 14, 1992.
STN Registry No. 138904-42-4, 1 page, dated Feb. 14, 1992.
STN Registry No. 138904-43-5, 1 page, dated Feb. 14, 1992.
STN Registry No. 138904-44-6, 1 page, dated Feb. 14, 1992.
STN Registry No. 138904-45-7, 1 page, dated Feb. 14, 1992.
STN Registry No. 138904-46-8, 1 page, dated Feb. 14, 1992.
STN Registry No. 140706-37-2, 1 page, dated Apr. 26, 1992.
STN Registry No. 144488-64-2, 1 page, dated Nov. 13, 1992.

Singapore Office Action for Application No. 11201803920T, dated Jul. 8, 2019, 13 pages.

U.S. Appl. No. 16/002,587, filed Jun. 7, 2018—Abandoned.

Russian Office Action for Application No. 2018110379, dated Dec. 25, 2019, 16 pages.

Doebele et al., An oncogenic NTRK fusion in a patient with soft-tissue sarcoma with response to the Tropomyosin-related kinase inhibitor LOXO-101. Cancer Discov. Oct. 2015;5(10):1049-57.

U.S. Appl. No. 15/248,207, filed Aug. 26, 2016, U.S. Pat. No. 10,017,512, Issued.

U.S. Appl. No. 15/355,425, filed Nov. 18, 2016, U.S. Pat. No. 10,370,379, Issued.

U.S. Appl. No. 16/527,773, filed Jul. 31, 2019, 2019-0382410, Published.

Figure 1A

| # | Structure | NMR; LCMS |
|---|---|---|
| 1 | 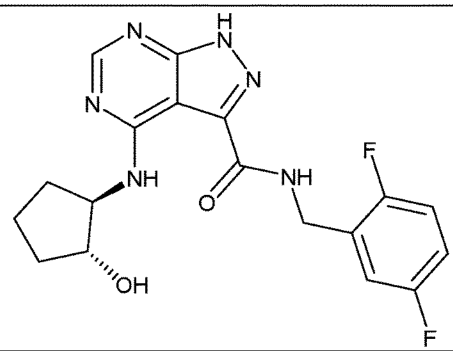 | 1H-NMR (400 MHz, CD3OD) δ ppm 8.34 (s, 1H), 7.13-7.02 (m, 3H), 4.66 (s, 2H), 4.17 (d, 2H, J = 3.2 Hz), 2.32-2.29 (m, 1H), 2.11-2.08 (m, 1H), 1.91-1.87 (m, 2H), 1.86-1.74 (m, 2H).; LCMS: 389.1 |
| 2 | 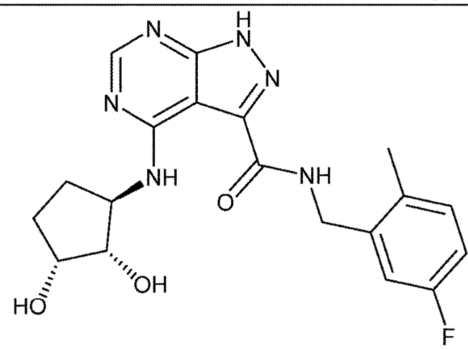 | 1H-NMR (400 MHz, CD3OD) δ ppm 8.37 (s, 1H), 7.319-7.15 (m, 1H), 7.02-7.01 (m, 1H), 6.99-6.88 (m, 1H), 4.61 (s, 2H), 4.38-4.31 (m, 1H), 4.13-4.11 (m, 1H), 4.03-4.02 (m, 1H), 2.44-2.41 (m, 1H), 2.34 (s, 3H), 2.16-2.13 (m, 1H), 1.79-1.70 (m, 2H).; LCMS: 401.1 |
| 3 | 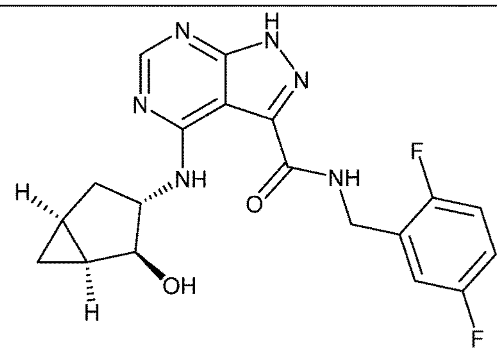 | 1H-NMR (400 MHz, CD3OD) δ ppm 8.21 (s, 1H), 7.15-7.09 (m, 2H), 7.08-7.01 (m, 1H), 4.65 (s, 2H), 4.41-4.38 (m, 1H), 4.03-3.96 (m, 1H), 2.41-2.36 (m, 1H), 1.90-1.89 (m, 1H), 1.58-1.56 (m, 1H), 1.44-1.41 (m, 1H), 0.76-0.73 (m, 1H), 0.50-0.47 (m, 1H).; LCMS: 401.1 |
| 4 | 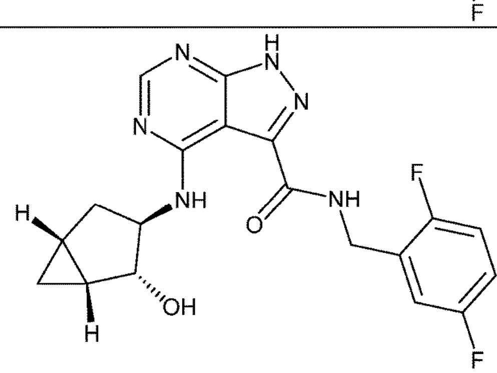 | 1H-NMR (400 MHz, CD3OD) δ ppm 8.12 (s, 1H), 7.06-6.99 (m, 2H), 6.93-6.92 (m, 1H), 4.56 (s, 2H), 4.32-4.29 (m, 1H), 3.93-3.87 (m, 1H), 2.32-2.25 (m, 1H), 1.81-1.80 (m, 1H), 1.49-1.47 (m, 1H), 1.35-1.33 (m, 1H), 0.67-0.64 (m, 1H), 0.41-0.40 (m, 1H).; LCMS: 401.1 |

| | | |
|---|---|---|
| 5 |  | 1H-NMR (400 MHz, CD3OD) δ ppm 8.51-8.47 (m, 2H), 8.38 (d, 1H, J = 2.0 Hz), 7.74 (d, 1H, J = 9.2 Hz), 5.50 (s, 1H), 4.94 (s, 1H), 4.39-4.34 (m, 1H), 4.15-4.13 (m, 1H), 4.07-4.01 (m, 1H), 3.70 (s, 1.5H), 3.20 (s, 1.5H), 2.47-2.44 (m, 1H), 2.19-2.16 (m, 1H), 1.84-1.71 (m, 2H).; LCMS: 402.1 |
| 6 |  | 1H-NMR (400 MHz, CD3OD) δ ppm 8.40 (d, 1H, J = 4.0 Hz), 7.22-7.07 (m, 3H), 5.51 (s, 1H), 4.26-4.17 (m, 2H), 3.70 (s, 1.5H), 3.21 (s, 1.5H), 2.38-2.36 (m, 1H), 2.17-2.06 (m, 1H), 1.96-1.76 (m, 4H).; LCMS: 403.1 |
| 7 |  | 1H-NMR (400 MHz, CD3OD) δ ppm 8.34 (s, 1H), 7.22-7.21 (m, 1H), 7.13-7.11 (m, 1H), 7.04-7.02 (m, 1H), 5.56-5.51 (m, 1H), 4.16-4.13 (m, 2H), 2.32-2.29 (m, 1H), 2.09-2.08 (m, 1H), 1.90-1.70 (m, 4H), 1.59 (d, 3H, J = 7.2 Hz).; LCMS: 403.1 |
| 8 |  | 1H-NMR (400 MHz, CD3OD) δ ppm 8.32 (s, 1H), 7.15-7.09 (m, 2H), 7.05-7.03 (m, 1H), 4.67 (s, 2H), 4.15-4.11 (m, 1H), 4.05-4.04 (m, 1H), 3.98-3.95 (m, 1H), 3.85-3.84 (m, 1H), 3.56 (t, 1H, J = 10.8 Hz), 3.43 (t, 1H, J = 10.8 Hz), 2.10-2.07 (m, 1H), 1.76-1.68 (m, 1H).; LCMS: 405.0 |

Figure 1C

| | | |
|---|---|---|
| 9 | (structure: pyrazolo[3,4-d]pyrimidine with (1S,2R,3S)-2,3-dihydroxycyclopentylamino and 2,5-difluorobenzylamide) | 1H-NMR (400 MHz, CD3OD) δ ppm 8.35 (s, 1H), 7.16-7.03 (m, 3H), 4.68 (s, 2H), 4.37 (q, 1H, J = 8.4 Hz), 4.12 (d, 1H, J = 4.4 Hz), 4.02 (dd, 1H, J = 8.4, 4.4 Hz), 2.45-2.42 (m, 1H), 2.17-2.14 (m, 1H), 1.82-1.71 (m, 2H).; LCMS: 405.1 |
| 10 | (structure: pyrazolo[3,4-d]pyrimidine with dihydroxycyclopentylamino and 2,5-difluorobenzylamide) | 1H-NMR (400 MHz, CD3OD) δ ppm 8.35 (s, 1H), 7.16-7.03 (m, 3H), 4.68 (s, 2H), 4.40-4.36 (m, 1H), 4.12 (d, 1H, J = 4.0 Hz), 4.02 (dd, 1H, J = 8.4, 4.4 Hz), 2.45-2.42 (m, 1H), 2.17-2.13 (m, 1H), 1.81-1.70 (m, 2H).; LCMS: 405.1 |
| 11 | (structure: pyrazolo[3,4-d]pyrimidine with hydroxytetrahydropyranylamino and 2,5-difluorobenzylamide) | 1H-NMR (400 MHz, CD3OD) δ ppm 8.34 (s, 1H), 7.16-7.10 (m, 2H), 704-7.03 (m, 1H), 4.68 (s, 2H), 4.07-4.01 (m, 1H), 4.00-3.97 (m, 2H), 3.67-3.65 (m, 1H), 3.52-3.51 (m, 1H), 3.27-3.24 (m, 1H), 2.19-2.15 (m, 1H), 1.83-1.79 (m, 1H).; LCMS: 405.1 |
| 12 | (structure: pyrazolo[3,4-d]pyrimidine with hydroxycyclopentylamino and 2,5-difluorobenzylamide) | 1H-NMR (400 MHz, CD3OD) δ ppm 8.17 (s, 1H), 7.05-7.00 (m, 2H), 6.93-6.92 (m, 1H), 4.60-4.56 (m, 2H), 4.42-4.38 (m, 1H), 4.28-4.26 (m, 1H), 4.03-3.97 (m, 1H), 2.41-2.36 (m, 1H), 2.17-2.14 (m, 1H), 1.90-1.85 (m, 1H), 1.60-1.57 (m, 1H).; LCMS: 405.1 |

Figure 1D

| | | |
|---|---|---|
| 13 | (structure) | 1H-NMR (400 MHz, CD3OD) δ ppm 8.26 (s, 1H), 7.15-7.09 (m, 2H), 7.03-7.02 (m, 1H), 4.65 (s, 2H), 4.53-4.49 (m, 1H), 4.39-4.35 (m, 1H), 4.12-4.07 (m, 1H), 2.50-2.45 (m, 1H), 2.26-2.25 (m, 1H), 1.99-1.92 (m, 1H), 1.70-1.66 (m, 1H).; LCMS: 405.1 |
| 14 | (structure) | 1H-NMR (400 MHz, CD3OD) δ ppm 8.26 (s, 1H), 7.16-7.09 (m, 2H), 7.02-7.01(m, 1H), 5.27-5.13 (m, 1H), 4.65 (s, 2H), 4.38-4.33 (m, 2H), 2.79-2.70 (m, 1H), 2.37-2.35 (m, 1H), 1.99-1.88 (m, 2H).; LCMS: 407.1 |
| 15 | (structure) | 1H-NMR (400 MHz, CDCl3) δ ppm 9.76 (s, 1H), 8.35 (s, 1H), 7.57 (t, 1H, J = 5.6 Hz), 7.05-6.90 (m, 3H), 5.16 (d, 1H, J = 52.4 Hz), 4.68-4.62 (m, 2H), 4.39-4.34 (m, 1H), 4.15-4.12 (m, 1H), 2.78-2.70 (m, 1H), 2.48-2.40 (m, 1H), 2.18-2.08 (m, 1H), 1.93-1.81 (m, 1H).; LCMS: 407.1 |
| 16 | (structure) | 1H-NMR (400 MHz, CD3OD) δ ppm 8.26 (s, 1H), 7.12-7.07 (m, 2H), 7.02-7.00 (m, 1H), 5.15 (d, 1H, J = 53.6 Hz), 4.64 (s, 2H), 4.58-4.52 (m, 1H), 4.17 (dd, 1H, J = 12.8, 6.4 Hz), 2.59-2.51 (m, 2H), 1.99-1.87 (m, 2H).; LCMS: 407.1 |

Figure 1E

| | | |
|---|---|---|
| 17 | *(structure)* | 1H-NMR (400 MHz, CD3OD) δ ppm 8.26 (s, 1H), 7.14-7.08 (m, 2H), 7.02-7.00 (m, 1H), 5.13 (d, 1H, J = 53.2 Hz), 4.64 (s, 2H), 4.57-4.52 (m, 1H), 4.19-4.16 (m, 1H), 2.59-2.51 (m, 2H), 1.99-1.90 (m, 2H).; LCMS: 407.1 |
| 18 | *(structure)* | 1H-NMR (400 MHz, CD3OD) δ ppm 8.14 (s, 1H), 7.04-6.97 (m, 2H), 6.91-6.90 (m, 1H), 4.89-4.88 (m, 1H), 4.55 (s, 2H), 4.53-4.46 (m, 1H), 3.98-3.89 (m, 1H), 2.38-2.3 (m, 1H), 2.18-2.00 (m, 1H), 1.90-1.83 (m, 1H), 1.56-1.52 (m, 1H).; LCMS: 407.1 |
| 19 | *(structure)* | 1H-NMR (400 MHz, CD3OD) δ ppm 8.13 (s, 1H), 7.05-6.98 (m, 2H), 6.91-6.90 (m, 1H), 4.89-4.87 (m, 1H), 4.55 (s, 2H), 4.50-4.46 (m, 1H), 3.98-3.89 (m, 1H), 2.37-2.32 (m, 1H), 2.19-2.00 (m, 1H), 1.90-1.83 (m, 1H), 1.56-1.51 (m, 1H).; LCMS: 407.1 |
| 20 | *(structure)* | 1H-NMR (400 MHz, CD3OD) δ ppm 8.26 (s, 1H), 7.15-7.01 (m, 3H), 4.94-4.92 (m, 1H), 4.66 (s, 2H), 4.32-4.28 (m, 1H), 4.17-4.10 (m, 1H), 2.34-1.88 (m, 4H).; LCMS: 407.2 |

Figure 1F

| | | |
|---|---|---|
| 21 | (structure) | 1H-NMR (400 MHz, CD3OD) δ ppm 8.17 (s, 1H), 7.05-6.92 (m, 3H), 4.86-4.83 (m, 1H), 4.56 (s, 2H), 4.23-4.21 (m, 1H), 4.08-4.02 (m, 1H), 2.24-1.78 (m, 4H).; LCMS: 407.2 |
| 22 | (structure) | 1H-NMR (400 MHz, CD3OD) δ ppm 8.36 (s, 1H), 7.58 (s, 1H), 7.47 (s, 2H), 4.67 (s, 2H), 4.39-4.37 (m, 1H), 4.13 (s, 1H), 4.02 (s, 1H), 2.44 (br.s, 1H), 2.16-2.15 (m, 1H), 1.79-1.69 (m, 2H).; LCMS: 412.1 |
| 23 | (structure) | 1H-NMR (400 MHz, CD3OD) δ ppm 8.37, 8.34 (s, 1H), 7.25-7.18 (m, 1H), 6.93-6.82 (m, 2H), 5.40 (s, 1H), 4.42-4.35 (m, 1H), 4.16-3.99 (m, 2H), 3.61 (s, 1.5H), 3.22 (s, 1.5H), 2.47-2.43 (m, 1H), 2.31 (s, 1.5H), 2.28 (s, 1.5H), 2.18-2.12 (m, 1H), 1.83-1.75 (m, 2H).; LCMS: 415.1 |
| 24 | (structure) | $^1$H NMR (500 MHz, DMSO-$d_6$) δ 14.07 (s, 1H), 9.45 (d, $J$ = 7.7 Hz, 1H), 9.26 (t, $J$ = 6.4 Hz, 1H), 8.27 (s, 1H), 7.11 – 6.81 (m, 3H), 6.51 (s, 0H), 5.10 (d, $J$ = 4.8 Hz, 1H), 4.47 (d, $J$ = 6.3 Hz, 2H), 4.04 (dd, $J$ = 7.8, 4.0 Hz, 1H), 3.96 (dd, $J$ = 11.2, 3.9 Hz, 1H), 3.82 (s, 3H), 3.81 – 3.71 (m, 1H), 3.65 (s, 1H), 3.43 (t, $J$ = 9.3 Hz, 1H), 3.18 (dd, $J$ = 11.2, 7.6 Hz, 1H), 1.93 – 1.85 (m, 1H), 1.53 – 1.43 (m, 1H); LCMS: 417 |

Figure 1G

| 25 | (structure) | ¹H NMR (500 MHz, DMSO-$d_6$) δ 14.09 (s, 1H), 9.48 – 9.31 (m, 2H), 8.30 (s, 1H), 7.25 (td, $J$ = 9.4, 4.5 Hz, 1H), 7.15 (td, $J$ = 7.5, 6.7, 4.1 Hz, 2H), 4.81 (d, $J$ = 4.1 Hz, 1H), 4.55 (d, $J$ = 6.2 Hz, 2H), 4.40 (d, $J$ = 7.1 Hz, 1H), 4.35 (d, $J$ = 7.7 Hz, 2H), 3.64 (t, $J$ = 5.1 Hz, 1H), 1.56 (dq, $J$ = 8.7, 4.2 Hz, 1H), 1.32 (p, $J$ = 4.6 Hz, 1H), 1.07 (q, $J$ = 4.1 Hz, 1H), 0.43 (td, $J$ = 8.3, 4.6 Hz, 1H); LCMS: 417 |
|---|---|---|
| 26 | (structure) | 1H-NMR (400 MHz, CD3OD) δ ppm 8.37-8.36 (m, 1H), 7.17-7.07 (m, 3H), 4.81 (s, 2H), 4.16-4.13 (m, 2H), 3.66-3.60 (m, 2H), 2.40-2.27 (m, 1H), 2.20-2.03 (m, 1H), 1.91-1.72 (m, 4H), 1.40-1.24 (m, 3H).; LCMS: 417.1 |
| 27 | (structure) | ¹H NMR (400 MHz, DMSO-$d_6$) δ 14.06 (s, 1H), 9.24 (d, $J$ = 7.2 Hz, 1H), 9.11 (d, $J$ = 8.6 Hz, 1H), 8.20 (s, 1H), 7.35 (ddd, $J$ = 9.1, 5.7, 3.2 Hz, 1H), 7.20 (td, $J$ = 9.3, 4.6 Hz, 1H), 7.10 (ddt, $J$ = 9.0, 7.3, 3.6 Hz, 1H), 5.44 – 5.32 (m, 1H), 5.11 (t, $J$ = 5.9 Hz, 1H), 5.02 – 4.91 (m, 1H), 4.16 (p, $J$ = 6.6 Hz, 1H), 3.86 (ddt, $J$ = 9.1, 6.2, 3.6 Hz, 1H), 3.77 – 3.60 (m, 2H), 2.15 – 2.02 (m, 1H), 1.78 (m, 1H), 1.64 (m, 2H), 1.42 (m, 2H); LCMS: 419 |
| 28 | (structure) | ¹H NMR (400 MHz, DMSO-$d_6$) δ 14.08 (br s, 1H), 9.30 (m, 1H), 8.28 (s, 1H), 7.31 (m, 1H), 7.20 (m, 2H), 5.36 (d, $J$ = 2.4 Hz, 1H), 4.90 – 4.76 (m, 1H), 4.40 (q, $J$ = 7.5 Hz, 1H), 3.94 (dtd, $J$ = 11.7, 5.6, 5.1, 3.4 Hz, 1H), 3.72 (ddd, $J$ = 22.6, 7.5, 4.5 Hz, 2H), 3.60 (br s, 1H), 3.07 (s, 3H), 2.32 – 2.19 (m, 1H), 1.94 (m, 1H), 1.58 (m, 1H), 1.41 – 1.26 (m, 1H); LCMS: 419 |

Figure 1H

| 29 | (structure) | 1H-NMR (400 MHz, CDCl3) δ ppm 10.62-10.49 (m, 1H), 8.39 (d, 1H, J = 5.6 Hz), 7.10-6.97 (m, 3H), 5.47-5.34 (m, 1H), 4.83 (s, 1H), 4.26-4.16 (m, 2H), 4.02-3.89 (m, 2H), 3.60-3.45 (m, 3.5H), 3.13 (s,1.5H), 2.17-2.13 (m, 1H), 1.81 (br.s, 1H).; LCMS: 419.1 |
|---|---|---|
| 30 | (structure) | 1H-NMR (400 MHz, CDCl3) δ ppm 13.68 (br.s, 1H), 9.40 (d, 1H, J = 6.8 Hz), 8.33 (s, 1H), 7.61 (d, 1H, J = 9.2 Hz), 7.03-6.88 (m, 3H), 5.40 (t, 1H, J = 7.6 Hz), 4.13-4.09 (m, 2H), 3.95-3.92 (m, 1H), 3.78-3.76 (m, 1H), 3.42-3.34 (m, 2H), 2.04 (dd, 1H, J = 10.8, 2.0 Hz), 1.73-1.70 (m, 1H), 1.57 (d, 3H, J = 7.2 Hz).; LCMS: 419.1 |
| 31 | (structure) | 1H-NMR (400 MHz, CD3OD) δ ppm 8.34 (s, 1H), 7.23-7.21 (m, 1H), 7.13-7.10 (m, 1H), 7.04-7.01 (m, 1H), 5.58-5.52 (m, 1H), 4.03-3.94 (m, 3H), 3.62-3.61 (m, 1H), 3.52-3.49 (m, 1H), 3.27-3.22 (m, 1H), 2.17-2.13 (m, 1H), 1.86-1.80 (m, 1H), 1.60 (d, 3H, J = 7.2 Hz).; LCMS: 419.1 |
| 32 | (structure) | 1H-NMR (400 MHz, CD3OD) δ ppm 8.21 (s, 1H), 7.14-7.10 (m, 2H), 7.03-7.01 (m, 1H), 4.66 (s, 2H), 4.51-4.45 (m, 1H), 4.00 (s, 1H), 3.70-3.63 (m, 1H), 2.09-2.07 (m, 1H), 1.85-1.78 (m, 2H), 1.61-1.56 (m, 2H), 1.45-1.36 (m, 1H).; LCMS: 419.1 |

| 33 |  | 1H-NMR (400 MHz, CD3OD) δ ppm 8.36 (d, 1H, J = 5.6 Hz), 6.99-6.96 (m, 2H), 6.92-6.88 (m, 1H), 5.43 (s, 1H), 4.90 (s, 1H), 4.43-4.37 (m, 1H), 4.15-4.13 (m, 1H), 4.05-4.01 (m, 1H), 3.64 (s, 1.5H), 3.16 (s, 1.5H), 2.46-2.43 (m, 1H), 2.19-2.15 (m, 1H), 1.82-1.65 (m, 2H).; LCMS: 419.1 |
| --- | --- | --- |
| 34 |  | 1H-NMR (400 MHz, CD3OD) δ ppm 8.34 (s, 1H), 7.21 (br.s, 1H), 7.11-7.09 (m, 1H), 7.01 (br.s, 1H), 5.54 (d, 1H, J = 7.2 Hz), 4.39-4.32 (m, 1H), 4.10 (br.s, 1H), 3.99-3.96 (m, 1H), 2.43-2.40 (m, 1H), 2.14-2.12 (m, 1H), 1.78-1.74 (m, 1H), 1.69 (br.s, 1H), 1.59 (d, 3H, J = 6.8 Hz).; LCMS: 419.2 |
| 35 |  | 1H-NMR (400 MHz, CD3OD) δ ppm 8.34 (s, 1H), 7.21 (br.s, 1H), 7.13-7.09 (m, 1H), 7.03-7.01 (m, 1H), 5.55-5.51 (m, 1H), 4.37-4.31 (m, 1H), 4.11 (s, 1H), 4.02-3.99 (m, 1H), 2.42-2.38 (m, 1H), 2.15-2.11 (m, 1H), 1.78-1.76 (m, 1H), 1.67-1.64 (m, 1H), 1.59 (d, 3H, J = 6.8 Hz).; LCMS: 419.2 |
| 36 |  | $^1$H NMR (400 MHz, DMSO-$d_6$) δ 14.10 (s, 1H), 9.49 (m, 1H), 9.37 (d, J = 7.3 Hz, 1H), 8.27 (s, 1H), 7.53 (dd, J = 8.8, 5.1 Hz, 1H), 7.18 (td, J = 8.4, 2.9 Hz, 1H), 7.12 (dd, J = 9.4, 3.5 Hz, 1H), 5.68 (d, J = 7.4 Hz, 1H), 4.87 (m, 1H), 4.56 (m, 1H), 4.48 (m, 1H), 4.39 (p, J = 7.6 Hz, 2H), 3.90 (m, 1H), 3.70 (m, 1H), 2.22 (m, 1H), 1.91 (m, 1H), 1.60 – 1.47 (m, 1H), 1.31 (m, 1H); LCMS: 421 |

Figure 1J

| | | |
|---|---|---|
| 37 | 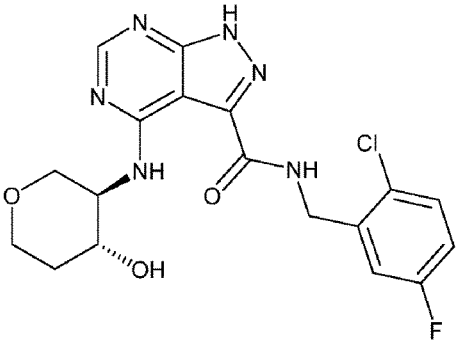 | ¹H NMR (400 MHz, DMSO-$d_6$) δ 13.80 (s, 1H), 9.43 (t, $J$ = 6.2 Hz, 1H), 9.31 (d, $J$ = 7.8 Hz, 1H), 8.22 (s, 1H), 7.47 (dd, $J$ = 8.8, 5.1 Hz, 1H), 7.13 (td, $J$ = 8.4, 3.1 Hz, 1H), 7.06 (dd, $J$ = 9.6, 3.1 Hz, 1H), 5.06 (d, $J$ = 4.8 Hz, 1H), 4.51 (d, $J$ = 6.2 Hz, 2H), 3.99 (qd, $J$ = 7.7, 3.8 Hz, 1H), 3.91 (dd, $J$ = 11.1, 4.0 Hz, 1H), 3.72 (dt, $J$ = 11.3, 4.6 Hz, 1H), 3.59 (tt, $J$ = 8.5, 4.5 Hz, 1H), 3.38 (ddd, $J$ = 11.7, 9.0, 3.1 Hz, 1H), 3.12 (dd, $J$ = 11.1, 7.7 Hz, 1H), 1.84 (ddt, $J$ = 9.2, 7.6, 3.6 Hz, 1H), 1.43 (dtd, $J$ = 13.0, 8.7, 4.0 Hz, 1H); LCMS: 421 |
| 38 | 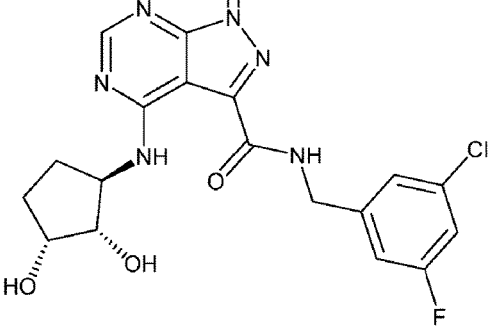 | 1H-NMR (400 MHz, CD3OD) δ ppm 8.24 (s, 1H), 7.23 (s, 1H), 7.08 (d, 2H, $J$ = 8.8 Hz), 4.60 (s, 2H), 4.51-4.46 (m, 1H), 4.13 (br.s, 1H), 3.94-3.90 (m, 1H), 2.46-2.40 (m, 1H), 2.11-2.06 (m, 1H), 1.78-1.74 (m, 1H), 1.62-1.58 (m, 1H).; LCMS: 421.2 |
| 39 | 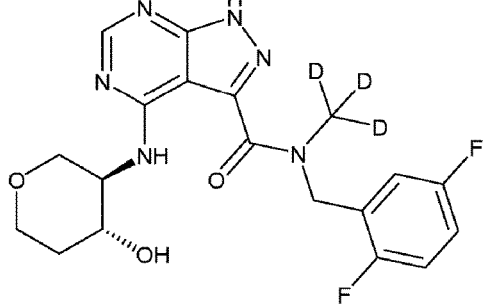 | ¹H NMR (500 MHz, DMSO-$d_6$) δ 9.19 (d, $J$ = 145.0 Hz, 1H), 8.08 (d, $J$ = 31.1 Hz, 1H), 7.37 – 7.02 (m, 3H), 5.58 (s, 1H), 5.18 (s, 1H), 4.78 (s, 1H), 4.08 – 3.90 (m, 2H), 3.78 (s, 1H), 3.63 (s, 1H), 3.43 (d, $J$ = 11.5 Hz, 1H), 3.17 (dd, $J$ = 11.2, 7.4 Hz, 1H), 1.92 (s, 2H), 1.48 (s, 1H); LCMS: 422 |
| 40 | 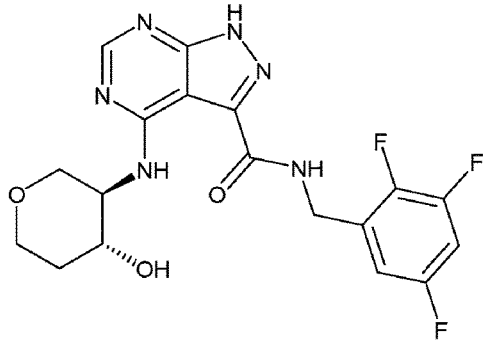 | ¹H NMR (500 MHz, DMSO-$d_6$) δ 14.19 (s, 1H), 9.51 (t, $J$ = 6.3 Hz, 2H), 7.57 – 7.35 (m, 1H), 7.11 – 6.94 (m, 1H), 4.60 (d, $J$ = 6.1 Hz, 2H), 4.04 (dt, $J$ = 11.7, 5.8 Hz, 1H), 3.97 (dd, $J$ = 11.1, 4.0 Hz, 1H), 3.78 (dd, $J$ = 11.3, 5.1 Hz, 1H), 3.60 (tt, $J$ = 6.6, 3.4 Hz, 1H), 3.48 – 3.40 (m, 1H), 3.19 (dd, $J$ = 11.1, 7.7 Hz, 1H), 3.12 (qd, $J$ = 7.3, 4.2 Hz, 2H), 1.91 (d, $J$ = 13.1 Hz, 1H), 1.50 (dq, $J$ = 8.7, 4.6 Hz, 1H); LCMS: 423 |

Figure 1K

| | | |
|---|---|---|
| 41 | (structure) | 1H-NMR (400 MHz, CD3OD) δ ppm 8.37 (s, 1H), 7.09-6.98 (m, 2H), 4.71 (s, 2H), 4.41-4.34 (m, 1H), 4.13 (br.s, 1H), 4.04-4.02 (m, 1H), 2.45-2.43 (m, 1H), 2.17-2.13 (m, 1H), 1.82-1.69 (m, 2H).; LCMS: 423.1 |
| 42 | (structure) | 1H-NMR (400 MHz, CD3OD) δ ppm 8.33 (s, 1H), 7.14-6.99 (m, 3H), 4.65 (s, 2H), 4.49-4.43 (m, 1H), 4.35-4.32 (m, 1H), 2.85-2.80 (m, 1H), 2.67-2.58 (m, 1H), 2.26-2.16 (m, 2H).; LCMS: 425.1 |
| 43 | (structure) | 1H-NMR (400 MHz, CD3OD) δ ppm 8.28 (s, 1H), 7.13-6.99 (m, 3H), 4.65 (s, 2H), 4.52-4.46 (m, 1H), 4.33-4.28 (m, 1H), 2.87-2.79 (m, 1H), 2.64-2.59 (m, 1H), 2.22-2.14 (m, 2H).; LCMS: 425.1 |
| 44 | (structure) | 1H-NMR (400 MHz, CD3OD) δ ppm 8.33 (d, 1H, J = 6.0 Hz), 7.60 (d, 1H, J = 9.2 Hz), 7.52-7.49 (m, 2H), 5.43 (d, 1H, J = 3.6 Hz), 4.90 (d, 1H, J = 3.2 Hz), 4.43-4.38 (m, 1H), 4.13 (br.s, 1H), 4.03-3.96 (m, 1H), 3.65 (s, 1.5H), 3.17 (s, 1.5H), 2.48-2.44 (m, 1H), 2.17-2.13 (m, 1H), 1.83-1.66 (m, 2H).; LCMS: 426.1 |

| 45 |  | 1H-NMR (400 MHz, CDCl3) δ ppm 11.58-11.21 (m, 1H), 8.47 (br.s, 0.5H), 6.98-6.55 (m, 3.5H), 6.33 (d, 0.5H, J = 8.0 Hz), 5.51-5.49 (m, 0.5H), 4.38-3.83 (m, 4H), 2.37-2.32 (m, 2H), 2.05-1.64 (m, 8H).; LCMS: 429.1 |
| --- | --- | --- |
| 46 |  | 1H-NMR (400 MHz, CD3OD) δ ppm 8.50 (br.s, 1H), 8.40 (br.s, 1H), 8.38 (s, 1H), 7.72 (d, 1H, J = 9.2 Hz), 5.54-5.41 (m, 2H), 4.97-4.92 (m, 1H), 4.59-4.45 ((m, 1H), 4.09-4.04 (m, 2H), 2.91-2.84 (m, 1H), 2.29-2.26 (m, 2H), 1.79-1.66 (m, 5H).; LCMS: 430.1 |
| 47 |  | 1H-NMR (400 MHz, CD3OD) δ ppm 9.57 (s, 1H), 8.34 (s, 1H), 7.38-7.37 (m, 1H), 7.06-6.96 (m, 2H), 4.13-4.09 (m, 1H), 4.00-3.96 (m, 2H), 3.87-3.76 (m, 1H), 3.58-3.47(m, 1H), 3.45-3.44 (m, 1H), 2.11-2.07 (m, 1H), 1.75-1.66 (m, 1H), 1.37 (s, 4H).; LCMS: 431.1 |
| 48 |  | 1H-NMR (400 MHz, CD3OD) δ ppm 8.36 (d, 1H, J = 4.8 Hz), 6.73 (d, 1H, J = 12.0 Hz), 6.69-6.63 (m, 2H), 5.40 (s, 1H), 4.82 (s, 1H), 4.39-4.36 (m, 1H), 4.15-4.12 (m, 1H), 4.06-4.02 (m, 1H), 3.78 (d, 3H, J = 6.4 Hz), 3.62 (s, 1.5H), 3.14 (s, 1.5H), 2.47-2.44 (m, 1H), 2.18-2.15 (m, 1H), 1.82-1.70 (m, 2H).; LCMS: 431.1 |

Figure 1M

| | | |
|---|---|---|
| 49 | (structure) | 1H-NMR (400 MHz, CD3OD) δ ppm 8.35 (d, 1H, J = 3.6 Hz), 7.01-6.93 (m, 1H), 5.44-5.33 (m, 1H), 4.83 (s, 1H), 4.40-4.35 (m, 1H), 4.14-4.12 (m, 1H), 4.05-4.01 (m, 1H), 3.86 (s, 1.5H), 3.75 (s, 1.5H), 3.63 (s, 1.5H), 3.12 (s, 1.5H), 2.46-2.43 (m, 1H), 2.17-2.15 (m, 1H), 1.82-1.63 (m, 2H).; LCMS: 431.1 |
| 50 | (structure) | 1H-NMR (400 MHz, CD3OD) δ ppm 8.60 (br.s, 1H), 8.50 (br.s, 1H), 8.43 (s, 1H), 7.89 (d, 1H, J = 9.2 Hz), 5.57-5.35 (m, 2H), 4.58-4.38 (m, 3H), 4.25-4.13 (m, 2H), 4.00-3.93 (m, 1H), 3.84-3.71 (m, 2H), 2.90-2.82 (m, 1H), 2.34-2.21 (m, 1H).; LCMS: 432.1 |
| 51 | (structure) | 1H-NMR (400 MHz, CD3OD) δ ppm 8.36 (s, 1H), 7.22-7.19 (m, 1H), 7.12-7.11 (m, 1H), 7.02-7.01 (m, 1H), 5.52-5.50 (m, 1H), 5.04-5.02 (m, 1H), 4.78-4.76 (m, 2H), 4.30-3.89 (m, 1H), 3.80-3.75 (m, 2H), 3.36-3.34 (m, 2H), 1.59 (d, 3H, J = 6.8 Hz), 1.50-1.34 (m, 3H).; LCMS: 432.2 |
| 52 | (structure) | 1H-NMR (400 MHz, CD3OD) δ ppm 8.35 (d, 1H, J = 6.0 Hz), 7.94 (dd, 1H, J = 9.2, 2.4 Hz), 7.47-7.41 (m, 1H), 5.31 (s, 1H), 4.78 (s, 1H), 4.41-4.35 (m, 1H), 4.14-4.11 (m, 1H), 4.04-4.02 (m, 1H), 3.97 (s, 1.5H), 3.89 (s, 1.5H), 3.70 (s, 1.5H), 3.17 (s, 1.5H), 2.47-2.40 (m, 1H), 2.18-2.14 (m, 1H), 1.81-1.64 (m, 2H).; LCMS: 432.2 |

Figure 1N

| 53 | | 1H-NMR (400 MHz, CD3OD) δ ppm 8.38 (d, 1H, J = 5.2 Hz), 7.20-7.05 (m, 3H), 4.87 (s, 2H), 4.17-4.11 (m, 2H), 4.00-3.97 (m, 3H), 3.64-3.44 (m, 3H), 2.13-2.06 (m, 1H), 1.76-1.70 (m, 1H), 1.39-1.18 (m, 3H).; LCMS: 433.1 |
|---|---|---|
| 54 | | $^1$H NMR (500 MHz, DMSO-$d_6$) δ 14.19 (s, 1H), 9.51 (t, J = 6.3 Hz, 2H), 7.57 – 7.35 (m, 1H), 7.11 – 6.94 (m, 1H), 4.60 (d, J = 6.1 Hz, 2H), 4.04 (dt, J = 11.7, 5.8 Hz, 1H), 3.97 (dd, J = 11.1, 4.0 Hz, 1H), 3.78 (dd, J = 11.3, 5.1 Hz, 1H), 3.60 (tt, J = 6.6, 3.4 Hz, 1H), 3.48 – 3.40 (m, 1H), 3.19 (dd, J = 11.1, 7.7 Hz, 1H), 3.12 (qd, J = 7.3, 4.2 Hz, 2H), 1.91 (d, J = 13.1 Hz, 1H), 1.50 (dq, J = 8.7, 4.6 Hz, 1H); LCMS: 435 |
| 55 | | LCMS: 435 |
| 56 | | 1H-NMR (400 MHz, CD3OD) δ ppm 8.37 (s, 1H), 7.23-7.21 (m, 1H), 7.13-7.12 (m, 1H), 7.11-7.03 (m, 1H), 5.57-5.54 (m, 1H), 4.14-4.01 (m, 1H), 4.00-3.92 (m, 4H), 3.91-3.90 (m, 1H), 3.61-3.44 (m, 2H), 2.05-2.02 (m, 1H), 1.72-1.68 (m, 1H).; LCMS: 435.1 |

Figure 10

| | | |
|---|---|---|
| 57 | | 1H-NMR (400 MHz, CD3OD) δ ppm 8.36 (d, 1H, J = 14.8 Hz), 7.50-7.45 (m, 1H), 7.09-7.04 (m, 2H), 5.46 (s, 1H), 4.96 (s, 1H), 4.40-4.35 (m, 1H), 4.16-3.97 (m, 2H), 3.67 (s, 1.5H), 3.22 (s, 1.5H), 2.47-2.45 (m ,1H), 2.20-2.16 (m, 1H), 1.87-1.77 (m, 2H).; LCMS: 435.1 |
| 58 | | 1H-NMR (400 MHz, CD3OD) δ ppm 8.36 (d, 1H, J = 5.2 Hz), 7.23 (d, 1H, J = 12.0 Hz), 7.16-7.09 (m, 2H), 5.42 (s, 1H), 4.85 (s, 1H), 4.40-4.36 (m, 1H), 4.15-4.13 (m, 1H), 4.06-4.02 (m, 1H), 3.64 (s, 1.5H), 3.16 (s, 1.5H), 2.47-2.44 (m, 1H), 2.19-2.15 (m, 1H), 1.84-1.72 (m, 2H).; LCMS: 435.1 |
| 59 | | 1H-NMR (400 MHz, CD3OD) δ ppm 8.24 (s, 1H), 6.94-6.89 (m, 2H), 4.64 (s, 2H), 4.52-4.48 (m, 1H), 4.14-4.12 (m, 1H), 3.95 (s, 3H), 3.93-3.92 (m, 1H), 2.43-2.40 (m, 1H), 2.10-2.08 (m, 1H), 1.78-1.75 (m, 1H), 1.61-1.57 (m, 1H).; LCMS: 435.2 |
| 60 | | 1H-NMR (400 MHz, CD3OD) δ ppm 8.26-8.22 (m, 2H), 7.64-7.59 (m, 1H), 5.34 (s, 1H), 4.89 (s, 1H), 4.51-4.47 (m, 1H), 4.15-4.09 (m, 1H), 3.95-3.86 (m, 1H), 3.68 (s, 1.2H), 3.22 (s, 1.8H), 2.46-2.40 (m, 1H), 2.11-2.09 (m, 1H), 1.80-1.49 (m, 2H).; LCMS: 436.2 |

| | | |
|---|---|---|
| 61 |  | 1H-NMR (400 MHz, CD3OD) δ ppm 8.30 (s, 1H), 7.25-7.15 (m, 2H), 7.08-7.07 (m, 1H), 5.55-5.52 (m, 1H), 5.15 (d, 1H, J = 53.6 Hz), 4.60-4.55 (m, 1H), 4.21-4.18 (m, 1H), 3.95-3.88 (m, 2H), 2.62-2.51 (m, 2H), 2.00-1.89 (m, 2H).; LCMS: 436.4 |
| 62 |  | 1H-NMR (400 MHz, CD3OD) δ ppm 8.30 (s, 1H), 7.25-7.15 (m, 2H), 7.08-7.07 (m, 1H), 5.55-5.52 (m, 1H), 5.16 (d, 1H, J = 53.6 Hz), 4.60-4.54 (m, 1H), 4.18-4.14 (m, 1H), 3.94-3.89 (m, 2H), 2.60-2.51 (m, 2H), 1.99-1.90 (m, 2H).; LCMS: 436.4 |
| 63 |  | $^1$H NMR (400 MHz, DMSO-$d_6$) δ 14.09 (br s, 1H), 9.25 (Abqd, 1H), 8.33 (d, $J$ = 8.2 Hz, 1H), 7.67 – 7.47 (m, 1H), 7.14 (m, 1H), 5.46 (m, 1H), 4.96 (m, 1H), 4.59 (dd, $J$ = 9.6, 4.0 Hz, 1H), 4.47 (q, $J$ = 7.8 Hz, 1H), 4.00 (m, 1H), 3.84 – 3.71 (m, 1H), 3.58 (s, 1H), 3.40 (s, 3H), 2.42 – 2.26 (m, 1H), 2.08 – 1.92 (m, 1H), 1.72 – 1.57 (m, 1H), 1.37 (m, 1H); LCMS: 437 |
| 64 |  | $^1$H NMR (400 MHz, DMSO-$d_6$) δ 14.12 (s, 1H), 9.58 – 9.35 (m, 2H), 8.29 (s, 1H), 7.37 – 7.12 (m, 3H), 5.72 (d, $J$ = 6.2 Hz, 1H), 4.67 – 4.49 (m, 2H), 4.29 (s, 1H), 3.76 (m, 1H), 2.04 (m, 2H), 1.99 – 1.79 (m, 1H), 1.71 (s, 1H), 1.47 (m, 2H); LCMS: 439 |

Figure 1Q

| | | |
|---|---|---|
| 65 | (structure) | LCMS: 439 |
| 66 | (structure) | 1H-NMR (400 MHz, CD3OD) δ ppm 8.17 (s, 1H), 7.38-7.34 (m, 3H), 7.10-7.06 (m, 1H), 6.01-5.95 (m, 1H), 4.17-4.12 (m, 1H), 4.07-4.03 (m, 1H), 2.19-2.17 (m, 1H), 1.96-1.94 (m, 1H), 1.76-1.73 (m, 2H), 1.60-1.57 (m, 2H).; LCMS: 439.2 |
| 67 | (structure) | 1H-NMR (400 MHz, CD3OD) δ ppm 8.15 (s, 1H), 7.38-7.35 (m, 3H), 7.10-7.05 (m, 1H), 6.02-5.96 (m, 1H), 4.24-4.14 (m, 1H), 4.03-3.99 (m, 1H), 2.24-2.19 (m, 1H), 1.94-1.93 (m, 1H), 1.77-1.74 (m, 2H), 1.60-1.55 (m, 2H).; LCMS: 439.2 |
| 68 | (structure) | $^1$H NMR (400 MHz, DMSO-$d_6$) δ 14.09 (s, 1H), 9.01 (d, $J$ = 7.1 Hz, 1H), 8.19 (s, 1H), 7.31 (m, 1H), 7.16 – 7.10 (m, 2H), 7.00 (m, 1H), 5.43-5.30 (m, 2H), 4.79 (d, $J$ = 5.6 Hz, 1H), 4.60 (m, 1H), 4.48 – 4.33 (m, 2H), 4.33 – 4.22 (m, 1H), 3.78 (m, 1H), 3.56 (m, 1H), 2.77 – 2.59 (m, 1H), 2.10 (m, 2H), 1.99 – 1.76 (m, 2H), 1.46 (m, 1H), 1.27 – 1.15 (m, 1H); LCMS: 445 |

| 69 |  | 1H-NMR (400 MHz, CDCl3) δ ppm 11.87-11.48 (m, 1H), 8.50-8.46 (m, 1H), 7.06-6.65 (m, 3H), 6.40-6.39 (m, 0.5H), 5.62-5.59 (m, 0.5H), 4.46-3.95 (m, 6H), 3.55-3.51 (m, 2H), 2.42-2.11 (m, 1H), 2.04-1.76 (m, 5H).; LCMS: 445.1 |
|---|---|---|
| 70 |  | 1H-NMR (400 MHz, CD3OD) δ ppm 8.35, 8.28 (s, 1H), 7.14-6.80 (m, 3H), 6.43 (d, 0.5H, J = 7.6 Hz), 5.60 (dd, 0.5H, J = 7.6, 4.0 Hz), 4.52-4.31 (m, 2H), 4.05-3.89 (m, 3H), 2.48-2.41 (m, 2H), 2.12-2.06 (m, 4H), 1.94-1.61 (m, 2H).; LCMS: 445.1 |
| 71 |  | 1H-NMR (400 MHz, CD3OD) δ ppm 8.33, 8.27 (s, 1H), 7.14-6.92 (m, 3H), 6.43 (d, 0.5H, J = 8.0 Hz), 5.58 (dd, 0.5H, J = 8.0, 4.4 Hz), 4.39-4.31 (m, 2H), 4.15-4.08 (m, 2H), 394-3.91 (m, 1H), 2.48-2.43 (m, 2H), 2.12-2.06 (m, 3H), 1.76-1.51 (m, 3H).; LCMS: 445.1 |
| 72 |  | 1H-NMR (400 MHz, CD3OD) δ ppm 8.42 (br.s, 1H), 8.31 (br.s, 1H), 8.26 (s, 1H), 7.63-7.61 (m, 1H), 5.46-5.26 (m, 2H), 4.50-4.37 (m, 1H), 4.26-4.21 (m, 1H), 3.97 (br.s, 2H), 3.80-3.77 (m, 1H), 2.80-2.76 (m, 1H), 2.33-2.30 (m, 1H), 2.29-2.27 (m, 1H), 2.07-2.00 (m, 1H), 1.69-1.67 (m, 1H), 1.52-1.51 (m, 1H).; LCMS: 446.1 |

| 73 |  | 1H-NMR (400 MHz, CD3OD) δ ppm 8.52 (s, 1H), 8.41 (s, 1H), 8.35-8.29 (m, 1H), 7.76 (d, 1H, J = 9.2 Hz), 5.57-5.36 (m, 2H), 4.96-4.94 (m, 1H), 4.60-4.51 (m, 1H), 3.98-3.89 (m, 3H), 3.50-3.47 (m, 2H), 3.24-3.21 (m, 1H), 2.88-2.86 (m, 1H), 2.18-2.09 (m, 2H), 1.75-1.71 (m, 1H).; LCMS: 446.1 |
|---|---|---|
| 74 |  | 1H-NMR (400 MHz, CD3OD) δ ppm 8.60 (br.s, 2H), 8.35 (s, 1H), 7.75 (d, 1H, J = 9.2 Hz), 5.57-5.35 (m, 2H), 4.59-4.45 (m, 1H), 4.09-4.05 (m, 1H), 3.95-3.91 (m, 2H), 3.65-3.75 (m, 1H), 3.53-3.50 (m, 1H), 3.40-3.35 (m, 1H), 2.88-2.86 (m, 1H), 2.29-2.27 (m, 2H), 1.97-1.93 (m, 1H), 1.66-1.63 (m, 1H).; LCMS: 446.2 |
| 75 |  | 1H-NMR (400 MHz, CD3OD) δ ppm 8.89-8.87 (m, 0.5H), 8.52-8.43 (m, 1H), 8.39 (s, 1H), 8.13-8.10 (m, 0.5H), 7.77 (d, 1H, J = 9.2 Hz), 5.55-5.40 (m, 2H), 5.16-5.01 (m, 2H), 4.60-4.37 (m, 2H), 4.17-4.15 (m, 1H), 2.89-2.86 (m, 1H), 2.66-2.56 (m, 1H), 2.44-2.42 (m, 1H), 2.30-2.20 (m, 1H), 1.98-1.88 (m, 2H).; LCMS: 448.1 |
| 76 |  | 1H-NMR (400 MHz, CD3OD) δ ppm 8.87-8.86 (m, 0.5H), 8.67-8.50 (m, 1H), 8.46 (s, 1H), 8.12-8.10 (m, 0.5H), 7.75-7.73 (m, 1H), 5.54-5.24 (m, 2H), 5.16-5.03 (m, 2H), 4.58-4.37 (m, 2H), 4.11-4.07 (m, 1H), 2.87-2.85 (m, 1H), 2.55-2.47 (m, 2H), 2.26-2.01 (m, 1H), 1.95-1.84 (m, 2H).; LCMS: 448.1 |

Figure 1T

| 77 | [structure] | 1H-NMR (400 MHz, CD3OD) δ ppm 8.43 (d, 1H, J = 5.2 Hz), 7.06-6.99 (m, 1H), 6.96-6.87 (m, 1H), 5.57-5.48 (m, 1H), 5.00 (s, 1H), 4.45-4.41 (m, 1H), 4.20-4.19 (m, 1H), 4.12-4.07 (m, 1H), 3.98 (s, 1.5H), 3.89 (s, 1.5H), 3.71 (s, 1.5H), 3.22 (s, 1.5H), 2.53-2.49 (m, 1H), 2.25-2.21 (m, 1H), 1.90-1.79 (m, 2H).; LCMS: 449.1 |
|---|---|---|
| 78 | [structure] | 1H-NMR (400 MHz, CD3OD) δ ppm 8.34 (s, 1H), 7.14-7.00 (m, 3H), 5.59-5.55 (m, 1H), 5.48-5.32 (m, 1H), 4.46-4.33 (m, 3H), 4.23-4.12 (m, 2H), 3.97-3.94 (m, 1H), 3.69-3.68 (m, 2H), 2.85-2.75 (m, 1H), 2.16-2.09 (m, 1H).; LCMS: 449.1 |
| 79 | [structure] | 1H-NMR (400 MHz, CD3OD) δ ppm 8.41 (s, 1H), 8.35 (s, 1H), 7.20-7.16 (m, 1H), 7.07-7.01 (m, 2H), 5.76-5.73 (m, 1H), 4.84-4.75 (m, 1H), 4.25-4.08 (m, 3H), 3.64-3.61 (m, 1H), 2.81-2.78 (m, 1H), 2.41-2.38 (m, 2H), 2.00-1.68 (m, 5H).; LCMS: 453.5 |
| 80 | [structure] | $^1$H NMR (500 MHz, DMSO-$d_6$) δ 14.35 (s, 1H), 9.60 (q, J = 7.8, 7.0 Hz, 1H), 8.33 (s, 1H), 7.84 (dd, J = 8.7, 5.4 Hz, 1H), 7.39 – 7.16 (m, 2H), 4.72 (d, J = 6.1 Hz, 2H), 4.04 (qd, J = 7.9, 4.0 Hz, 1H), 3.96 (dd, J = 11.1, 4.0 Hz, 1H), 3.78 (dt, J = 11.5, 4.5 Hz, 1H), 3.65 (td, J = 8.2, 4.3 Hz, 1H), 3.48 – 3.38 (m, 1H), 3.23 – 3.15 (m, 1H), 1.89 (dq, J = 12.7, 4.1 Hz, 1H), 1.49 (dtd, J = 13.2, 8.9, 4.0 Hz, 1H), 1.25 (dt, J = 13.3, 7.9 Hz, 1H); LCMS: 455 |

| | | |
|---|---|---|
| 81 |  | 1H-NMR (400 MHz, CD3OD) δ ppm 8.37 (s, 1H), 7.80-7.71 (m, 1H), 7.29-7.27 (m, 1H), 7.21-7.17 (m, 1H), 4.74-4.67 (m, 2H), 4.44-4.30 (m, 1H), 4.11 (s, 1H), 4.02-4.01 (m, 1H), 2.50-2.40 (m, 1H), 2.15-2.12 (m, 1H), 1.78-1.77 (m, 1H), 1.70-1.67 (m, 1H).; LCMS: 455.1 |
| 82 |  | 1H-NMR (400 MHz, CD3OD) δ ppm 8.39 (s, 1H), 8.33 (s, 1H), 7.22-6.90 (m, 3H), 5.74 (br.s, 1H), 4.83-4.73 (m, 1H), 4.51-4.42 (m, 2H), 4.26-4.17 (m, 2H), 3.98-3.95 (m, 1H), 3.82-3.71 (m, 3H), 2.87-2.75 (m, 1H), 2.53-2.50 (m, 1H).; LCMS: 455.4 |
| 83 |  | $^1$H NMR (500 MHz, DMSO-$d_6$) δ 14.12 (s, 1H), 9.51 (t, $J$ = 6.2 Hz, 1H), 9.33 (d, $J$ = 7.7 Hz, 1H), 8.28 (s, 1H), 7.64 (dd, $J$ = 8.2, 3.0 Hz, 1H), 7.15 (dd, $J$ = 9.2, 3.1 Hz, 1H), 5.09 (d, $J$ = 4.9 Hz, 1H), 4.60 (d, $J$ = 6.1 Hz, 2H), 4.05 (dd, $J$ = 7.7, 4.1 Hz, 1H), 3.96 (dd, $J$ = 11.2, 4.1 Hz, 1H), 3.82 – 3.75 (m, 1H), 3.65 (d, $J$ = 4.9 Hz, 1H), 3.43 (t, $J$ = 9.4 Hz, 1H), 3.17 (dd, $J$ = 11.2, 7.6 Hz, 1H), 1.89 (d, $J$ = 12.9 Hz, 1H), 1.52 – 1.44 (m, 1H); LCMS: 456 |
| 84 |  | $^1$H NMR (400 MHz, DMSO-$d_6$) δ 14.11 (s, 1H), 9.60 – 9.39 (m, 2H), 8.28 (s, 1H), 7.32 – 7.24 (m, 1H), 7.17 (m, 1H), 5.21 (d, $J$ = 5.2 Hz, 1H), 4.56 (d, $J$ = 6.1 Hz, 2H), 4.29 (m, 1H), 3.96 (d, $J$ = 6.7 Hz, 1H), 3.29 – 3.18 (m, 1H), 2.97 (s, 3H), 2.84 (s, 3H), 2.30 (m, 1H), 2.14 (m, 1H), 1.78 – 1.61 (m, 2H); LCMS: 460 |

| 85 |  | 1H-NMR (400 MHz, CD3OD) δ ppm 8.51 (s, 1H), 8.41 (s, 1H), 8.32 (s, 1H), 7.76 (d, 1H, J = 9.2 Hz), 5.56-5.40 (m, 2H), 4.87-4.82 (m, 1H), 4.59-4.50 (m, 1H), 4.11-3.97 (m, 2H), 3.48-3.45 (m, 1H), 2.88-2.86 (m, 1H), 2.27-1.80 (m, 2H), 1.78-1.67 (m, 2H), 1.59-1.46 (m, 3H).; LCMS: 460.1 |
| --- | --- | --- |
| 86 |  | 1H-NMR (400 MHz, CD3OD) δ ppm 8.25-8.19 (m, 1H), 7.14-6.85 (m, 3H), 5.63-5.59 (m, 1H), 5.42 (d, 1H, J = 52.4 Hz), 4.83 (br.s, 1H), 4.48-4.31 (m, 3H), 4.12-3.99 (m, 1H), 2.88-2.80 (m, 1H), 2.42-2.39 (m, 1H), 2.25-2.20 (m, 2H), 1.92-1.89 (m, 1H), 1.69-1.64 (m, 1H).; LCMS: 462.4 |
| 87 |  | 1H-NMR (400 MHz, CD3OD) δ ppm 8.26-8.19 (m, 1H), 7.15-6.86 (m, 3H), 5.63-5.59 (m, 1H), 5.42 (d, 1H, J = 52.0 Hz), 4.85-4.80 (m, 1H), 4.47-4.31 (m, 3H), 4.11-4.03 (m, 1H), 2.83-2.78 (m, 1H), 2.49-2.43 (m, 1H), 2.23-2.20 (m, 2H), 1.87-1.83 (m, 1H), 1.70-1.65 (m, 1H).; LCMS: 462.4 |
| 88 |  | $^1$H-NMR (400 MHz, CD$_3$OD) δ ppm 8.25 (s, 1H), 7.17-7.03 (m, 3H), 5.62 (t, 1H, J = 8.8 Hz), 5.43 (d, 1H, J = 52.0 Hz), 4.86-4.81 (m, 1H), 4.50-4.40 (m, 2H), 4.12-4.08 (m, 1H), 3.93-3.84 (m, 1H), 2.89-2.79 (m, 1H), 2.41-2.38 (m, 1H), 2.12-2.05 (m, 2H), 1.76-1.75 (m, 1H), 1.56-1.55 (m, 1H); LCMS: 463 |

| | | |
|---|---|---|
| 89 |  | $^1$H NMR (400 MHz, DMSO-$d_6$) δ 14.02 (s, 1H), 9.23 (d, $J$ = 7.0 Hz, 1H), 8.24 (s, 1H), 7.41 (qd, $J$ = 9.4, 4.9 Hz, 1H), 7.12 (ddt, $J$ = 11.4, 7.6, 2.0 Hz, 1H), 5.48 (m, 1H), 4.90 (m, 1H), 4.46 (m, 1H), 4.36 (m, 2H), 4.09 (m, 1H), 3.89 – 3.83 (m, 1H), 3.59 (m, 1H), 2.49 – 2.38 (m, 1H), 2.30 – 2.10 (m, 2H), 1.97 – 1.79 (m, 3H), 1.54 (m, 2H), 1.37 – 1.24 (m, 2H); LCMS: 463 |
| 90 |  | LCMS: 463 |
| 91 |  | LCMS: 463 |
| 92 |  | 1H-NMR (400 MHz, CD3OD) δ ppm 8.34 (s, 1H), 7.14-6.86 (m, 3H), 5.63-5.59 (m, 1H), 5.51-5.35 (m, 1H), 4.50-4.41 (m, 1H), 4.10-4.06 (m, 1H), 3.98-3.92 (m, 2H), 3.75-3.70 (m, 1H), 3.52-3.41 (m, 1H), 3.39-3.36 (m, 1H), 2.84-2.81 (m, 1H), 2.25-2.00 (m, 1H), 2.00-1.96 (m, 1H), 1.67-1.64 (m, 1H), 1.38-1.28 (m, 1H).; LCMS: 463.1 |

| | | |
|---|---|---|
| 93 |  | 1H-NMR (400 MHz, CD3OD) δ ppm 8.14-8.04 (m, 1H), 7.02-6.74 (m, 3H), 5.73-5.48 (m, 1H), 5.37-5.24 (m, 1H), 4.36-4.10 (m, 2H), 3.87-3.76 (m, 2H), 3.44-3.38 (m, 2H), 3.18-3.10 (m, 1H), 2.76-2.72 (m, 1H), 2.10-1.88 (m, 2H), 1.52 (br.s, 1H), 1.33-1.17 (m, 1H).; LCMS: 463.1 |
| 94 |  | 1H-NMR (400 MHz, CD3OD) δ ppm 8.53 (s, 1H), 8.46-8.43 (m, 1H), 8.29-8.24 (m, 1H), 7.81-7.66 (m, 1H), 5.81-5.78 (m, 1H), 4.89-4.85 (m, 1H), 4.57-4.52 (m, 2H), 4.50-4.48 (m, 1H), 4.13-4.11 (m, 1H), 3.88-3.85 (m, 1H), 3.12-3.11 (m, 1H), 2.62-2.59 (m, 1H), 2.44-2.42 (m, 1H), 2.08-2.05 (m, 1H), 1.82-1.77 (m, 1H), 1.55-1.53 (m, 1H).; LCMS: 464.1 |
| 95 |  | 1H-NMR (400 MHz, CD3OD) δ ppm 8.15-8.09 (m, 1H), 7.03-6.74 (m, 3H), 5.52-5.47 (m, 1H), 5.31 (d, 1H, J = 52.0 Hz), 5.06-4.92 (m, 2H), 4.44-4.38 (m, 2H), 3.99-3.96 (m, 1H), 2.72-2.70 (m, 1H), 2.45-2.32 (m, 2H), 1.84-1.75 (m, 3H).; LCMS: 465.1 |
| 96 |  | 1H-NMR (400 MHz, CD3OD) δ ppm 8.22-8.10 (m, 1H), 7.05-6.75 (m, 3H), 5.51-5.47 (m, 1H), 5.31 (d, 1H, J = 52.0 Hz), 4.99 (d, 1H, J = 54.0 Hz), 4.44-4.29 (m, 2H), 4.02-3.99 (m, 1H), 2.90-2.72 (m, 1H), 2.47-2.35 (m, 2H), 2.12-1.64 (m, 3H).; LCMS: 465.1 |

| | | |
|---|---|---|
| 97 |  | 1H-NMR (400 MHz, CD3OD) δ ppm 8.28 (s, 1H), 7.15-7.11 (m, 2H), 7.04-7.02 (m, 1H), 4.66 (s, 2H), 4.51-4.45 (m, 1H), 4.28-4.23 (m, 1H), 3.84-3.80 (m, 1H), 2.96 (s, 3H), 2.75-2.70 (m, 1H), 2.53-2.50 (m, 1H), 2.15-2.06 (m, 2H).; LCMS: 467.1 |
| 98 |  | 1H-NMR (400 MHz, CD3OD) δ ppm 8.28 (s, 1H), 7.15-7.11 (m, 2H), 7.09-7.02 (m, 1H), 4.66 (s, 2H), 4.51-4.45 (m, 1H), 4.28-4.25 (m, 1H), 3.84-3.80 (m, 1H), 2.96 (s, 3H), 2.75-2.70 (m, 1H), 2.54-2.52 (m, 1H), 2.13-2.06 (m, 2H).; LCMS: 467.1 |
| 99 |  | 1H-NMR (400 MHz, CD3OD) δ ppm 8.40, 8.36 (d, 1H, J = 11.6 Hz), 7.85-7.80 (m, 1H), 7.25-7.17 (m, 2H), 5.60 (s, 1H), 5.57 (s, 1H), 4.40-4.35 (m, 1H), 4.16-3.98 (m, 2H), 3.69 (s, 1.5H), 3.23 (s, 1.5H), 2.49-2.43 (m, 1H), 2.21-2.20 (m, 1H), 1.85-1.64 (m, 2H).; LCMS: 469.1 |
| 100 |  | 1H-NMR (400 MHz, CD3OD) δ ppm 8.28-8.22 (m, 1H), 7.19-6.90 (m, 3H), 5.78-5.76 (m, 1H), 4.85-4.80 (m, 1H), 4.71-4.69 (m, 1H), 4.19-4.17 (m, 2H), 4.09-4.08 (m, 2H), 3.75-3.74 (m, 1H), 3.59-3.48 (m, 2H), 2.86-2.76 (m, 1H), 2.51-2.35 (m, 1H), 2.13-1.96 (m, 1H), 1.71-1.60 (m, 1H).; LCMS: 469.4 |

| | | |
|---|---|---|
| 101 |  | 1H-NMR (400 MHz, CD3OD) δ ppm 8.34 (s, 1H), 7.35 (br.s, 1H), 7.20 (d, 1H, J = 6.8 Hz), 7.13 (t, 1H, J = 8.0 Hz), 4.71 (s, 2H), 4.41-4.35 (m, 1H), 4.12 (br.s, 1H), 4.01-3.99 (m, 1H), 2.45-2.40 (m, 1H), 2.15-2.11 (m, 1H), 1.80-1.68 (m, 2H).; LCMS: 471.1 |
| 102 |  | 1H-NMR (400 MHz, CDCl3) δ ppm 11.11 (d, 1H, J = 6.0 Hz), 8.67 (s, 1H), 7.84-7.82 (m, 1H), 7.04-6.92 (m, 3H), 4.64 (d, 2H, J = 6.4 Hz), 4.41 (br.s, 1H), 4.29 (br.s, 1H), 3.42-3.38 (m, 2H), 3.25-3.22 (m, 2H), 3.09-3.07 (m, 1H), 2.79-2.77 (m, 1H).; LCMS: 472.2 |
| 103 |  | $^1$H NMR (400 MHz, DMSO-$d_6$) δ 14.32 (s, 1H), 10.13 (d, J = 9.9 Hz, 1H), 8.99 (d, J = 7.6 Hz, 1H), 8.30 (s, 1H), 8.14 – 8.03 (m, 1H), 7.41 (m, 2H), 6.40 (m, 1H), 5.11 (s, 1H), 4.03 (m, 3H), 3.80 (m, 1H), 3.67 (m, 1H), 3.54 – 3.42 (m, 1H), 3.21 (m, 1H), 1.90 (dq, J = 12.7, 4.3 Hz, 1H), 1.50 (dq, J = 13.7, 5.1 Hz, 1H); LCMS: 473 |
| 104 |  | LCMS: 475 |

Figure 1A-1
| 105 | 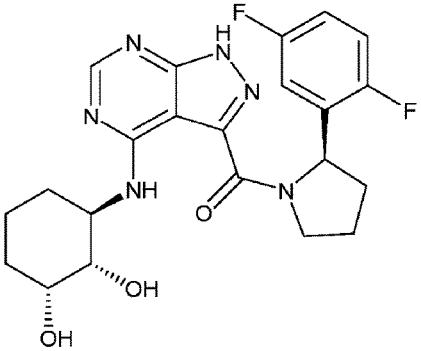 | 1H-NMR (400 MHz, CD3OD) δ ppm 8.32-8.25 (m, 1H), 7.15-6.87 (m, 3H), 5.62-5.58 (m, 1H), 5.51-5.38 (m, 1H), 4.94-4.90 (m, 1H), 4.51-4.47 (m, 1H), 4.14-4.07 (m, 1H), 4.02 (br.s, 1H), 3.52-3.49 (m, 1H), 2.83-2.79 (m, 1H), 2.27-2.24 (m, 1H), 2.14-2.05 (m, 1H), 1.88-1.80 (m, 2H), 1.60-1.48 (m, 3H).; LCMS: 477.1 |
|---|---|---|
| 106 | 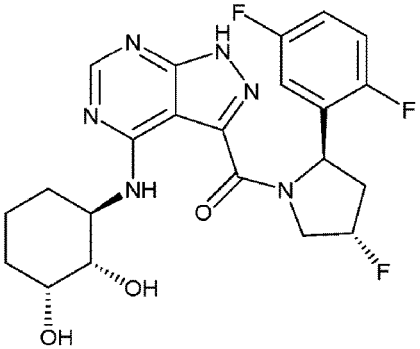 | 1H-NMR (400 MHz, CD3OD) δ ppm 8.32-8.25 (m, 1H), 7.15-6.87 (m, 3H), 5.62-5.58 (m, 1H), 5.51-5.38 (m, 1H), 4.94-4.90 (m, 1H), 4.51-4.47 (m, 1H), 4.14-4.07 (m, 1H), 4.02 (br.s, 1H), 3.52-3.49 (m, 1H), 2.83-2.79 (m, 1H), 2.27-2.24 (m, 1H), 2.14-2.05 (m, 1H), 1.88-1.80 (m, 2H), 1.60-1.48 (m, 3H).; LCMS: 477.1 |
| 107 | 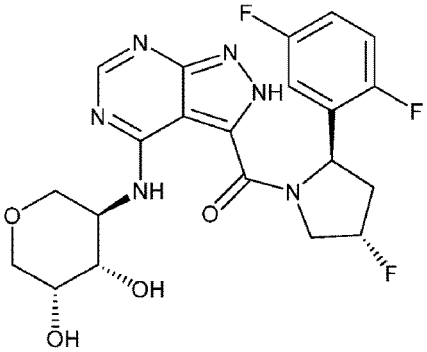 | 1H-NMR (400 MHz, CD3OD) δ ppm 8.35-8.27 (m, 1H), 7.16-7.01 (m, 3H), 5.63-5.59 (m, 1H), 5.44 (d, 1H, J = 52.0 Hz), 4.51-4.32 (m, 2H), 4.04-3.75 (m, 5H), 3.60-3.57 (m, 1H), 3.39-3.38 (m, 1H), 2.86-2.80 (m, 1H), 2.27-2.13 (m, 1H); LCMS: 479 |
| 108 | 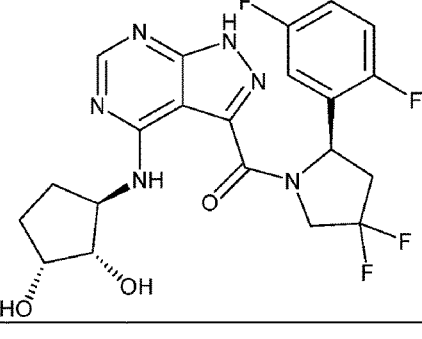 | 1H-NMR (400 MHz, CD3OD) δ ppm 8.22-8.16 (m, 1H), 7.15-7.11 (m, 1H), 7.05-7.01 (m, 1H), 6.94-6.92 (m, 1H), 5.79-5.75 (m, 1H), 4.82-4.75 (m, 1H), 4.46-4.41 (m, 1H), 4.04-4.02 (m, 1H), 3.82-3.79 (m, 1H), 2.98-2.94 (m, 1H), 2.52-2.36 (m, 2H), 2.01-1.92 (m, 1H), 1.71-1.60 (m, 1H), 1.32-1.29 (m, 1H), 1.23-1.19 (m, 1H).; LCMS: 481.1 |

Figure 1A-2
| | | |
|---|---|---|
| 109 | 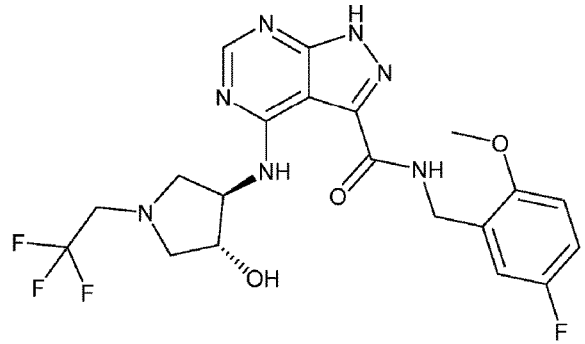 | 1H-NMR (400 MHz, CDCl3) δ ppm 11.26 (d, 1H, J = 6.0 Hz), 8.67 (s, 1H), 7.94-7.91 (m, 1H), 7.00-6.76 (m, 3H), 4.55 (d, 2H, J = 6.0 Hz), 4.39 (br.s, 1H), 4.28 (br.s, 1H), 3.82 (s, 3H), 3.39-3.35 (m, 2H), 3.25-3.22 (m, 2H), 3.09-3.08 (m, 1H), 2.79-2.78 (m, 1H).; LCMS: 484.2 |
| 110 | 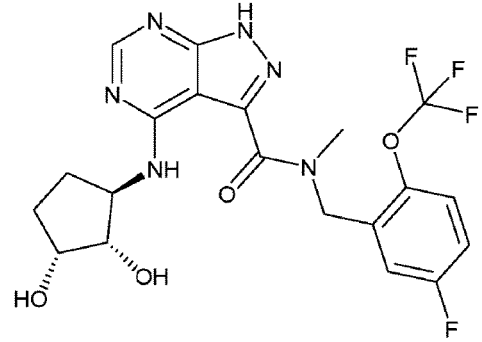 | 1H-NMR (400 MHz, CD3OD) δ ppm 8.40, 8.35 (s, 1H), 7.40 (br.s, 1H), 7.20-7.14 (m, 2H), 5.51 (s, 1H), 4.94 (d, 1H, J = 9.6 Hz), 4.41-4.36 (m, 1H), 4.15-3.97 (m, 2H), 3.65 (s, 1.5H), 3.18 (s, 1.5H), 2.48-2.42 (m, 1H), 2.19-2.14 (m, 1H), 1.82-1.65 (m, 2H).; LCMS: 485.1 |
| 111 | 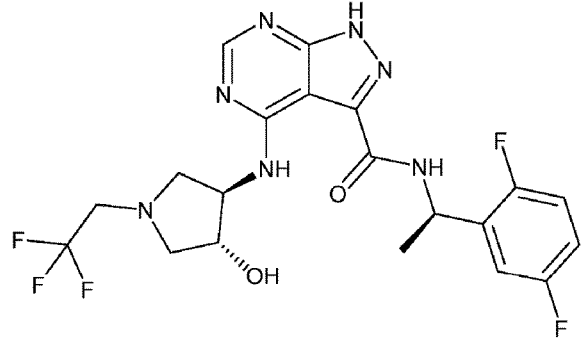 | 1H-NMR (400 MHz, CDCl3) δ ppm 8.77 (br.s, 1H), 7.83 (d, 1H, J = 8.4 Hz), 7.10-6.97 (m, 3H), 5.45-5.41 (m, 1H), 4.44 (br.s, 1H), 4.35 (br.s, 1H), 3.51-3.43 (m, 2H), 3.36-3.33 (m, 2H), 3.21 (d, 1H, J = 8.0 Hz), 2.85 (d, 1H, J = 2.0 Hz), 1.67 (d, 1H, J = 6.8 Hz).; LCMS: 486.2 |
| 112 | 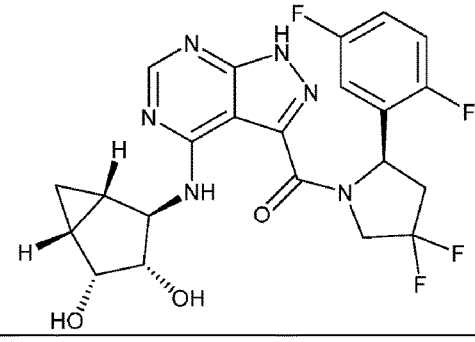 | 1H-NMR (400 MHz, CD3OD) δ ppm 8.38-8.32 (m, 1H), 7.17-6.67 (m, 3H), 5.77 (dd, 1H, J = 9.2, 6.0 Hz), 4.83-4.77 (m, 1H), 4.40-4.37 (m, 1H), 4.30-4.26 (m, 1H), 3.94-3.76 (m, 1H), 3.05-2.99 (m, 1H), 2.57-2.50 (m, 1H), 1.70-1.65 (m, 1H), 1.48-1.46 (m, 1H), 1.25-1.23 (m, 1H), 0.64-0.61 (m, 1H).; LCMS: 493.1 |

| 113 |  | 1H-NMR (400 MHz, CDCl3) δ ppm 11.10 (d, 1H, J = 6.0 Hz), 8.69 (s, 1H), 7.80 (s, 1H), 7.28-7.26 (m, 1H), 6.92-6.87 (m, 2H), 4.33 (br.s, 1H), 4.26 (br.s, 1H), 3.46-3.44 (m, 1H), 3.31-3.25 (m, 1H), 3.12-3.10 (m, 1H), 2.73-2.72 (m, 1H), 1.32-1.24 (m, 4H).; LCMS: 498.2 |
|---|---|---|
| 114 |  | LCMS: 513 |
| 115 |  | 1H-NMR (400 MHz, CD3OD) δ ppm 8.26 (s, 1H), 7.15-7.01 (m, 3H), 5.62-5.57 (m, 1H), 5.49-5.36 (m, 1H), 4.44-4.41 (m, 2H), 4.17-4.12 (m, 1H), 3.75-3.68 (m, 1H), 2.96 (s, 3H), 2.80-2.70 (m, 1H), 2.68-2.64 (m, 1H), 2.41-2.39 (m, 1H), 2.10-2.00 (m, 4H).; LCMS: 525.1 |
| 116 |  | 1H-NMR (400 MHz, CD3OD) δ ppm 8.26 (s, 1H), 7.15-7.01 (m, 3H), 5.61-5.57 (m, 1H), 5.49-5.36 (m, 1H), 4.44-4.41 (m, 2H), 4.17-4.12 (m, 1H), 3.75-3.68 (m, 1H), 2.96 (s, 3H), 2.80-2.70 (m, 1H), 2.68-2.64 (m, 1H), 2.41-2.39 (m, 1H), 2.10-2.00 (m, 4H).; LCMS: 525.1 |

Figure 1A-4

| 117 | *(structure)* | 1H-NMR (400 MHz, CD3OD) δ ppm 8.36 (s, 1H), 7.01-6.96 (m, 3H), 4.62 (s, 2H), 4.37-4.31 (m, 1H), 4.13 (br.s, 1H), 4.04-4.01 (m, 1H), 3.88 (s, 3H), 2.26-2.24 (m, 1H), 2.46-2.39 (m, 1H), 2.16-2.14 (m, 1H), 1.82-1.72 (m, 2H).; LCMS:ND |
|---|---|---|
| 118 | *(structure)* | $^1$H NMR (500 MHz, DMSO-$d_6$) δ 14.01 (d, $J$ = 41.7 Hz, 1H), 9.31 (d, $J$ = 7.6 Hz, 1H), 8.98 (d, $J$ = 7.5 Hz, 1H), 8.29 (d, $J$ = 9.0 Hz, 1H), 7.36 – 7.07 (m, 3H), 5.33 (s, 1H), 4.81 (dd, $J$ = 9.2, 5.0 Hz, 2H), 4.48 – 4.23 (m, 3H), 3.72 – 3.55 (m, 1H), 3.49 (s, 2H), 3.05 (s, 1H), 1.56 (dt, $J$ = 29.6, 6.3 Hz, 1H), 1.38 – 1.20 (m, 1H), 1.08 (dq, $J$ = 8.5, 4.1 Hz, 1H) |
| 119 | *(structure)* | 1H-NMR (400 MHz, CD3OD) δ ppm 8.37 (s, 1H), 7.18-7.04 (m, 3H), 5.61 (t, 1H, J = 8.4 Hz), 5.47 (d, 1H, J = 51.6 Hz), 4.51-4.38 (m, 1H), 4.14-4.08 (m, 2H), 2.89-2.81 (m, 1H), 2.33-1.69 (m, 8H); LCMS: 447 |
| 120 | *(structure)* | 1H-NMR (400 MHz, CD3OD) δ ppm 8.28 (s, 0.2H), 8.26 (s, 0.8H), 7.24-7.20 (m, 1H), 7.11-7.09 (m, 1H), 5.77-5.67 (m, 1H), 5.04-4.95 (m, 1H), 4.33-4.27 (m, 1H), 4.05-4.04 (m, 1H), 3.93-3.89 (m, 1H), 3.43 (s, 1.8H), 2.92 (s, 1.2H), 2.40-2.35 (m, 1H), 2.08-2.07 (m, 1H), 1.72-1.71 (m, 1H), 1.62-1.59 (m, 1H); LCMS: 453 |

Figure 1A-5
| | | | |
|---|---|---|---|
| 121 | 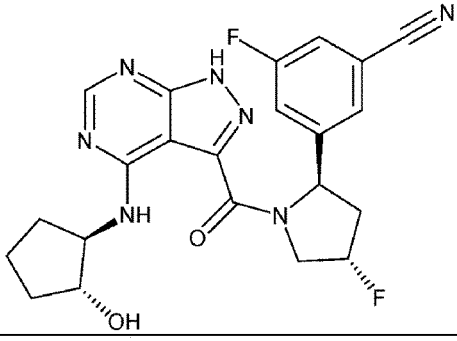 | | ¹H NMR (500 MHz, DMSO-$d_6$) δ 14.14 (s, 1H), 9.01 (d, $J$ = 7.2 Hz, 1H), 8.38 – 8.05 (m, 1H), 7.78 (t, $J$ = 1.5 Hz, 1H), 7.74 – 7.62 (m, 2H), 5.44 – 5.31 (m, 2H), 4.92 (d, $J$ = 4.0 Hz, 1H), 4.77 (dd, $J$ = 21.4, 14.1 Hz, 1H), 4.46 (dd, $J$ = 39.9, 14.0 Hz, 1H), 4.18 (d, $J$ = 4.8 Hz, 1H), 3.79 (t, $J$ = 4.7 Hz, 1H), 2.73 (dt, $J$ = 16.8, 8.4 Hz, 1H), 2.20 – 1.99 (m, 2H), 1.78 – 1.60 (m, 3H), 1.56 – 1.32 (m, 2H) |
| 122 | 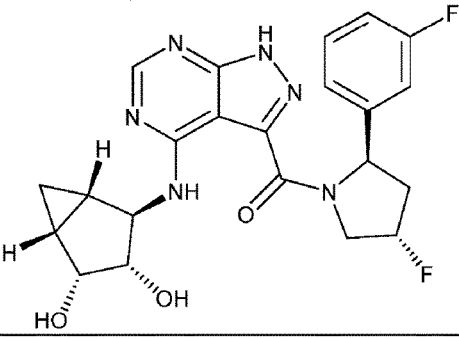 | | 1H-NMR (400 MHz, CD3OD) δ ppm 8.23-8.15 (m, 1H), 7.36-7.31 (m, 1H), 7.15-7.14 (m, 1H), 7.06 (d, 1H, J = 9.6 Hz), 6.96-6.94 (m, 1H), 5.41 (br.s, 1H), 5.37 (d, 1H, J = 50.4 Hz), 4.60-4.33 (m, 4H), 4.81-4.70 (m, 1H), 2.83-2.74 (m, 1H), 2.20-2.15 (m, 1H), 1.75-1.63 (m, 1H), 1.46-1.40 (m, 1H), 1.38-1.17 (m, 2H), 0.54-0.51 (m, 1H); LCMS: 457 |
| 123 | 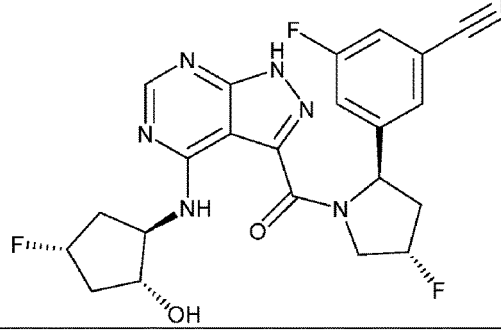 | | 1H-NMR (400 MHz, CD3OD) δ ppm 8.26 (s, 1H), 7.60 (s, 1H), 7.48-7.43 (m, 2H), 5.48-5.45 (m, 1H), 5.43-5.33 (m, 1H), 5.16-5.02 (m, 1H), 4.80-4.75 (m, 1H), 4.55-4.48 (m, 2H), 4.06-4.03 (m, 1H), 2.83-2.81 (m, 1H), 2.55-2.43 (m, 2H), 1.93-1.85 (m, 3H).; LCMS: 472.1 |
| 124 | 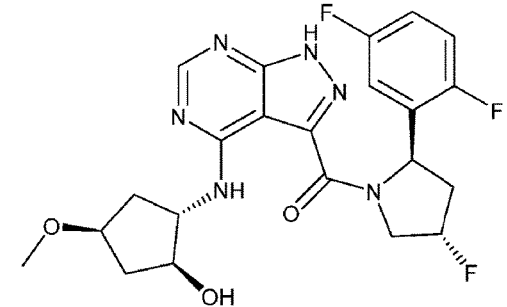 | | 1H-NMR (400 MHz, CD3OD) δ ppm 8.24-8.17 (m, 1H), 7.15-7.01 (m, 3H), 5.61-5.57 (m, 1H), 5.41 (d, 1H, J = 51.6 Hz), 4.88-4.86 (m, 1H), 4.43-4.37 (m, 2H), 4.09-4.00 (m, 1H), 3.87-3.85 (m, 1H), 3.28 (s, 3H), 2.82-2.80 (m, 1H), 2.45-2.24 (m, 3H), 1.78-1.69 (m, 2H); LCMS: 477 |

Figure 1A-6

| 125 | (structure) | 1H-NMR (400 MHz, CD3OD) δ ppm 8.24-8.17 (m, 1H), 7.14-6.84 (m, 3H), 5.61-5.57 (m, 1H), 5.41 (d, 1H, J = 51.6 Hz), 4.89-4.86 (m, 1H), 4.46-4.36 (m, 2H), 4.00-3.96 (m, 1H), 3.88-3.86 (m, 1H), 3.29 (s, 3H), 2.82-2.75 (m, 1H), 2.38-2.25 (m, 3H), 1.86-1.80 (m, 1H), 1.67-1.64 (m, 1H); LCMS:477 |
|---|---|---|
| 126 | (structure) | 1H-NMR (400 MHz, CD3OD) δ ppm 8.19 (s, 1H), 6.96-6.94 (m, 2H), 6.80-6.77 (m, 1H), 5.44-5.30 (m, 2H), 4.79-4.76 (m, 1H), 4.48-4.38 (m, 2H), 3.87 (br.s, 1H), 3.65-3.53 (m, 1H), 2.84-2.74 (m, 1H), 2.05-2.00 (m, 2H), 1.78-1.72 (m, 2H), 1.53-1.35 (m, 3H).; LCMS: 477.1 |
| 127 | (structure) | 1H-NMR (400 MHz, CD3OD) δ ppm 8.23-8.16 (m, 1H), 7.21 (s, 1H), 7.08-7.05 (m, 2H), 5.44-5.31 (m, 2H), 4.80-4.79 (m, 1H), 4.50-4.41 (m, 2H), 4.06-4.04 (m, 1H), 3.85-3.82 (m, 1H), 2.83-2.77 (m, 1H), 2.38-2.36 (m, 1H), 2.07-2.00 (m, 2H), 1.74-1.71 (m, 1H), 1.52-1.49 (m, 1H).; LCMS: 479 |
| 128 | (structure) | 1H-NMR (400 MHz, CD3OD) δ ppm 8.23-8.20 (m, 2H), 7.59 (dd, 1H, J = 8.8, 3.2 Hz), 5.67-5.62 (m, 1H), 5.40 (d, 1H, J = 52.8 Hz), 4.63-4.40 (m, 3H), 4.03-4.01 (m, 1H), 3.80 (dd, 1H, J = 7.2, 4.4 Hz), 2.95-2.87 (m, 1H), 2.37-2.35 (m, 1H), 2.06-1.99 (m, 2H), 1.71-1.68 (m, 1H), 1.49-1.46 (m, 1H). ; LCMS: 480 |

Figure 1A-7
| | | |
|---|---|---|
| 129 | 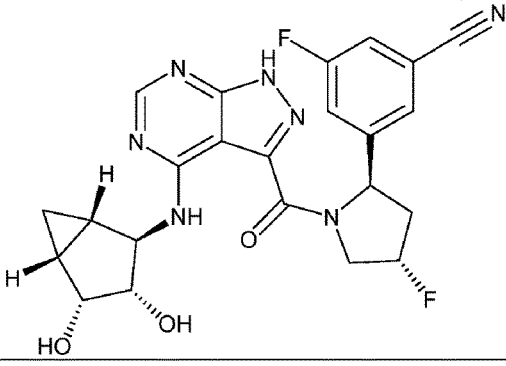 | ND |
| 130 | 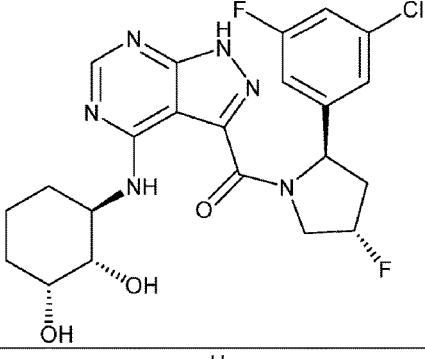 | 1H-NMR (400 MHz, CD3OD) δ ppm 8.19-8.12 (m, 1H), 7.20 (s, 1H), 7.05 (d, 2H, J = 8.8 Hz), 5.43-5.30 (m, 2H), 4.77-4.76 (m, 1H), 4.49-4.39 (m, 2H), 3.87 (br.s, 1H), 3.56-3.53 (m, 1H), 2.81-2.75 (m, 1H), 2.15-2.13 (m, 1H), 1.81-1.73 (m, 2H), 1.58-1.35 (m, 4H).; LCMS: 493.1 |
| 131 | 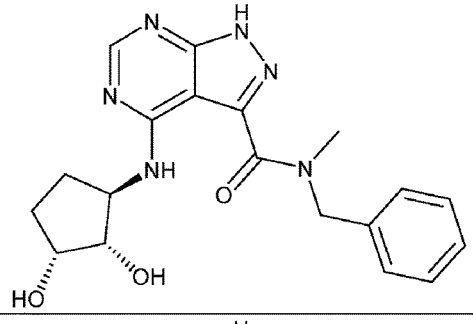 | 1H-NMR (400 MHz, CDCl3) δ ppm 8.38 (br.s, 1H), 7.32-7.22 (m, 5H), 5.42-5.28 (m, 1H), 4.84-4.69 (m, 1H), 4.55 (br.s, 1H), 4.22 (br.s, 1H), 4.04 (br.s, 1H), 3.51 (s, 1.5H), 3.07 (s, 1.5H), 2.42 (br.s, 1H), 2.13 (br.s, 1H), 1.87 (br.s, 1H),1.71 (br.s, 1H).; LCMS: 383.2 |
| 132 | 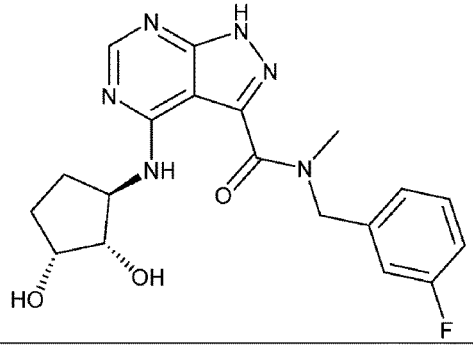 | 1H-NMR (400 MHz, CDCl3) δ ppm 9.80 (s, 0.5H), 9.64 (s, 0.5H), 8.38 (d, 1H, J = 5.2 Hz), 7.35-7.27 (m, 1H), 7.13-7.02 (m, 3H), 5.40 (s, 1H), 4.82 (d, 1H, J = 4.8 Hz), 4.38 (br.s, 1H), 4.22 (s, 1H), 3.95 (s, 1H), 3.57 (s, 1.5H), 3.09 (s, 1.5H), 2.52 (br.s, 1H), 2.10-2.05 (m, 1H), 1.96 (m, 1H), 1.89-1.82 (m, 1H).; LCMS: 401.1 |

Figure 1A-8
| | | |
|---|---|---|
| 133 | 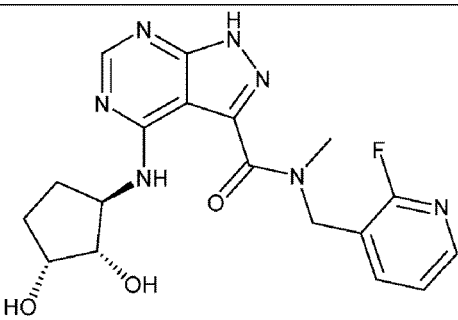 | 1H-NMR (400 MHz, CD3OD) δ ppm 8.35-8.33 (m, 1H), 8.16-8.12 (m, 1H), 7.97-7.88 (m, 1H), 7.34-7.30 (m, 1H), 5.47 (s, 1H), 4.85 (s, 1H), 4.38 (br.s, 1H), 4.15-4.12 (m, 1H), 4.03-3.98 (m, 1H), 3.70 (s, 1.5H), 3.35-3.25 (m, 1H), 3.22 (s, 1.5H), 2.48-2.40 (m, 1H), 2.14 (br.s, 1H), 1.81-1.75 (m, 1H).; LCMS: 402.1 |
| 134 | 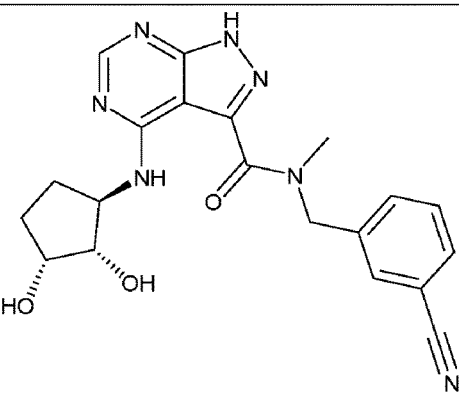 | 1H-NMR (400 MHz, CD3OD) δ ppm 8.36 (d, 1H, J = 4.8 Hz), 7.76-7.67 (m, 3H), 7.58-7.56 (m, 1H), 5.47 (d, 1H, J = 2.4 Hz), 4.91 (s, 1H), 4.42-4.37 (m, 1H), 4.15-4.14 (m, 1H), 4.04-3.99 (m, 1H), 3.65 (s, 1.5H), 3.16 (s, 1.5H), 2.48-2.45 (m, 1H), 1.84-1.81 (m, 1H), 1.71-1.66 (m, 2H).; LCMS: 408.1 |
| 135 | 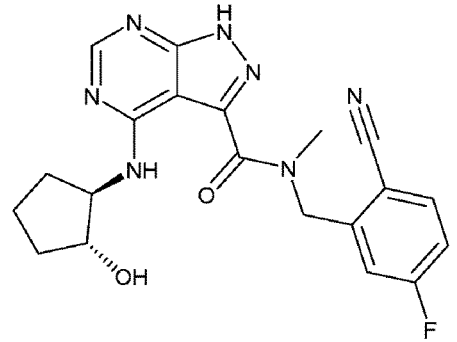 | 1H NMR (400 MHz, DMSO-d6) δ 13.98 (s, 1H), 9.26 (m, 1H), 8.26 (d, J = 11.5 Hz, 1H), 7.99 (m, 1H), 7.45 – 7.28 (m, 2H), 5.47 (m, 1H), 5.02 (m, 1H), 4.25 (m, 1H), 3.94 (m, 1H), 3.56 (s, 1H), 3.30 (s, 3H), 3.09 (s, 1H), 2.22 – 2.03 (m, 1H), 1.91 (m, 1H), 1.84 – 1.64 (m, 2H), 1.64 – 1.34 (m, 2H).; LCMS: 410.2 |
| 136 | 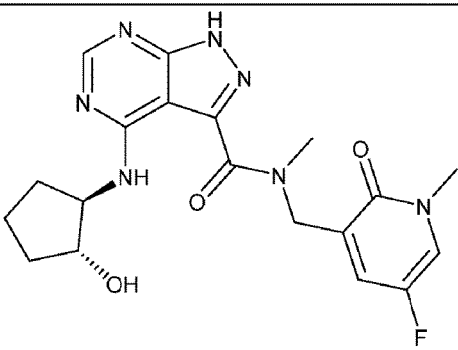 | 1H NMR (400 MHz, DMSO-d6) δ 13.89 (s, 1H), 9.10 (ABqd, 1H), 8.21 (d, J = 10.6 Hz, 1H), 7.87 (ddd, J = 8.3, 4.7, 3.3 Hz, 1H), 7.33 (ddd, J = 9.4, 7.9, 3.2 Hz, 1H), 4.97 (m, 2H), 4.46 (s, 1H), 4.27 – 4.12 (m, 1H), 3.99 – 3.81 (m, 1H), 3.39 (d, J = 6.3 Hz, 3H), 3.29 (s, 3H), 2.18 – 2.01 (m, 1H), 1.86 – 1.35 (m, 5H).; LCMS: 416.1 |

Figure 1A-9
| | | |
|---|---|---|
| 137 | 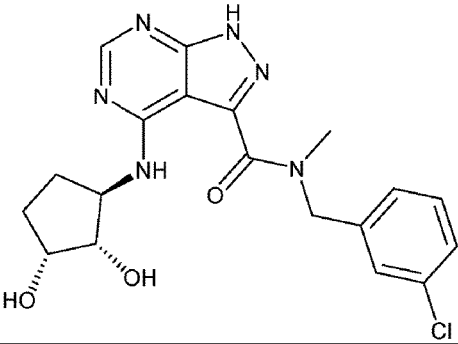 | 1H-NMR (400 MHz, CD3OD) δ ppm 8.36 (s, 1H), 7.52-7.41 (m, 4H), 5.49 (s, 1H), 4.91 (s, 1H), 4.63-4.60 (m, 1H), 4.27 (br.s, 1H), 4.04 (b.s, 1H), 3.67 (s, 1.7H), 3.21 (s, 1.3H), 2.56-2.55 (m, 1H), 2.23 (br.s, 1H), 1.90 (br.s, 1H), 1.71 (br.s, 1H).; LCMS: 417.1 |
| 138 | 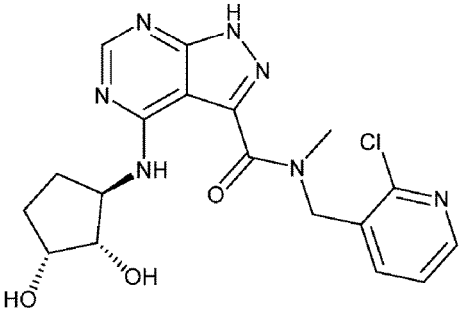 | 1H-NMR (400 MHz, CD3OD) δ ppm 8.36-8.30 (m, 2H), 7.79-7.74 (m, 1H), 7.42-7.38 (m, 1H), 5.44 (s, 1H), 4.96 (s, 1H), 4.41-4.34 (m, 1H), 4.15-3.97 (m, 2H), 3.97 (s, 1H), 3.25 (s, 2H), 2.47-2.42 (m, 1H), 2.17-2.15 (m, 1H), 1.82-1.74 (m, 2H).; LCMS: 418.0 |
| 139 | 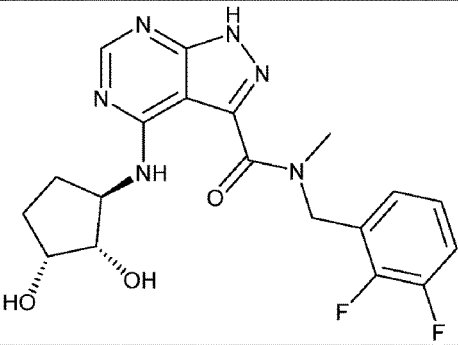 | 1H-NMR (400 MHz, CD3OD) δ ppm 8.25 (d, 1H, J = 5.2 Hz), 7.23-7.14 (m, 3H), 5.51 (s, 1H), 4.94 (s, 1H), 4.51-4.47 (m, 1H), 4.15-4.13 (m, 1H), 3.94-3.89 (m, 1H), 3.89 (s, 1.5H), 3.15 (s, 1.5H), 2.45-2.41 (m, 1H), 2.12-2.04 (m, 1H), 1.80-1.77 (m, 1H), 1.60-1.58 (m, 1H), 1.38-1.29 (m, 1H).; LCMS: 419.1 |
| 140 | 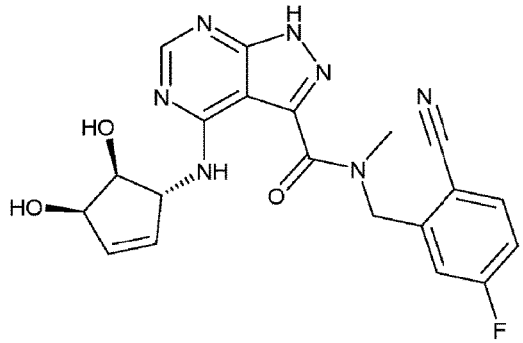 | 1H-NMR (400 MHz, CD3OD) δ ppm 8.40 (d, 1H, J = 8.8 Hz), 7.85 (dd, 1H, J = 7.6, 5.6 Hz), 7.31-7.22 (m, 2H), 6.22-6.17 (m, 1H), 6.09-6.04 (m, 1H), 5.61 (s, 1H), 5.05 (s, 1H), 5.02-5.01 (m, 1H), 4.61 (dd, 1H, J = 14.8, 2.8 Hz), 4.12 (td, 1H, J = 18.4, 5.6 Hz), 3.69 (s, 1.5H), 3.21 (s, 1.5H).; LCMS: 424.1 |

Figure 1A-10

| | | |
|---|---|---|
| 141 | (structure) | 1H-NMR (400 MHz, CDCl3) δ ppm 8.38 (br.s, 1H), 7.68-7.65 (m, 1H), 7.10-7.03 (m, 2H), 5.55-5.46 (m, 1H), 4.94-4.83 (m, 1H), 4.56 (br.s, 1H), 4.21 (br.s, 1H), 4.09-4.02 (m, 1H), 3.58 (s, 1.5H), 3.11 (s, 1.5H), 2.42 (br.s, 1H), 2.10 (br.s, 1H), 1.85 (br.s, 1H), 1.69 (s, 1H).; LCMS: 426.1 |
| 142 | (structure) | 1H-NMR (400 MHz, CD3OD) δ ppm 8.35 (d, 1H, J = 5.6 Hz), 7.75-7.65 (m, 2H), 7.37-7.34 (m, 1H), 5.53 (s, 1H), 4.95 (s, 1H), 4.38-4.33 (m, 1H), 4.13-4.11 (m, 1H), 4.04-3.96 (m, 1H), 3.68 (s, 1.5H), 3.20 (s, 1.5H), 2.45-2.42 (m, 1H), 2.17-2.13 (m, 1H), 1.80-1.69 (m, 2H).; LCMS: 426.1 |
| 143 | (structure) | 1H-NMR (400 MHz, CD3OD) δ ppm 8.32 (d, 1H, J = 8.4 Hz), 7.87-7.82 (m, 1H), 7.33-7.23 (m, 2H), 5.66-5.55 (m, 1H), 5.11-5.02 (m, 1H), 4.06-3.95 (m, 3H), 3.68 (s, 1.5H), 3.67-3.58 (m, 1H), 3.52-3.49 (m, 1H), 3.25-3.23 (m, 1H), 3.22 (s, 1.5H), 2.20-2.11 (m, 1H), 1.82-1.74 (m, 1H).; LCMS: 426.1 |
| 144 | (structure) | 1H-NMR (400 MHz, CD3OD) δ ppm 8.34 (s, 1H), 7.32-7.25 (m, 3H), 7.24-7.19 (m, 2H), 5.47-5.35 (m, 2H), 4.84-4.83 (m, 1H), 4.53-4.29 (m, 2H), 4.05-3.97 (m, 1H), 3.90-3.87 (m, 1H), 2.89-2.78 (m, 1H), 2.38-2.35 (m, 1H), 2.18-2.06 (m, 2H), 1.77-1.61 (m, 2H).; LCMS: 427.1 |

Figure 1A-11
| 145 | 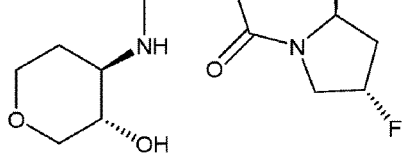 | 1H-NMR (400 MHz, CD3OD) δ ppm 8.33 (s, 1H), 7.34-7.19 (m, 5H), 5.48-5.36 (m, 2H), 4.93 (br.s, 1H), 4.53-4.44 (m, 1H), 3.98-3.91 (m, 3H), 3.50-3.46 (m, 2H), 3.23-3.20 (m, 1H), 2.80-2.79 (m, 1H), 2.13-2.07 (m, 2H), 1.77-1.74 (m, 1H).; LCMS: 427.2 |
|---|---|---|
| 146 | 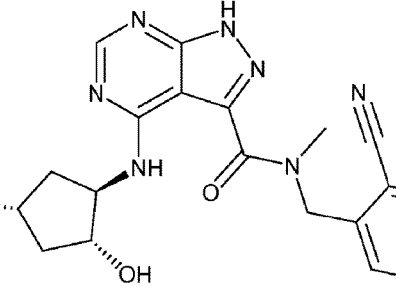 | 1H-NMR (400 MHz, CD3OD) δ ppm 8.17 (d, 1H, J = 8.4 Hz), 7.78-7.72 (m, 1H), 7.21-7.11 (m, 2H), 5.52 (s, 1H), 5.48-4.98 (m, 1H), 4.95 (s, 1H), 4.50-4.44 (m, 1H), 4.10-4.03 (m, 1H), 3.56 (s, 1.5H), 3.10 (s, 1.5H), 2.52-2.41 (m, 2H), 1.88-1.81 (m, 2H).; LCMS: 428.1 |
| 147 | 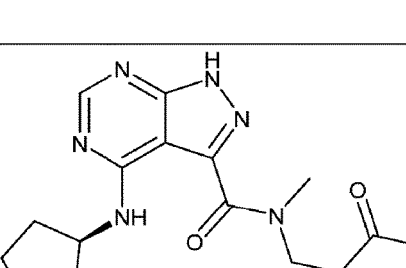 | 1H NMR (400 MHz, DMSO-d6) δ 13.92 (br d, 1H), 9.19 (ABqd, 1H), 9.05 (d, J = 7.2 Hz, 0H), 8.20 (d, J = 9.9 Hz, 1H), 7.87 (m, 1H), 7.33 (m, 1H), 4.97 (d, J = 3.8 Hz, 1H), 4.87 (dd, J = 14.6, 5.5 Hz, 1H), 4.51 – 4.42 (m, 2H), 4.34 (m, 1H), 3.88 (m, 1H), 3.65 (ddt, J = 26.8, 7.3, 5.1 Hz, 1H), 3.40 (d, J = 6.3 Hz, 3H), 3.29 (s, 3H), 2.20 (m, 1H), 1.87 (m, 1H), 1.52 (m, 1H), 1.36 – 1.15 (m, 1H).; LCMS: 432.1 |
| 148 | 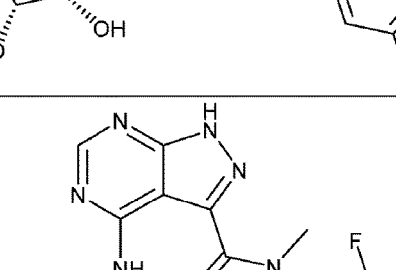 | 1H-NMR (400 MHz, CD3OD) δ ppm 8.35 (d, 1H, J = 4.4 Hz), 7.42 (d, 1H, J = 2.4 Hz), 7.41-7.32 (m, 1H), 7.18-7.14 (m, 1H), 5.48 (s, 1H), 4.91-4.89 (m, 1H), 4.40-4.36 (m, 1H), 4.15-4.13 (m, 1H), 4.05-3.99 (m, 1H), 3.66 (s, 1.5H), 3.17 (s, 1.5H), 3.47-2.44 (m, 1H), 2.18-2.14 (m, 1H), 1.82-1.80 (m, 1H), 1.71-1.65 (m, 1H).; LCMS: 435.1 |

Figure 1A-12
| 149 | 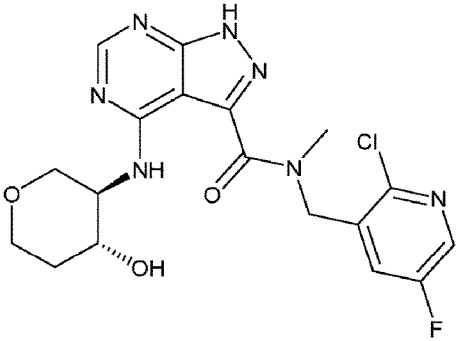 | 1H-NMR (400 MHz, CD3OD) δ ppm 8.35 (d, 1H, J = 12.4 Hz), 8.25 (d, 1H, J = 8.8 Hz), 7.64-7.59 (m, 1H), 5.38 (s, 1H), 4.92 (s, 1H), 4.16-3.88 (m, 4H), 3.72 (s, 1H), 3.59-3.39 (m, 2H), 3.26 (s, 2H), 2.13-2.00 (m, 1H), 1.78-1.68 (m, 1H).; LCMS: 436.1 |
|---|---|---|
| 150 | 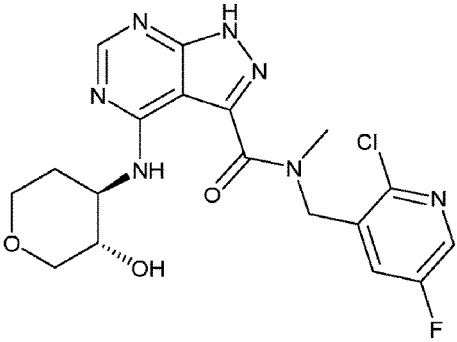 | 1H-NMR (400 MHz, CD3OD) δ ppm 8.36 (dd, 1H, J = 12.8, 2.0 Hz), 8.25 (dd, 1H, J = 9.2, 2.0 Hz), 7.64-7.59 (m, 1H), 5.38 (s, 1H), 4.02-3.94 (m, 3H), 3.72 (s, 1H), 3.68-3.48 (m, 2H), 3.24 (s, 2H), 3.23-3.22 (m, 1H), 2.19-2.10 (m, 1H), 1.88-1.75 (m, 1H).; LCMS: 436.1 |
| 151 | 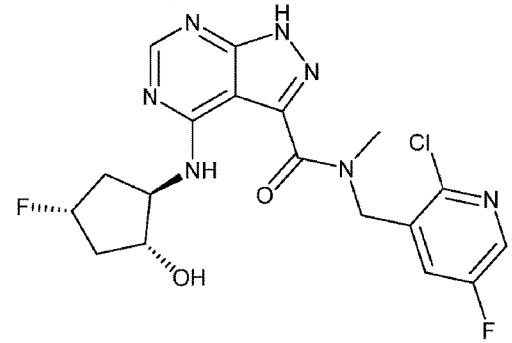 | 1H-NMR (400 MHz, CD3OD) δ ppm 8.27-8.23 (m, 2H), 7.61-7.57 (m, 1H), 5.32 (s, 1H), 5.24-5.10 (m, 1H), 4.94 (s, 1H), 4.58-4.49 (m, 1H), 4.18-4.08 (m, 1H), 3.67 (s, 1H), 3.20 (s, 2H), 2.65-2.48 (m, 2H), 1.99-1.82 (m, 2H).; LCMS: 438.1 |
| 152 | 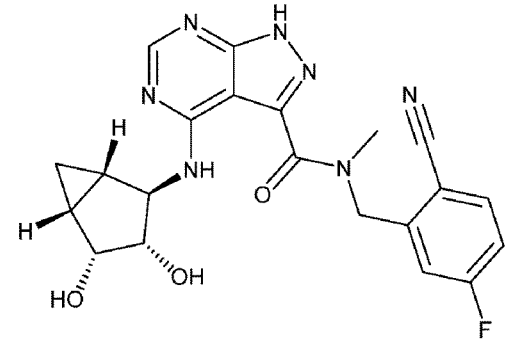 | 1H-NMR (400 MHz, CD3OD) δ ppm 8.40 (d, 1H, J = 6.0 Hz), 7.88-7.84 (m, 1H), 7.36-7.24 (m, 2H), 5.62 (d, 1H, J = 4.0 Hz), 5.07 (d, 1H, J = 5.6 Hz), 4.61 (dt, 1H, J = 32.0, 5.6 Hz), 4.30 (d, 1H, J = 10.4 Hz), 3.94 (dd, 1H, J = 20.8, 6.0 Hz), 3.72 (s, 1.5H), 3.23 (s, 1.5H), 1.84-1.78 (m, 1H), 1.59-1.53 (m, 1H), 1.32-1.28 (m, 1H), 0.71-0.66 (m, 1H).; LCMS: 438.1 |

Figure 1A-13
| 153 | 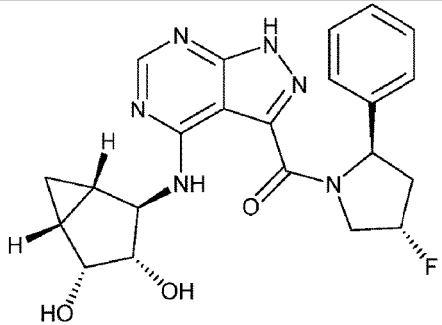 | 1H-NMR (400 MHz, CD3OD) δ ppm 8.33-8.32 (m, 1H), 7.32-7.18 (m, 6H), 5.48-5.35 (m, 2H), 4.92-4.90 (m, 1H), 4.49-4.45 (m, 1H), 4.39-4.36 (m, 1H), 4.24-4.20 (m, 1H), 3.74-3.73 (m, 1H), 2.83-2.75 (m, 1H), 2.24-2.10 (m, 1H), 1.70-1.67 (m, 1H), 1.48-1.46 (m, 1H), 1.28-1.20 (m, 1H), 0.65-0.59 (m, 1H).; LCMS: 439.1 |
|---|---|---|
| 154 | 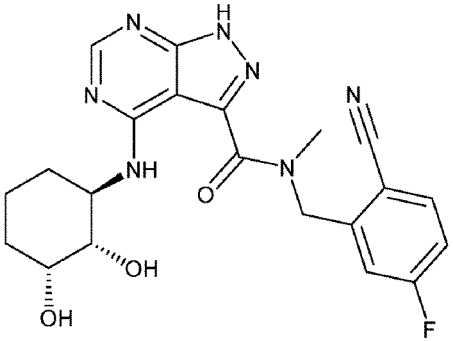 | 1H-NMR (400 MHz, CD3OD) δ ppm 8.13 (br.s, 1H), 7.81 (br.s, 1H), 7.29 (br.s, 1H), 7.20 (br.s, 1H), 5.61 (br.s, 1H), 5.02-4.99 (m, 1H), 4.42 (br.s, 1H), 4.02-3.97 (m, 1H), 3.62 (s, 2H), 3.14 (s, 1H), 2.06 (s, 1H), 1.82-1.40 (m, 5H). ; LCMS: 440.3 |
| 155 | 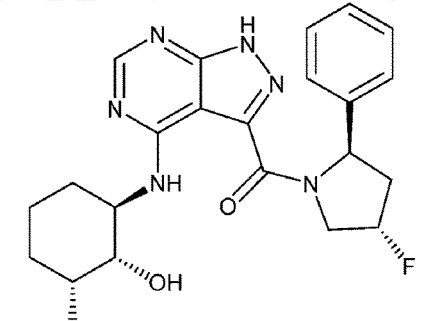 | 1H-NMR (400 MHz, CD3OD) δ ppm 8.31 (s, 1H), 7.32-7.25 (m, 3H), 7.24-7.20 (m, 2H), 5.47-5.35 (m, 2H), 4.53-4.43 (m, 1H), 4.10-3.97 (m, 3H), 3.49-3.46 (m, 1H), 2.81-2.79 (m, 1H), 2.17-2.03 (m, 2H), 1.88-1.83 (m, 2H), 1.59-1.49 (m, 3H).; LCMS: 441.1 |
| 156 | 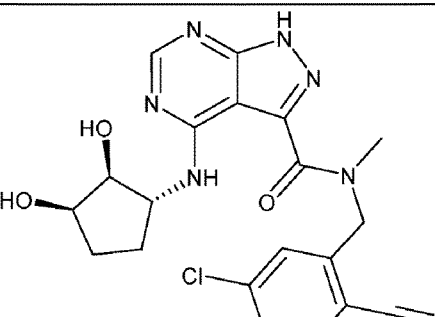 | 1H-NMR (400 MHz, CD3OD) δ ppm 8.33 (d, 1H, J = 8.0 Hz), 7.80-7.77 (m, 1H), 7.58-7.50 (m, 2H), 5.61-5.60 (m, 1H), 5.05 (d, 1H, J = 4.8 Hz), 4.42-4.37 (m, 1H), 4.15-4.11 (m, 1H), 4.04-3.97 (m, 1H), 3.69 (s, 1.5H), 3.22 (s, 1.5H), 2.47-2.41 (m, 1H), 2.16-2.13 (m, 1H), 1.81-1.69 (m, 2H).; LCMS: 442.1 |

Figure 1A-14
| 157 | 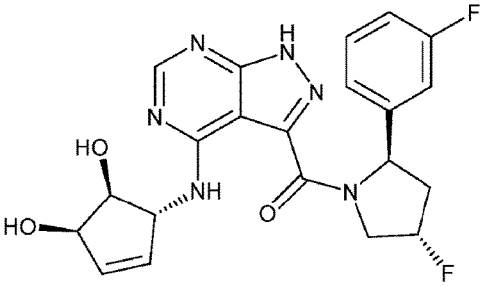 | 1H-NMR (400 MHz, CD3OD) δ ppm 8.32-8.24 (m, 1H), 7.35-7.31 (m, 1H), 7.14-6.93 (m, 3H), 6.10-5.96 (m, 2H), 5.47-5.03 (m, 2H), 4.83-4.87 (m, 1H), 4.52-4.38 (m, 2H), 4.07-3.94 (m, 1H), 2.83-2.67 (m, 1H), 2.17-2.01 (m, 1H).; LCMS: 443.1 |
|---|---|---|
| 158 | 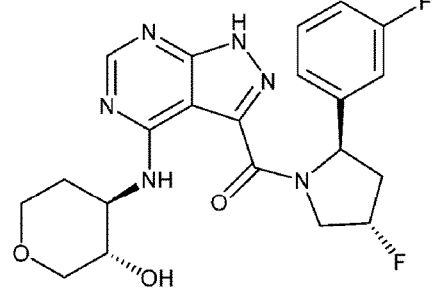 | 1H-NMR (400 MHz, CD3OD) δ ppm 8.39-8.32 (m, 1H), 7.39-6.97 (m, 4H), 5.51-5.35 (m, 2H), 4.96-4.91 (m, 1H), 4.49-4.46 (m, 1H), 4.06-3.92 (m, 3H), 3.55-3.49 (m, 2H), 3.26-3.24 (m, 1H), 2.85-2.83 (m, 1H), 2.21-2.11 (m, 2H), 1.78-1.72 (m, 1H).; LCMS: 445.2 |
| 159 | 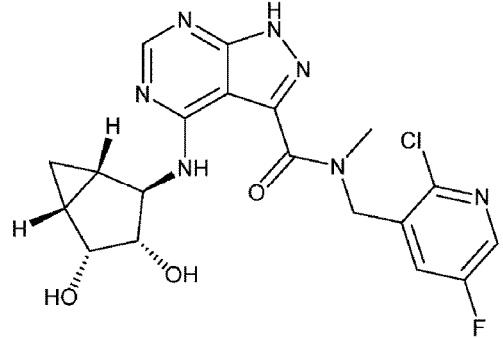 | 1H-NMR (400 MHz, CD3OD) δ ppm 8.40 (s, 0.5H), 8.37 (s, 0.5H), 8.23 (dd, 1H, J = 8.8, 2.8 Hz), 7.64-7.59 (m, 1H), 5.36 (s, 1H), 4.89 (s, 1H), 4.57 (td, 1H, J = 49.2, 4.2 Hz), 4.29 (s, 0.5H), 4.26 (s, 0.5H), 3.90 (dd, 1H, J = 26.4, 6.0 Hz), 3.70 (s, 1.5H), 3.25 (s, 1.5H), 1.82-1.81 (m, 1H), 1.56-1.48 (m, 1H), 1.30-1.27 (m, 1H), 1.68-1.62 (m, 1H).; LCMS: 448.1 |
| 160 | 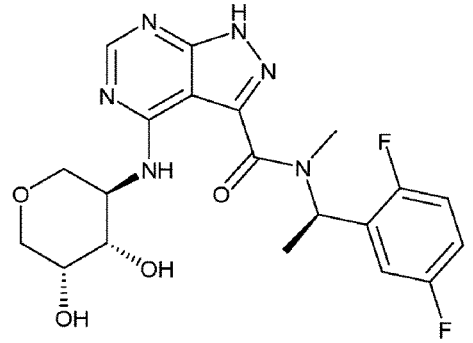 | 1H-NMR (400 MHz, CD3OD) δ ppm 8.37 (d, 1H, J = 4.4 Hz), 7.31-7.29 (m, 1H), 7.13-7.06 (m, 2H), 6.24-6.19 (m, 1H), 4.37-4.35 (m, 1H), 4.12-4.09 (m, 1H), 3.95 (s, 1H), 3.90-3.87 (m, 2H), 3.67-3.65 (m, 1H), 3.47-3.44 (m, 1H), 3.33 (s, 1.5H), 2.86 (s, 1.5H), 1.79 (d, 1.5H, J = 6.8 Hz), 1.66 (d, 1.5H, J = 6.4 Hz).; LCMS: 449.1 |

Figure 1A-15

| 161 | *structure* | 1H-NMR (400 MHz, CD3OD) δ ppm 8.25-8.19 (m, 2H), 7.16 (s, 1H), 5.33 (s, 1H), 4.94-4.88 (m, 1H), 4.54-4.46 (m, 1H), 4.03-3.95 (m, 1H), 3.66 (s, 1.5H), 3.60-3.58 (m, 1H), 3.21 (s, 1.5H), 2.20-2.00 (m, 1H), 1.85-1.81 (m, 2H), 1.60-1.35 (m, 3H).; LCMS: 450.1 |
|---|---|---|
| 162 | *structure* | 1H-NMR (400 MHz, CD3OD) δ ppm 8.40-8.37 (m, 1H), 7.49-7.44 (m, 1H), 7.10-7.03 (m, 2H), 5.46 (s, 2H), 4.36-4.35 (m, 1H), 4.11-4.10 (m, 1H), 3.97-3.85 (m, 3H), 3.67-3.65 (m, 2.5H), 3.49-3.40 (m, 1H), 3.22 (s, 1.5H).; LCMS: 451 |
| 163 | *structure* | 1H-NMR (400 MHz, CD3OD) δ ppm 8.36 (d, 1H, J = 4.0 Hz), 7.43-7.30 (m, 2H), 7.17-7.12 (m, 1H), 5.45 (s, 1H), 4.88-4.86 (m, 1H), 4.41-4.37 (m, 1H), 4.16-4.11 (m, 1H), 3.97-3.95 (m, 1H), 3.89-3.86 (m, 2H), 3.69-3.65 (m, 1H), 3.64 (s, 1.5H), 3.47-3.45 (m, 1H), 3.16 (s, 1.5H).; LCMS: 451.1 |
| 164 | *structure* | 1H-NMR (400 MHz, CD3OD) δ ppm 8.30 (d, 1H, J = 5.6 Hz), 7.11-6.96 (m, 2H), 5.48 (s, 1H), 4.93 (s, 1H), 4.46 (d, 1H, J = 7.6 Hz), 4.12-4.09 (m, 1H), 3.95-3.80 (m, 3H), 3.66-3.64 (m, 2.5H), 3.44-3.41 (m, 1H), 3.18 (s, 1.5H).; LCMS: 453.1 |

Figure 1A-16
| 165 | 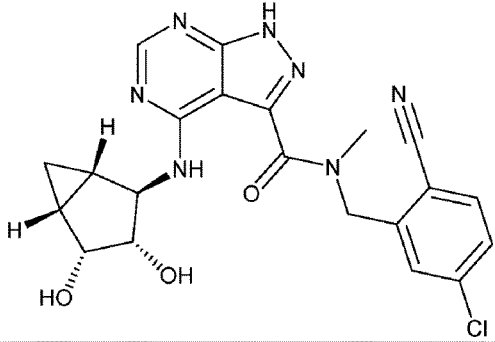 | 1H-NMR (400 MHz, CD3OD) δ ppm 8.33 (d, 1H, J = 6.4 Hz), 7.79-7.76 (m, 1H), 7.60-7.53 (m, 2H), 5.58 (d, 1H, J = 5.2 Hz), 5.03 (d, 1H, J = 5.2 Hz), 4.64-4.57 (m, 1H), 4.36-4.33 (m, 1H), 3.93-3.87 (dd, 1H, J = 17.2, 6.4 Hz), 3.69 (s, 1.5H), 3.02 (s, 1.5H), 1.80-1.76 (m, 1H), 1.55-1.51 (m, 1H), 1.29-1.25 (m, 1H), 0.67-0.62 (m, 1H). ; LCMS: 454.1 |
|---|---|---|
| 166 | 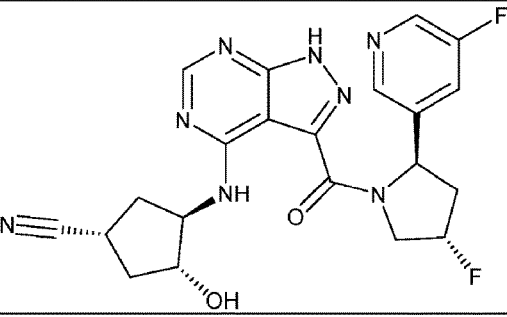 | 1H-NMR (400 MHz, CD3OD) δ ppm 8.47 (s, 1H), 8.38-8.23 (m, 2H), 7.70 (d, 1H, J = 9.6 Hz), 5.52-5.38 (m, 2H), 4.93-4.89 (m, 1H), 4.56-4.43 (m, 1H), 4.34-4.32 (m, 1H), 4.11-4.07 (m, 1H), 3.18-3.14 (m, 1H), 2.86-2.82 (m, 1H), 2.56-2.52 (m, 1H), 2.51-2.38 (m, 1H), 2.19-2.16 (m, 2H), 1.94-1.91 (m, 1H).; LCMS: 455.1 |
| 167 | 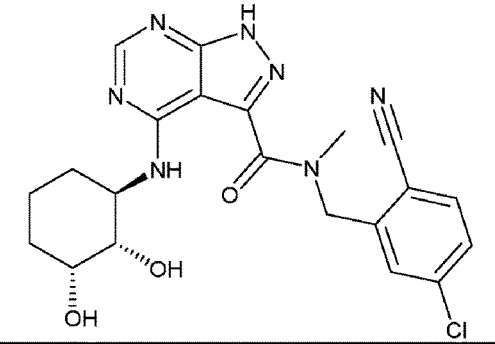 | 1H-NMR (400 MHz, CD3OD) δ ppm 8.32 (s, 0.5H), 8.30 (s, 0.5H), 7.80-7.77 (m, 1H), 7.58-7.52 (m, 2H), 5.66-5.55 (m, 1H), 5.10-5.00 (m, 1H), 4.20-4.07 (m, 2H), 3.70 (s, 1.5 H), 3.66-3.59 (m, 1H), 3.22 (s, 1.5H), 2.14-2.07 (m, 1H), 1.90-1.82 (m, 2H), 1.64-1.55 (m, 3H). ; LCMS: 456.1 |
| 168 | 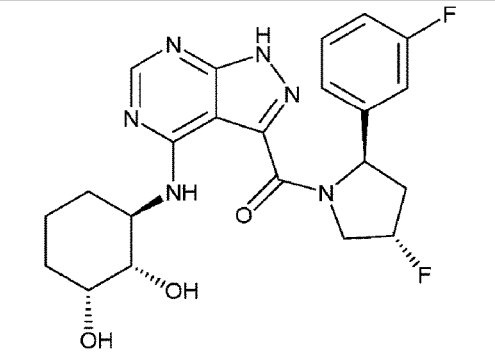 | 1H-NMR (400 MHz, CD3OD) δ ppm 8.31-8.23 (m, 1H), 7.37-7.33 (m, 1H), 7.15 (d, 1H, J = 8.0 Hz), 7.06 (d, 1H, J = 10.0 Hz), 7.00-6.96 (m, 1H), 5.48-5.35 (m, 2H), 4.54-4.44 (m, 1H), 4.13-4.01 (m, 2H), 3.51-3.48 (m, 1H), 2.84-2.80 (m, 1H), 2.32-2.04 (m, 2H), 1.84-1.79 (m, 2H), 1.59-1.50 (m, 3H).; LCMS: 459.2 |

Figure 1A-17
| | | |
|---|---|---|
| 169 | 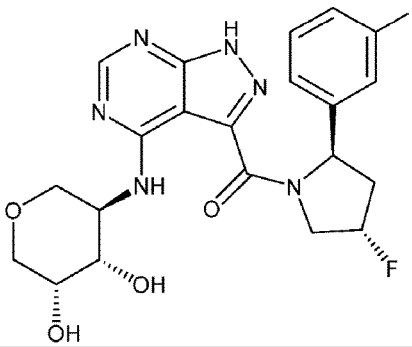 | 1H-NMR (400 MHz, CD3OD) δ ppm 8.37-8.29 (m, 1H), 7.44-6.96 (m, 4H), 5.46 (br.s, 1H), 5.40 (d, 1H, J = 52.0 Hz), 4.87-4.82 (m, 1H), 4.47 (dd, 1H, J = 38.4, 14.8 Hz), 4.30 (br.s, 1H), 4.05-3.83 (m, 2H), 3.75-3.58 (m, 2H), 3.55-3.36 (m, 2H), 3.09-2.81 (m, 1H), 2.21-2.08 (m, 1H).; LCMS: 461.1 |
| 170 | 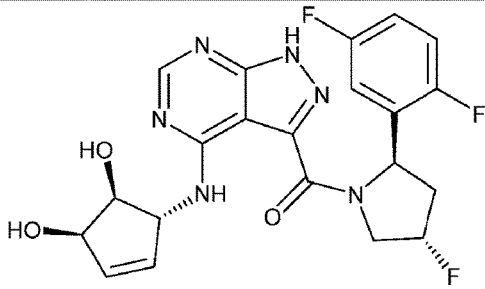 | 1H-NMR (400 MHz, CD3OD) δ ppm 8.29 (s, 1H), 7.16-7.02 (m, 3H), 6.08-6.00 (m, 2H), 5.62-5.58 (m, 1H), 5.42 (d, 1H, J = 52.4 Hz), 5.16 (br.s, 1H), 4.66-4.58 (m, 2H), 4.49-4.36 (m, 1H), 4.07-3.94 (m, 1H), 2.88-2.78 (m, 1H), 2.25-2.09 (m, 1H).; LCMS: 461.1 |
| 171 | 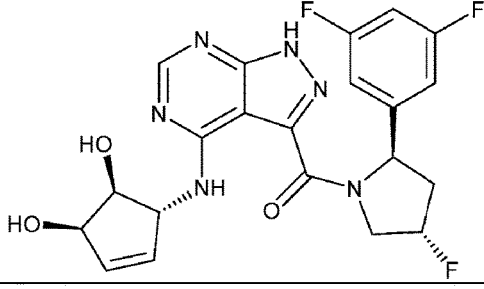 | 1H-NMR (400 MHz, CD3OD) δ ppm 8.35-8.28 (m, 1H), 6.96-6.94 (m, 1H), 6.85-6.78 (m, 2H), 6.23-6.04 (m, 2H), 5.46-5.33 (m, 2H), 5.04 (br.s, 1H), 4.56-4.40 (m, 2H), 4.11-3.97 (m, 1H), 2.86-2.76 (m, 1H), 2.19-2.03 (m, 1H).; LCMS: 461.1 |
| 172 | 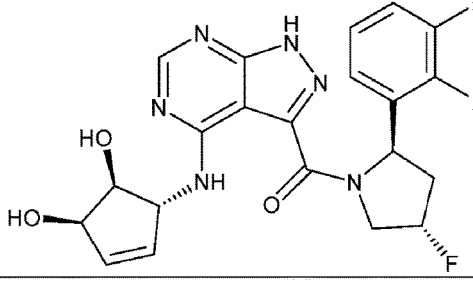 | 1H-NMR (400 MHz, CD3OD) δ ppm 8.32-8.23 (m, 1H), 7.16-7.09 (m, 3H), 6.10-5.98 (m, 2H), 5.66-5.61 (m, 1H), 5.43 (d, 1H, J = 52.0 Hz), 5.06-5.05 (m, 1H), 4.55-4.39 (m, 3H), 3.96-3.93 (m, 1H), 2.87-2.77 (m, 1H), 2.26-2.12 (m, 1H). ; LCMS: 461.1 |

Figure 1A-18
| 173 | 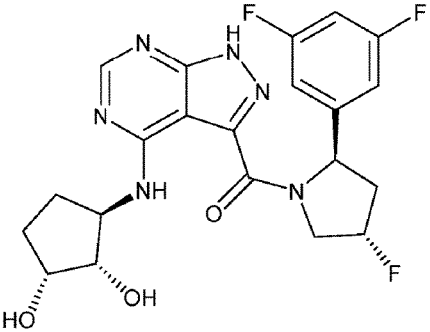 | 1H-NMR (400 MHz, CD3OD) δ ppm 8.34 (s, 1H), 6.95 (d, 2H, J = 6.8 Hz), 6.87-6.67 (m, 1H), 5.46-5.33 (m, 2H), 4.91-4.89 (m, 1H), 4.53-4.50 (m, 1H), 4.34-4.30 (m, 1H), 4.05-4.04 (m, 1H), 3.91-3.88 (m, 1H), 2.84-2.78 (m, 1H), 2.38-2.37 (m, 1H), 2.10-2.06 (m, 2H), 1.74-1.61 (m, 2H).; LCMS: 463.1 |
|---|---|---|
| 174 | 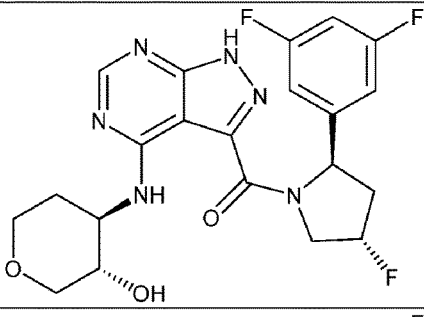 | 1H-NMR (400 MHz, CD3OD) δ ppm 8.33-8.26 (m, 1H), 6.98 (d, 1H, J = 6.4 Hz), 6.88-6.70 (m, 2H), 5.48-5.35 (m, 2H), 4.55-4.52 (m, 1H), 4.01-3.90 (m, 3H), 3.55-3.48 (m, 2H), 3.25-3.19 (m, 1H), 2.84-2.78 (m, 1H), 2.18-2.09 (m, 2H), 1.76-1.66 (m, 2H).; LCMS: 463.1 |
| 175 | 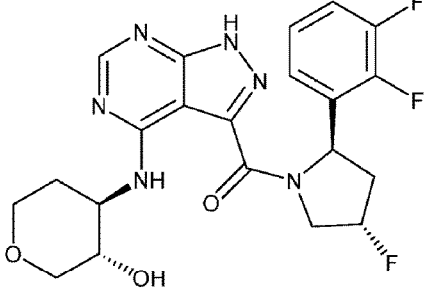 | 1H-NMR (400 MHz, CD3OD) δ ppm 8.32-8.24 (m, 1H), 7.17-6.96 (m, 3H), 5.69-5.65 (m, 1H), 5.46 (d, 1H, J = 52.0 Hz), 4.94-4.89 (m, 1H), 4.57-4.37 (m, 1H), 4.03-3.88 (m, 3H), 3.52-3.48 (m, 2H), 3.24-3.22 (m, 1H), 2.87-2.81 (m, 1H), 2.16-2.10 (m, 2H), 1.74-1.71 (m, 1H).; LCMS: 463.1 |
| 176 | 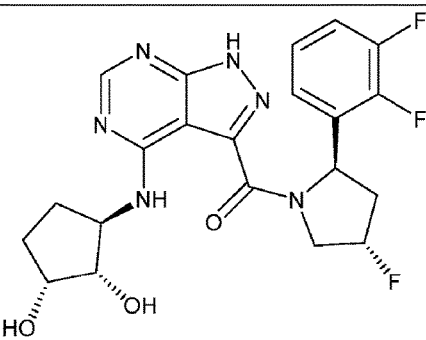 | 1H-NMR (400 MHz, CD3OD) δ ppm 8.24-8.16 (m, 1H), 7.16-6.92 (m, 3H), 5.68-5.64 (m, 1H), 5.42 (d, 1H, J = 52.0 Hz), 4.91-4.89 (m, 1H), 4.48-4.41 (m, 2H), 4.06-4.04 (m, 1H), 3.84-3.81 (m, 1H), 2.86-2.80 (m, 1H), 2.40-2.35 (m, 1H), 2.09-2.01 (m, 2H), 1.74-1.72 (m, 1H), 1.53-1.51 (m, 1H).; LCMS: 463.1 |

Figure 1A-19
| 177 | 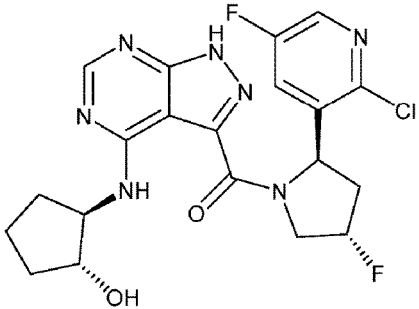 | 1H NMR (400 MHz, DMSO-d6) δ 14.17 (s, 1H), 8.99 (d, J = 7.2 Hz, 1H), 8.38 (d, J = 2.9 Hz, 1H), 8.26 (s, 1H), 7.87 (dd, J = 8.9, 3.0 Hz, 1H), 5.67 – 5.34 (m, 3H), 4.92 (d, J = 3.9 Hz, 1H), 4.80 (dd, J = 21.4, 14.0 Hz, 1H), 4.59 – 4.34 (m, 1H), 4.18 (s, 1H), 3.85 – 3.75 (m, 1H), 2.87 – 2.71 (m, 1H), 2.26 – 2.00 (m, 2H), 1.66 (dq, J = 13.1, 5.5 Hz, 2H), 1.58 – 1.34 (m, 2H).; LCMS: 464 |
| --- | --- | --- |
| 178 | 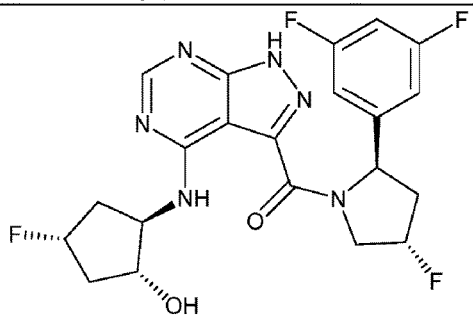 | 1H-NMR (400 MHz, CD3OD) δ ppm 8.37 (s, 1H), 6.97-6.95 (m, 2H), 6.84-6.79 (m, 1H), 5.47-5.41 (m, 1H), 5.10 (d, 1H, J = 53.6 Hz), 4.82 (s, 1H), 4.54-4.41 (m, 2H), 4.14-4.11 (m, 1H), 2.83-2.60 (m, 1H), 2.54-2.47 (m, 2H), 2.07-1.84 (m, 3H).; LCMS: 465.1 |
| 179 | 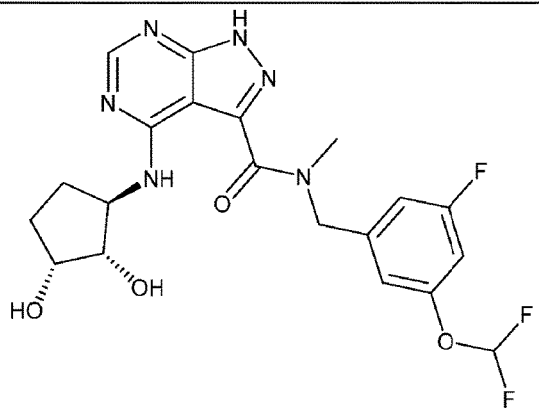 | 1H-NMR (400 MHz, CD3OD) δ ppm 8.42 (br.s, 1H), 7.13-7.03 (m, 2H), 6.97-6.74 (m, 2H), 5.48 (d, 1H, J = 1.6 Hz), 4.91 (s, 1H), 4.47-4.43 (m, 1H), 4.20-4.19 (m, 1H), 4.09-4.03 (m, 1H), 3.69 (s, 1.5H), 3.21 (s, 1.5H), 2.53-2.49 (m, 1H), 2.23-2.20 (m, 1H), 1.87-1.69 (m, 2H).; LCMS: 467.1 |
| 180 | 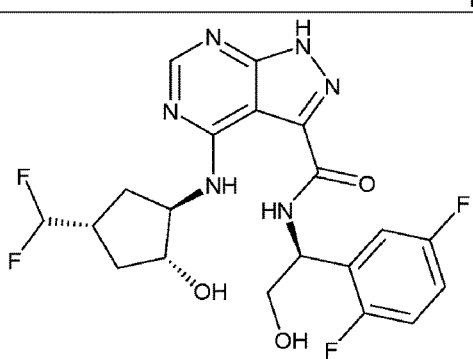 | 1H-NMR (400 MHz, CD3OD) δ ppm 8.34 (s, 1H), 7.22-7.04 (m, 3H), 5.85 (td, 1H, J = 57.2, 4.4 Hz), 5.54-5.51 (m, 1H), 4.25-4.16 (m, 2H), 3.90-3.83 (m, 2H), 3.35-3.33 (m, 1H), 2.31-2.19 (m, 2H), 1.92-1.85 (m, 1H), 69-1.66 (m, 1H).; LCMS: 469.1 |

Figure 1A-20
| | | |
|---|---|---|
| 181 | 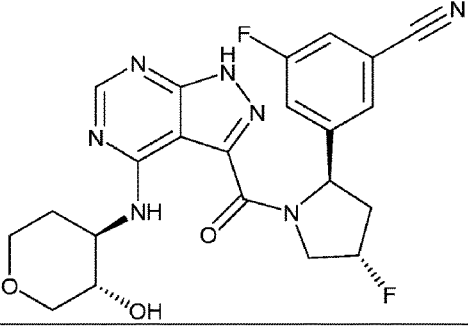 | 1H NMR (400 MHz, DMSO-d6) δ 14.18 (s, 1H), 9.10 (d, J = 7.3 Hz, 1H), 8.25 (s, 1H), 7.78 (s, 1H), 7.74 – 7.59 (m, 2H), 5.57 – 5.35 (m, 2H), 5.06 (d, J = 5.4 Hz, 1H), 4.76 – 4.63 (m, 1H), 4.50 (dd, J = 39.8, 14.4 Hz, 1H), 4.09 (s, 2H), 3.69 (dd, J = 11.3, 4.5 Hz, 2H), 3.42 – 3.37 (m, 1H), 3.09 (dd, J = 11.4, 8.7 Hz, 1H), 2.73 (dd, J = 33.7, 20.2 Hz, 1H), 2.09 (q, J = 13.8, 11.9 Hz, 2H), 1.50 – 1.33 (m, 1H).; LCMS: 470 |
| 182 | 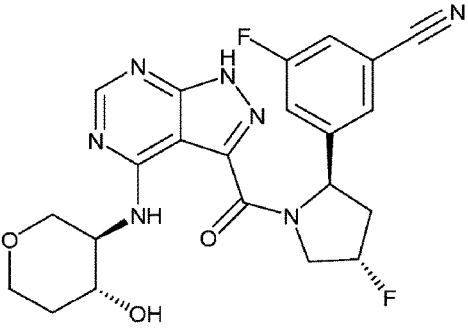 | 1H NMR (400 MHz, DMSO-d6) δ 14.17 (s, 1H), 9.11 (d, J = 7.8 Hz, 1H), 8.26 (s, 1H), 7.88 – 7.55 (m, 3H), 5.52 (s, 1H), 5.45 – 5.35 (m, 1H), 5.02 (d, J = 4.7 Hz, 1H), 4.73 (dd, J = 21.9, 13.9 Hz, 1H), 4.48 (dd, J = 39.7, 13.0 Hz, 1H), 4.03 (dd, J = 7.5, 3.7 Hz, 1H), 3.92 (dd, J = 11.1, 3.7 Hz, 1H), 3.73 (dd, J = 11.0, 5.7 Hz, 1H), 3.56 – 3.46 (m, 1H), 3.43 – 3.34 (m, 1H), 3.18 (dd, J = 11.3, 6.5 Hz, 1H), 2.83 – 2.63 (m, 1H), 2.19 – 1.95 (m, 1H), 1.81 – 1.65 (m, 1H), 1.42 (d, J = 4.4 Hz, 1H).; LCMS: 470 |
| 183 | 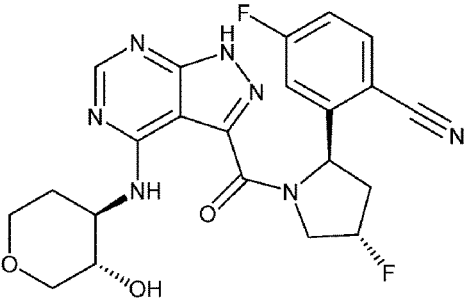 | 1H-NMR (400 MHz, CD3OD) δ ppm 8.33-8.26 (m, 1H), 7.84-7.81 (m, 1H), 7.36 (dd, 1H, J = 9.2, 2.0 Hz), 7.24-7.19 (m, 1H), 5.66 (dd, 1H, J = 10.4, 8.0 Hz), 5.49 (d, 1H, J = 52.0 Hz), 4.95-4.89 (m, 1H), 4.65-4.56 (m, 1H), 3.97-3.89 (m, 3H), 3.51-3.48 (m, 2H), 3.25-3.22 (m, 1H), 2.90-2.86 (m, 1H), 2.28-2.11 (m, 2H), 1.74-1.70 (m, 1H).; LCMS: 470.1 |
| 184 | 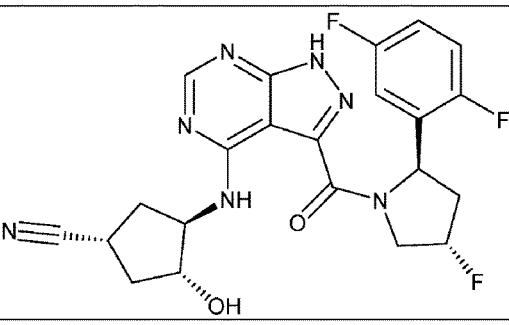 | 1H-NMR (400 MHz, CD3OD) δ ppm 8.33-8.26 (m, 1H), 7.13-7.07 (m, 3H), 5.60-5.55 (m, 1H), 5.43 (d, 1H, J = 52.0 Hz), 4.47-4.33 (m, 2H), 4.13-4.09 (m, 1H), 3.20-3.14 (m, 2H), 2.83-2.78 (m, 1H), 2.53-2.51 (m, 1H), 2.49-2.38 (m, 1H), 2.21-2.15 (m, 2H), 1.92-1.89 (m, 1H).; LCMS: 472.1 |

Figure 1A-21
| | | |
|---|---|---|
| 185 | 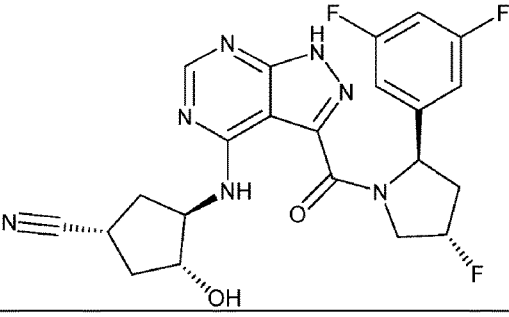 | 1H-NMR (400 MHz, CD3OD) δ ppm 8.34-8.27 (m, 1H), 6.97 (d, 2H, J = 6.0 Hz), 6.85-6.80 (m, 1H), 5.48-5.34 (m, 2H), 4.92-4.86 (m, 1H), 4.72-4.61 (m, 1H), 4.42-4.36 (m, 2H), 4.13-4.12 (m, 1H), 3.17-3.13 (m, 1H), 2.85-2.80 (m, 1H), 2.54-2.51 (m, 1H), 2.44-2.40 (m, 1H), 2.21-2.16 (m, 1H), 1.94-1.90 (m, 1H).; LCMS: 472.1 |
| 186 | 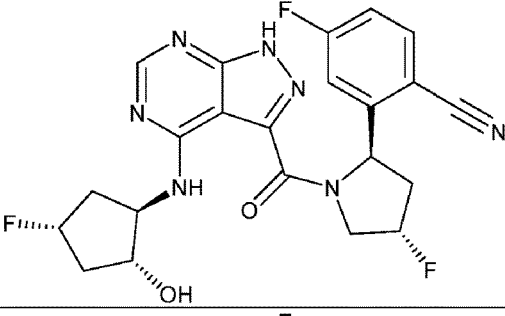 | 1H-NMR (400 MHz, CD3OD) δ ppm 8.24 (s, 1H), 7.82-7.79 (m, 1H), 7.34-7.31 (m, 1H), 7.21-7.03 (m, 1H), 5.65-5.61 (m, 1H), 5.45 (d, 1H, J = 52.0 Hz), 5.10 (d, 1H, J = 53.6 Hz), 4.89 (s, 1H), 4.61-4.47 (m, 2H), 4.06-4.01 (m, 1H), 2.87-2.85 (m, 1H), 2.53-2.46 (m, 2H), 2.44-2.41 (m, 1H), 1.92-1.84 (m, 2H).; LCMS: 472.1 |
| 187 | 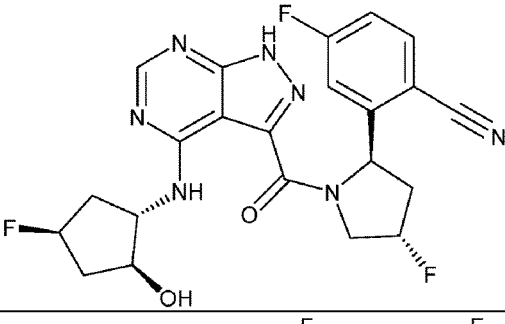 | 1H-NMR (400 MHz, CD3OD) δ ppm 8.25 (s, 1H), 7.83-7.80 (m, 1H), 7.34-7.31 (m, 1H), 7.21-7.13 (m, 1H), 5.65-5.61 (m, 1H), 5.45 (d, 1H, J = 51.6 Hz), 5.08 (d, 1H, J = 54.0 Hz), 4.78 (s, 1H), 4.61-4.47 (m, 2H), 4.15-4.07 (m, 1H), 3.06-2.85 (m, 1H), 2.55-2.42 (m, 2H), 2.25-2.00 (m, 1H), 1.94-1.82 (m, 2H).; LCMS: 472.1 |
| 188 | 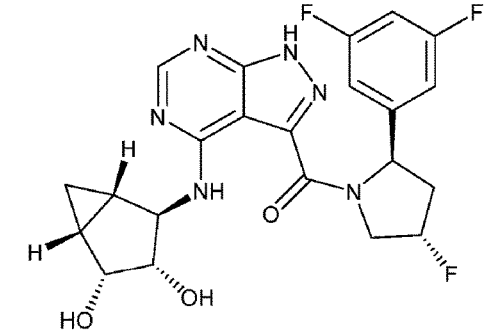 | 1H-NMR (400 MHz, CD3OD) δ ppm 8.34-8.27 (m, 1H), 6.98 (d, 1H, J = 6.4 Hz), 6.85-6.69 (m, 2H), 5.48-5.35 (m, 2H), 4.64-4.42 (m, 3H), 4.29-4.25 (m, 1H), 3.78 (d, 1H, J = 5.6 Hz), 2.82 (br.s, 1H), 2.19-2.08 (m, 1H), 1.70-1.64 (m, 1H), 1.55-1.47 (m, 1H), 1.23 (s, 1H), 0.66-0.63 (m, 1H).; LCMS: 475.1 |

Figure 1A-22

| | Structure | NMR / LCMS |
|---|---|---|
| 189 | 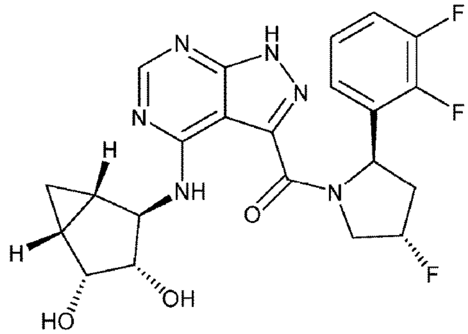 | 1H-NMR (400 MHz, CD3OD) δ ppm 8.31-8.23 (m, 1H), 7.18-6.95 (m, 3H), 5.66-5.62 (m, 1H), 5.45 (d, 1H, J = 52.0 Hz), 4.97-4.95 (m, 1H), 4.46-4.28 (m, 3H), 3.89-3.72 (m, 1H), 2.88-2.79 (m, 1H), 2.30-2.16 (m, 1H), 1.70-1.67 (m, 1H), 1.49-1.46 (m, 1H), 1.27-1.20 (m, 1H), 0.65-0.58 (m, 1H).; LCMS: 475.1 |
| 190 | 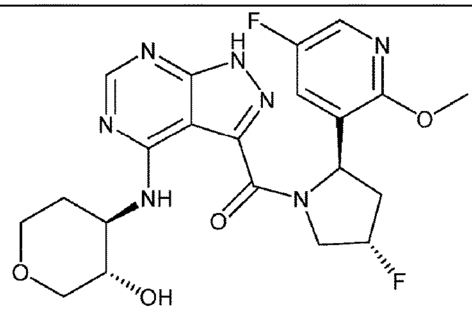 | 1H NMR (400 MHz, DMSO-d6) δ 14.16 (s, 1H), 9.15 (d, J = 7.4 Hz, 1H), 8.25 (s, 1H), 8.05 (d, J = 2.9 Hz, 1H), 7.54 (dd, J = 8.5, 3.1 Hz, 1H), 5.56 – 5.32 (m, 2H), 5.07 (d, J = 5.4 Hz, 1H), 4.79 – 4.62 (m, 1H), 4.53 – 4.27 (m, 1H), 4.09 (m, 1H), 3.91 (s,3H), 3.71 (m, 2H), 3.48 – 3.32 (m, 2H), 3.11 (m, 1H), 2.84 – 2.61 (m, 1H), 2.23 – 1.97 (m, 2H), 1.53 – 1.32 (m, 1H).; LCMS: 476.1 |
| 191 | 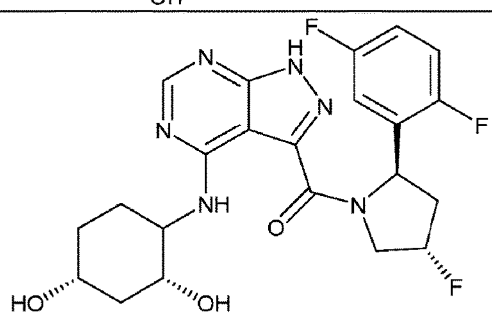 | 1H NMR (400 MHz, DMSO-d6) δ 14.11 (s, 1H), 8.90 (d, J = 7.4 Hz, 1H), 8.23 (s, 1H), 7.34 – 7.07 (m, 3H), 5.59 – 5.43 (m, 2H), 4.76 – 4.58 (m, 3H), 4.50 – 4.29 (m, 1H), 3.91 – 3.76 (m, 1H), 3.58 – 3.39 (m, 1H), 2.82 – 2.63 (m, 1H), 2.23 – 1.91 (m, 3H), 1.74 (d, J = 12.7 Hz, 1H), 1.32 – 1.05 (m, 2H).; LCMS: 477.1 |
| 192 | 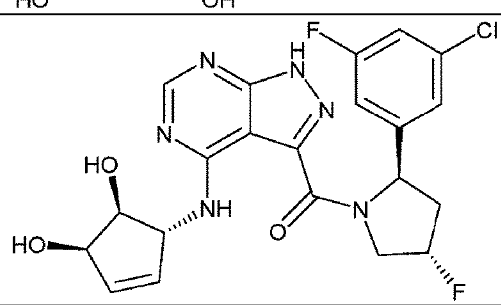 | 1H-NMR (400 MHz, CD3OD) δ ppm 8.35-8.28 (m, 1H), 7.20 (s, 1H), 7.07-6.93 (m, 2H), 6.22-5.98 (m, 2H), 5.46-5.33 (m, 2H), 5.04-5.03 (m, 1H), 4.64-4.43 (m, 2H), 4.00-3.97 (m, 1H), 2.85-2.76 (m, 1H), 2.19-2.03 (m, 1H).; LCMS: 477.1 |

Figure 1A-23
| 193 | 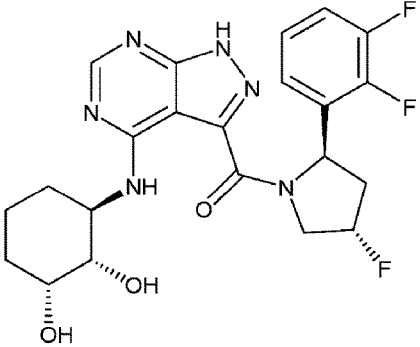 | 1H-NMR (400 MHz, CD3OD) δ ppm 8.30-8.22 (m, 1H), 7.17-6.95 (m, 3H), 5.67-5.63 (m, 1H), 5.44 (d, 1H, J = 52.0 Hz), 4.93-4.87 (m, 1H), 4.50-4.37 (m, 1H), 4.11-4.08 (m, 1H), 3.99 (s, 1H), 3.49-3.46 (m, 1H), 2.83-2.82 (m, 1H), 2.24-2.03 (m, 2H), 1.86-1.78 (m, 2H), 1.59-1.47 (m, 3H).; LCMS: 477.1 |
|---|---|---|
| 194 | 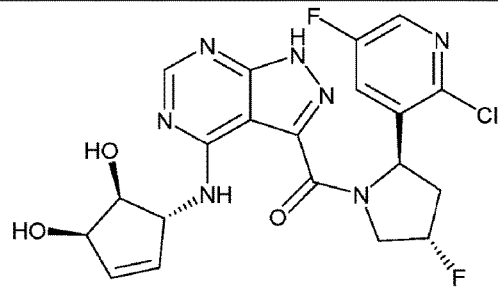 | 1H-NMR (400 MHz, CD3OD) δ ppm 8.32-8.25 (m, 1H), 8.21-8.09 (m, 1H), 7.61-7.48 (m, 1H), 6.10-6.08 (m, 1H), 5.98-5.96 (m, 1H), 5.65-5.61 (m, 1H), 5.48-5.35 (m, 1H), 5.04-5.03 (m, 1H), 4.55-4.51 (m, 2H), 4.08-3.92 (m, 1H), 2.96-2.87 (m, 1H), 2.19-2.04 (m, 1H).; LCMS: 478.1 |
| 195 | 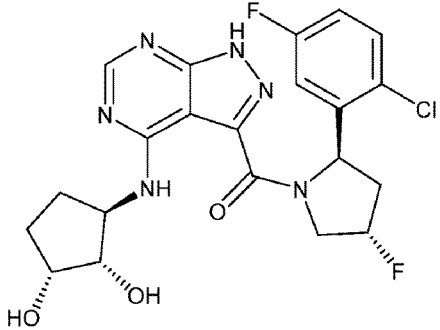 | 1H-NMR (400 MHz, CD3OD) δ ppm 9.28 (br.s, 1H), 8.30-8.21 (m, 1H), 7.51 (br.s, 1H), 7.18-7.00 (m, 2H), 5.58-5.39 (m, 2H), 4.65-4.31 (m, 3H), 3.84-3.62 (m, 2H), 2.65 (br.s, 4H), 2.19-1.28 (m, 2H).; LCMS: 479.1 |
| 196 | 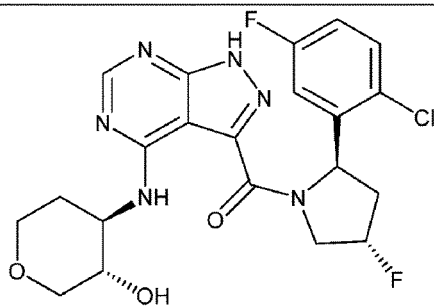 | 1H-NMR (400 MHz, CD3OD) δ ppm 8.36-8.28 (m, 1H), 7.46-7.42 (m, 1H), 7.09-6.91 (m, 2H), 5.75 (t, 1H, J = 8.8 Hz), 5.50-5.33 (m, 1H), 4.61-4.53 (m, 1H), 4.03-3.89 (m, 4H), 3.52-3.47 (m, 2H), 3.24-3.19 (m, 1H), 2.93-2.91 (m, 1H), 2.17-2.10 (m, 2H), 1.75-1.71 (m, 1H).; LCMS: 479.1 |

Figure 1A-24
| | | |
|---|---|---|
| 197 | 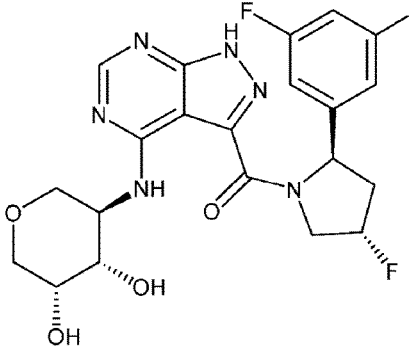 | 1H-NMR (400 MHz, CD3OD) δ ppm 8.35-8.28 (m, 1H), 6.97 (d, 1H, J = 6.4 Hz), 6.87-6.80 (m, 2H), 5.48-5.34 (m, 2H), 4.54-4.33 (m, 1H), 4.32-4.07 (m, 1H), 4.05-4.03 (m, 2H), 3.85-3.84 (m, 2H), 3.77-3.75 (m, 1H), 3.59-3.57 (m, 1H), 3.41-3.36 (m, 1H), 2.86-2.79 (m, 1H), 2.20-2.04 (m, 1H).; LCMS: 479.1 |
| 198 | 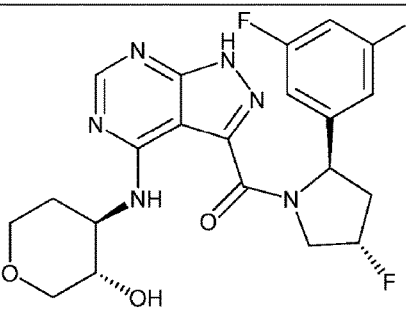 | 1H-NMR (400 MHz, CD3OD) δ ppm 8.34 (s, 1H), 7.22 (s, 1H), 7.08 (d, 2H, J = 8.8 Hz), 5.47-5.34 (m, 2H), 4.86-4.82 (m, 1H), 4.55-4.50 (m, 1H), 3.97-3.90 (m, 3H), 3.54-3.46 (m, 2H), 3.23-3.21 (m, 1H), 2.83-2.81 (m, 1H), 2.17-2.07 (m, 2H), 1.76-1.73 (m, 1H).; LCMS: 479.1 |
| 199 | 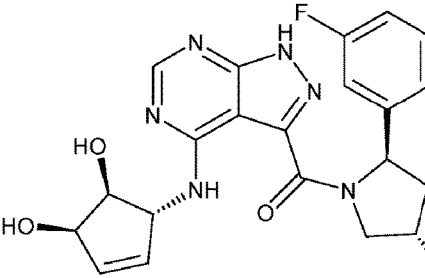 | 1H-NMR (400 MHz, CD3OD) δ ppm 8.30-8.23 (m, 1H), 7.07-7.03 (m, 1H), 6.92-6.91 (m, 1H), 6.13-6.06 (m, 1H), 6.04-5.97 (m, 1H), 5.62-5.58 (m, 1H), 5.41 (d, 1H, J = 51.6 Hz), 5.08-5.07 (m, 1H), 4.55-4.35 (m, 2H), 4.05-3.93 (m, 1H), 2.86-2.76 (m, 1H), 2.24-2.08 (m, 1H).; LCMS: 479.1 |
| 200 | 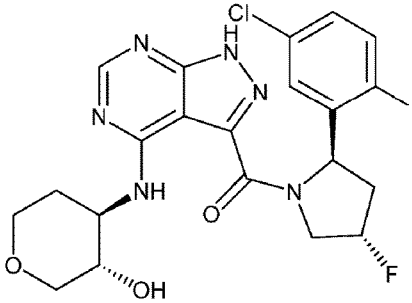 | 1H-NMR (400 MHz, CD3OD) δ ppm 8.30-8.23 (m, 1H), 7.35-7.26 (m, 3H), 5.61-5.57 (m, 1H), 5.40 (d, 1H, J = 52.4 Hz), 4.52-4.36 (m, 1H), 4.03-3.87 (m, 4H), 3.53-3.47 (m, 2H), 3.24-3.21 (m, 1H), 2.80-2.80 (m, 1H), 2.24-2.10 (m, 2H), 1.69-1.67 (m, 1H).; LCMS: 479.1 |

Figure 1A-25
| | | |
|---|---|---|
| 201 | 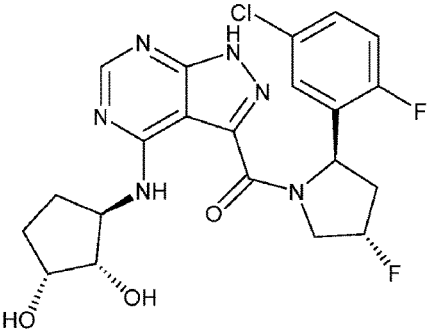 | 1H-NMR (400 MHz, CDCl3) δ ppm 8.37-8.29 (m, 1H), 7.35-7.10 (m, 3H), 5.60 (dd, 1H, J = 10.0, 8.4 Hz), 5.45 (d, 1H, J = 52.0 Hz)), 4.87-4.85 (m, 1H), 4.55-4.32 (m, 2H), 4.07-3.91 (m, 2H), 2.88-2.82 (m, 1H), 2.41-2.11 (m, 3H), 1.79-1.63 (m, 2H).; LCMS: 479.1 |
| 202 | 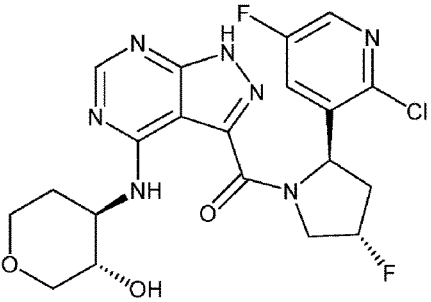 | 1H NMR (400 MHz, DMSO-d6) δ 14.20 (s, 1H), 9.07 (d, J = 7.4 Hz, 1H), 8.39 (d, J = 3.0 Hz, 1H), 8.25 (d, J = 6.0 Hz, 1H), 7.84 (dd, J = 8.8, 3.0 Hz, 1H), 5.60 – 5.42 (m, 2H), 5.05 (d, J = 5.3 Hz, 1H), 4.75 (dd, J = 21.3, 14.1 Hz, 1H), 4.51 (dd, J = 39.5, 15.0 Hz, 1H), 4.09 (s, 2H), 3.71 – 3.62 (m, 2H), 3.13 – 3.02 (m, 1H), 2.08 (s, 2H), 1.44 (dd, J = 27.0, 9.2 Hz, 2H), 1.21 (d, J = 13.5 Hz, 1H).; LCMS: 480 |
| 203 | 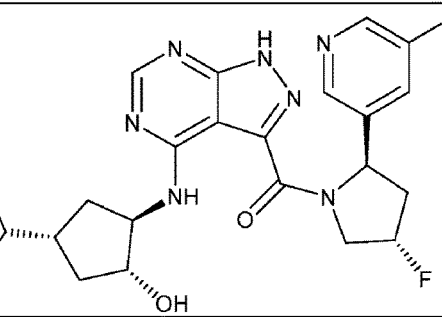 | 1H-NMR (400 MHz, CD3OD) δ ppm 8.49 (br.s, 1H), 8.38 (br.s, 1H), 8.33 (br.s, 1H), 7.69 (d, 1H, J = 9.2 Hz), 5.97-5.77 (m, 1H), 5.64-5.39 (m, 2H), 4.57-4.44 (m, 1H), 4.24-4.21 (m, 2H), 4.07 (d, 1H, J = 6.4 Hz), 2.89-2.85 (m, 1H), 2.46-2.44 (m, 1H), 2.27-2.25 (m, 1H), 2.15-2.12 (m, 1H), 1.92-1.81 (m, 2H), 1.66-1.62 (m, 1H).; LCMS: 480.1 |
| 204 | 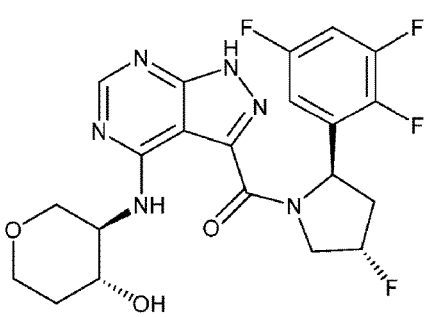 | 1H NMR (400 MHz, DMSO-d6) δ 14.19 (s, 1H), 9.13 (d, J = 7.8 Hz, 1H), 8.26 (s, 1H), 7.47 – 7.34 (m, 1H), 7.14 (d, J = 8.1 Hz, 1H), 5.59 – 5.48 (m, 2H), 4.80 – 4.60 (m, 1H), 4.41 (dd, J = 39.5, 14.0 Hz, 1H), 4.09 – 3.96 (m, 1H), 3.92 (dd, J = 11.1, 3.7 Hz, 1H), 3.75 (dd, J = 12.0, 5.6 Hz, 1H), 3.47 (dtd, J = 59.1, 8.2, 7.8, 4.5 Hz, 2H), 3.19 (dd, J = 11.2, 6.9 Hz, 1H), 2.85 – 2.60 (m, 1H), 2.33 – 2.04 (m, 1H), 1.79 (dd, J = 11.3, 4.7 Hz, 1H), 1.53 – 1.33 (m, 1H).; LCMS: 481 |

Figure 1A-26
| | | |
|---|---|---|
| 205 | 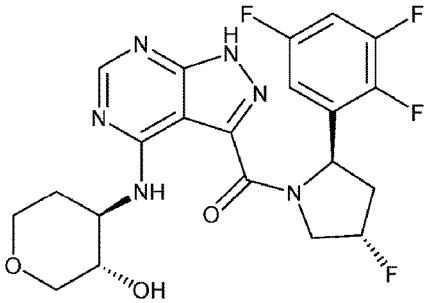 | 1H-NMR (400 MHz, CD3OD) δ ppm 8.37-9.30 (m, 1H), 7.08-6.98 (m, 2H), 5.68-5.63 (m, 1H), 5.53-5.36 (m, 1H), 4.53-4.40 (m, 1H), 4.02-3.91 (m, 4H), 3.55-3.46 (m, 2H), 3.26-3.21 (m, 1H), 2.86-2.82 (m, 1H), 2.30-2.12 (m, 2H), 1.78-1.70 (m, 1H).; LCMS: 481.1 |
| 206 | 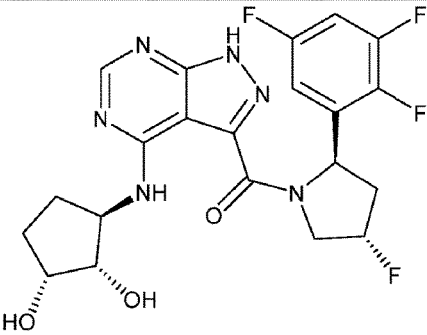 | 1H-NMR (400 MHz, CD3OD) δ ppm 8.36 (s, 1H), 7.10-6.95 (m, 2H), 5.72-5.62 (m, 1H), 5.52-5.39 (m, 1H), 4.93-4.92 (m, 1H), 4.52-4.08 (m, 2H), 4.07-5.06 (m, 1H), 3.93-3.90 (m, 1H), 2.88-2.82 (m, 1H), 2.41-2.10 (m, 3H), 1.78-1.63 (m, 2H).; LCMS: 481.1 |
| 207 | 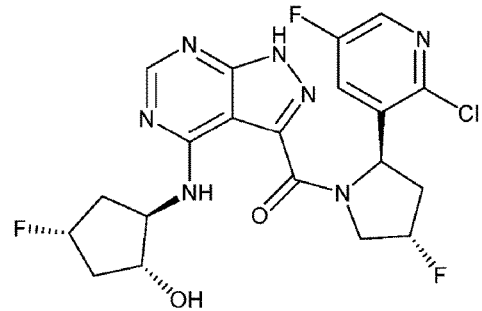 | 1H-NMR (400 MHz, CD3OD) δ ppm 8.25-8.20 (m, 2H), 7.61-7.58 (m, 1H), 5.66-5.62 (m, 1H), 5.25 (d, 1H, J = 52.0 Hz), 5.14-5.00 (m, 1H), 4.91-4.87 (m, 1H), 4.53-4.44 (m, 2H), 4.06-4.03 (m, 1H), 2.94-2.91 (m, 1H), 2.54-2.43 (m, 2H), 1.91-1.83 (m, 3H).; LCMS: 482.1 |
| 208 | 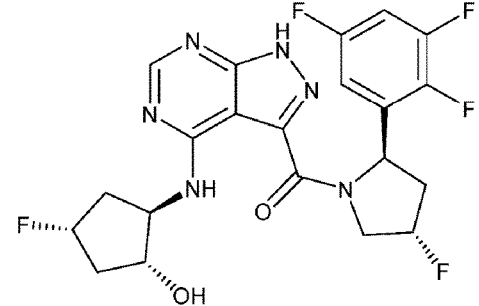 | 1H-NMR (400 MHz, CD3OD) δ ppm 8.26-8.20 (m, 1H), 7.08-7.02 (m, 1H), 6.94-6.92 (m, 1H), 5.64-5.60 (m, 1H), 5.42 (d, 1H, J = 52.0 Hz), 5.10 (dt, 1H, J = 52.0, 6.0 Hz), 4.80 (s, 1H), 4.55-4.44 (m, 2H), 4.09-4.04 (m, 1H), 2.92-2.54 (m, 1H), 2.52-2.43 (m, 2H), 1.93-1.89 (m, 1H), 1.86-1.83 (m, 2H).; LCMS: 483.1 |

Figure 1A-27
| 209 | 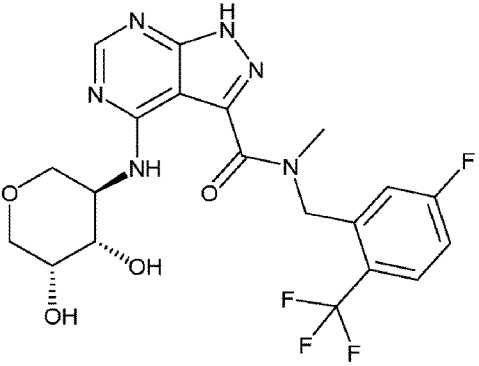 | 1H-NMR (400 MHz, CD3OD) δ ppm 8.38-8.35 (m, 1H), 7.84-7.80 (m, 1H), 7.24-7.15 (m, 2H), 5.58 (s, 1H), 5.07 (s, 1H), 4.40-4.39 (m, 1H), 4.11-4.10 (m, 1H), 3.98-3.90 (m, 3H), 3.68-3.61 (m, 2.5H), 3.48-3.41 (m, 1H), 3.22 (s, 1.5H).; LCMS: 485.1 |
| --- | --- | --- |
| 210 | 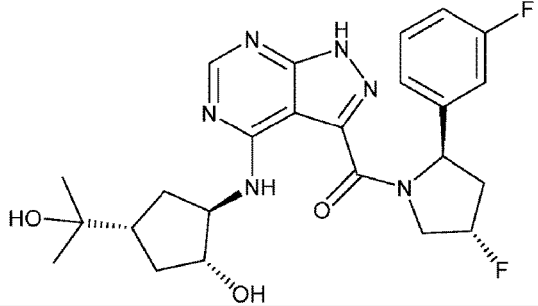 | 1H-NMR (400 MHz, CD3OD) δ ppm 8.26 (s, 1H), 7.36-7.32 (m, 1H), 7.15 (d, 1H, J = 7.6 Hz), 7.07 (d, 1H, J = 9.6 Hz), 6.97-6.93 (m, 1H), 5.45-5.41 (m, 2H), 4.49-4.36 (m, 1H), 4.13-4.09 (m, 1H), 4.01-3.97 (m, 1H), 3.13-3.09 (m, 1H), 2.84-2.75 (m, 1H), 2.26-2.16 (m, 3H), 1.68-1.59 (m, 2H), 1.50-1.37 (m, 1H), 1.20-1.14 (m, 6H).; LCMS: 487.1 |
| 211 | 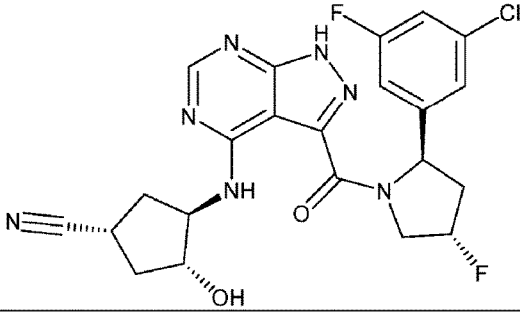 | 1H-NMR (400 MHz, CD3OD) δ ppm 8.34-8.27 (m, 1H), 7.22 (s, 1H), 7.07 (d, 2H, J = 6.8 Hz), 5.47-5.34 (m, 2H), 4.88-4.87 (m, 1H), 4.79-4.77 (m, 1H), 4.42-4.37 (m, 2H), 4.13-4.12 (m, 1H), 3.17-3.13 (m, 1H), 2.83-2.80 (m, 1H), 2.54-2.51 (m, 1H), 2.44-2.40 (m, 1H), 2.21-2.17 (m, 1H), 1.94-1.91 (m, 1H).; LCMS: 488.1 |
| 212 | 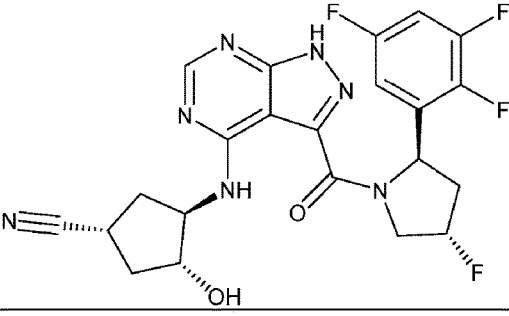 | 1H-NMR (400 MHz, CD3OD) δ ppm 8.36-8.30 (m, 1H), 7.09-6.95 (m, 2H), 5.65-5.62 (m, 1H), 5.61-5.39 (m, 1H), 4.95-4.91 (m, 1H), 4.50-4.36 (m, 2H), 4.14-4.11 (m, 1H), 3.21-3.16 (m, 1H), 2.82-2.75 (m, 1H), 2.57-2.54 (m, 1H), 2.52-2.42 (m, 1H), 2.23-2.18 (m, 2H), 2.00-1.94 (m, 1H).; LCMS: 490.0 |

Figure 1A-28
| 213 | 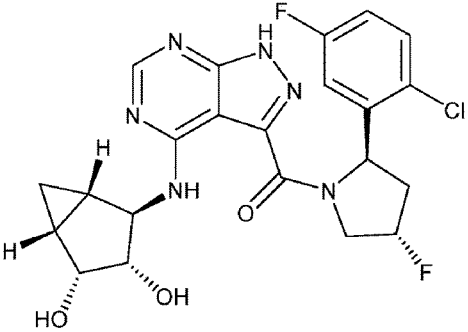 | 1H-NMR (400 MHz, CD3OD) δ ppm 7.49-7.46 (m, 1H), 7.12-7.06 (m, 2H), 5.76 (t, 1H, J = 8.4 Hz), 5.47 (d, 1H, J = 52.4 Hz), 4.46-4.28 (m, 3H), 4.00 (s, 1H), 3.79 (d, 1H, J = 6.4 Hz), 2.20-2.04 (m, 1H), 1.71 (br.s, 1H), 1.50 (br.s, 1H), 1.31-1.25 (m, 2H), 0.67-0.64 (m, 1H).; LCMS: 491.1 |
|---|---|---|
| 214 | 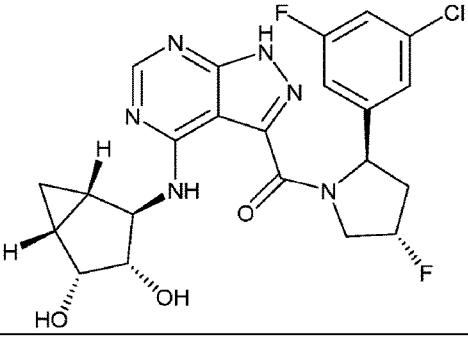 | 1H-NMR (400 MHz, CD3OD) δ ppm 8.33-8.27 (m, 1H), 7.22 (s, 1H), 7.10-7.07 (m, 2H), 5.47-5.34 (m, 2H), 4.51-4.38 (m, 2H), 4.27-4.23 (m, 1H), 3.91-3.77 (m, 1H), 3.35-3.33 (m, 1H), 2.84-2.78 (m, 1H), 2.19-2.18 (m, 1H), 1.72-1.68 (m, 1H), 1.48-1.45 (m, 1H), 1.24-1.21 (m, 1H), 0.67-0.60 (m, 1H).; LCMS: 491.1 |
| 215 | 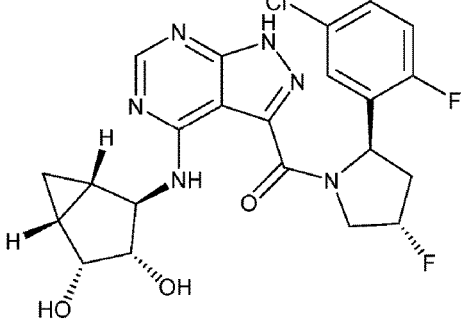 | 1H-NMR (400 MHz, CD3OD) δ ppm 8.41-8.28 (m, 1H), 7.36-6.33 (m, 3H), 5.58-5.54 (m, 1H), 5.51-5.38 (m, 1H), 4.98-4.96 (m, 1H), 4.52-3.76 (m, 4H), 2.97-2.74 (m, 1H), 2.30-2.15 (m, 1H), 1.73-1.48 (m, 2H), 1.26-1.22 (m, 1H), 0.66-0.61 (m, 1H).; LCMS: 491.1 |
| 216 | 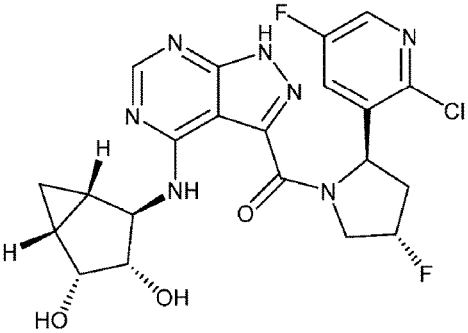 | 1H NMR (400 MHz, DMSO-d6) δ 14.19 (s, 1H), 9.02 (d, J = 7.6 Hz, 1H), 8.39 (d, J = 2.8 Hz, 1H), 8.29 (s, 1H), 7.89 (dd, J = 9.0, 3.0 Hz, 1H), 5.64 – 5.37 (m, 3H), 4.92 – 4.71 (m, 2H), 4.43 (d, J = 9.1 Hz, 1H), 4.30 (dd, J = 13.2, 7.4 Hz, 2H), 4.14 (q, J = 6.0 Hz, 1H), 3.48 (t, J = 5.3 Hz, 1H), 2.79 (td, J = 16.6, 16.1, 7.2 Hz, 1H), 1.43 (dd, J = 8.9, 4.7 Hz, 1H), 1.24 (d, J = 16.9 Hz, 1H), 1.02 (q, J = 4.2 Hz, 1H), 0.48 – 0.33 (m, 1H).; LCMS: 492 |

Figure 1A-29

| 217 | | 1H-NMR (400 MHz, CD3OD) δ ppm 8.39-8.30 (m, 1H), 7.51-7.48 (m, 1H), 7.11-6.95 (m, 2H), 5.79 (t, 1H, J = 9.2 Hz), 5.55-5.38 (m, 1H), 4.89 (br.s, 1H), 4.62-4.49 (m, 1H), 4.17-4.07 (m, 2H), 3.57-3.55 (m, 1H), 3.04-2.91 (m, 1H), 2.17-2.10 (m, 2H), 1.93-1.85 (m, 2H), 1.67-1.54 (m, 3H).; LCMS: 493.1 |
|---|---|---|
| 218 | | 1H-NMR (400 MHz, CD3OD) δ ppm 8.34-8.28 (m, 1H), 6.95-6.86 (m, 2H), 5.66 (t, 1H, J = 8.4 Hz), 5.50-5.37 (m, 1H), 4.52-4.43 (m, 1H), 4.03-3.91 (m, 7H), 3.54-3.49 (m, 2H), 3.26-3.21 (m, 1H), 2.86-2.75 (m, 1H), 2.24-2.11 (m, 2H), 1.76-1.71 (m, 1H).; LCMS: 493.1 |
| 219 | | 1H-NMR (400 MHz, CD3OD) δ ppm 8.36-8.30 (m, 1H), 6.93-6.85 (m, 2H), 5.66 (t, 1H, J = 8.8 Hz), 5.50-5.37 (m, 1H), 4.52-4.31 (m, 2H), 4.07-4.04 (m, 2H), 3.98 (s, 3H), 3.93-3.90 (m, 1H), 2.79-2.75 (m, 1H), 2.43-2.39 (m, 1H), 2.20-2.07 (m, 2H), 1.79-1.77 (m, 1H), 1.64-1.62 (m, 1H).; LCMS: 493.1 |
| 220 | | 1H-NMR (400 MHz, CD3OD) δ ppm 8.37 (s, 1H), 7.10-6.98 (m, 2H), 5.63 (t, 1H, J = 8.4 Hz), 5.54-5.36 (m, 1H), 4.98-4.95 (m, 1H), 4.50-4.37 (m, 2H), 4.29-4.25 (m, 1H), 3.80-3.78 (m, 1H), 2.89-2.79 (m, 1H), 2.31-2.15 (m, 1H), 1.78-1.72 (m, 1H), 1.56-1.50 (m, 1H), 1.30-1.25 (m, 1H), 0.68-0.62 (m, 1H).; LCMS: 493.1 |

Figure 1A-30

| 221 | *(structure)* | 1H-NMR (400 MHz, CD3OD) δ ppm 8.30-8.22 (m, 1H), 7.33-6.35 (m, 3H), 5.85-5.56 (m, 1H), 5.49-5.36 (m, 1H), 4.91-4.88 (m, 1H), 4.50-4.40 (m, 1H), 4.15-4.08 (m, 1H), 3.99 (br.s, 1H), 3.52-3.49 (m, 1H), 2.82-2.80 (m, 1H), 2.24-2.03 (m, 2H), 1.86-1.78 (m, 2H), 1.58-1.47 (m, 3H).; LCMS: 493.1 |
|---|---|---|
| 222 | *(structure)* | 1H-NMR (400 MHz, CD3OD) δ ppm 8.38 (s, 1H), 7.49-7.45 (m, 1H), 7.10-7.03 (m, 2H), 5.77 (d, 1H, J = 8.4 Hz) 5.44 (d, 1H, J = 51.6 Hz), 4.59-4.49 (m, 1H), 4.38-4.36 (m, 1H), 4.09-3.61 (m, 6H), 3.42-3.39 (m, 1H), 2.99-2.90 (m, 0.5H), 2.16-2.01 (m, 0.5H).; LCMS: 495.1 |
| 223 | *(structure)* | 1H-NMR (400 MHz, CD3OD) δ ppm 8.36-8.28 (m, 1H), 7.21 (s, 1H), 7.11-7.06 (m, 2H), 5.46-5.33 (m, 2H), 4.84-4.80 (m, 1H), 4.55-4.51 (m, 1H), 4.28-4.27 (m, 1H), 4.05-4.02 (m, 1H), 3.86-3.83 (m, 2H), 3.76-3.73 (m, 1H), 3.58-3.56 (m, 1H), 3.40-3.38 (m, 1H), 2.84-2.78 (m, 1H), 2.19-2.05 (m, 1H).; LCMS: 495.1 |
| 224 | *(structure)* | 1H-NMR (400 MHz, CD3OD) δ ppm 8.33-8.32 (m, 1H), 7.09-7.03 (m, 1H), 6.95-6.93 (m, 1H), 5.65-5.61 (m, 1H), 5.51-5.38 (m, 1H), 4.52-4.42 (m, 1H), 4.10-4.02 (m, 3H), 3.51-3.48 (m, 1H), 2.84-2.82 (m, 1H), 2.24-2.04 (m, 2H), 1.87-1.79 (m, 2H), 1.62-1.48 (m, 3H). ; LCMS: 495.2 |

Figure 1A-31

| 225 | (structure) | N/A; LCMS: 497.1 |
|---|---|---|
| 226 | (structure) | 1H-NMR (400 MHz, CD3OD) δ ppm 8.34-8.27 (m, 1H), 7.15-7.02 (m, 3H), 5.99-5.62 (m, 1H), 5.60-5.58 (m, 1H), 5.51-5.38 (m, 1H), 4.96-4.90 (m, 1H), 4.49-4.40 (m, 1H), 4.23-4.18 (m, 1H), 4.12-4.09 (m, 1H), 2.87-2.79 (m, 1H), 2.58-2.50 (m, 1H), 2.30-2.23 (m, 2H), 2.15-2.11 (m, 1H), 1.87-1.77 (m, 1H), 1.67-1.64 (m, 1H).; LCMS: 497.1 |
| 227 | (structure) | N/A; LCMS: 499.1 |
| 228 | (structure) | 1H-NMR (400 MHz, CD3OD) δ ppm 8.36 (d, 1H, J = 8.4 Hz), 7.40 (br.s, 1H), 7.20-7.14 (m, 2H), 5.50 (s, 1H), 4.94 (d, 1H, J = 7.2 Hz), 4.40-4.38 (m, 1H), 4.11-4.10 (m, 1H), 3.97-3.85 (m, 3H), 3.68-3.61 (m, 2.5H), 3.47-3.40 (m, 1H), 3.17 (s, 1.5H).; LCMS: 501.1 |

Figure 1A-32

| 229 | [structure] | N/A; LCMS: 504.1 |
|---|---|---|
| 230 | [structure] | 1H-NMR (400 MHz, CD3OD) δ ppm 8.19 (s, 1H), 7.59 (s, 1H), 7.48-7.41 (m, 2H), 5.47-5.30 (m, 2H), 4.78-4.75 (m, 1H), 4.53-4.43 (m, 1H), 4.34-4.30 (m, 1H), 3.75-3.70 (m, 1H), 2.84-2.79 (m, 1H), 2.18-2.07 (m, 3H), 1.75-1.49 (m, 4H).; LCMS: 504.1 |
| 231 | [structure] | 1H-NMR (400 MHz, CD3OD) δ ppm 8.45 (s, 1H), 8.33 (d, 1H, J = 2.8 Hz), 8.21 (s, 1H), 7.64 (d, 1H, J = 9.6 Hz), 5.51-5.34 (m, 2H), 4.82-4.79 (m, 1H), 4.53-4.40 (m, 1H), 4.33 (br.s, 1H), 3.74-3.66 (m, 1H), 2.84-2.80 (m, 1H), 2.21-2.08 (m, 3H), 1.78-1.71 (m, 2H), 1.61-1.46 (m, 2H).; LCMS: 504.1 |
| 232 | [structure] | 1H-NMR (400 MHz, CD3OD) δ ppm 8.22-8.15 (m, 1H), 7.13-6.83 (m, 3H), 5.61-5.56 (m, 1H), 5.41 (d, 1H, J = 52.0 Hz), 4.91-4.89 (m, 1H), 4.46-4.36 (m, 1H), 4.21-4.20 (m, 1H), 4.10-3.97 (m, 1H), 2.85-2.79 (m, 1H), 2.29-2.00 (m, 4H), 1.63-1.58 (m, 2H), 1.22-1.18 (m, 6H); LCMS: 505.2 |

Figure 1A-33

| | | |
|---|---|---|
| 233 | [structure] | 1H-NMR (400 MHz, CD3OD) δ ppm 8.30-8.24 (m, 1H), 6.94-6.83 (m, 2H), 5.64 (t, 1H, J = 8.8 Hz), 5.41 (d, 1H, J = 52.0 Hz), 4.48-4.29 (m, 4H), 4.00 (s, 3H), 3.74 (d, 1H, J = 6.0 Hz), 2.79-2.71 (m, 1H), 2.20-2.06 (m, 2H), 1.65-1.60 (m, 1H), 1.47-1.45 (m, 1H), 1.23-1.20 (m, 1H), 0.61-0.55 (m, 1H).; LCMS: 505.3 |
| 234 | [structure] | 1H-NMR (400 MHz, CD3OD) δ ppm 8.33-8.27 (m, 1H), 6.95-6.84 (m, 2H), 5.65 (t, 1H, J = 8.8 Hz), 5.50-5.31 (m, 1H), 4.52-4.39 (m, 1H), 4.11-4.08 (m, 1H), 4.03 (s, 1H), 3.98 (s, 3H), 3.73-3.50 (m, 2H), 2.84-2.74 (m, 1H), 2.20-2.06 (m, 2H), 1.86-1.81 (m, 2H), 1.61-1.47 (m, 3H).; LCMS: 507.1 |
| 235 | [structure] | 1H-NMR (400 MHz, CD3OD) δ ppm 8.37-8.30 (m, 1H), 7.04-6.95 (m, 2H), 6.85-6.67 (m, 2H), 6.15-6.13 (m, 1H), 5.99-5.97 (m, 1H), 5.46-5.33 (m, 2H), 4.98 (d, 1H, J = 4.4 Hz), 4.80 (s, 1H), 4.53-4.42 (m, 2H), 4.00-3.97 (m, 1H), 2.85-2.75 (m, 1H), 2.19-2.02 (m, 1H).; LCMS: 509 |
| 236 | [structure] | 1H-NMR (400 MHz, CD3OD) δ ppm 8.36-8.30 (m, 1H), 6.94-6.84 (m, 2H), 5.67 (t, 1H, J = 8.4 Hz), 5.50-5.31 (m, 1H), 4.52-4.42 (m, 1H), 4.31-4.30 (m, 1H), 4.07-3.89 (m, 5H), 3.83-3.76 (m, 3H), 3.58-3.40 (m, 2H), 2.81-2.75 (m, 1H), 2.22-2.03 (m, 1H).; LCMS: 509.1 |

Figure 1A-34
| 237 | 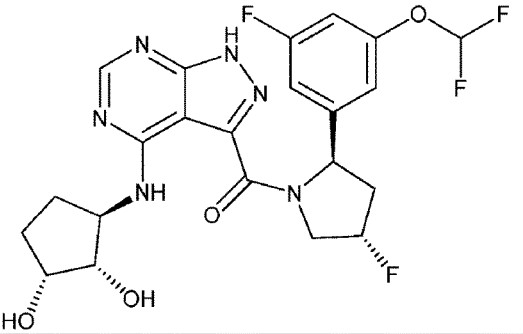 | 1H-NMR (400 MHz, CD3OD) δ ppm 8.34-8.27 (m, 1H), 7.05-6.96 (m, 2H), 6.86-6.68 (m, 2H), 5.47-5.34 (m, 2H), 4.81 (s, 1H), 4.54-4.49 (m, 1H), 4.31-4.29 (m, 1H), 4.06-4.04 (m, 1H), 3.91-3.88 (m, 1H), 2.86-2.83 (m, 1H), 2.40-2.36 (m, 1H), 2.17-2.06 (m, 2H), 1.76-1.62 (m, 2H).; LCMS: 511 |
|---|---|---|
| 238 | 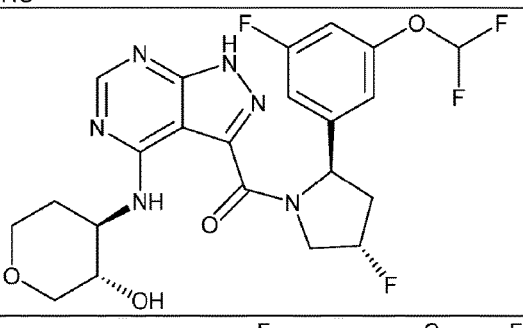 | 1H-NMR (400 MHz, CD3OD) δ ppm 8.32 (s, 1H), 7.06-6.97 (m, 2H), 6.87-6.69 (m, 2H), 5.47-5.34 (m, 2H), 4.54-4.50 (m, 1H), 4.01-3.88 (m, 3H), 3.53-3.46 (m, 3H), 3.23-3.18 (m, 1H), 2.83-2.81 (m, 1H), 2.17-2.08 (m, 2H), 1.74-1.65 (m, 1H).; LCMS: 511.1 |
| 239 | 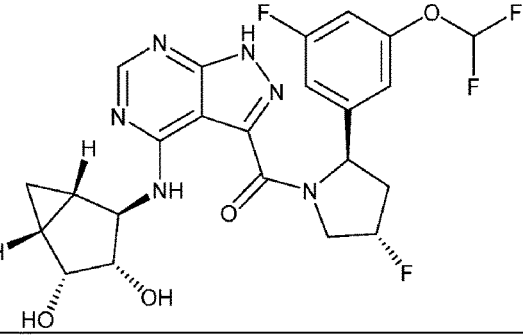 | 1H-NMR (400 MHz, CD3OD) δ ppm 8.34-8.27 (m, 1H), 7.05-6.97 (m, 2H), 6.87-6.68 (m, 2H), 5.47-5.34 (m, 2H), 4.89 (s, 1H), 4.62-4.47 (m, 1H), 4.40-4.37 (m, 1H), 4.27-4.23 (m, 1H), 3.77 (d, 1H, J = 6.0 Hz), 2.86-2.80 (m, 1H), 2.22-2.18 (m, 1H), 1.71-1.68 (m, 1H), 1.48-1.46 (m, 1H), 1.27-1.20 (m, 1H), 0.65-0.59 (m, 1H).; LCMS: 523 |
| 240 | 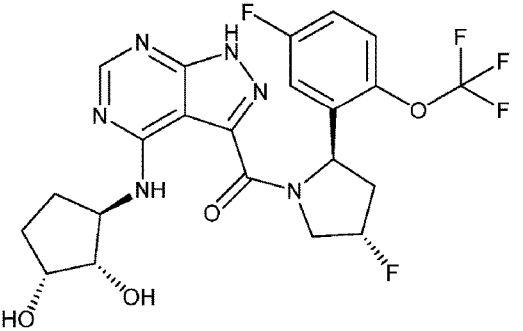 | 1H-NMR (400 MHz, CD3OD) δ ppm 8.23 (s, 1H), 7.36 (br.s, 1H), 7.16-7.08 (m, 2H), 5.65-5.61 (m, 1H), 5.41 (d, 1H, J = 52.0 Hz), 4.80 (s, 1H), 4.57-4.38 (m, 2H), 4.14-4.05 (m, 1H), 3.82-3.79 (m, 1H), 2.80-2.76 (m, 1H), 2.38-2.34 (m, 1H), 2.15-2.01 (m, 2H), 1.74-1.71 (m, 1H), 1.52-1.49 (m, 1H).; LCMS: 529.1 |

Figure 1A-35
| 241 | 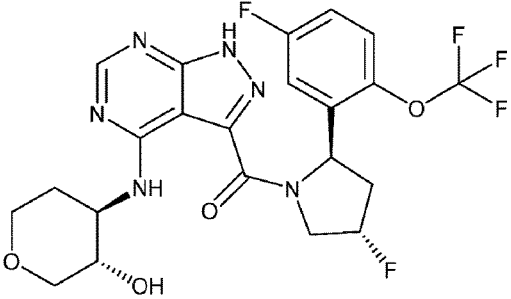 | 1H-NMR (400 MHz, CD3OD) δ ppm 8.22 (s, 1H), 7.36 (br.s, 1H), 7.17-7.15 (m, 1H), 7.11-7.08 (m, 1H), 5.67-5.62 (m, 1H), 5.41 (d, 1H, J = 52.0 Hz), 4.91 (s, 1H), 4.51-4.38 (m, 1H), 4.20 (br.s, 1H), 3.86-3.83 (m, 2H), 3.54-3.49 (m, 2H), 3.27-3.22 (m, 1H), 2.82-2.73 (m, 1H), 2.19-2.03 (m, 2H), 1.63-1.56 (m, 1H).; LCMS: 529.1 |
|---|---|---|
| 242 | 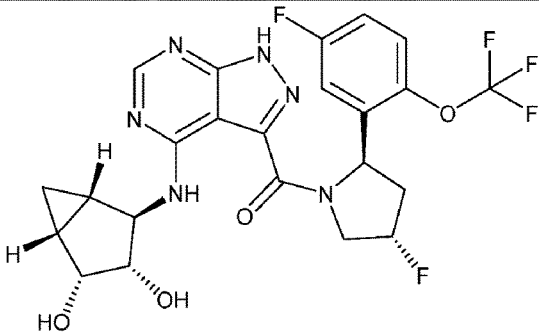 | 1H-NMR (400 MHz, CD3OD) δ ppm 8.34 (s, 1H), 7.38 (br.s, 1H), 7.18-7.10 (m, 2H), 5.65-5.61 (m, 1H), 5.46 (d, 1H, J = 52.0 Hz), 4.98-4.92 (m, 1H), 4.64-4.53 (m, 1H), 4.49-4.40 (m, 1H), 4.37-4.26 (m, 1H), 3.73 (d, 1H, J = 5.6 Hz), 2.82-2.73 (m, 1H), 2.24-2.07 (m, 1H), 1.67 (br.s, 1H), 1.47 (br.s, 1H), 1.29-1.23 (m, 1H), 0.68-0.59 (m, 1H).; LCMS: 541.2 |
| 243 | 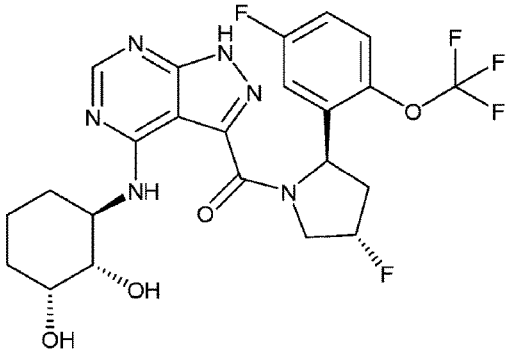 | 1H-NMR (400 MHz, CD3OD) δ ppm 8.19 (s, 1H), 7.35-7.34 (m, 1H), 7.16-7.07 (m, 2H), 5.63-5.59 (m, 1H), 5.40 (d, 1H, J = 52.4 Hz), 4.86-4.80 (m, 1H), 4.49-4.41 (m, 2H), 3.81 (br.s, 1H), 3.56-3.54 (m, 1H), 2.81-2.75 (m, 1H), 2.15-1.97 (m, 2H), 1.77-1.71 (m, 2H), 1.52-1.47 (m, 2H), 1.47-1.27 (m, 1H).; LCMS: 543.1 |
| 244 | 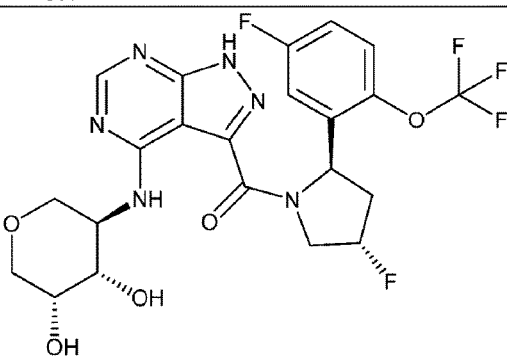 | 1H-NMR (400 MHz, CD3OD) δ ppm 8.23 (s, 1H), 7.35 (br.s, 1H), 7.16-7.07 (m, 2H), 5.67-5.62 (m, 1H), 5.40 (d, 1H, J = 52.0 Hz), 4.77 (s, 1H), 4.54-4.40 (m, 2H), 4.01-3.86 (m, 2H), 3.79-3.72 (m, 3H), 3.57-3.54 (m, 1H), 2.82-2.72 (m, 1H), 2.22-2.12 (m, 1H).; LCMS: 545.1 |

COMPOUNDS AND COMPOSITIONS USEFUL FOR TREATING DISORDERS RELATED TO NTRK

CLAIM OF PRIORITY

This application is a divisional of U.S. patent application Ser. No. 15/248,207, filed Aug. 26, 2016, which claims priority from U.S. Provisional Application No. 62/210,264, filed Aug. 26, 2015, each of which is incorporated herein by reference in its entirety.

BACKGROUND

Neurotrophic Tyrosine Receptor Kinase (NTRK) 1, 2 and 3 are receptor tyrosine kinases (RTKs) that activate multiple downstream pathways involved in cell proliferation and survival. Various genetic fusions, arising from aberrant chromosomal translocations of the genes coding for these RTKs, are implicated in the etiology of multiple cancers including high and low grade glioma, cholangiocarcinoma, papillary thyroid carcinoma, colon cancer and non-small cell lung cancer. A genomics analysis on the landscape of kinase fusions identified NTRK fusions in a wide array of additional cancer types including head and neck squamous cell carcinoma, pancreatic adenocarcinoma, sarcoma and melanoma, thereby providing further therapeutic rationale for deploying inhibitors of these kinases to treat multiple oncologic indications.

The identification of NTRK fusions as the underlying cause of certain cancers prompted the discovery and clinical development of several NTRK kinase inhibitors to treat tumors that harbor an NTRK fusion protein. Early clinical data support the viability of this approach in providing benefit to patients with specific human malignancies. Ultimately however, despite clear signs of clinical activity, most patients' cancers will become resistant to kinase inhibitor therapy leading to relapse and progression of the disease. Kinase reactivation via an intrinsic mutation is a frequent mechanism of resistance. When resistance occurs, the patient's treatment options are often very limited. There is thus a need for compounds that inhibit NTRK, as well as its resistant mutants.

SUMMARY OF THE INVENTION

The invention features compounds and pharmaceutical compositions comprising compounds of Formula (I) or pharmaceutically acceptable salts thereof, wherein:

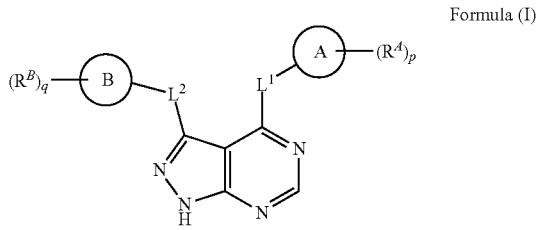

Formula (I)

Rings A and B are each independently selected from aryl, heteroaryl, cycloalkyl and heterocyclyl;

each $L^1$ and $L^2$ is independently selected from a bond, —C(O)—, —N($R^1$)—, —N($R^1$)—C(O)—, —C(O)—N($R^1$)—, —(C$_1$-C$_6$ alkylene)-N($R^1$)—, —N($R^1$)—(C$_1$-C$_6$ alkylene)-, —N($R^1$)—C(O)—(C$_1$-C$_6$ alkylene)-, and —C(O)—N($R^1$)—(C$_1$-C$_6$ alkylene)-; wherein each alkylene, is independently substituted with 0-5 occurrences of R';

each $R^A$ and $R^B$ is independently selected from hydroxyl, C$_1$-C$_6$ alkyl, C$_2$-C$_6$ alkenyl, C$_2$-C$_6$ alkynyl, C$_1$-C$_6$ alkoxyl, halo, C$_1$-C$_6$ heteroalkyl, C$_1$-C$_6$ haloalkyl, C$_1$-C$_6$ haloalkoxyl, C$_1$-C$_6$ hydroxyalkyl, cycloalkyl, aryl, heteroaryl, aryloxy, aralkyl, heterocyclyl, heterocyclylalkyl, nitro, cyano, —C(O)$R^1$, —OC(O)$R^1$, —C(O)O$R^1$, —(C$_1$-C$_6$ alkylene)-C(O)$R^1$, —S$R^1$, —S(O)$_2$$R^1$, —S(O)$_2$—N($R^1$)($R^1$), —(C$_1$-C$_6$ alkylene)-S(O)$_2$$R^1$, —(C$_1$-C$_6$ alkylene)-S(O)$_2$—N($R^1$)($R^1$), —N($R^1$)($R^1$), —C(O)—N($R^1$)($R^1$), —N($R^1$)—C(O)$R^1$, —N($R^1$)—C(O)O$R^1$, —(C$_1$-C$_6$ alkylene)-N($R^1$)—C(O)$R^1$, —N($R^1$)S(O)$_2$$R^1$, and —P(O)($R^1$)($R^1$); wherein each of alkyl, alkenyl, alkynyl, alkoxyl, heteroalkyl, haloalkyl, haloalkoxyl, hydroxyalkyl, cycloalkyl, aryl, heteroaryl, aryloxy, aralkyl, heterocyclyl, and heterocyclylalkyl is independently substituted with 0-5 occurrences of $R^a$; or 2 $R^A$ or 2 $R^B$ together with the carbon atom(s) to which they are attached form a cycloalkyl or heterocyclyl ring independently substituted with 0-5 occurrences of $R^a$;

each $R^1$ is independently selected from hydrogen, hydroxyl, halo, thiol, C$_1$-C$_6$ alkyl, C$_1$-C$_6$ thioalkyl, C$_1$-C$_6$ alkoxyl, C$_1$-C$_6$ haloalkyl, C$_1$-C$_6$ hydroxyalkyl, C$_1$-C$_6$ heteroalkyl, cycloalkyl, cycloalkylalkyl, heteroarylalkyl, heterocyclyl, and heterocyclylalkyl, wherein each of alkyl, thioalkyl, alkoxyl, haloalkyl, hydroxyalkyl, heteroalkyl, cycloalkyl, cycloalkylalkyl, heteroarylalkyl, heterocyclyl, and heterocyclylalkyl is independently substituted with 0-5 occurrences of $R^b$, or 2 $R^1$ together with the atom(s) to which they are attached form a cycloalkyl or heterocyclyl ring independently substituted with 0-5 occurrences of $R^b$;

each $R^a$ and $R^b$ is independently selected from C$_1$-C$_6$ alkyl, halo, hydroxyl, C$_1$-C$_6$ haloalkyl, C$_1$-C$_6$ heteroalkyl, C$_1$-C$_6$ hydroxyalkyl, C$_1$-C$_6$ alkoxyl, cycloalkyl, heterocyclyl, and cyano, wherein each of alkyl, haloalkyl, heteroalkyl, hydroxyalkyl, alkoxyl, cycloalkyl and heterocyclyl is independently substituted with 0-5 occurrences of R';

each R' is independently selected from C$_1$-C$_6$ alkyl, C$_1$-C$_6$ heteroalkyl, halo, hydroxyl, C$_1$-C$_6$ haloalkyl, C$_1$-C$_6$ hydroxyalkyl, cycloalkyl and cyano; or 2 R' together with the atom(s) to which they are attached form a cycloalkyl or heterocyclyl ring;

p is 0, 1, 2, 3, 4, or 5; and q is 0, 1, 2, 3, or 4.

Any of the compounds disclosed herein may be used, alone or in combination with another therapeutic agent, to treat any of the diseases disclosed herein.

BRIEF DESCRIPTION OF THE DRAWINGS

FIGS. 1A to 1A-35 depict the structure of various exemplary compounds of the invention, as well as their NMR peaks and mass as determined by LC-MS.

DETAILED DESCRIPTION OF THE INVENTION

Definitions

Figure 1B:
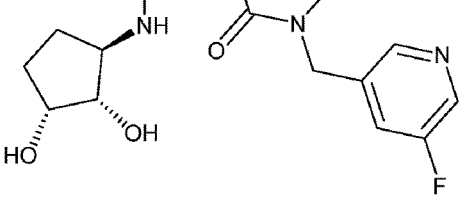
Figure 1B:
Figure 1B:
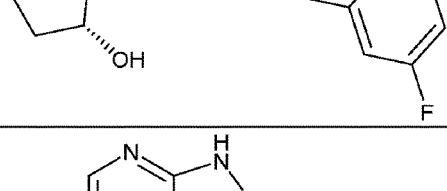
Figure 1B:
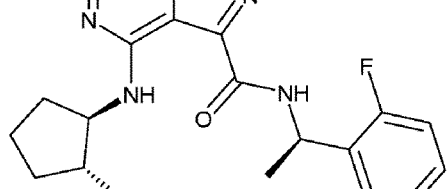
Figure 1I:
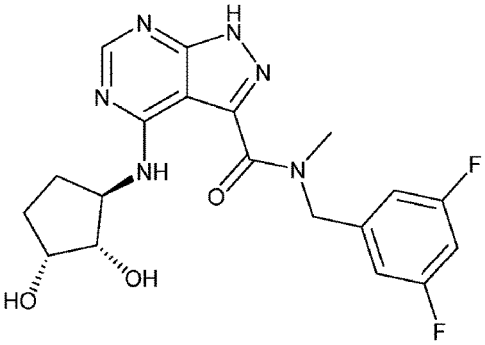
Figure 1I:
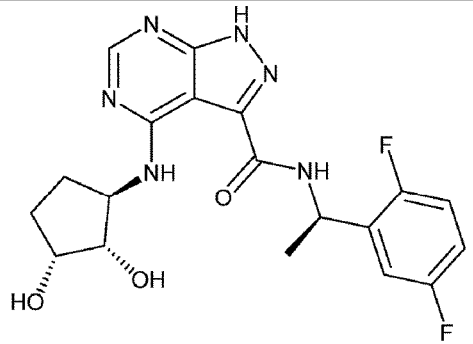
Figure 1I:
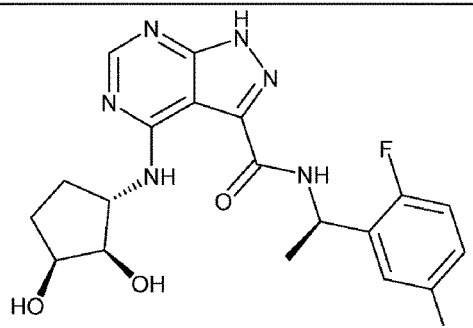
Figure 1I:
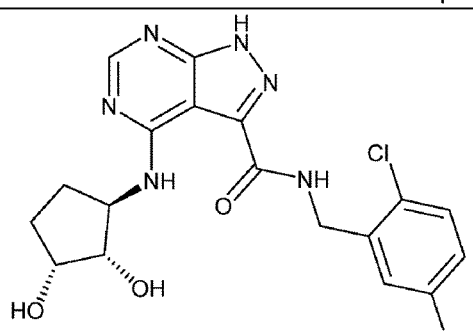
Figure 1L:
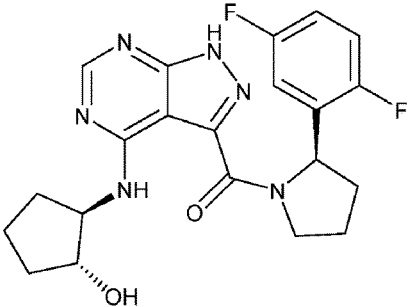
Figure 1L:
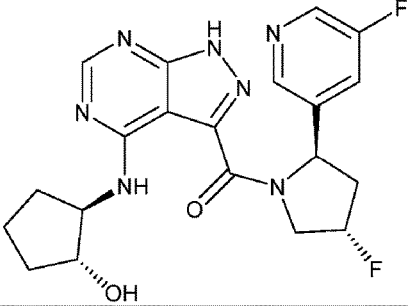
Figure 1L:
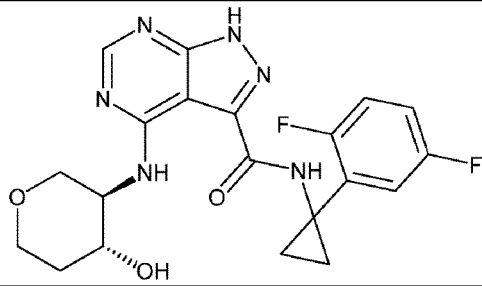
Figure 1L:
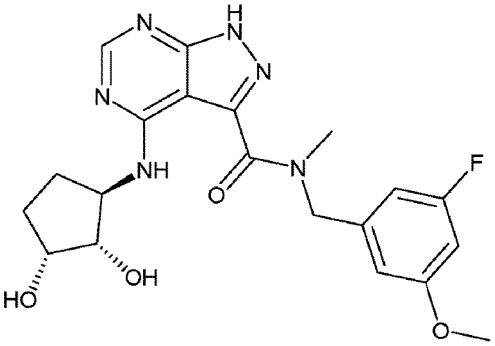
Figure 1P:
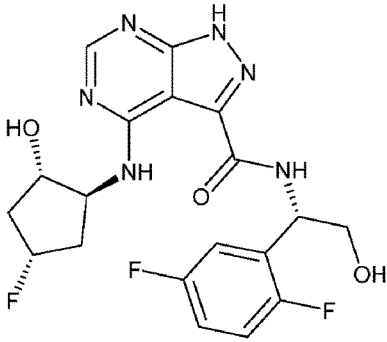
Figure 1P:
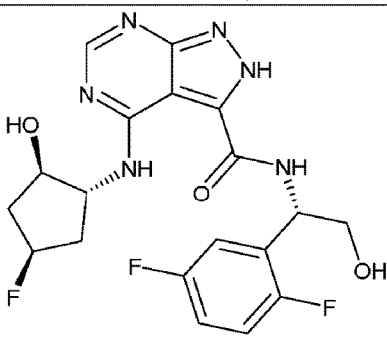
Figure 1P:
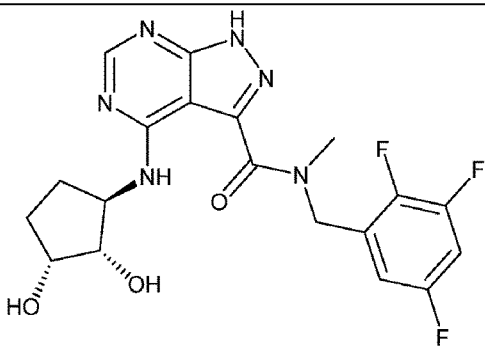
Figure 1P:
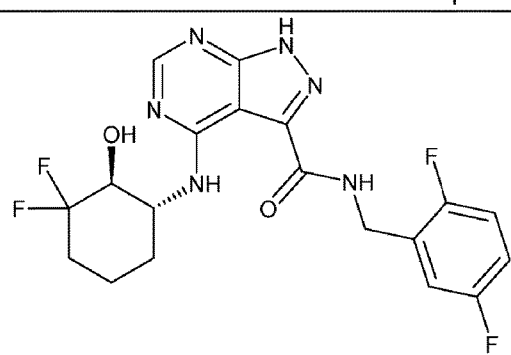
Figure 1R:
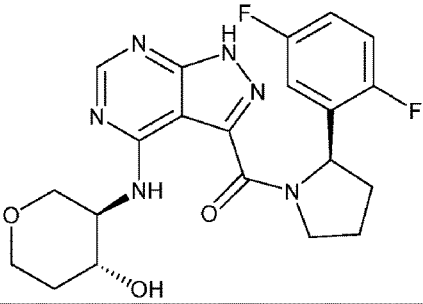
Figure 1R:
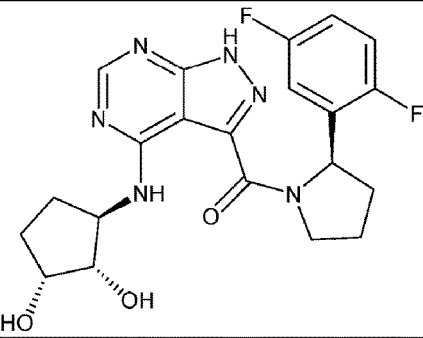
Figure 1R:
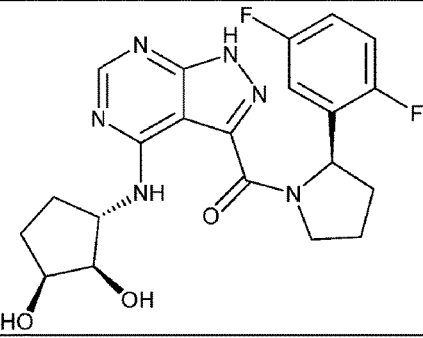
Figure 1R:
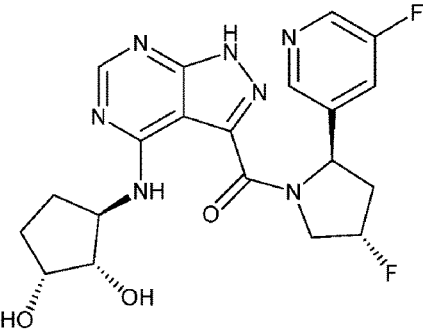
Figure 1S:
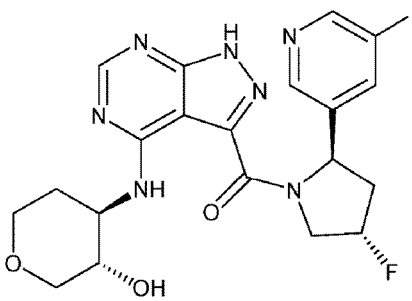
Figure 1S:
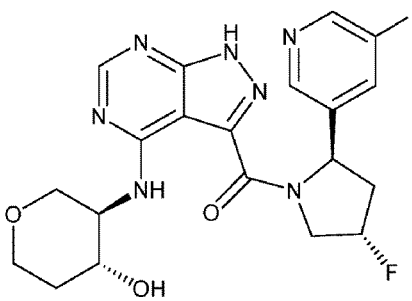
Figure 1S:
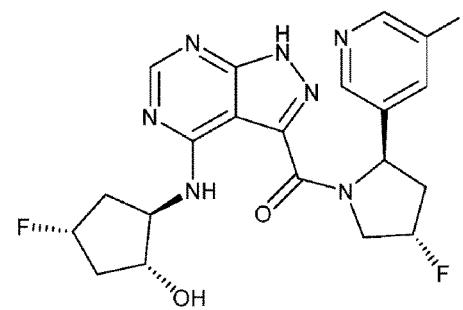
Figure 1S:
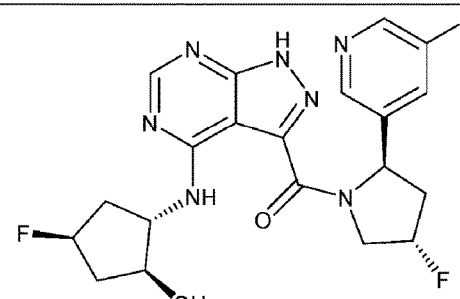
Figure 1U:
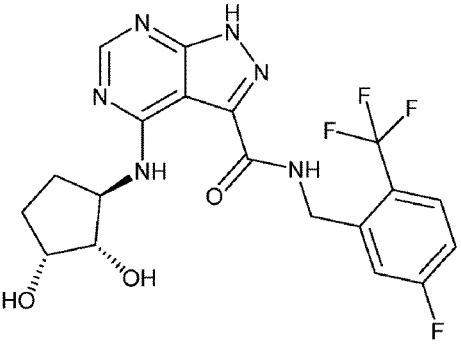
Figure 1U:
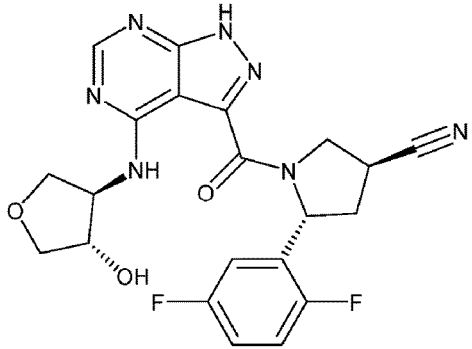
Figure 1U:
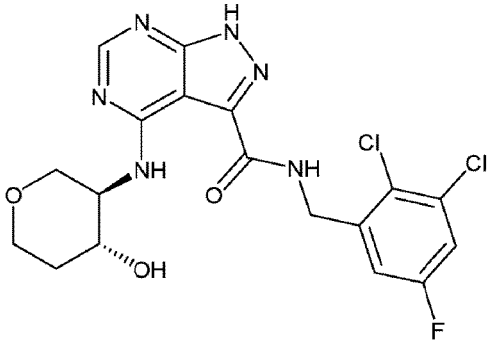
Figure 1U:
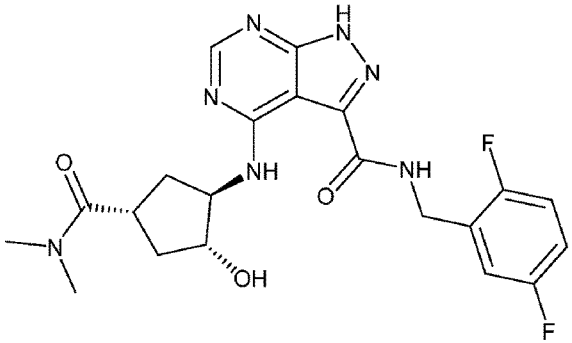
Figure 1V:
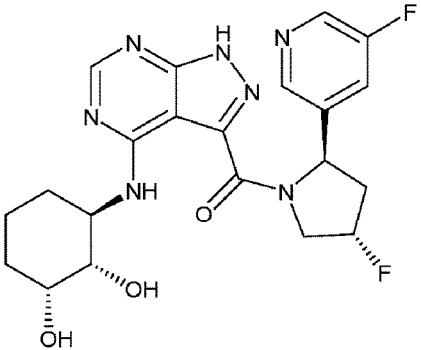
Figure 1V:
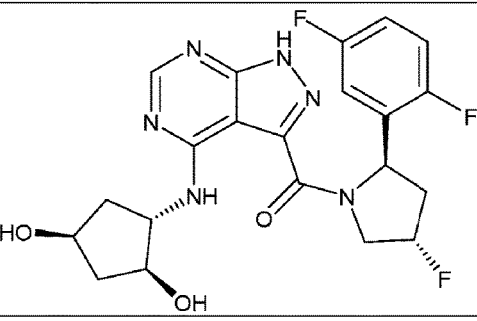
Figure 1V:
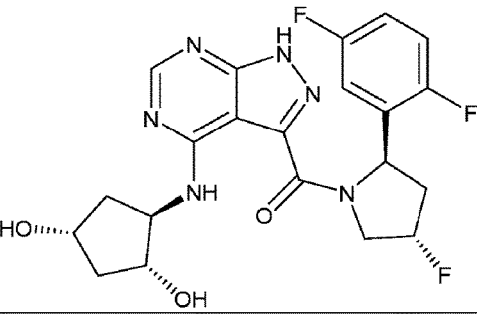
Figure 1V:
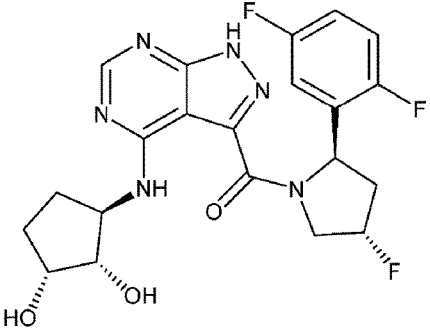
Figure 1W:
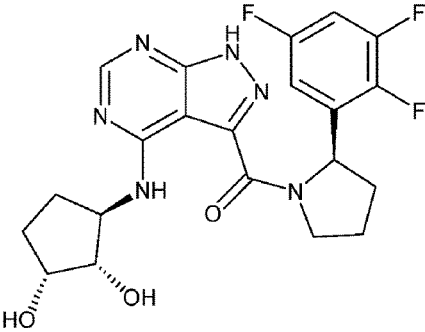
Figure 1W:
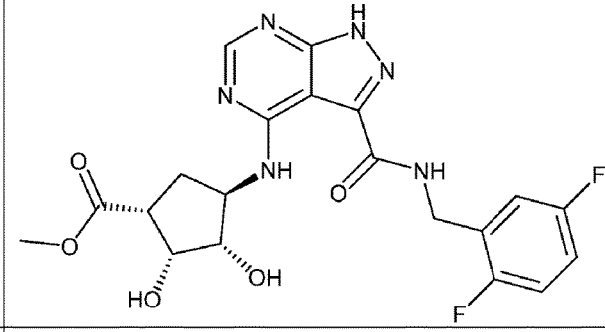
Figure 1W:
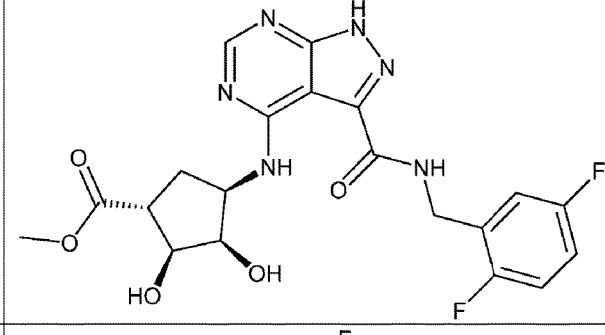
Figure 1W:
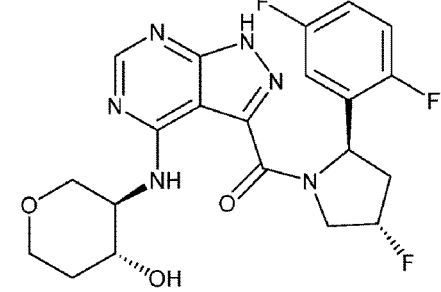
Figure 1X:
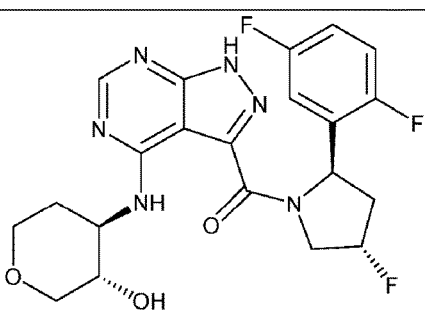
Figure 1X:
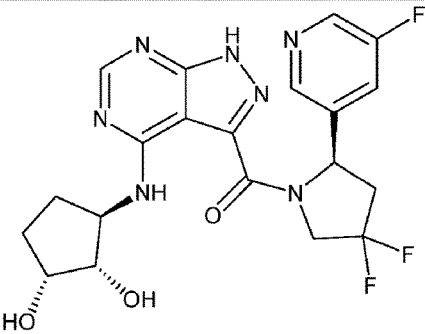
Figure 1X:
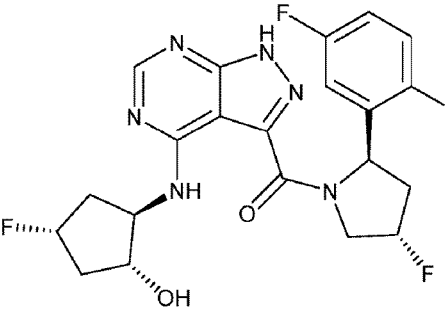
Figure 1X:
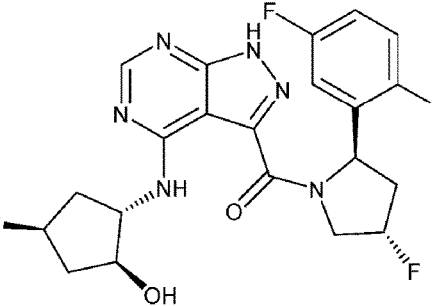
Figure 1Y:
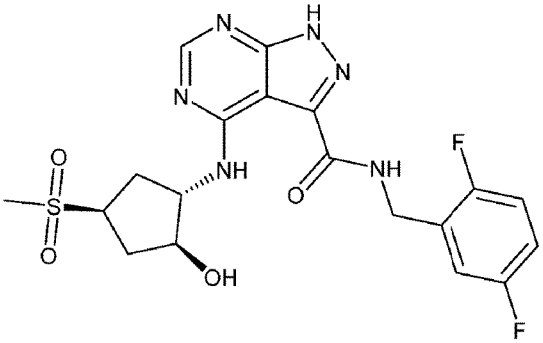
Figure 1Y:
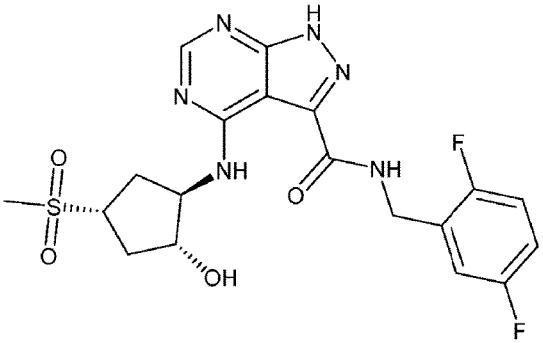
Figure 1Y:
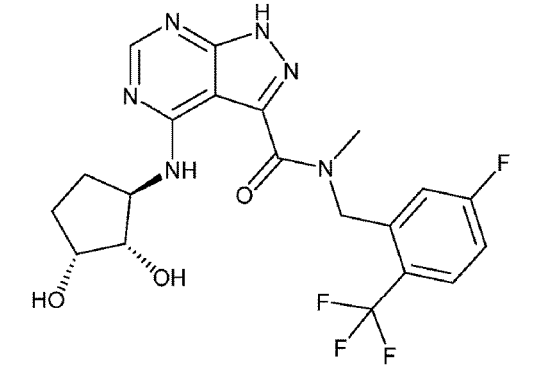
Figure 1Y:
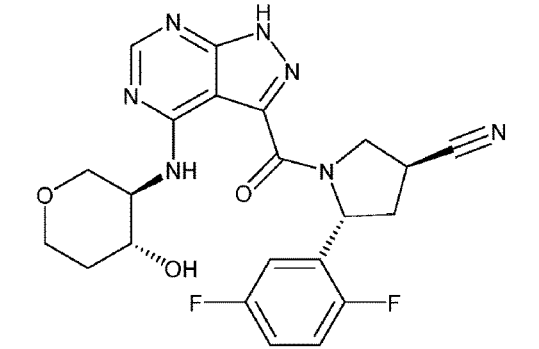
Figure 1Z:
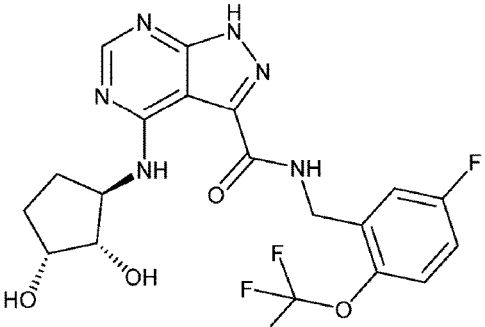
Figure 1Z:
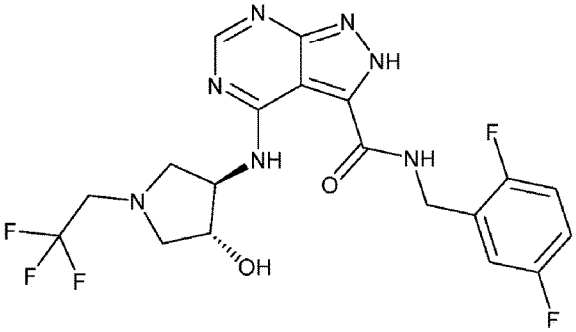
Figure 1Z:
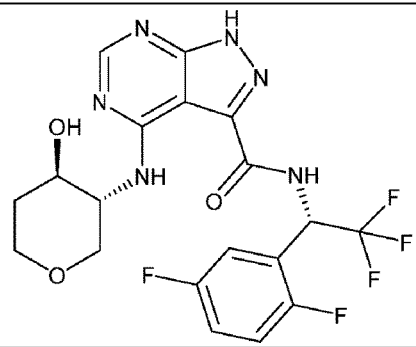
Figure 1Z:
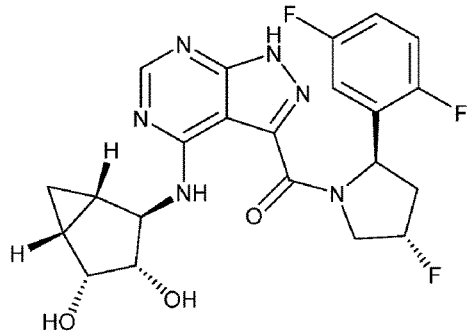
Figure 1A:
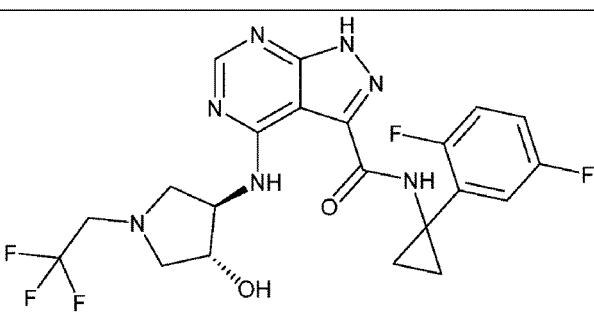

As used herein, the terms a "patient," "subject," "individual," and "host" refer to either a human or a non-human animal suffering from or suspected of suffering from a disease or disorder associated with aberrant NTRK expression (i.e., increased NTRK activity caused by signaling through NTRK) or biological activity.

"Treat" and "treating" such a disease or disorder refers to ameliorating at least one symptom of the disease or disorder. These terms, when used in connection with a condition such as a cancer, refer to one or more of: impeding growth of the cancer, causing the cancer to shrink by weight or volume, extending the expected survival time of the patient, inhibiting tumor growth, reducing tumor mass, reducing size or number of metastatic lesions, inhibiting the development of new metastatic lesions, prolonging survival, prolonging progression-free survival, prolonging time to progression, and/or enhancing quality of life.

The term "preventing" when used in relation to a condition or disease such as cancer, refers to a reduction in the frequency of, or delay in the onset of, symptoms of the condition or disease. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

The term "therapeutic effect" refers to a beneficial local or systemic effect in animals, particularly mammals, and more particularly humans, caused by administration of a compound or composition of the invention. The phrase "therapeutically-effective amount" means that amount of a compound or composition of the invention that is effective to treat a disease or condition caused by over expression of NTRK or aberrant NTRK biological activity at a reasonable benefit/risk ratio. The therapeutically effective amount of such substance will vary depending upon the subject and disease condition being treated, the weight and age of the subject, the severity of the disease condition, the manner of administration and the like, which can readily be determined by one of skill in the art.

As used herein, "developing resistance" means that when a drug is first administered to the patient, the patient's symptoms improve, whether measured by decrease in tumor volume, a decrease in the number of new lesions, or some other means that a physician uses to judge disease progression; however, those symptoms stop improving, or even worsen at some point. At that time, the patient is said to have developed resistance to the drug.

"Aliphatic group" means a straight-chain, branched-chain, or cyclic hydrocarbon group and includes saturated and unsaturated groups, such as an alkyl group, an alkenyl group, and an alkynyl group.

"Alkylene" refers to a divalent radical of an alkyl group, e.g., —$CH_2$—, —$CH_2CH_2$—, and $CH_2CH_2CH_2$—.

"Alkenyl" means an aliphatic group containing at least one double bond.

"Alkoxyl" or "alkoxy" means an alkyl group having an oxygen radical attached thereto. Representative alkoxyl groups include methoxy, ethoxy, propyloxy, tert-butoxy and the like. The term "haloalkoxy" refers to an alkoxyl in which one or more hydrogen atoms are replaced by halo, and includes alkoxyl moieties in which all hydrogens have been replaced by halo (e.g., perfluoroalkoxy).

"Alkyl" refers to a monovalent radical of a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

"Alkenylene" refers to an alkenyl group having two connecting points. For example, "ethenylene" represents the group —CH=CH—. Alkenylene groups can also be in an unsubstituted form or substituted form with one or more substituents.

"Alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

"Alkynylene" refers to an alkynyl having two connecting points. For example, "ethynylene" represents the group —C≡—. Alkynylene groups can also be in an unsubstituted form or substituted form with one or more substituents.

"Hydroxyalkylene" or "hydroxyalkyl" refers to an alkylene or alkyl moiety in which an alkylene or alkyl hydrogen atom is replaced by a hydroxyl group. Hydroxyalkylene or hydroxyalkyl includes groups in which more than one hydrogen atom has been replaced by a hydroxyl group.

"Aromatic ring system" is art-recognized and refers to a monocyclic, bicyclic or polycyclic hydrocarbon ring system, wherein at least one ring is aromatic.

"Aryl" refers to a monovalent radical of an aromatic ring system. Representative aryl groups include fully aromatic ring systems, such as phenyl, naphthyl, and anthracenyl, and ring systems where an aromatic carbon ring is fused to one or more non-aromatic carbon rings, such as indanyl, phthalimidyl, naphthimidyl, or tetrahydronaphthyl, and the like.

"Arylalkyl" or "aralkyl" refers to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

"Aryloxy" refers to —O-(aryl), wherein the heteroaryl moiety is as defined herein.

"Halo" refers to a radical of any halogen, e.g., —F, —Cl, —Br, or —I.

"Haloalkyl" and "haloalkoxy" refers to alkyl and alkoxyl structures that are substituted with one or more halo groups or with combinations thereof. For example, the terms "fluoroalkyl" and "fluoroalkoxy" include haloalkyl and haloalkoxyl groups, respectively, in which the halo is fluorine.

"Haloalkylene" refers to a divalent alkyl, e.g., —$CH_2$—, —$CH_2CH_2$—, and —$CH_2CH_2CH_2$—, in which one or more hydrogen atoms are replaced by halo, and includes alkyl moieties in which all hydrogens have been replaced by halo.

"Heteroalkyl" refers to an optionally substituted alkyl, which has one or more skeletal chain atoms selected from an atom other than carbon, e.g., oxygen, nitrogen, sulfur, phosphorus or combinations thereof. A numerical range may be given, e.g. $C_1$-$C_6$ heteroalkyl which refers to the number of carbons in the chain, which in this example includes 1 to 6 carbon atoms. For example, a —$CH_2OCH_2CH_3$ radical is referred to as a "$C_3$" heteroalkyl. Connection to the rest of the molecule may be through either a heteroatom or a carbon in the heteroalkyl chain. "Heteroalkylene" refers to a divalent optionally substituted alkyl, which has one or more skeletal chain atoms selected from an atom other than carbon, e.g., oxygen, nitrogen, sulfur, phosphorus or combinations thereof.

"Carbocyclic ring system" refers to a monocyclic, bicyclic or polycyclic hydrocarbon ring system, wherein each ring is either completely saturated or contains one or more units of unsaturation, but where no ring is aromatic.

"Carbocyclyl" refers to a monovalent radical of a carbocyclic ring system. Representative carbocyclyl groups include cycloalkyl groups (e.g., cyclopentyl, cyclobutyl, cyclopentyl, cyclohexyl and the like), and cycloalkenyl groups (e.g., cyclopentenyl, cyclohexenyl, cyclopentadienyl, and the like).

"Cycloalkyl" refers to a cyclic, bicyclic, tricyclic, or polycyclic non-aromatic hydrocarbon groups having 3 to 12 carbons. Any substitutable ring atom can be substituted (e.g., by one or more substituents). The cycloalkyl groups can contain fused or Spiro rings. Fused rings are rings that share a common carbon atom. Examples of cycloalkyl moieties include, but are not limited to, cyclopropyl, cyclohexyl, methylcyclohexyl, adamantyl, and norbornyl. In some embodiments, the cycloalkyl is bicyclo[3.1.0]hexanyl.

"Cycloalkylalkyl" refers to a -(cycloalkyl)-alkyl radical where cycloalkyl and alkyl are as disclosed herein. The "cycloalkylalkyl" is bonded to the parent molecular structure through the cycloalkyl group.

"Heteroaromatic ring system" is art-recognized and refers to monocyclic, bicyclic or polycyclic ring system wherein at least one ring is both aromatic and comprises at least one heteroatom (e.g., N, O or S); and wherein no other rings are heterocyclyl (as defined below). In certain instances, a ring which is aromatic and comprises a heteroatom contains 1, 2, 3, or 4 ring heteroatoms in such ring.

"Heteroaryl" refers to a monovalent radical of a heteroaromatic ring system. Representative heteroaryl groups include ring systems where (i) each ring comprises a heteroatom and is aromatic, e.g., imidazolyl, oxazolyl, thiazolyl, triazolyl, pyrrolyl, furanyl, thiophenyl pyrazolyl, pyridinyl, pyrazinyl, pyridazinyl, pyrimidinyl, indolizinyl, purinyl, naphthyridinyl, and pteridinyl; (ii) each ring is aromatic or carbocyclyl, at least one aromatic ring comprises a heteroatom and at least one other ring is a hydrocarbon ring or e.g., indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, pyrido[2,3-b]-1,4-oxazin-3-(4H)-one, 5,6,7,8-tetrahydroquinolinyl and 5,6,7,8-tetrahydroisoquinolinyl; and (iii) each ring is aromatic or carbocyclyl, and at least one aromatic ring shares a bridgehead heteroatom with another aromatic ring, e.g., 4H-quinolizinyl.

"Heterocyclic ring system" refers to monocyclic, bicyclic and polycyclic ring systems where at least one ring is saturated or partially unsaturated (but not aromatic) and comprises at least one heteroatom. A heterocyclic ring system can be attached to its pendant group at any heteroatom or carbon atom that results in a stable structure and any of the ring atoms can be optionally substituted.

"Heterocyclyl" refers to a monovalent radical of a heterocyclic ring system. Representative heterocyclyls include ring systems in which (i) every ring is non-aromatic and at least one ring comprises a heteroatom, e.g., tetrahydrofuranyl, tetrahydropyranyl, tetrahydrothienyl, pyrrolidinyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl; (ii) at least one ring is non-aromatic and comprises a heteroatom and at least one other ring is an aromatic carbon ring, e.g., 1,2,3,4-tetrahydroquinolinyl, 1,2,3,4-tetrahydroisoquinolinyl; and (iii) at least one ring is non-aromatic and comprises a heteroatom and at least one other ring is aromatic and comprises a heteroatom, e.g., 3,4-dihydro-1H-pyrano[4,3-c]pyridine, and 1,2,3,4-tetrahydro-2,6-naphthyridine.

"Heterocyclylalkyl" refers to an alkyl group substituted with a heterocyclyl group.

"Cyano" refers to a —CN radical.

"Nitro" refers to —$NO_2$.

"Hydroxy" or "hydroxyl" refers to —OH.

"Hydroxyalkylene" refers to a divalent alkyl, e.g., —$CH_2$—, —$CH_2CH_2$—, and —$CH_2CH_2CH_2$—, in which one or more hydrogen atoms are replaced by a hydroxy, and includes alkyl moieties in which all hydrogens have been replaced by hydroxy.

"Substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

As used herein, the definition of each expression, e.g., alkyl, m, n, etc., when it occurs more than once in any structure, is intended to be independent of its definition elsewhere in the same structure.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Unless otherwise indicated, when a disclosed compound is named or depicted by a structure without specifying the stereochemistry and has one or more chiral centers, it is understood to represent all possible stereoisomers of the compound, as well as enantiomeric mixtures thereof. The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer.

ee=(90−10)/100=80%.

Thus, a composition containing 90% of one enantiomer and 10% of the other enantiomer is said to have an enantiomeric excess of 80%.

The compounds or compositions described herein may contain an enantiomeric excess of at least 50%, 75%, 90%, 95%, or 99% of one form of the compound, e.g., the S-enantiomer. In other words such compounds or compositions contain an enantiomeric excess of the S enantiomer over the R enantiomer.

The compounds described herein may also contain unnatural proportions of atomic isotopes at one or more of the atoms that constitute such compounds. For example, the compounds may be radiolabeled with radioactive isotopes, such as for example deuterium ($^2H$), tritium ($^3H$), carbon-13 ($^{13}C$), or carbon-14 ($^{14}C$). All isotopic variations of the compounds disclosed herein, whether radioactive or not, are intended to be encompassed within the scope of the present invention. In addition, all tautomeric forms of the compounds described herein are intended to be within the scope of the invention.

The compound can be useful as the free base or as a salt. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, for example, Berge et al. (1977) "Pharmaceutical Salts", *J. Pharm. Sci.* 66:1-19.)

Compounds

The invention features compounds of Formula (I), or a stereoisomer, enantiomer, tautomer, or isotopically labeled form thereof, or a pharmaceutically acceptable salt of any of the foregoing, wherein:

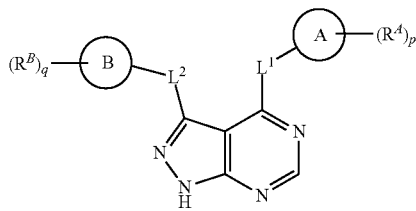

Formula (I)

Rings A and B are each independently selected from aryl, heteroaryl, cycloalkyl and heterocyclyl;

each $L^1$ and $L^2$ is independently selected from a bond, —C(O)—, —N($R^1$)—, —N($R^1$)—C(O)—, —C(O)—N($R^1$)—, —($C_1$-$C_6$ alkylene)-N($R^1$)—, —N($R^1$)—($C_1$-$C_6$ alkylene)-, —N($R^1$)—C(O)—($C_1$-$C_6$ alkylene)-, and —C(O)—N($R^1$)—($C_1$-$C_6$ alkylene)-; wherein each alkylene, is independently substituted with 0-5 occurrences of R';

each $R^A$ and $R^B$ is independently selected from hydroxyl, $C_1$-$C_6$ alkyl, $C_2$-$C_6$ alkenyl, $C_2$-$C_6$ alkynyl, $C_1$-$C_6$ alkoxyl, halo, $C_1$-$C_6$ heteroalkyl, $C_1$-$C_6$ haloalkyl, $C_1$-$C_6$ haloalkoxyl, $C_1$-$C_6$ hydroxyalkyl, cycloalkyl, aryl, heteroaryl, aryloxy, aralkyl, heterocyclyl, heterocyclylalkyl, nitro, cyano, —C(O)$R^1$, —OC(O)$R^1$, —C(O)O$R^1$, —($C_1$-$C_6$ alkylene)-C(O)$R^1$, —S$R^1$, —S(O)$_2R^1$, —S(O)$_2$—N($R^1$)($R^1$), —($C_1$-$C_6$ alkylene)-S(O)$_2R^1$, —($C_1$-$C_6$ alkylene)-S(O)$_2$—N($R^1$)($R^1$), —N($R^1$)($R^1$), —C(O)—N($R^1$)($R^1$), —N($R^1$)—C(O)$R^1$, —N($R^1$)—C(O)O$R^1$, —($C_1$-$C_6$ alkylene)-N($R^1$)—C(O)$R^1$, —N($R^1$)S(O)$_2R^1$, and —P(O)($R^1$)($R^1$); wherein each of alkyl, alkenyl, alkynyl, alkoxyl, heteroalkyl, haloalkyl, haloalkoxyl, hydroxyalkyl, cycloalkyl, aryl, heteroaryl, aryloxy, aralkyl, heterocyclyl, and heterocyclylalkyl is independently substituted with 0-5 occurrences of $R^a$; or 2 $R^A$ or 2 $R^B$ together with the carbon atom(s) to which they are attached form a cycloalkyl or heterocyclyl ring independently substituted with 0-5 occurrences of $R^a$;

each $R^1$ is independently selected from hydrogen, hydroxyl, halo, thiol, $C_1$-$C_6$ alkyl, $C_1$-$C_6$ thioalkyl, $C_1$-$C_6$ alkoxyl, $C_1$-$C_6$ haloalkyl, $C_1$-$C_6$ hydroxyalkyl, $C_1$-$C_6$ heteroalkyl, cycloalkyl, cycloalkylalkyl, heteroarylalkyl, heterocyclyl, and heterocyclylalkyl, wherein each of alkyl, thioalkyl, alkoxyl, haloalkyl, hydroxyalkyl, heteroalkyl, cycloalkyl, cycloalkylalkyl, heteroarylalkyl, heterocyclyl, and heterocyclylalkyl is independently substituted with 0-5 occurrences of $R^b$, or 2 $R^1$ together with the atom(s) to which they are attached form a cycloalkyl or heterocyclyl ring independently substituted with 0-5 occurrences of $R^b$;

each $R^a$ and $R^b$ is independently selected from $C_1$-$C_6$ alkyl, halo, hydroxyl, $C_1$-$C_6$ haloalkyl, $C_1$-$C_6$ heteroalkyl, $C_1$-$C_6$ hydroxyalkyl, $C_1$-$C_6$ alkoxyl, cycloalkyl, heterocyclyl, and cyano, wherein each of alkyl, haloalkyl, heteroalkyl, hydroxyalkyl, alkoxyl, cycloalkyl and heterocyclyl is independently substituted with 0-5 occurrences of R';

each R' is independently selected from $C_1$-$C_6$ alkyl, $C_1$-$C_6$ heteroalkyl, halo, hydroxyl, $C_1$-$C_6$ haloalkyl, $C_1$-$C_6$ hydroxyalkyl, cycloalkyl and cyano; or 2 R' together with the atom(s) to which they are attached form a cycloalkyl or heterocyclyl ring; and p is 0, 1, 2, 3, 4, or 5; and q is 0, 1, 2, 3, or 4.

In some embodiments, Ring A is cycloalkyl. In some embodiments, Ring A is a 5-membered or 6-membered cycloalkyl ring. In some embodiments, Ring A is cyclopentyl or cyclohexyl. In some embodiments, Ring A is heterocyclyl. In some embodiments, Ring A is a 5-membered or 6-membered heterocyclyl. In some embodiments, Ring A is tetrahydropyranyl, tetrahydrofuranyl, or pyrrolidinyl. In some embodiments, Ring A is a cycloalkenyl ring. In some embodiments, Ring A is cyclopentenyl.

In some embodiments, Ring B is aryl. In some embodiments, Ring B is phenyl. In some embodiments, Ring B is heteroaryl. In some embodiments, Ring B is pyridyl. In some embodiments, Ring B is heterocyclyl. In some embodiments, Ring B is pyrrolidinyl.

In some embodiments, $L^1$ is a bond, —C(O)—, or —N($R^1$)—; and $L^2$ is —N($R^1$)—C(O)—($C_1$-$C_6$ alkylene)- or —C(O)—N($R^1$)—($C_1$-$C_6$ alkylene)-. In some embodiments, $L^1$ is —NH— and $L^2$ is —C(O)—NH—CH(CH$_2$OH)—*, —C(O)—N(CH$_3$)—CH$_2$—*, —C(O)—N(CH$_3$)—CH(CH$_3$)—*, —C(O)N(CH$_2$CH$_3$)CH$_2$—*, —C(O)NHCH(CH$_3$)—*, —C(O)N(CD$_3$)CH$_2$—*, —C(O)NHCH(CF$_3$)—*, and

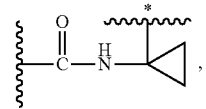

wherein "*" represents a portion of $L^2$ bound to ring B. In some embodiments, $L^1$ is —NH—, $L^2$ is —C(O)— and ring B is pyrrolidinyl. In some embodiments, $L^1$ is —NH—, $L^2$ is —C(O)— and ring B is pyrrolidin-1-yl.

In some embodiments, each $R^1$ is independently selected from hydrogen and $C_1$-$C_6$ alkyl substituted with 0-5 occurrences of $R^b$. In some embodiments, each $R^1$ is independently selected from hydrogen and —$CH_3$.

In some embodiments, each $R^A$ and $R^B$ is independently selected from hydroxyl, $C_1$-$C_6$ alkyl, $C_1$-$C_6$ alkoxyl, halo, $C_1$-$C_6$ heteroalkyl, $C_1$-$C_6$ haloalkyl, $C_1$-$C_6$ haloalkoxyl, $C_1$-$C_6$ hydroxyalkyl, cycloalkyl, aryl, heteroaryl, nitro, cyano, —C(O)$R^1$, —OC(O)$R^1$, —C(O)O$R^1$, —S$R^1$, —S(O)$_2$ $R^1$, —S(O)$_2$—N($R^1$)($R^1$), —N($R^1$)($R^1$), —C(O)—N($R^1$)($R^1$), —N($R^1$)—C(O)$R^1$, —N($R^1$)—C(O)O$R^1$, and —N($R^1$)S(O)$_2$$R^1$; wherein each of alkyl, alkoxyl, heteroalkyl, haloalkyl, haloalkoxyl, hydroxyalkyl, cycloalkyl, aryl, and heteroaryl, is independently substituted with 0-5 occurrences of $R^a$; or 2 $R^A$ or 2 $R^B$ together with the carbon atom(s) to which they are attached form a cycloalkyl or heterocyclyl ring independently substituted with 0-5 occurrences of $R^a$.

In some embodiments, each $R^A$ is independently selected from hydroxyl, $C_1$-$C_6$ alkyl, $C_1$-$C_6$ alkoxyl, halo, —C(O)—N($R^1$)($R^1$), —C(O)O$R^1$, —S(O)$_2$$R^1$, and $C_1$-$C_6$ haloalkyl. In some embodiments, each $R^A$ is additionally and independently selected from —CN, oxetanyl, and $C_1$-$C_6$ hydroxyalkyl, or two $R^A$ bound to adjacent ring carbon atoms on ring A are taken together to form a $C_3$-$C_6$ cycloalkyl fused to ring A. In some embodiments each $R^A$ is independently selected from hydroxyl, fluoro, oxetan-3-yl, —CHF$_2$, —CH$_2$CH$_3$, —C(CH$_3$)$_2$OH, —OCH$_3$, —C(O)N(CH$_3$)$_2$, —C(O)OCH$_3$, —S(O)$_2$CH$_3$; or two $R^A$ bound to adjacent ring carbon atoms on ring A are taken together to form a cyclopropyl fused to ring A.

In some embodiments, each $R^B$ is independently selected from halo, $C_1$-$C_6$ alkyl, cyano, $C_1$-$C_6$ alkoxyl, aryl, heteroaryl, and $C_1$-$C_6$ haloalkoxy. In some embodiments, each $R^B$ is additionally selected from oxo.

In some embodiments, Ring B is pyrrolidinyl and at least one $R^B$ is optionally substituted aryl or heteroaryl. In some embodiments, Ring B is pyrrolidinyl and at least one $R^B$ is optionally substituted phenyl or pyridyl.

In some embodiments, Ring B is pyrrolidinyl, and at least one $R^B$ is selected from 2,3,5-trifluorphenyl, 2,3-difluorophenyl, 2,5-difluorophenyl, 2-chloro-5-fluorophenyl, 2-chloro-5-fluoropyridin-3-yl, 2-cyano-5-fluorophenyl, 2-fluoro-5-chlorophenyl, 2-methoxy-3,5-difluorophenyl, 2-methoxy-5-fluoropyridin-3-yl, 2-trifluoromethoxy-5-fluorophenyl, 3,5-difluorophenyl, 3-chloro-5-fluorophenyl, 3-cyano-5-fluorophenyl, 3-difluoromethoxy-5-fluorophenyl, 3-fluorophenyl, 5-fluoropyridin-3-yl, and phenyl.

In some embodiments, Ring B is pyrrolidinyl and one additional $R^B$, if present, is fluoro.

In some embodiments, Ring B is other than pyrrolidinyl, and each $R^B$ is independently selected from chloro, fluoro, oxo, —CH$_3$, —CF$_3$, —CN, —OCH$_3$, —OCF$_3$, and —OCHF).

In another aspect, the invention features compounds of Formula (Ia):

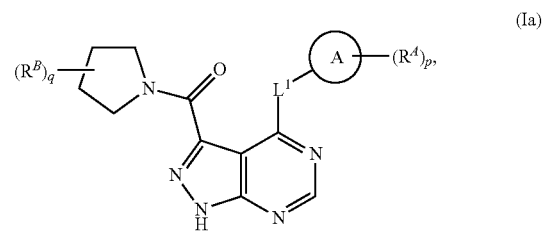

(Ia)

or a stereoisomer, enantiomer, tautomer, or isotopically labeled form thereof, or a pharmaceutically acceptable salt of any of the foregoing, wherein:

Ring A is selected from aryl, heteroaryl, cycloalkyl and heterocyclyl;

$L^1$ is selected from a bond, —C(O)—, —N($R^1$)—, —N($R^1$)—C(O)—, —C(O)—N($R^1$)—, —($C_1$-$C_6$ alkylene)-N($R^1$)—, —N($R^1$)—($C_1$-$C_6$ alkylene)-, —N($R^1$)—C(O)—($C_1$-$C_6$ alkylene)-, and —C(O)—N($R^1$)—($C_1$-$C_6$ alkylene)-; wherein each alkylene, is independently substituted with 0-5 occurrences of R';

each $R^A$ and $R^B$ is independently selected from hydroxyl, $C_1$-$C_6$ alkyl, $C_2$-$C_6$ alkenyl, $C_2$-$C_6$ alkynyl, $C_1$-$C_6$ alkoxyl, halo, $C_1$-$C_6$ heteroalkyl, $C_1$-$C_6$ haloalkyl, $C_1$-$C_6$ haloalkoxyl, $C_1$-$C_6$ hydroxyalkyl, cycloalkyl, aryl, heteroaryl, aryloxy, aralkyl, heterocyclyl, heterocyclylalkyl, nitro, cyano, —C(O)$R^1$, —OC(O)$R^1$, —C(O)O$R^1$, —($C_1$-$C_6$ alkylene)-C(O)$R^1$, —S$R^1$, —S(O)$_2$$R^1$, —S(O)$_2$—N($R^1$)($R^1$), —($C_1$-$C_6$ alkylene)-S(O)$_2$$R^1$, —($C_1$-$C_6$ alkylene)-S(O)$_2$—N($R^1$)($R^1$), —N($R^1$)($R^1$), —C(O)—N($R^1$)($R^1$), —N($R^1$)—C(O)$R^1$, —N($R^1$)—C(O)O$R^1$, —($C_1$-$C_6$ alkylene)-N($R^1$)—C(O)$R^1$, —N($R^1$)S(O)$_2$$R^1$, and —P(O)($R^1$)($R^1$); wherein each of alkyl, alkenyl, alkynyl, alkoxyl, heteroalkyl, haloalkyl, haloalkoxyl, hydroxyalkyl, cycloalkyl, aryl, heteroaryl, aryloxy, aralkyl, heterocyclyl, and heterocyclylalkyl is independently substituted with 0-5 occurrences of $R^a$; or 2 $R^A$ or 2 $R^B$ together with the carbon atom(s) to which they are attached form a cycloalkyl or heterocyclyl ring independently substituted with 0-5 occurrences of $R^a$;

each $R^1$ is independently selected from hydrogen, hydroxyl, halo, thiol, $C_1$-$C_6$ alkyl, $C_1$-$C_6$ thioalkyl, $C_1$-$C_6$ alkoxyl, $C_1$-$C_6$ haloalkyl, $C_1$-$C_6$ hydroxyalkyl, $C_1$-$C_6$ heteroalkyl, cycloalkyl, cycloalkylalkyl, heteroarylalkyl, heterocyclyl, and heterocyclylalkyl, wherein each of alkyl, thioalkyl, alkoxyl, haloalkyl, hydroxyalkyl, heteroalkyl, cycloalkyl, cycloalkylalkyl, heteroarylalkyl, heterocyclyl, and heterocyclylalkyl is independently substituted with 0-5 occurrences of $R^b$, or 2 $R^1$ together with the atom(s) to which they are attached form a cycloalkyl or heterocyclyl ring independently substituted with 0-5 occurrences of $R^b$;

each $R^a$ and $R^b$ is independently selected from $C_1$-$C_6$ alkyl, halo, hydroxyl, $C_1$-$C_6$ haloalkyl, $C_1$-$C_6$ heteroalkyl, $C_1$-$C_6$ hydroxyalkyl, $C_1$-$C_6$ alkoxyl, cycloalkyl, heterocyclyl, and cyano, wherein each of alkyl, haloalkyl, heteroalkyl, hydroxyalkyl, alkoxyl, cycloalkyl and heterocyclyl is independently substituted with 0-5 occurrences of R';

each R' is independently selected from $C_1$-$C_6$ alkyl, $C_1$-$C_6$ heteroalkyl, halo, hydroxyl, $C_1$-$C_6$ haloalkyl, $C_1$-$C_6$ hydroxyalkyl, cycloalkyl and cyano; or 2 R' together with the atom(s) to which they are attached form a cycloalkyl or heterocyclyl ring; and p is 0, 1, 2, 3, 4, or 5; and
q is 0, 1, 2, 3, or 4.

In some embodiments, Ring A is cycloalkyl. In some embodiments, Ring A is a 5-membered or 6-membered cycloalkyl ring. In some embodiments, Ring A is cyclopentyl or cyclohexyl. In some embodiments, Ring A is heterocyclyl. In some embodiments, Ring A is a 5-membered or 6-membered heterocyclyl. In some embodiments, Ring A is tetrahydropyran, tetrahydrofuran, or pyrrolidinyl. In some embodiments, Ring A is a cycloalkenyl ring. In some embodiments, Ring A is cyclopentenyl.

In some embodiments, $L^1$ is a bond, —C(O)—, or —N($R^1$)—. In some embodiments, $L^1$ is —NH—.

In some embodiments, each $R^1$ is independently selected from hydrogen and $C_1$-$C_6$ alkyl substituted with 0-5 occurrences of $R^b$. In some embodiments, each $R^1$ is independently selected from hydrogen and —$CH_3$.

In some embodiments, each $R^A$ and $R^B$ is independently selected from hydroxyl, $C_1$-$C_6$ alkyl, $C_1$-$C_6$ alkoxyl, halo, $C_1$-$C_6$ heteroalkyl, $C_1$-$C_6$ haloalkyl, $C_1$-$C_6$ haloalkoxyl, $C_1$-$C_6$ hydroxyalkyl, cycloalkyl, aryl, heteroaryl, nitro, cyano, —C(O)$R^1$, —OC(O)$R^1$, —C(O)O$R^1$, —S(O)$_2R^1$, —S(O)$_2$—N($R^1$)($R^1$), —N($R^1$)($R^1$), —C(O)—N($R^1$)($R^1$), —N($R^1$)—C(O)$R^1$, —N($R^1$)—C(O)O$R^1$, and —N($R^1$)S(O)$_2$ $R^1$; wherein each of alkyl, alkoxyl, heteroalkyl, haloalkyl, haloalkoxyl, hydroxyalkyl, cycloalkyl, aryl, and heteroaryl, is independently substituted with 0-5 occurrences of $R^a$; or 2 $R^A$ or 2 $R^B$ together with the carbon atom(s) to which they are attached form a cycloalkyl or heterocyclyl ring independently substituted with 0-5 occurrences of $R^a$.

In some embodiments, each $R^A$ is independently selected from hydroxyl, $C_1$-$C_6$ alkyl, $C_1$-$C_6$ alkoxyl, halo, —C(O)—N($R^1$)($R^1$), —C(O)O$R^1$, —S(O)$_2R^1$, and $C_1$-$C_6$ haloalkyl. In some embodiments, each $R^A$ is additionally and independently selected from —CN, oxetanyl, and $C_1$-$C_6$ hydroxyalkyl, or two $R^A$ bound to adjacent ring carbon atoms on ring A are taken together to form a $C_3$-$C_6$ cycloalkyl fused to ring A. In some embodiments each $R^A$ is independently selected from hydroxyl, fluoro, oxetan-3-yl, —$CHF_2$, —$CH_2CH_3$, —C($CH_3$)$_2$OH, —O$CH_3$, —C(O)N($CH_3$)$_2$, —C(O)O$CH_3$, —S(O)$_2CH_3$; or two $R^A$ bound to adjacent ring carbon atoms on ring A are taken together to form a cyclopropyl fused to ring A.

In some embodiments, each $R^B$ is independently selected from halo, $C_1$-$C_6$ alkyl, cyano, $C_1$-$C_6$ alkoxyl, aryl, heteroaryl, and $C_1$-$C_6$ haloalkoxy. In some embodiments, each $R^B$ is additionally selected from oxo.

In some embodiments, when ring B is pyrrolidinyl, at least one $R^B$ is selected from 2,3,5-trifluorphenyl, 2,3-difluorophenyl, 2,5-difluorophenyl, 2-chloro-5-fluorophenyl, 2-chloro-5-fluoropyridin-3-yl, 2-cyano-5-fluorophenyl, 2-fluoro-5-chlorophenyl, 2-methoxy-3,5-difluorophenyl, 2-methoxy-5-fluoropyridin-3-yl, 2-trifluoromethoxy-5-fluorophenyl, 3,5-difluorophenyl, 3-chloro-5-fluorophenyl, 3-cyano-5-fluorophenyl, 3-difluoromethoxy-5-fluorophenyl, 3-fluorophenyl, 5-fluoropyridin-3-yl, and phenyl.

In some embodiments, when ring B is pyrrolidinyl one additional $R^B$, if present, is fluoro.

In some embodiments, p is 0, 1 or 2.

In some embodiments, q is 1, 2 or 3.

In another aspect, the invention features compounds of Formula (II):

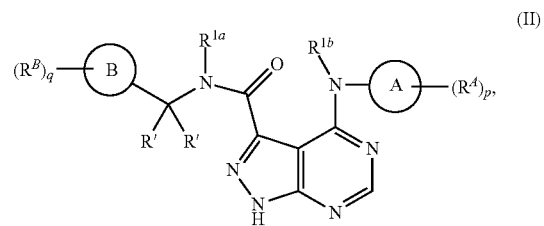

or a stereoisomer, enantiomer, tautomer, or isotopically labeled form thereof, or a pharmaceutically acceptable salt of any of the foregoing, wherein:

Rings A and B are each independently selected from aryl, heteroaryl, cycloalkyl and heterocyclyl;

each $R^A$ and $R^B$ is independently selected from hydroxyl, $C_1$-$C_6$ alkyl, $C_2$-$C_6$ alkenyl, alkynyl, $C_1$-$C_6$ alkoxyl, halo, $C_1$-$C_6$ heteroalkyl, $C_1$-$C_6$ haloalkyl, $C_1$-$C_6$ haloalkoxyl, $C_1$-$C_6$ hydroxyalkyl, cycloalkyl, aryl, heteroaryl, aryloxy, aralkyl, heterocyclyl, heterocyclylalkyl, nitro, cyano, —C(O)$R^1$, —OC(O)$R^1$, —C(O)O$R^1$, —($C_1$-$C_6$ alkylene)-C(O)$R^1$, —S$R^1$, —S(O)$_2R^1$, —S(O)$_2$—N($R^1$)($R^1$), alkylene)-S(O)$_2R^1$, —($C_1$-$C_6$ alkylene)-S(O)$_2$—N($R^1$)($R^1$), —N($R^1$)($R^1$), —C(O)—N($R^1$)($R^1$), —N($R^1$)—C(O)$R^1$, —N($R^1$)—C(O)O$R^1$, —($C_1$-$C_6$ alkylene)-N($R^1$)—C(O)$R^1$, —N($R^1$)S(O)$_2R^1$, and —P(O)($R^1$)($R^1$); wherein each of alkyl, alkenyl, alkynyl, alkoxyl, heteroalkyl, haloalkyl, haloalkoxyl, hydroxyalkyl, cycloalkyl, aryl, heteroaryl, aryloxy, aralkyl, heterocyclyl, and heterocyclylalkyl is independently substituted with 0-5 occurrences of $R^a$; or 2 $R^A$ or 2 $R^B$ together with the carbon atom(s) to which they are attached form a cycloalkyl or heterocyclyl ring independently substituted with 0-5 occurrences of $R^a$;

each $R^1$ is independently selected from hydrogen, hydroxyl, halo, thiol, $C_1$-$C_6$ alkyl, $C_1$-$C_6$ thioalkyl, $C_1$-$C_6$ alkoxyl, $C_1$-$C_6$ haloalkyl, $C_1$-$C_6$ hydroxyalkyl, $C_1$-$C_6$ heteroalkyl, cycloalkyl, cycloalkylalkyl, heteroarylalkyl, heterocyclyl, and heterocyclylalkyl, wherein each of alkyl, thioalkyl, alkoxyl, haloalkyl, hydroxyalkyl, heteroalkyl, cycloalkyl, cycloalkylalkyl, heteroarylalkyl, heterocyclyl, and heterocyclylalkyl is independently substituted with 0-5 occurrences of $R^b$, or 2 $R^1$ together with the atom(s) to which they are attached form a cycloalkyl or heterocyclyl ring independently substituted with 0-5 occurrences of $R^b$;

$R^{1a}$ is selected from hydrogen, $C_1$-$C_6$ alkyl, and deuterated $C_1$-$C_6$ alkyl;

$R^{1b}$ is selected from hydrogen and $C_1$-$C_6$ alkyl;

each $R^a$ and $R^b$ is independently selected from $C_1$-$C_6$ alkyl, halo, hydroxyl, $C_1$-$C_6$ haloalkyl, $C_1$-$C_6$ heteroalkyl, $C_1$-$C_6$ hydroxyalkyl, $C_1$-$C_6$ alkoxyl, cycloalkyl, heterocyclyl, and cyano, wherein each of alkyl, haloalkyl, heteroalkyl, hydroxyalkyl, alkoxyl, cycloalkyl and heterocyclyl is independently substituted with 0-5 occurrences of R';

each R' is independently selected from $C_1$-$C_6$ alkyl, $C_1$-$C_6$ heteroalkyl, halo, hydroxyl, $C_1$-$C_6$ haloalkyl, $C_1$-$C_6$ hydroxyalkyl, cycloalkyl and cyano; or 2 R' together with the atom(s) to which they are attached form a cycloalkyl or heterocyclyl ring; and p is 0, 1, 2, 3, 4, or 5; and q is 0, 1, 2, 3, or 4.

In some embodiments, Ring A is cycloalkyl. In some embodiments, Ring A is a 5-membered or 6-membered cycloalkyl ring. In some embodiments, Ring A is cyclopentyl or cyclohexyl. In some embodiments, Ring A is heterocyclyl. In some embodiments, Ring A is a 5-membered or 6-membered heterocyclyl. In some embodiments, Ring A is tetrahydropyran, tetrahydrofuran, or pyrrolidinyl. In some embodiments, Ring A is a cycloalkenyl ring. In some embodiments, Ring A is cyclopentenyl.

In some embodiments, Ring B is aryl. In some embodiments, Ring B is phenyl. In some embodiments, Ring B is heteroaryl. In some embodiments, Ring B is pyridyl.

In some embodiments, each $R^1$ is independently selected from hydrogen and $C_1$-$C_6$ alkyl substituted with 0-5 occurrences of $R^b$.

In some embodiments, $R^{1a}$ is hydrogen, —$CH_3$, —$CD_3$, or —$CH_2CH_3$.

In some embodiments, $R^{1b}$ is hydrogen.

In some embodiments, each $R^A$ and $R^B$ is independently selected from hydroxyl, $C_1$-$C_6$ alkyl, $C_1$-$C_6$ alkoxyl, halo, $C_1$-$C_6$ heteroalkyl, $C_1$-$C_6$ haloalkyl, $C_1$-$C_6$ haloalkoxyl, $C_1$-$C_6$ hydroxyalkyl, cycloalkyl, aryl, heteroaryl, nitro, cyano, —C(O)$R^1$, —OC(O)$R^1$, —C(O)O$R^1$, —S$R^1$, —S(O)$_2$ $R^1$, —S(O)$_2$—N($R^1$)($R^1$), —N($R^1$)($R^1$), —C(O)—N($R^1$)($R^1$), —N($R^1$)—C(O)$R^1$, —N($R^1$)—C(O)O$R^1$, and —N($R^1$)S(O)$_2$$R^1$; wherein each of alkyl, alkoxyl, heteroalkyl, haloalkyl, haloalkoxyl, hydroxyalkyl, cycloalkyl, aryl, and heteroaryl, is independently substituted with 0-5 occurrences of $R^a$; or 2 $R^A$ or 2 $R^B$ together with the carbon atom(s) to which they are attached form a cycloalkyl or heterocyclyl ring independently substituted with 0-5 occurrences of $R^a$.

In some embodiments, each $R^A$ is independently selected from hydroxyl, $C_1$-$C_6$ alkyl, $C_1$-$C_6$ alkoxyl, halo, —C(O)—N($R^1$)($R^1$), —C(O)O$R^1$, —S(O)$_2$$R^1$, and $C_1$-$C_6$ haloalkyl. In some embodiments, each $R^A$ is additionally and independently selected from —CN, oxetanyl, and $C_1$-$C_6$ hydroxyalkyl, or two $R^A$ bound to adjacent ring carbon atoms on ring A are taken together to form a $C_3$-$C_6$ cycloalkyl fused to ring A. In some embodiments each $R^A$ is independently selected from hydroxyl, fluoro, oxetan-3-yl, —CHF$_2$, —CH$_2$CH$_3$, —C(CH$_3$)$_2$OH, —OCH$_3$, —C(O)N(CH$_3$)$_2$, —C(O)OCH$_3$, —S(O)$_2$CH$_3$; or two $R^A$ bound to adjacent ring carbon atoms on ring A are taken together to form a cyclopropyl fused to ring A.

In some embodiments, each $R^B$ is independently selected from halo, $C_1$-$C_6$ alkyl, cyano, $C_1$-$C_6$ alkoxyl, aryl, heteroaryl, and $C_1$-$C_6$ haloalkoxy. In some embodiments, each $R^B$ is additionally selected from oxo. In some embodiments, each $R^B$ is independently selected from chloro, fluoro, oxo, —CH$_3$, —CF$_3$, —CN, —OCH$_3$, —OCF$_3$, and —OCHF$_2$.

In some embodiments, each R' is independently selected from $C_1$-$C_6$ alkyl, $C_1$-$C_6$ haloalkyl and $C_1$-$C_6$ hydroxyalkyl; or 2 R' together with the atom(s) to which they are attached form a cycloalkyl or heterocyclyl ring. In some embodiments one R' is hydrogen, and the other R' is selected from hydrogen, $C_1$-$C_6$ alkyl, $C_1$-$C_6$ haloalkyl and $C_1$-$C_6$ hydroxyalkyl; or 2 R' together with the atom(s) to which they are attached form a cycloalkyl ring. In some embodiments one R' is hydrogen, and the other R' is selected from hydrogen, —CH$_2$OH, —CH$_3$, or —CF$_3$, or 2 R' together with the atom(s) to which they are attached form a cycloprop-1,1-diyl ring.

In some embodiments, p is 0, 1 or 2.

In some embodiments, q is 0, 1, 2 or 3.

Although, as indicated above, various embodiments and aspects thereof for a variable in Formula (I), (Ia), or (II), may be selected from a group of chemical moieties, the invention also encompasses as further embodiments and aspects thereof situations where such variable is: a) selected from any subset of chemical moieties in such a group; and b) any single member of such a group.

Although various embodiments and aspects thereof are set forth (or implied, as discussed in the preceding paragraph) individually for each variable in Formula (I), (Ia) and (II), the invention encompasses all possible combinations of the different embodiments and aspects for each of the variables in Formula (I), (Ia), and (II).

Figure 1:
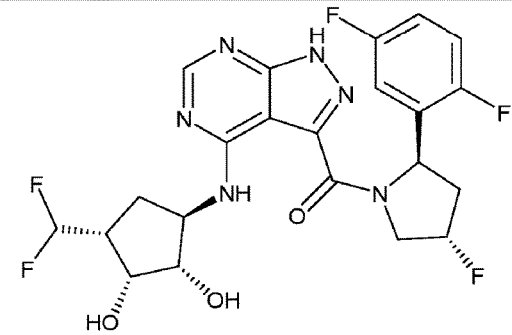
Figure 2:
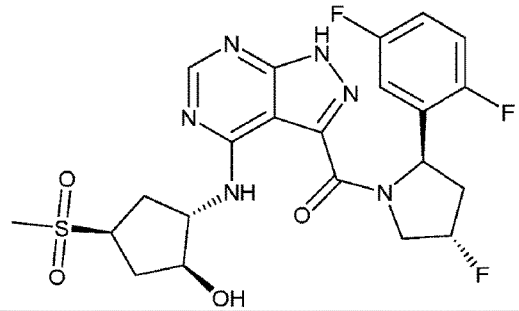
Figure 3:
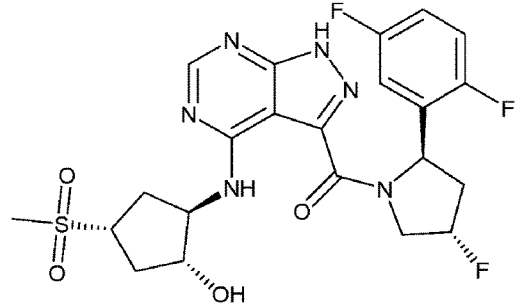

The structures, as well as the NMR and LCMS data of exemplary compounds of the invention are shown in FIG. 1. In certain embodiments, the compound of the invention is selected from the group consisting of any one of the compounds in FIG. 1 and pharmaceutically acceptable salts, solvates, hydrates, tautomers, stereoisomers, and isotopically labeled derivatives thereof.

The invention also features pharmaceutical compositions containing a pharmaceutically acceptable carrier and any compound of Formulas (I), (Ia) and (II).

Pharmaceutically acceptable salts of these compounds are also contemplated for the uses described herein.

"Pharmaceutically acceptable salt" refers to any salt of a compound of the invention which retains its biological properties and which is not toxic or otherwise undesirable for pharmaceutical use. Pharmaceutically acceptable salts may be derived from a variety of organic and inorganic counter-ions well known in the art and include. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo [2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like. Pharmaceutically acceptable salts further include, by way of example only, sodium, potassium, calcium, magnesium, ammonium, tetraalkylammonium and the like, and when the compound contains a basic functionality, salts of non-toxic organic or inorganic acids, such as hydrochloride, hydrobromide, tartrate, mesylate, besylate, acetate, maleate, oxalate and the like.

Pharmaceutical Compositions

Pharmaceutical compositions of the invention comprise one or more compounds of the invention and one or more physiologically or pharmaceutically acceptable carrier. The term "pharmaceutically acceptable carrier" refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compositions of the invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions of the invention are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tween, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

Dosages

Toxicity and therapeutic efficacy of compounds of the invention, including pharmaceutically acceptable salts and deuterated variants, can be determined by standard pharmaceutical procedures in cell cultures or experimental animals. The $LD_{50}$ is the dose lethal to 50% of the population. The $ED_{50}$ is the dose therapeutically effective in 50% of the population. The dose ratio between toxic and therapeutic effects ($LD_{50}/ED_{50}$) is the therapeutic index. Compounds that exhibit large therapeutic indexes are preferred. While compounds that exhibit toxic side effects may be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Treatment

NTRK fusions have been implicated in several types of cancers. These fusions harbor an intact NTRK kinase domain that is identical to the native or wild-type form of the receptor; therefore, as used herein, any NTRK protein (NTRK1, 2 or 3) with the same kinase domain as wild-type NTRK will be referred to as "wild-type NTRK." Mutations can occur in the NTRK kinase domain, leading to mutants that are resistant to kinase inhibitor therapy. These resistance mutations can be predicted using structural biology and computational analyses, as well as by examining codon sequences in which a sequence change gives rise to a codon for a different amino acid. Alternatively, resistance mutations for a given inhibitor can be identified experimentally by administration of that inhibitor (e.g., a known NTRK wild-type inhibitor) and exposing cells to a mutation-promoting agent, such as ENU. The cells are washed, then plated with increasing concentrations (2-100× proliferation $IC_{50}$) of the compound of choice. The wells with cellular outgrowth are then collected after 3-4 weeks. In particular, a mutation at amino acid position 595 within the NTRK fusion (NTRK1 wt numbering), effecting a change from a glycine to an arginine residue (heretofore designated 'G595R') was identified via both methods. This mutation was subsequently demonstrated to confer significant resistance to two NTRK inhibitors that are being clinically evaluated (shown in the table below). As shown in the table, the compounds are active against the wild-type NTRK, but are markedly less active against the G595R mutant form of the NTRK fusion.

| Compound | NTRK wt Enzyme Assay $IC_{50}$ (nM) | NTRK wt Cellular $GI_{50}$ (nM) | NTRK G595R Cellular $GI_{50}$ (nM) |
|---|---|---|---|
| Entrectinib | 0.6 | 2 | 2700 |
| TSR-011 | 2.3 | 32 | 12000 |
| Crizotinib | 9.3 | 87 | 9000 |

Accordingly, in another aspect the invention provides a method for treating a subject suffering from a condition mediated by aberrant neurotrophic tyrosine receptor kinase (NTRK) activity, comprising administering to the subject a therapeutically effective amount of a compound or pharmaceutical composition of a compound described herein.

The invention provides compounds that inhibit both wild-type NTRK and resistant G595R mutants of NTRK.

In another aspect, the invention provides a method for treating a subject who has developed resistance to a cancer treatment, comprising administering to the subject a therapeutically effective amount of a compound or pharmaceutical composition of a compound described herein.

Furthermore, the inhibitors can be selective for wild-type NTRK, over other kinases, thus leading to reduced toxicities associated with inhibiting other kinases. Because of their activity against wild-type and mutant NTRK, the compounds described herein can be used to treat a patient with a condition associated with aberrant NTRK activity. They can also be used to treat various cancers. In some embodiments, the cancer is selected from non-small cell lung cancer, breast cancer, melanoma, low and high grade glioma, glioblastoma, pediatric astrocytoma, colorectal cancer, papillary thyroid carcinoma, pancreatic adenocarcinoma, head and neck cancer, cholangiocarcinoma, acute myelogenous leukemia, secretory breast cancer, salivary cancer and spitzoid neoplasms.

The compounds can also be used to treat a patient who has developed resistance to a wild-type NTRK inhibitor, or a patient with a mutant form of NTRK, such as the G595R mutant. The method includes the step of administering a compound or composition of the invention that is active against the NTRK resistant mutant. By "active" is meant that a compound has an $IC_{50}$ of less than 1 μM, 500 nM, 250 nM, 100 nM, 75 nM, 50 nM, 25 nM, 10 nM, or 5 nM when measured in a biochemical assay, against at least one resistant mutant.

The compounds and compositions described herein can be administered alone or in combination with other compounds, including other NTRK-modulating compounds, or other therapeutic agents. In some embodiments, the compound or composition of the invention may be administered in combination with one or more compounds selected from cabozantinib (COMETRIQ®), vandetanib (CALPRESA®), sorafenib (NEXAVAR®), sunitinib (SUTENT®), regorafenib (STAVARGA®), ponatinib (ICLUSIG®), bevacizumab (AVASTIN®), crizotinib (XALKORI®), or gefitinib (IRESSA®). The compound or composition of the invention may be administered simultaneously or sequentially with the other therapeutic agent by the same or different routes of administration. The compound of the invention may be included in a single formulation with the other therapeutic agent or in separate formulations.

Synthesis

Compounds of the invention, including salts and N-oxides thereof, can be prepared using known organic synthesis techniques and can be synthesized according to any of numerous possible synthetic routes, such as those in the Schemes below. The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 4th ed., John Wiley & Sons: New Jersey, (2006), which is incorporated herein by reference in its entirety.

Reactions can be monitored according to any suitable method known in the art. For example, product formation can be monitored by spectroscopic means, such as nuclear magnetic resonance (NMR) spectroscopy (e.g., $^1$H or $^{13}$C), infrared (IR) spectroscopy, spectrophotometry (e.g., UV-visible), mass spectrometry (MS), or by chromatographic methods such as high performance liquid chromatography (HPLC) or thin layer chromatography (TLC). Analytical instruments and methods for compound characterization:

LC-MS:

Unless otherwise indicated, all liquid chromatography-mass spectrometry (LC-MS) data (sample analyzed for purity and identity) were obtained with an Agilent model-1260 LC system using an Agilent model 6120 mass spectrometer utilizing ES-API ionization fitted with an Agilent Poroshel 120 (EC-C18, 2.7 um particle size, 3.0×50 mm dimensions) reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 4 minutes was utilized. The flow rate was constant at 1 mL/min.

Prep LC-MS:

Preparative HPLC was performed on a Shimadzu Discovery VP® Preparative system fitted with a Luna 5 u C18(2) 100 A, AXIA packed, 250×21.2 mm reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 25 minutes was utilized. The flow rate was constant at 20 mL/min. Reactions carried out in a microwave were done so in a Biotage Initiator microwave unit.

Chiral HPLC:

Preparative HPLC to resolve chiral mixtures was performed on a Thar SFC Pre-80 instrument fitted with a Chiralpak AS-H column (5 mm, 3.0 cm id×25 cm L). The mobile phases consisted of SFC $CO_2$ (A) and MeOH/0.1% $NH_4OH$ (B). A constant gradient from 67% to 33% (B) was maintained at a flow rate of 65 g/min, with a system back pressure of 100 bar. The separation progress was monitored by UV detection at a wavelength of 220 nm.

Silica Gel Chromatography:

Silica gel chromatography was performed on either a Teledyne Isco CombiFlash® Rf unit or a Biotage® Isolera Four unit.

Proton NMR:

Unless otherwise indicated, all $^1$H NMR spectra were obtained with a Varian 400 MHz Unity Inova 400 MHz NMR instrument (acquisition time=3.5 seconds with a 1 second delay; 16 to 64 scans). Where characterized, all protons were reported in DMSO-$d_6$ solvent as parts-per million (ppm) with respect to residual DMSO (2.50 ppm).

EXAMPLES

The following examples are intended to be illustrative, and are not meant in any way to be limiting.

The below Schemes are meant to provide general guidance in connection with preparing the compounds of the invention. One skilled in the art would understand that the preparations shown in the Schemes can be modified or optimized using general knowledge of organic chemistry to prepare various compounds of the invention.

General Synthesis 1:

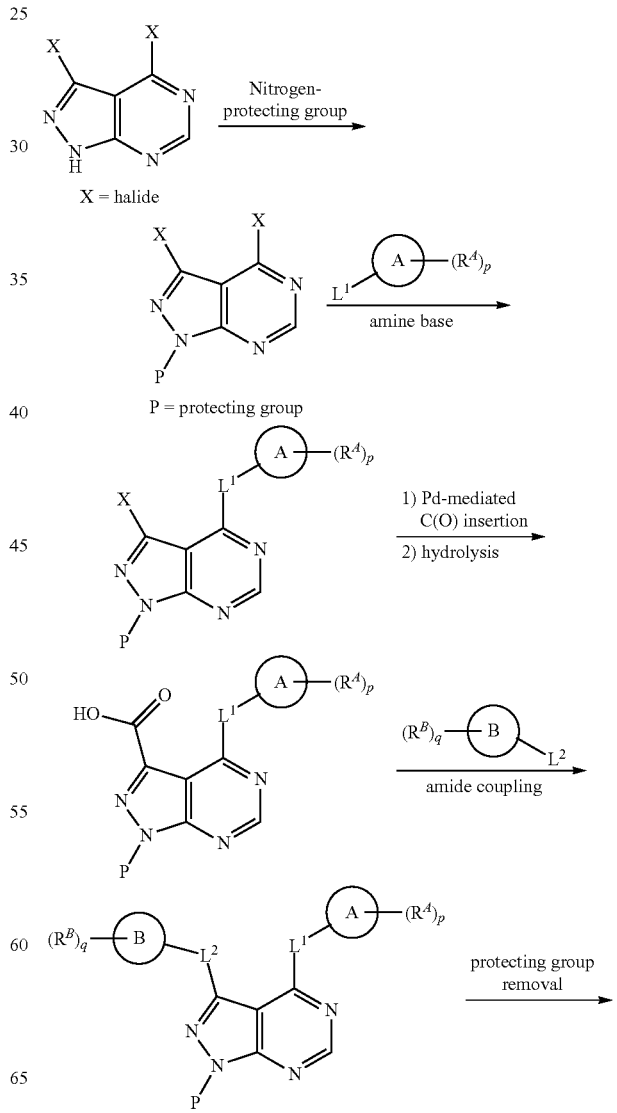

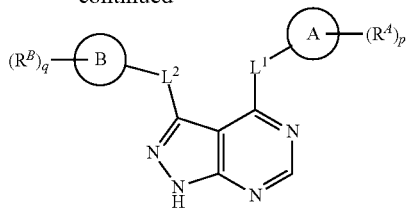

For certain compounds, the general synthesis begins with appropriate nitrogen-protection (P) of a di-halide substituted 1H-pyrazolo[3,4-d]pyrimidine. The nitrogen-protected bicycle can be substituted at the halide on the pyrimidine ring with an appropriately substituted Ring A under appropriate conditions, for example, nucleophilic aromatic substitution reaction conditions, using a base, such as diisopropylethylamine (DIPEA), in a polar solvent such as dioxane to provide the bicycle substituted with Ring A. The halide of the pyrazole ring can be substituted under Palladium-mediated carbonyl insertion reaction conditions followed by hydrolysis to provide the resultant carboxylic acid. The carboxylic acid can be reacted with Ring B under appropriate coupling conditions, for example amide coupling reaction conditions, to afford the nitrogen-protected compound substituted with Rings A and B. The removal of the protecting group can afford compounds of Formula I.

Synthetic Protocol 1:

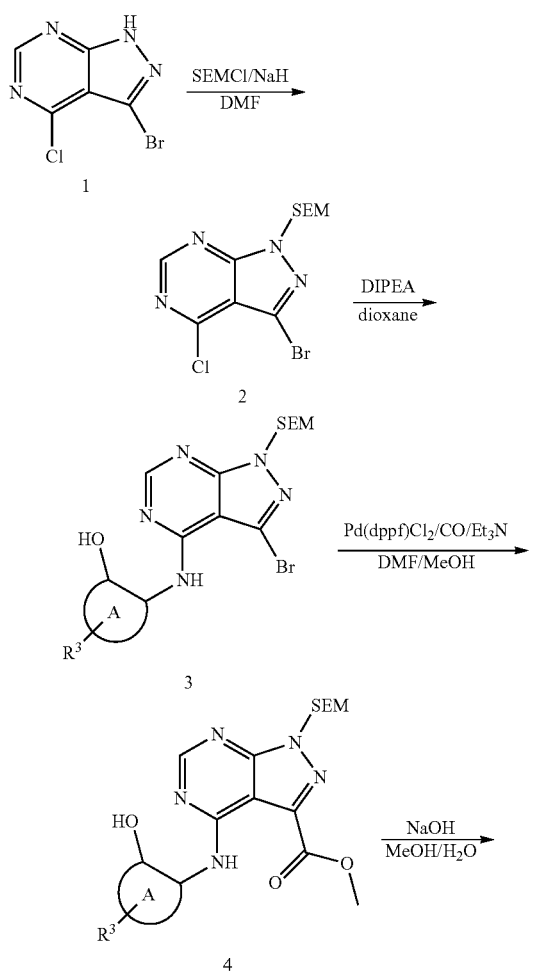

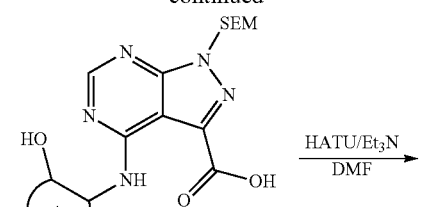

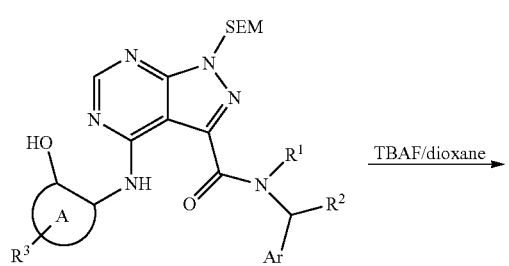

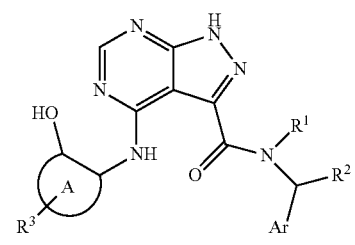

A slightly more specific version of General Synthesis scheme 1 is shown above in Synthetic Protocol 1. The synthetic protocol begins with SEM-group protection of 3-bromo-4-chloro-1H-pyrazolo[3,4-d]pyrimidine 1. The SEM-protected heterocycle 2 can be substituted with an amino alcohol under nucleophilic aromatic substitution reaction conditions using a base such as diisopropylethylamine (DIPEA) in a polar solvent such as dioxane to provide the amine-substituted heterocycle 3. The 3-bromo pyrazolo pyrimidine 3 is subjected to a palladium-mediated carbonyl insertion reaction in a DMF-MeOH solvent mixture to afford the methyl ester 4. Following the hydrolysis of the ester with NaOH treatment, the carboxylic acid is 5 reacted with a benzyl amine or a pyrrolidine under amide coupling reaction conditions to afford the SEM-protected compound 6. The SEM-protecting group can be removed using TBAF or under acidic conditions to afford the final compound 7. The compounds described below were prepared using General Synthesis 1, 2 or 3, as further detailed in Synthetic Protocol 1, 2, or 3, respectively.

General Synthesis 2

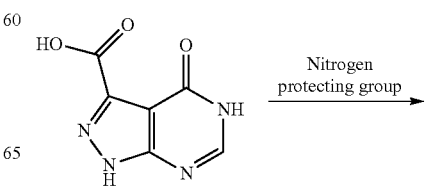

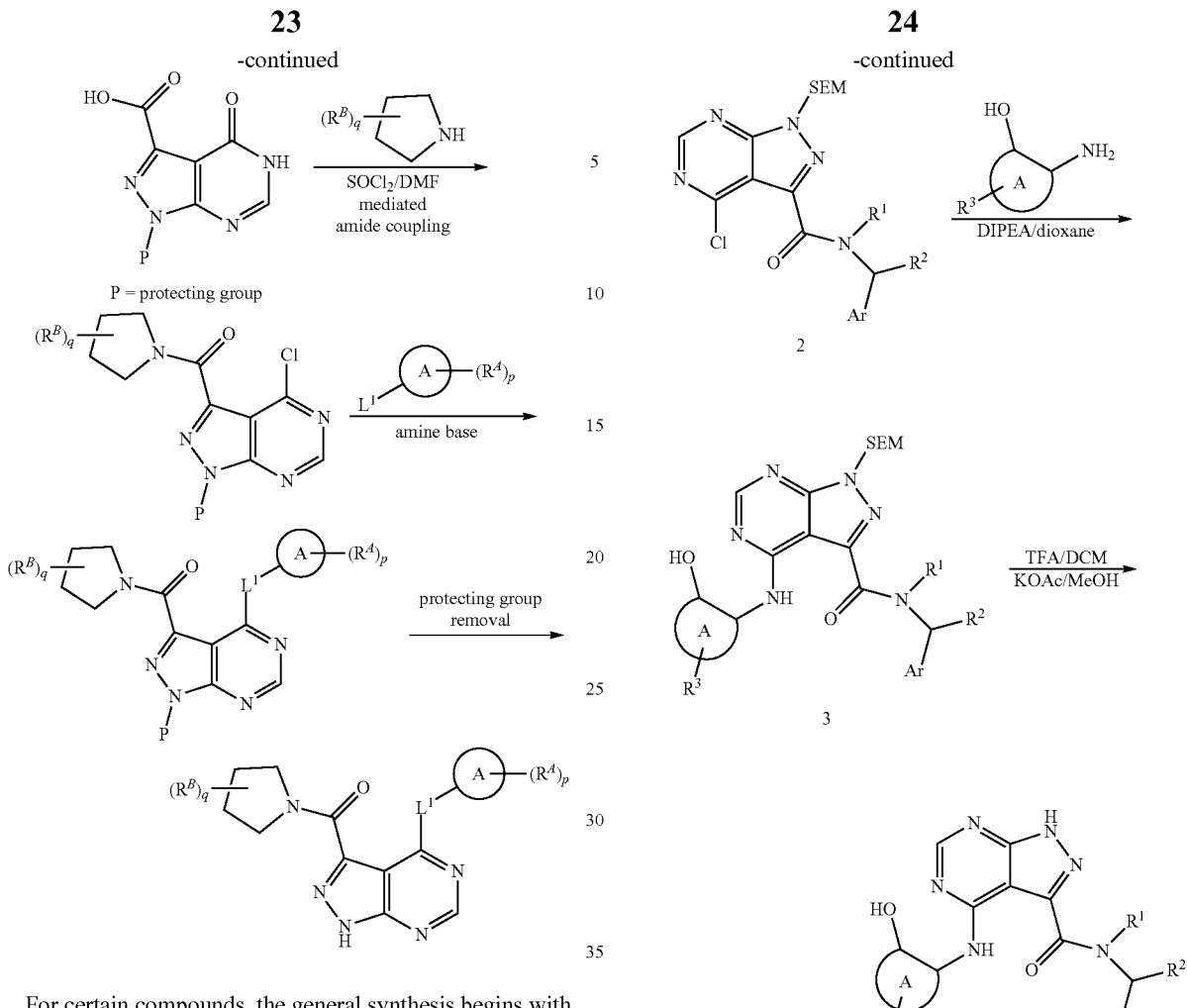

For certain compounds, the general synthesis begins with appropriate nitrogen-protection (P) of 4-oxo-4,5-dihydro-1H-pyrazolo[3,4-d]pyrimidine-3-carboxylic acid. The nitrogen-protected bicycle can be chlorinated and coupled with an amine in the presence of a chlorinating reagent such as thionyl chloride. The resulting compound can be substituted at the halide on the pyrimidine ring with an appropriately substituted Ring A under appropriate conditions, for example, nucleophilic aromatic substitution reaction conditions, using a base, such as diisopropylethylamine (DIPEA), in a polar solvent such as dioxane to provide the bicycle substituted with Ring A. The removal of the protecting group can afford compounds of Formula I. Compounds described below can be prepared using this general synthesis. Further, chiral HPLC can be employed to resolve chiral mixtures of compounds of Formula I, (Ia), (Ia-1), (Ia-2), (Ib), (Ib-1, (Ib-2), II, (IIa), (IIb), (IIc).

Synthetic Protocol 2

A slightly more specific version of General Synthesis scheme 2 is shown above in Synthetic Protocol 2. The synthetic protocol begins with SEM-protected 4-oxo-4,5-dihydro-1H-pyrazolo[3,4-d]pyrimidine-3-carboxylic acid 1 which can be chlorinate with thionyl chloride/DMF and then coupled with a benzyl amine or a pyrrolidine under mild heat to afford the SEM-protected compound 2. The SEM-protected heterocycle 2 can be substituted with an amino alcohol under nucleophilic aromatic substitution reaction conditions using a base such as diisopropylethylamine (DIPEA) in a polar solvent such as dioxane to provide the amine-substituted heterocycle 3. The SEM-protecting group can be removed using TBAF or under acidic conditions to afford the final compound 4.

General Synthesis 3

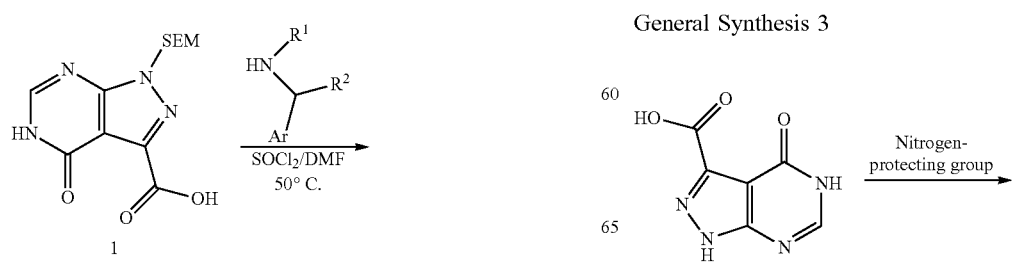

25
-continued

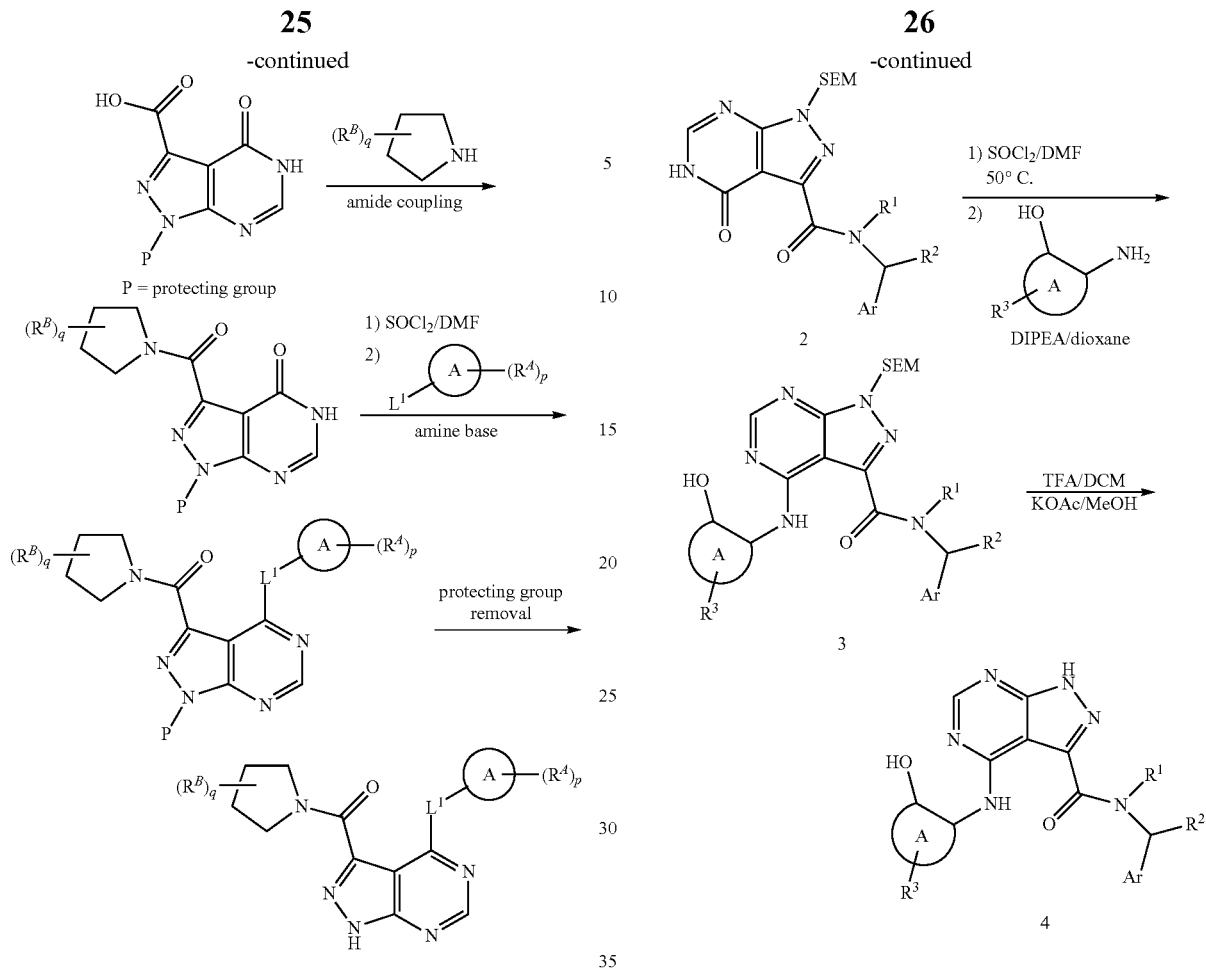

For certain compounds, the general synthesis begins with appropriate nitrogen-protection (P) of 4-oxo-4,5-dihydro-1H-pyrazolo[3,4-d]pyrimidine-3-carboxylic acid. The carboxylic acid can be coupled to an amine using amide coupling conditions. The resulting compound can be chlorinated using thionyl chloride followed by substitution at the chloride on the pyrimidine ring with an appropriately substituted Ring A under appropriate conditions, for example, nucleophilic aromatic substitution reaction conditions, using a base, such as diisopropylethylamine (DIPEA), in a polar solvent such as dioxane to provide the bicycle substituted with Ring A. The removal of the protecting group can afford compounds of Formula I. Compounds described below can be prepared using this general synthesis. Further, chiral HPLC can be employed to resolve chiral mixtures of compounds of Formula I, (Ia), (Ia-1), (Ia-2), (Ib), (Ib-1, (Ib-2), II, (IIa), (IIb), (IIc).

Synthetic Protocol 3

26
-continued

A slightly more specific version of General Synthesis scheme 3 is shown above in Synthetic Protocol 3. The synthetic protocol begins with SEM-protected 4-oxo-4,5-dihydro-1H-pyrazolo[3,4-d]pyrimidine-3-carboxylic acid 1 which can be coupled with a benzyl amine or a pyrrolidine under amide coupling conditions. The SEM-protected heterocycle 2 can be chlorinated with thionyl chloride/DMF and then substituted with an amino alcohol under nucleophilic aromatic substitution reaction conditions using a base such as diisopropylethylamine (DIPEA) in a polar solvent such as dioxane to provide the amine-substituted heterocycle 3. The SEM-protecting group can be removed using TBAF or under acidic conditions to afford the final compound 4.

All of the compounds set forth in FIG. 1, as well as other compounds of the invention were prepared using one of three general synthesis schemes and protocols depicted above. Further, chiral HPLC can be employed to resolve chiral mixtures of compounds of Formula I, (Ia), (Ia-1), (Ia-2), (Ib), (Ib-1, (Ib-2), II, (IIa), (IIb), (IIc). Certain specific examples of synthesis are set forth in the Examples.

Example 1. Synthesis of Compound 45

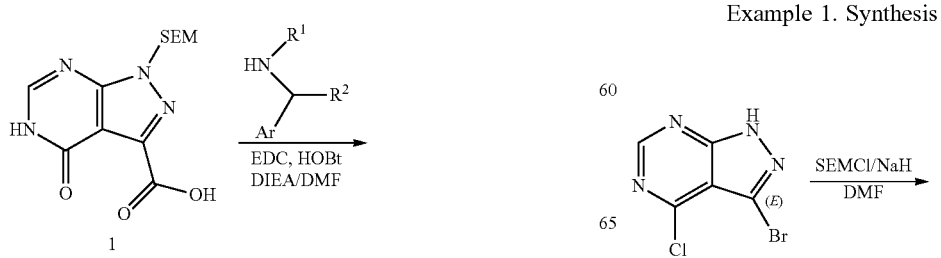

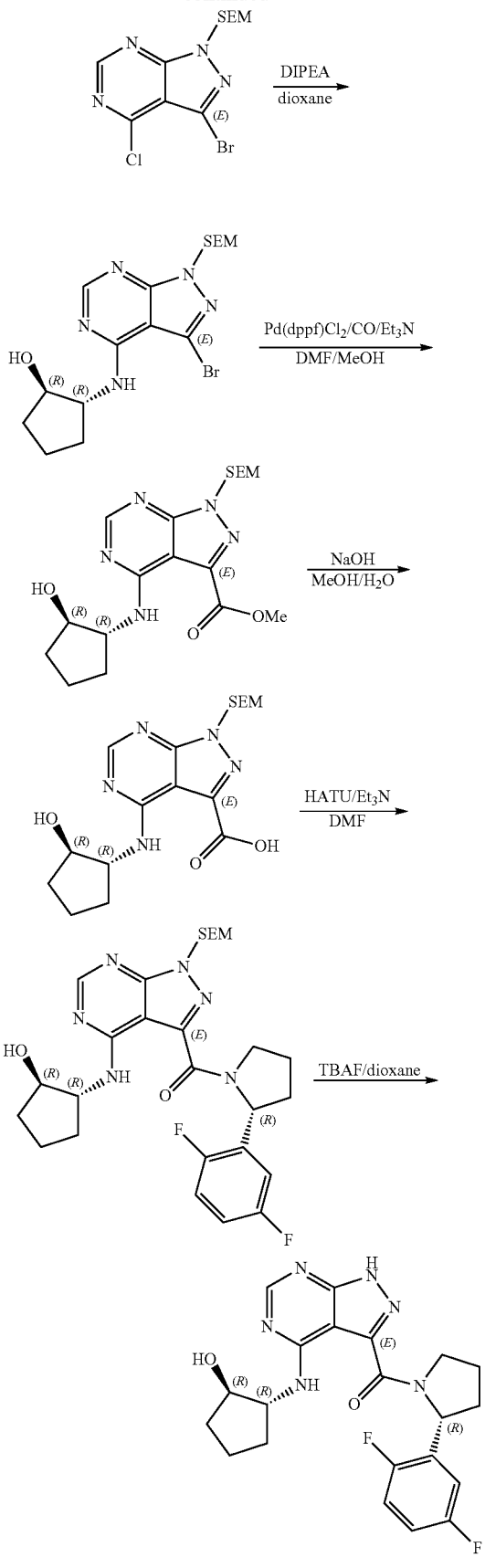

Step 1: Synthesis of 3-bromo-4-chloro-1-((2-(trimethylsilyl)ethoxy)methyl)-1H-pyrazolo[3,4-d]pyrimidine To a solution of 3-bromo-4-chloro-1H-pyrazolo[3,4-d]pyrimidine (10.00 g, 42.84 mmol) in DMF (50.00 mL) was added NaH (2.57 g, 64.25 mmol) in portions at 0° C. After stirring for 0.5 hr, SEM-Cl (8.57 g, 51.40 mmol) was added dropwise to the reaction at 0° C. over 0.5 hr. The reaction was slowly warmed to 25° C. and stirred for 16 hrs. After TLC (PE:EtOAc=1:1, $R_f$=0.88) showed the reaction was complete, the reaction was slowly quenched by 50 mL of $H_2O$. The mixture was extracted with EtOAc (50 mL*3), and the organic layer was washed with brine (20 mL*3), dried over $Na_2SO_4$, and concentrated. The residue was purified by column chromatography on silica gel (PE:EtOAc=20:1) to give 3-bromo-4-chloro-1-((2-(trimethylsilyl)ethoxy)methyl)-1H-pyrazolo[3,4-d]pyrimidine (6.20 g, yield: 39.80%) as a colorless oil. $^1$H-NMR (400 MHz, CDCl$_3$) δ ppm 8.83 (s, 1H), 5.82 (s, 2H), 3.70 (t, 2H, J=8.4 Hz), 0.97 (t, 2H, J=8.4 Hz), 0.00 (s, 9H).

Step 2: Synthesis of (1R,2R)-2-((3-bromo-1-((2-(trimethylsilyl)ethoxy)methyl)-1H-pyrazolo[3,4-d]pyrimidin-4-yl)amino)cyclopentan-1-ol To a mixture of 3-bromo-4-chloro-1-((2-(trimethylsilyl)ethoxy)methyl)-1H-pyrazolo[3,4-d]pyrimidine (2.50 g, 6.87 mmol) and (1R, 2R)-2-aminocyclopentenol hydrochloride (945.38 mg, 6.87 mmol) in dioxane (15 mL) was added DIPEA (1.78 g, 13.74 mmol), the reaction mixture was allowed to stir at 70° C. for 16 hrs. Once TLC (PE:EtOAc=5:1) showed the starting material was consumed completely, the mixture was concentrated in vacuum and purified by column chromatography on silica gel (PE:EtOAc=30:1~10:1) to provide (1R,2R)-2-((3-bromo-1-((2-(trimethylsilyl)ethoxy)methyl)-1H-pyrazolo[3,4-d]pyrimidin-4-yl)amino)cyclopentan-1-ol (2.10 g, 4.41 mmol, yield: 64.22%) as a yellow oil. $^1$H-NMR (400 MHz, CD$_3$OD) δ ppm 8.41 (s, 1H), 6.26 (s, 1H), 5.70 (s, 2H), 4.13-4.12 (m, 2H), 3.69-3.65 (m, 2H), 2.40-2.39 (m, 1H), 2.20-2.18 (m, 1H), 1.95-1.84 (m, 2H), 1.72-1.61 (m, 2H), 0.97 (d, 2H, J=4.0 Hz), 0.00 (s, 9H).

Step 3: Synthesis of methyl 4-(((1R,2R)-2-hydroxy-cyclopentyl)amino)-1-((2-(trimethylsilyl)ethoxy)methyl)-1H-pyrazolo[3,4-d]pyrimidine-3-carboxylate

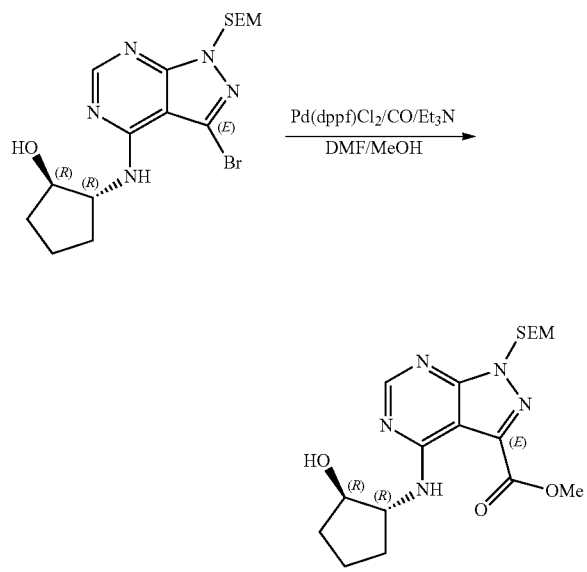

To a mixture of (1R,2R)-2-((3-bromo-1-((2-(trimethylsilyl)ethoxy)methyl)-1H-pyrazolo[3,4-d]pyrimidin-4-yl)amino)cyclopentan-1-ol (2.10 g, 4.90 mmol) in DMF (10 mL) and MeOH (15 mL) was added Pd(dppf)Cl$_2$ (717.07 mg, 980.00 umol) and Et$_3$N (1.49 g, 14.70 mmol) in one portion, and the reaction mixture was allowed to stir at 70° C. for 30 hrs under a CO (50 psi) atmosphere. Once TLC (PE:EtOAc=1:1) and LCMS showed the starting material was consumed completely, the mixture was filtered and the filtrate was concentrated in vacuum to get methyl 4-(((1R,2R)-2-hydroxycyclopentyl)amino)-1-((2-(trimethylsilyl)ethoxy)methyl)-1H-pyrazolo[3,4-d]pyrimidine-3-carboxylate (2.70 g, crude) as a yellow oil, which was used directly without further purification. $^1$H-NMR (400 MHz, CDCl$_3$) δ ppm 8.85 (s, 1H), 8.45 (s, 1H), 5.83 (s, 2H), 4.14 (br.s, 2H), 4.10 (s, 3H), 3.70 (t, 2H, J=8.4 Hz), 2.40-2.38 (m, 1H), 2.20-2.17 (m, 1H), 1.93-1.79 (m, 4H), 0.98 (t, 2H, J=8.4 Hz), 0.00 (s, 9H).

Step 4: Synthesis of 4-(((1R,2R)-2-hydroxycyclopentyl)amino)-1-((2-(trimethylsilyl)ethoxy)methyl)-1H-pyrazolo[3,4-d]pyrimidine-3-carboxylic acid

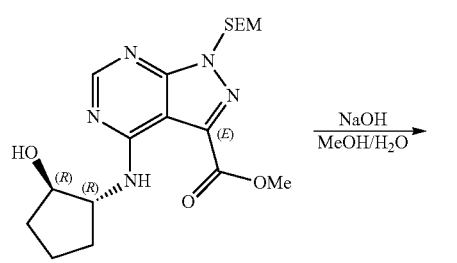

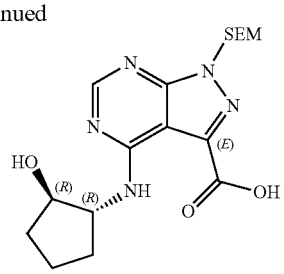

To a mixture of methyl 4-(((1R,2R)-2-hydroxycyclopentyl)amino)-1-((2-(trimethylsilyl)ethoxy)methyl)-1H-pyrazolo[3,4-d]pyrimidine-3-carboxylate (2.70 g, 6.63 mmol) in MeOH (10 mL), H$_2$O (10 mL) was added, followed by NaOH (530.01 mg, 13.25 mmol) in one portion. The reaction mixture was then allowed to stir at 26° C. for 16 hrs. Once LCMS and TLC (PE:EtOAc=1:1) showed the starting material was consumed completely, MeOH was removed by concentration in vacuum and the residue was washed with EtOAc (8 mL*2). Aqueous HCl (1 N) was then added until the pH<7 and the formation of white precipitate was observed. The solid was collected by filtration and dried in vacuo to provide 4-(((1R,2R)-2-hydroxycyclopentyl)amino)-1-((2-(trimethylsilyl)ethoxy)methyl)-1H-pyrazolo[3,4-d]pyrimidine-3-carboxylic acid (1.20 g, yield: 37.89%) as a white solid. $^1$H-NMR (400 MHz, CD$_3$OD) δ ppm 8.40 (s, 1H), 5.80 (s, 2H), 4.37-4.32 (m, 1H), 4.22-4.19 (m, 1H), 3.75 (t, 2H, J=8.0 Hz), 2.39-2.36 (m, 1H), 2.11-2.06 (m, 1H), 1.96-1.91 (m, 2H), 1.78-1.73 (m, 2H), 0.95 (t, 2H, J=8.0 Hz), 0.00 (s, 9H).

Step 5: Synthesis of ((R)-2-(2,5-difluorophenyl)pyrrolidin-1-yl)(4-(((1R,2R)-2-hydroxycyclopentyl)amino)-1-((2-(trimethylsilyl)ethoxy)methyl)-1H-pyrazolo[3,4-d]pyrimidin-3-yl)methanone

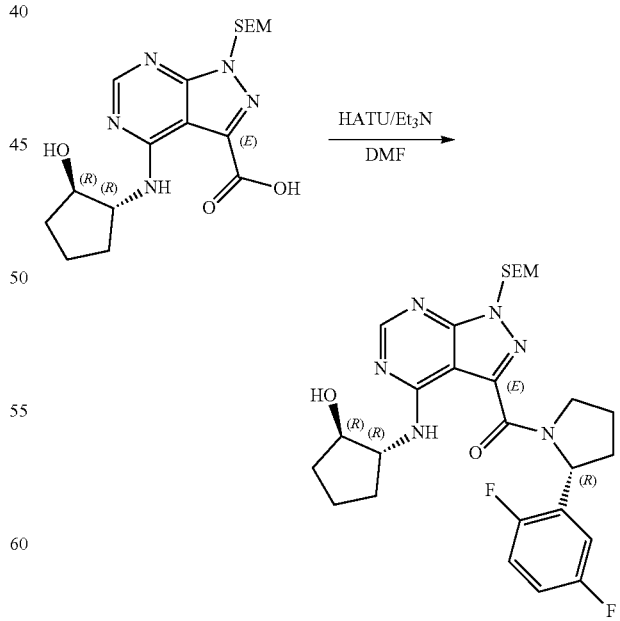

To a mixture of 4-(((1R,2R)-2-hydroxycyclopentyl)amino)-1-((2-(trimethylsilyl)ethoxy)methyl)-1H-pyrazolo[3,4-d]pyrimidine-3-carboxylic acid (100.00 mg, 254.12 umol) and (2R)-2-(2, 5-difluorophenyl) pyrrolidine (55.87 mg, 304.95 umol) in DMF (2 mL) was added HATU (144.94 mg, 381.18 umol) and Et₃N (128.57 mg, 1.27 mmol) at 20° C., and the reaction was stirred at 20° C. for 16 hrs. After LCMS showed the reaction was complete, H₂O (5 mL) was added to the mixture, and the reaction was extracted with EtOAc (10 mL*3) and washed with brine (5 mL*3). The organic layer was then dried over Na₂SO₄ and concentrated. The residue was purified by preparative TLC (PE:EtOAc=1:1, R$_f$=0.5) to give ((R)-2-(2,5-difluorophenyl)pyrrolidin-1-yl)(4-(((1R,2R)-2-hydroxycyclopentyl)amino)-1-((2-(trimethylsilyl)ethoxy)methyl)-1H-pyrazolo[3,4-d]pyrimidin-3-yl)methanone (20.00 mg, yield: 14.09%) as a colorless oil.

Step 6: Synthesis of ((R)-2-(2,5-difluorophenyl)pyrrolidin-1-yl)(4-(((1R,2R)-2-hydroxycyclopentyl)amino)-1H-pyrazolo[3,4-d]pyrimidin-3-yl)methanone

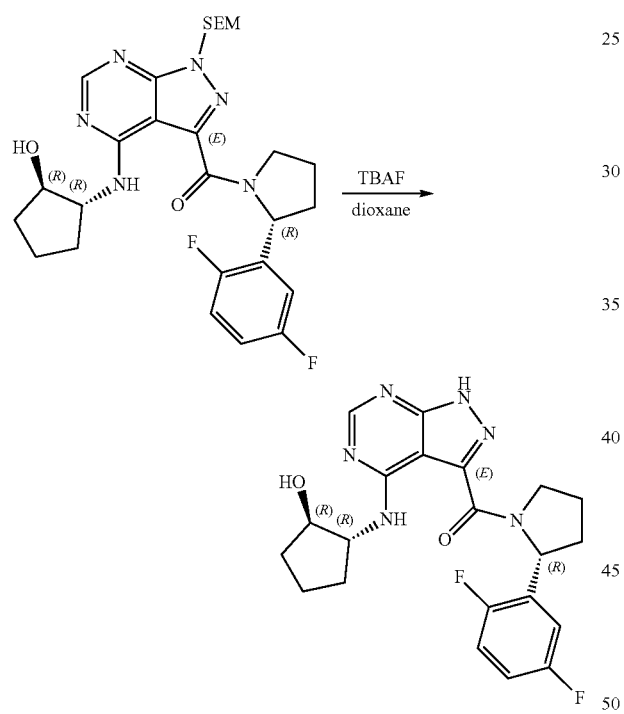

To a solution of ((R)-2-(2,5-difluorophenyl)pyrrolidin-1-yl)(4-(((1R,2R)-2-hydroxycyclopentyl)amino)-1-((2-(trimethylsilyl)ethoxy)methyl)-1H-pyrazolo[3,4-d]pyrimidin-3-yl)methanone (20.00 mg, 35.80 umol) in dioxane (20 mL) was added TBAF (80.61 mg, 358.00 umol) at 20° C., and the reaction was heated at 80° C. for 16 hrs. After TLC (EtOAc, R$_f$=0.1) showed the reaction was complete, the solution was concentrated And 10 mL of H₂O was added to the residue. The solution was extracted with EtOAc (10 mL*3), and the organic layer was dried over Na₂SO₄ and concentrated. The residue was purified by acidic preparative HPLC (MeOH/H₂O/TFA solvent system) to give ((R)-2-(2,5-difluorophenyl)pyrrolidin-1-yl)(4-(((1R,2R)-2-hydroxycyclopentyl)amino)-1H-pyrazolo[3,4-d]pyrimidin-3-yl)methanone (11.10 mg, yield: 72.37%) as a brown solid.

Example 2. Synthesis of Compound 97 and Compound 98

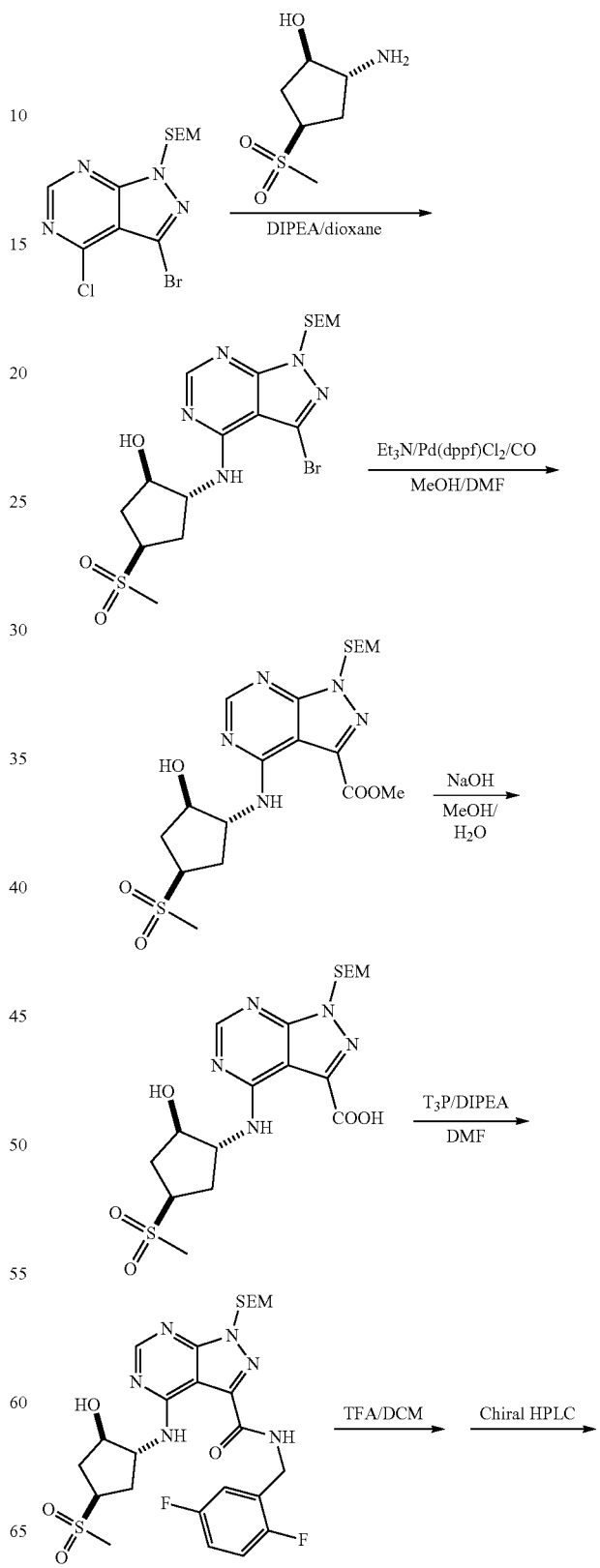

-continued

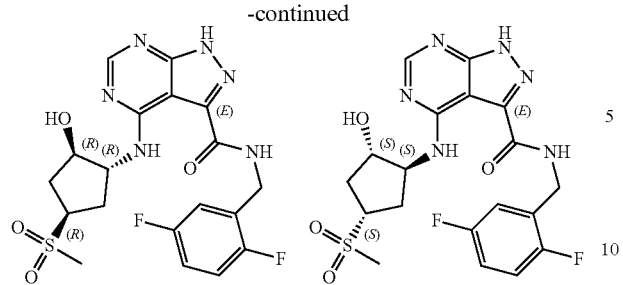

Step 1: Synthesis of (1R,2R,4R)-2-((3-bromo-1-((2-(trimethylsilyl)ethoxy)methyl)-1H-pyrazolo[3,4-d]pyrimidin-4-yl)amino)-4-(methylsulfonyl)cyclopentan-1-ol

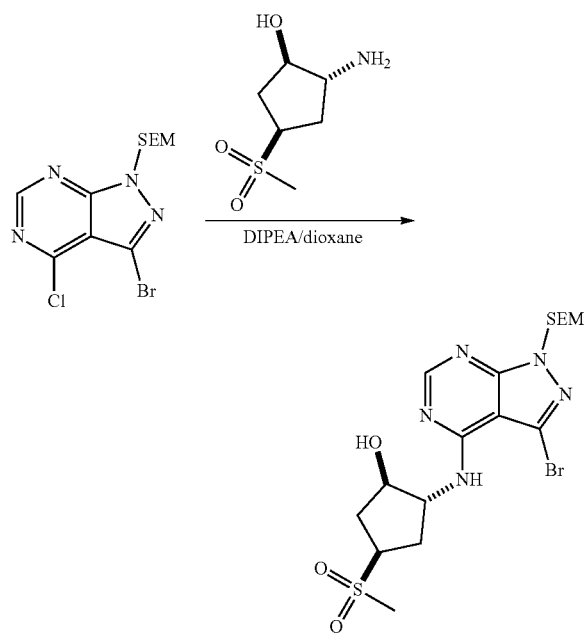

To a mixture of 3-bromo-4-chloro-1-((2-(trimethylsilyl)ethoxy)methyl)-1H-pyrazolo[3,4-d]pyrimidine (300.00 mg, 824.83 umol) in dioxane (10.00 mL) was added DIPEA (319.80 mg, 2.47 mmol) and (1R,2R,4R)-2-amino-4-(methylsulfonyl)cyclopentan-1-ol (195.71 mg, 907.31 umol), and the mixture was stirred at 90° C. for 32 hrs. After LCMS showed the reaction was complete, the mixture was concentrated to remove 1,4-dioxane, and the residue was dissolved in DCM (20 mL). The organic layer was washed with water (10 mL*4), dried over $Na_2SO_4$, and concentrated to give (1R,2R,4R)-2-((3-bromo-1-((2-(trimethylsilyl)ethoxy)methyl)-1H-pyrazolo[3,4-d]pyrimidin-4-yl)amino)-4-(methylsulfonyl)cyclopentan-1-ol (350.00 mg, yield: 83.78%) as a white solid. $^1$H-NMR (400 MHz, CDCl$_3$) δ ppm 8.43 (s, 1H), 6.23 (br.s, 1H), 5.71 (s, 2H), 4.50 (br.s, 1H), 4.26-4.24 (m, 1H), 3.70-3.66 (m, 3H), 2.97 (br.s, 4H), 2.65 (m, 1H), 2.37-2.20 (m, 2H), 0.97 (t, 2H, J=8.4 Hz), 0.00 (s, 9H).

Step 2: Synthesis of methyl 4-(((1R,2R,4R)-2-hydroxy-4-(methylsulfonyl)cyclopentyl)amino)-1-((2-(trimethylsilyl)ethoxy)methyl)-1H-pyrazolo[3,4-d]pyrimidine-3-carboxylate

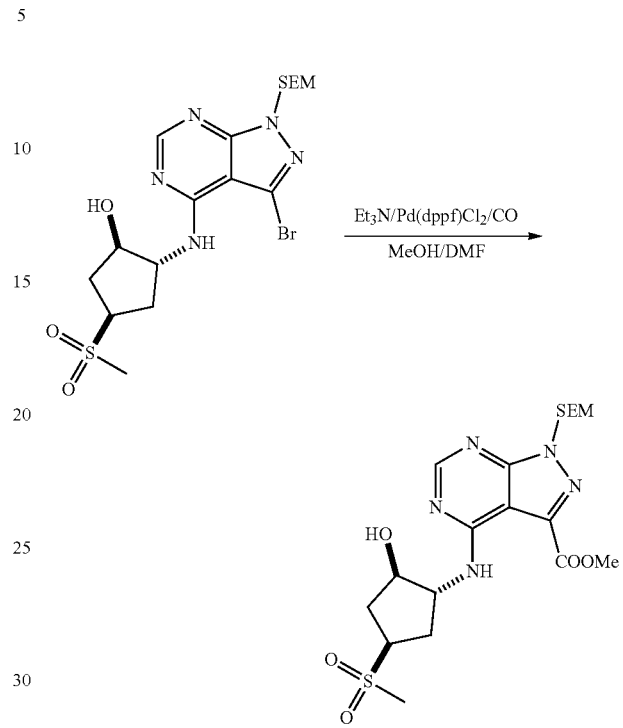

To a mixture of (1R,2R,4R)-2-((3-bromo-1-((2-(trimethylsilyl)ethoxy)methyl)-1H-pyrazolo[3,4-d]pyrimidin-4-yl)amino)-4-(methylsulfonyl)cyclopentan-1-ol (350.00 mg, 691.03 umol) in MeOH (10.00 mL)/DMF (2.00 mL) was added Et$_3$N (139.85 mg, 1.38 mmol) and Pd(dppf)Cl$_2$ (25.28 mg, 34.55 umol). After addition, the mixture was stirred at 75° C. for 16 hrs under CO (50 Psi). Once LCMS showed the reaction was complete, the mixture was concentrated to give the crude product, which was purified by preparative TLC (PE:EtOAc=0:1) to give methyl 4-(((1R,2R,4R)-2-hydroxy-4-(methylsulfonyl)cyclopentyl)amino)-1-((2-(trimethylsilyl)ethoxy)methyl)-1H-pyrazolo[3,4-d]pyrimidine-3-carboxylate (250.00 mg, yield: 74.50%) as a red solid.

Step 3: Synthesis of 4-(((1R,2R,4R)-2-hydroxy-4-(methylsulfonyl)cyclopentyl)amino)-1-((2-(trimethylsilyl)ethoxy)methyl)-1H-pyrazolo[3,4-d]pyrimidine-3-carboxylic Acid

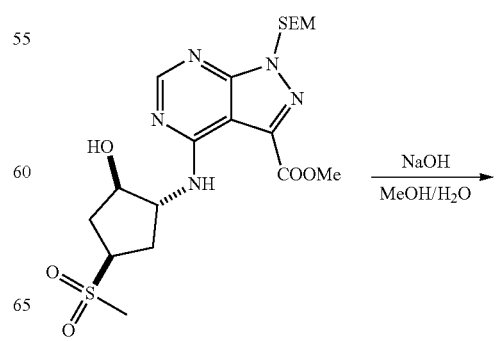

-continued

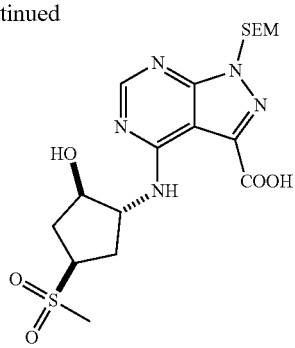

To a mixture of methyl 4-(((1R,2R,4R)-2-hydroxy-4-(methylsulfonyl)cyclopentyl)amino)-1-((2-(trimethylsilyl)ethoxy)methyl)-1H-pyrazolo[3,4-d]pyrimidine-3-carboxylate (250.00 mg, 514.80 umol) in MeOH (10.00 mL)/H$_2$O (5.00 mL) was added NaOH (41.18 mg, 1.03 mmol), which was stirred at 20° C. for 16 hrs. Once LCMS showed the reaction was complete, the mixture was concentrated to remove MeOH. The water layer was washed with EtOAc (3 mL*2) and acidified by HCl (1 M) until the pH=4, after which the mixture was filtered and the filter cake was dried under vacuum to afford 4-(((1R,2R,4R)-2-hydroxy-4-(methylsulfonyl)cyclopentyl)amino)-1-((2-(trimethylsilyl)ethoxy)methyl)-1H-pyrazolo[3,4-d]pyrimidine-3-carboxylic acid (180.00 mg, yield: 74.14%) as a black/brown solid. $^1$H-NMR (400 MHz, CDCl$_3$) δ ppm 8.47 (s, 1H), 5.77 (s, 2H), 4.43-4.40 (m, 1H), 4.17-4.12 (m, 1H), 3.85-8.82 (m, 1H), 3.69 (t, 2H, J=8.4 Hz), 3.03 (s, 3H), 2.45-2.41 (m, 2H), 1.99-1.91 (m, 2H), 0.92 (t, 2H, J=8.4 Hz), 0.00 (s, 9H).

Step 4: Synthesis of N-(2,5-difluorobenzyl)-4-(((1R,2R,4R)-2-hydroxy-4-(methylsulfonyl)cyclopentyl)amino)-1-((2-(trimethylsilyl)ethoxy)methyl)-1H-pyrazolo[3,4-d]pyrimidine-3-carboxamide

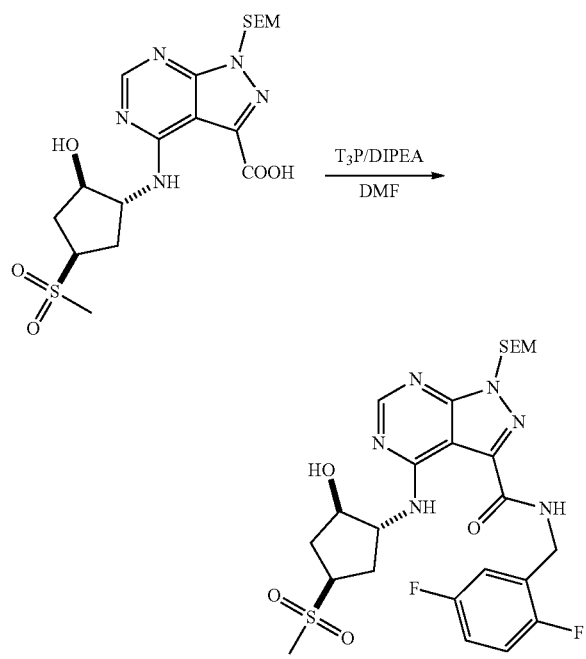

To a mixture of 4-(((1R,2R,4R)-2-hydroxy-4-(methylsulfonyl)cyclopentyl)amino)-1-((2-(trimethylsilyl)ethoxy)methyl)-1H-pyrazolo[3,4-d]pyrimidine-3-carboxylic acid (60.00 mg, 127.23 umol) in DMF (2.00 mL) was added DIPEA (16.44 mg, 127.23 umol), (2,5-difluorophenyl)methanamine (36.42 mg, 254.46 umol) and T$_3$P (40.48 mg, 127.23 umol). After addition, the mixture was stirred at 20° C. for 1 hr, wherein LCMS showed the reaction was complete. The mixture was added to water (4 mL) and extracted with EtOAc (5 mL*3), and the organic layer was dried over Na$_2$SO$_4$ and concentrated to give N-(2,5-difluorobenzyl)-4-(((1R,2R,4R)-2-hydroxy-4-(methylsulfonyl)cyclopentyl)amino)-1-((2-(trimethylsilyl)ethoxy)methyl)-1H-pyrazolo[3,4-d]pyrimidine-3-carboxamide (50.00 mg, crude) as a red oil.

Step 5: Synthesis of N-(2,5-difluorobenzyl)-4-(((1R,2R,4R)-2-hydroxy-4-(methylsulfonyl)cyclopentyl)amino)-1H-pyrazolo[3,4-d]pyrimidine-3-carboxamide

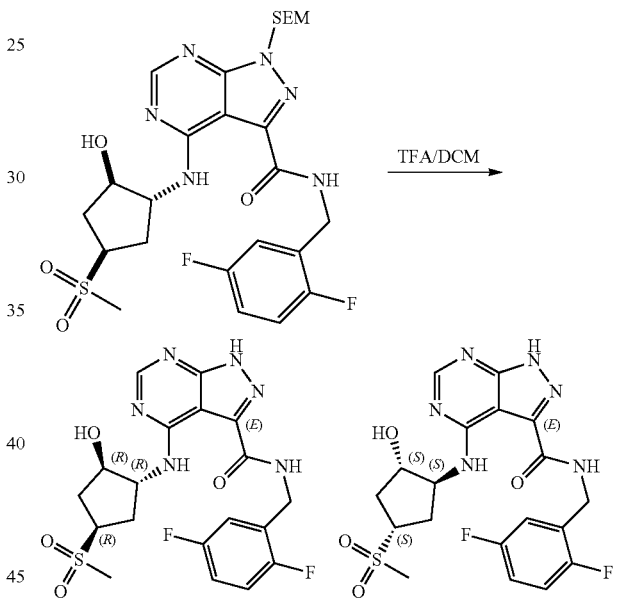

N-(2,5-difluorobenzyl)-4-(((1R,2R,4R)-2-hydroxy-4-(methylsulfonyl)cyclopentyl)amino)-1-((2-(trimethylsilyl)ethoxy)methyl)-1H-pyrazolo[3,4-d]pyrimidine-3-carboxamide (50.00 mg, 83.79 umol) in DCM (5.00 mL) was stirred in a mixture of TFA (5.00 mL) at 20° C. for 16 hrs, after which LCMS showed the reaction was complete. The mixture was concentrated to give the crude product, which was purified by preparative HPLC (TFA) and chiral HPLC (retention times of the resolved isomers were 7.46 min and 9.20 min, respectively). N-(2,5-difluorobenzyl)-4-(((1R,2R,4R)-2-hydroxy-4-(methylsulfonyl)cyclopentyl)amino)-1H-pyrazolo[3,4-d]pyrimidine-3-carboxamide (2.80 mg, yield: 7.16%) and N-(2,5-difluorobenzyl)-4-(((1S,2S,4S)-2-hydroxy-4-(methylsulfonyl)cyclopentyl)amino)-1H-pyrazolo[3,4-d]pyrimidine-3-carboxamide (4.00 mg, yield: 10.23%) were obtained as white solids. LC-MS conditions for these compounds were as follows: flow rate=0.8 mL·min$^{-1}$, mobile phase: from 99% [water+0.375‰ v/v TFA] and 1% [CH$_3$CN+0.188‰ v/v TFA], under this condition for 0.4 min, then changed to 10% [water+0.375‰ v/v TFA] and 90% [CH₃CN+0.188‰ v/v TFA] in 3.0 min, then changed to 100% [CH₃CN+0.188‰ v/v TFA] in 0.45 min, finally changed to 99% [water+0.375‰ v/v TFA] and 1% [CH₃CN+0.188‰ v/v TFA] in 0.01 min, then under this condition for 0.64 min; 98.887% purity and 96.551%, respectively.

Example 3. Synthesis of Compound 20 and Compound 21

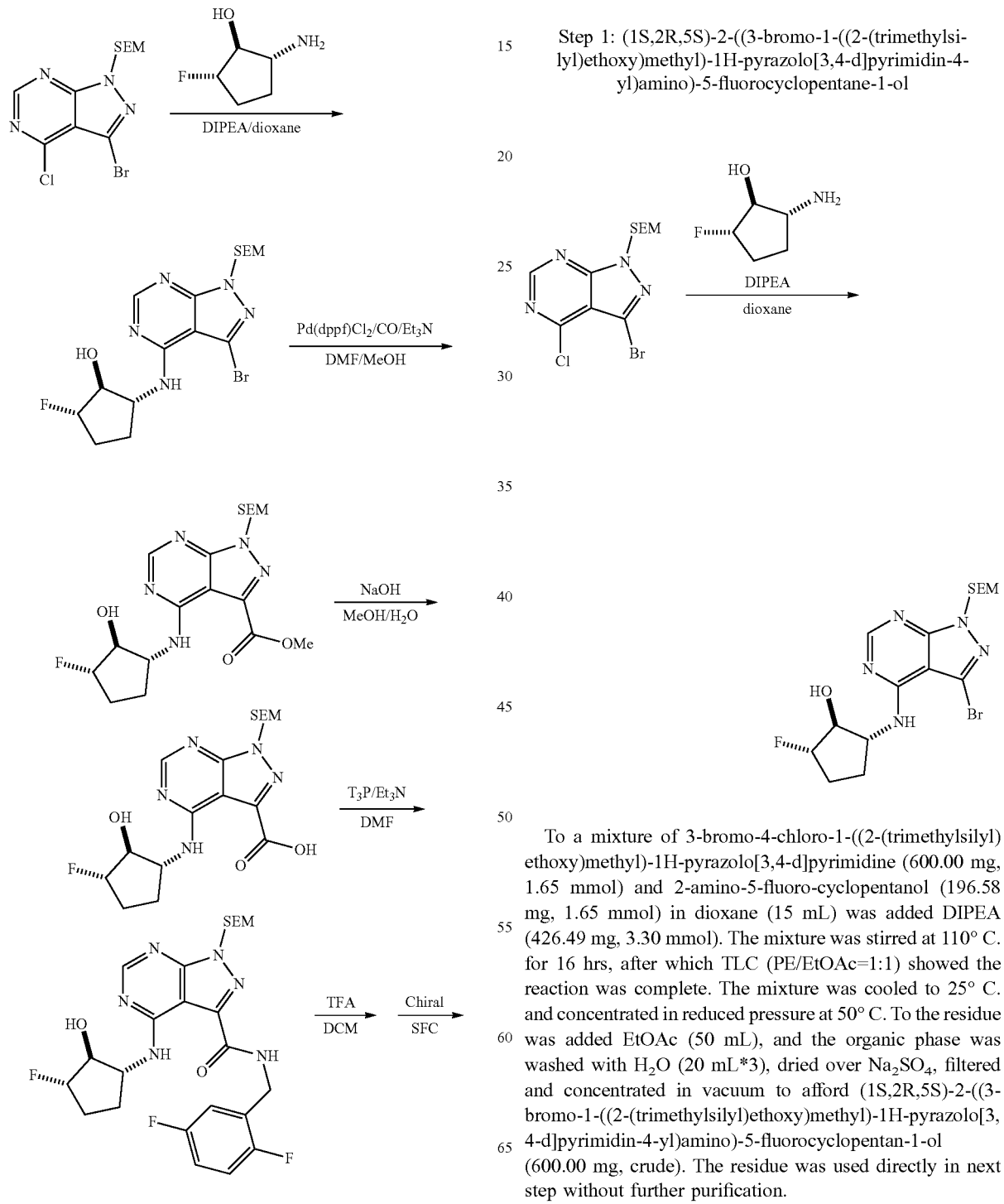

Step 1: (1S,2R,5S)-2-((3-bromo-1-((2-(trimethylsilyl)ethoxy)methyl)-1H-pyrazolo[3,4-d]pyrimidin-4-yl)amino)-5-fluorocyclopentane-1-ol To a mixture of 3-bromo-4-chloro-1-((2-(trimethylsilyl)ethoxy)methyl)-1H-pyrazolo[3,4-d]pyrimidine (600.00 mg, 1.65 mmol) and 2-amino-5-fluoro-cyclopentanol (196.58 mg, 1.65 mmol) in dioxane (15 mL) was added DIPEA (426.49 mg, 3.30 mmol). The mixture was stirred at 110° C. for 16 hrs, after which TLC (PE/EtOAc=1:1) showed the reaction was complete. The mixture was cooled to 25° C. and concentrated in reduced pressure at 50° C. To the residue was added EtOAc (50 mL), and the organic phase was washed with H₂O (20 mL*3), dried over Na₂SO₄, filtered and concentrated in vacuum to afford (1S,2R,5S)-2-((3-bromo-1-((2-(trimethylsilyl)ethoxy)methyl)-1H-pyrazolo[3,4-d]pyrimidin-4-yl)amino)-5-fluorocyclopentan-1-ol (600.00 mg, crude). The residue was used directly in next step without further purification.

Step 2: Methyl 4-(((1R,2S,3S)-3-fluoro-2-hydroxy-cyclopentyl)amino)-1-((2-(trimethylsilyl)ethoxy)methyl)-1H-pyrazolo[3,4-d]pyrimidine-3-carboxylate

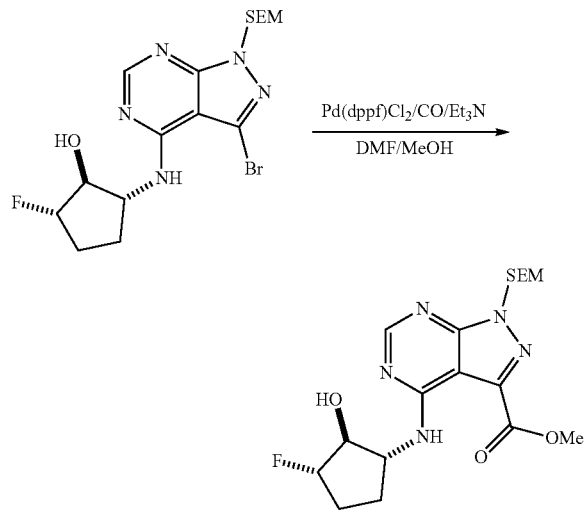

To a solution of (1S,2R,5S)-2-((3-bromo-1-((2-(trimethylsilyl)ethoxy)methyl)-1H-pyrazolo[3,4-d]pyrimidin-4-yl)amino)-5-fluorocyclopentan-1-ol (600.00 mg, 1.34 mmol) in MeOH/DMF (20 mL, v:v=2/1) was added Pd(dppf)Cl₂ (49.17 mg, 67.21 umol) and Et₃N (408.03 mg, 4.03 mmol) under N₂. The suspension was degassed under vacuum and purged with CO several times. The mixture was stirred under CO (50 psi) at 70° C. for 16 hrs, after which TLC (PE/EtOAc=1:1) showed the starting material was consumed completely. The reaction mixture was filtered and the filtrate was concentrated to afford methyl 4-(((1R,2S,3S)-3-fluoro-2-hydroxycyclopentyl)amino)-1-((2-(trimethylsilyl)ethoxy)methyl)-1H-pyrazolo[3,4-d]pyrimidine-3-carboxylate (700.00 mg, crude). The crude product was used directly without purification.

Step 3: 4-(((1R,2S,3S)-3-fluoro-2-hydroxycyclopentyl)amino)-1-((2-(trimethylsilyl)ethoxy)methyl)-1H-pyrazolo[3,4-d]pyrimidine-3-carboxylic Acid

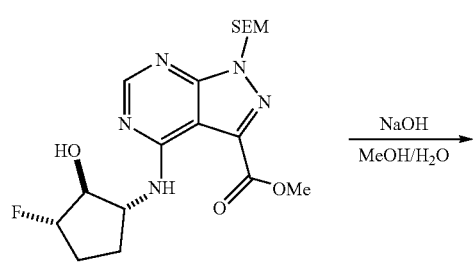

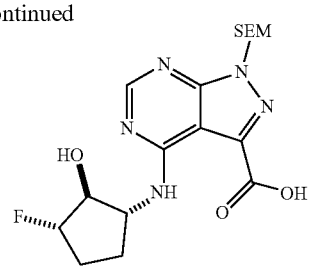

To a solution of methyl 4-(((1R,2S,3S)-3-fluoro-2-hydroxycyclopentyl)amino)-1-((2-(trimethylsilyl)ethoxy)methyl)-1H-pyrazolo[3,4-d]pyrimidine-3-carboxylate (700.00 mg, 1.65 mmol) in MeOH/H₂O (15 mL, v/v=2/1) was added NaOH (132.00 mg, 3.30 mmol) in one portion, which was stirred at 25° C. for 2 hrs. After LCMS showed the reaction was complete, the mixture was concentrated in reduced pressure at 40° C. The aqueous phase was adjusted to pH=4 and filtered to afford 4-(((1R,2S,3S)-3-fluoro-2-hydroxycyclopentyl)amino)-1-((2-(trimethylsilyl)ethoxy)methyl)-1H-pyrazolo[3,4-d]pyrimidine-3-carboxylic acid (700.00 mg, crude) as a white solid.

Step 4: N-(2,5-difluorobenzyl)-4-(((1R,2S,3S)-3-fluoro-2-hydroxycyclopentyl)amino)-1-((2-(trimethylsilyl)ethoxy)methyl)-1H-pyrazolo[3,4-d]pyrimidine-3-carboxamide

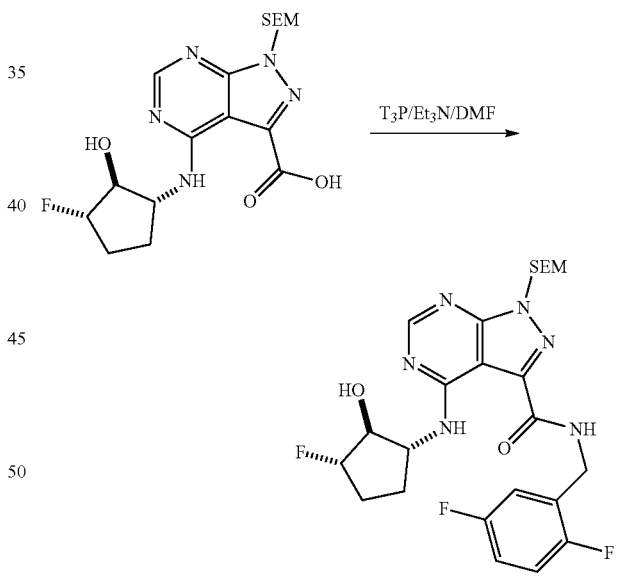

To a mixture of 4-(((1R,2S,3S)-3-fluoro-2-hydroxycyclopentyl)amino)-1-((2-(trimethylsilyl)ethoxy)methyl)-1H-pyrazolo[3,4-d]pyrimidine-3-carboxylic acid (100.00 mg, 243.01 umol) and T₃P (231.97 mg, 729.04 umol) was added Et₃N (49.18 mg, 486.03 umol) in DMF (2.00 mL) at 25° C., followed by the addition of (2,5-difluorophenyl)methanamine (69.57 mg, 486.03 umol) in one portion after 10 min. The mixture was stirred at 25° C. for 16 hrs. After LCMS showed the reaction was complete, the mixture was concentrated under reduced pressure at 60° C. to afford N-(2,5-difluorobenzyl)-4-(((1R,2S,3S)-3-fluoro-2-hydroxycyclopentyl)amino)-1-((2-(trimethylsilyl)ethoxy)methyl)-

1H-pyrazolo[3,4-d]pyrimidine-3-carboxamide (200 mg, crude). The residue was not purified and used directly.

Step 5: N-(2,5-difluorobenzyl)-4-(((1R,2S,3S)-3-fluoro-2-hydroxycyclopentyl)amino)-1H-pyrazolo[3,4-d]pyrimidine-3-carboxamide and N-(2,5-difluorobenzyl)-4-(((1S,2R,3R)-3-fluoro-2-hydroxycyclopentyl)amino)-1H-pyrazolo[3,4-d]pyrimidine-3-carboxamide

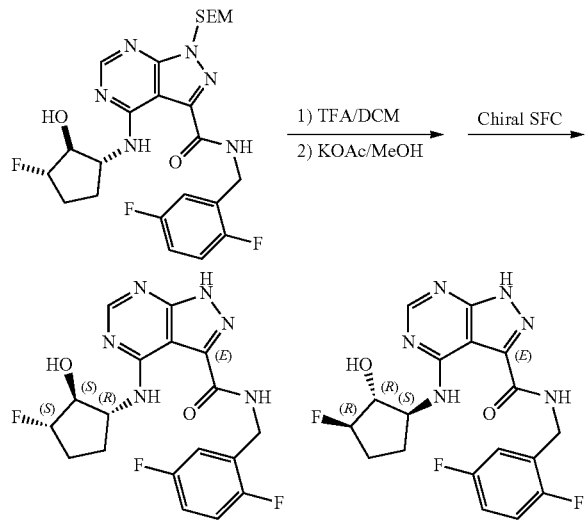

A mixture of N-(2,5-difluorobenzyl)-4-(((1R,2S,3S)-3-fluoro-2-hydroxycyclopentyl)amino)-1-((2-(trimethylsilyl)ethoxy)methyl)-1H-pyrazolo[3,4-d]pyrimidine-3-carboxamide (200.00 mg, 372.70 umol) in TFA/DCM (15.00 mL, v/v=1/1) was stirred at 25° C. for 3 hrs, then concentrated under reduced pressure at 30° C. To the residue was added MeOH (20 mL) and KOAc (100 mg), and the mixture was stirred for 16 hrs at 25° C. Once LCMS showed the reaction was complete, the mixture was concentrated under reduced pressure at 30° C. The residue was purified by acidic preparative HPLC followed by chiral preparative HPLC to afford N-(2,5-difluorobenzyl)-4-(((1R,2S,3S)-3-fluoro-2-hydroxycyclopentyl)amino)-1H-pyrazolo[3,4-d]pyrimidine-3-carboxamide (25.00 mg, yield: 16.51%) as a white solid and N-(2,5-difluorobenzyl)-4-(((1S,2R,3R)-3-fluoro-2-hydroxycyclopentyl)amino)-1H-pyrazolo[3,4-d]pyrimidine-3-carboxamide (30.00 mg, yield: 19.81%) as a grey solid. LC-MS conditions for these compounds were as follows: flow rate=0.8 mL·min$^{-1}$, mobile phase: from 95% [water+10 mM NH$_4$HCO$_3$] and 5% CH$_3$CN, under this condition for 0.4 min, then changed to 10% [water+10 mM NH$_4$HCO$_3$] and 90% CH$_3$CN in 2.6 min, then changed to 100% CH$_3$CN in 0.85 min, finally changed to 95% [water+10 mM NH$_4$HCO$_3$] and 5% CH$_3$CN in 0.01 min, then under this condition for 0.64 min. 97.125% purity and 97.690% purity, respectively.

Synthesis of Amine Intermediates

Example 4: Synthesis of (1R,2S,3R)-3-aminocyclopentane-1,2-diol

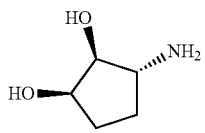

Step 1: (3aS,4S,6aR)-2,2-Dimethyltetrahydro-4H-cyclopenta[d][1,3]dioxol-4-ol

To a solution of (3aR,6aR)-2,2-dimethyl-3a,6a-dihydro-4H-cyclopenta[d][1,3]dioxol-4-one (92.00 g, 596.78 mmol, 1.00 eq) in MeOH (2.00 L) was added Pd—C (10%, 12 g). The suspension was degassed under vacuum and purged with H$_2$ several times. The mixture was stirred under H$_2$ (30 psi) at 20° C. for 4 hrs, at which point TLC (PE:EtOAc=3:1) showed the starting material was consumed completely. The reaction mixture was filtered, and to the filtrate was added NaBH$_4$ (34.09 g, 901.14 mmol, 1.51 eq) in portions at 0° C., and the resulting mixture was stirred at 20° C. for 0.5 hr. The mixture was then concentrated, and to the residue was added H$_2$O (500 mL). The mixture was extracted with EtOAc (500 mL*3), dried over Na$_2$SO$_4$, and concentrated to give (3aS,4S,6aR)-2,2-dimethyltetrahydro-4H-cyclopenta[d][1,3]dioxol-4-ol (84.00 g, yield: 88.98%) as a yellow oil. $^1$H-NMR (400 MHz, CDCl$_3$) δ ppm 4.60 (t, 1H, J=5.2 Hz), 4.39 (t, 1H, J=5.6 Hz), 3.83 (br.s, 1H), 2.37-2.35 (m, 1H), 1.88-1.76 (m, 2H), 1.65-1.56 (m, 1H), 1.48 (s, 3H), 1.45-1.36 (m, 1H), 1.33 (s, 3H).

Step 2: 2-((3aS,4R,6aR)-2,2-Dimethyltetrahydro-4H-cyclopenta[d][1,3]dioxol-4-yl)isoindoline-1,3-dione To a stirred mixture of (3aS,4S,6aR)-2,2-dimethyltetrahydro-4H-cyclopenta[d][1,3]dioxol-4-ol (70.00 g, 442.51 mmol, 1.00 eq), isoindoline-1,3-dione (80.00 g, 543.74 mmol, 1.23 eq) and PPh$_3$ (175.00 g, 667.20 mmol, 1.51 eq) in dry toluene (1.00 L) under N$_2$ was added DIAD (135.00 g, 667.62 mmol, 1.51 eq) dropwise. The resulting mixture was stirred at 80° C. for 20 hrs under N$_2$. After TLC (PE:EtOAc=3:1) showed the starting material was consumed completely, the mixture was concentrated, and the residue was purified by column chromatography on silica gel (PE:EtOAc=80:1/50:1/20:1/10:1) to give 2-((3aS,4R,6aR)-2,2-dimethyltetrahydro-4H-cyclopenta[d][1,3]dioxol-4-yl)isoindoline-1,3-dione (90.00 g, yield: 70.79%) as a white solid. $^1$H-NMR (400 MHz, CDCl$_3$) δ ppm 7.82-7.80 (m, 2H), 7.72-7.70 (m, 2H), 5.03-4.96 (m, 2H), 4.61-4.60 (m, 1H), 2.28-2.20 (m, 2H), 1.94-1.85 (m, 2H), 1.50 (s, 3H), 1.31 (s, 3H)

Step 3: 3aS,4R,6aR)-2,2-Dimethyltetrahydro-4H-cyclopenta[d][1,3]dioxol-4-amine

A mixture of 2-((3aS,4R,6aR)-2,2-dimethyltetrahydro-4H-cyclopenta[d][1,3]dioxol-4-yl)isoindoline-1,3-dione (90.00 g, 313.25 mmol, 1.00 eq) and NH$_2$NH$_2$.H$_2$O (32.00 g, 626.50 mmol, 2.00 eq) in EtOH (600.00 mL) was stirred at 80° C. for 16 hrs. After TLC (PE:EtOAc=3:1) showed the starting material was consumed completely, the mixture was filtered and concentrated, and EtOH (500 mL) was added to the residue. After concentration to remove the solvent, PE (1000 mL) was added and the mixture filtered and concentrated to give (3aS,4R,6aR)-2,2-dimethyltetrahydro-4H-cyclopenta[d][1,3]dioxol-4-amine (41.00 g, crude) as a yellow oil, which was solidified by standing as a yellow crystal. $^1$H-NMR (400 MHz, CDCl$_3$) δ ppm 4.72 (t, 1H, J=5.2 Hz), 4.18 (d, 1H, J=5.6 Hz), 3.39 (d, 1H, J=4.0 Hz), 2.01-1.93 (m, 2H), 1.78-1.77 (m, 1H), 1.40 (s, 3H), 1.38-1.35 (m, 1H), 1.26 (s, 3H), 1.10 (br.s, 2H).

Step 4: (1R,2S,3R)-3-Aminocyclopentane-1,2-diol Hydrochloride

A mixture of (3aS,4R,6aR)-2,2-dimethyltetrahydro-4H-cyclopenta[d][1,3]dioxol-4-amine (10.00 g, 63.61 mmol, 1.00 eq) in H$_2$O (55.00 mL) and HCl (5.00 mL, 12 M) was stirred at 20° C. for 2 hrs. TLC (EtOAc:MeOH=10:1) showed the starting material was consumed completely. The mixture was concentrated to give (1R,2S,3R)-3-aminocyclopentane-1,2-diol hydrochloride (9.20 g, yield: 94.15%) as a yellow solid. $^1$H-NMR (400 MHz, CD$_3$OD) δ ppm 4.03 (br.s, 1H), 3.90 (dd, 1H, J=8.4, 4.4 Hz), 3.48-3.41 (m, 1H), 2.25-2.19 (m, 1H), 2.05-2.02 (m, 1H), 1.75-1.65 (m, 1H), 1.58-1.56 (m, 1H).

Example 5: Synthesis of (1R,2R,3S,4R,5S)-4-Aminobicyclo[3.1.0]hexane-2,3-diol

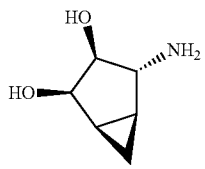

Step 1: (3aS,4S,6aR)-2,2-Dimethyl-3a,6a-dihydro-4H-cyclopenta[d][1,3]dioxol-4-ol To a 0° C. stirred mixture of (3aR,6aR)-2,2-dimethyl-3a,6a-dihydro-4H-cyclopenta[d][1,3]dioxol-4-one (90.00 g, 583.81 mmol, 1.00 eq) and CeCl$_3$.7H$_2$O (240.00 g, 644.16 mmol, 1.10 eq) in MeOH (2.00 L) was added NaBH$_4$ (44.00 g, 1.16 mol, 1.99 eq) in portions over 0.5 hr. After addition, the mixture was stirred at 18° C. for 0.5 hr. TLC (PE:EtOAc=3:1) showed the starting material was consumed completely. The mixture was concentrated, and to the residue was added EtOAc (2000 mL) and the solution stirred at 18° C. for 0.5 hr. The mixture was then filtered, the filtrate was dried over Na$_2$SO$_4$ and concentrated to give the crude product (3aS,4S,6aR)-2,2-dimethyl-3a,6a-dihydro-4H-cyclopenta[d][1,3]dioxol-4-ol (79.00 g, crude) as a light yellow oil which was used directly to the next step without further purification. $^1$H-NMR (400 MHz, CDCl$_3$) δ ppm 5.88 (s, 2H), 5.01 (d, 1H, J=5.6 Hz), 4.74 (t, 1H, J=5.6 Hz), 4.55 (dd, 1H, J=9.6, 5.6 Hz), 2.76 (d, 1H, J=9.6 Hz), 1.43 (s, 3H), 1.40 (s, 3H).

Step 2: 3aR,3bR,4aS,5S,5aS)-2,2-Dimethylhexahydrocyclopropa[3,4]cyclopenta[1,2-d][1,3]dioxol-5-ol To a 0° C. stirred mixture of (3aS,4S,6aR)-2,2-dimethyl-3a,6a-dihydro-4H-cyclopenta[d][1,3]dioxol-4-ol (40.00 g, 256.11 mmol, 1.00 eq) in DCM (50.00 mL) was added dropwise ZnEt$_2$ (1 M, 1.00 L, 3.90 eq). After 15 min, CH$_2$I$_2$ (550.00 g, 2.05 mol, 8.02 eq) was added into the mixture, which was stirred at 20° C. for 16 hrs. TLC (PE:EtOAc=1:1) showed the starting material was consumed. The mixture was quenched by saturated NH$_4$Cl solution (200 mL), followed by addition of H$_2$O (500 mL). The mixture was extracted with DCM (500 mL*5), and the combined organic layers were dried over Na$_2$SO$_4$ and concentrated to give the crude product. The crude product was purified by column chromatography on silica gel (PE:EtOAc=0:1/100:1/80:1/50:1/20:1/10:1/5:1) to give (3aR,3bR,4aS,5S,5aS)-2,2-dimethylhexahydrocyclopropa[3,4]-cyclopenta[1,2-d][1,3]dioxol-5-ol (18.00 g, yield: 41.29%) as a light yellow oil. $^1$H-NMR (400 MHz, CDCl$_3$) δ ppm 4.87 (t, 1H, J=6.0 Hz), 4.53-4.45 (m, 2H), 2.34 (br.s, 1H), 1.85-1.82 (m, 1H), 1.64-1.62 (m, 1H), 1.54 (s, 3H), 1.28 (s, 3H), 0.98-0.94 (m, 1H), 0.63-0.60 (m, 1H).

Step 3: 2-((3aR,3bR,4aS,5R,5aS)-2,2-dimethylhexahydrocyclopropa[3,4]cyclopenta[1,2-d][1,3]dioxol-5-yl)isoindoline-1,3-dione To a stirred mixture of (3aR,3bR,4aS,5S,5aS)-2,2-dimethylhexahydrocyclopropa[3,4]-cyclopenta[1,2-d][1,3]dioxol-5-ol (10.00 g, 58.75 mmol, 1.00 eq), isoindoline-1,3-dione (12.00 g, 81.56 mmol, 1.39 eq) and PPh$_3$ (24.00 g, 91.50 mmol, 1.56 eq) in dry toluene (500.00 mL) under N$_2$ was added DIAD (20.00 g, 98.91 mmol, 1.68 eq) dropwise. The resulting mixture was stirred at 80° C. for 20 hrs under N$_2$. TLC (PE:EtOAc=3:1) showed the starting material was consumed completely. The mixture was concentrated, and the residue was purified by column chromatography on silica gel (PE:EtOAc=80:1/50:1/30:1/20:1/10:1) to give 2-((3aR,3bR,4aS,5R,5aS)-2,2-dimethylhexahydrocyclopropa[3,4]-cyclopenta[1,2-d][1,3]dioxol-5-yl)isoindoline-1,3-dione (14.00 g, yield: 79.61%) as a light yellow oil. $^1$H-NMR (400 MHz, CDCl$_3$) δ ppm 7.86-7.83 (m, 2H), 7.74-7.72 (m, 2H), 5.37-5.34 (m, 1H), 4.78-4.76 (m, 1H), 4.73 (s, 1H), 2.01-1.95 (m, 1H), 1.51 (s, 3H), 1.47-1.42 (m, 1H), 1.24 (s, 3H), 0.85-0.79 (m, 2H).

Step 4: (3aR,3bR,4aS,5R,5aS)-2,2-Dimethylhexahydrocyclopropa[3,4]cyclopenta[1,2-d][1,3]dioxol-5-amine A mixture of 2-((3aR,3bR,4aS,5R,5aS)-2,2-dimethylhexahydrocyclopropa[3,4]cyclopenta[1,2-d][1,3]dioxol-5-yl)isoindoline-1,3-dione (14.00 g, 46.77 mmol, 1.00 eq) and NH$_2$NH$_2$.H$_2$O (4.78 g, 93.54 mmol, 2.00 eq) in EtOH (200.00 mL) was stirred at 70° C. for 16 hrs. TLC (PE:EtOAc=3:1) showed the starting material was consumed completely. The mixture was filtered, the filtrate was concentrated, and to the residue was added EtOAc (20 mL). The mixture was then filtered, and concentrated to give (3aR,3bR,4aS,5R,5aS)-2,2-dimethylhexahydrocyclopropa[3,4]cyclopenta[1,2-d][1,3]dioxol-5-amine (7.00 g, yield: 88.45%) as a yellow oil. $^1$H-NMR (400 MHz, CDCl$_3$) δ ppm 5.06-5.03 (m, 1H), 4.30 (d, 1H, J=6.8 Hz), 3.45 (s, 1H), 1.73-1.71 (m, 1H), 1.48 (s, 3H), 1.43-1.39 (m, 1H), 1.25 (s, 3H), 0.74-0.67 (m, 2H).

Step 5: (1R,2R,3S,4R,5S)-4-aminobicyclo[3.1.0]hexane-2,3-diol*HCl

A mixture of (3aR,3bR,4aS,5R,5aS)-2,2-dimethylhexahydrocyclopropa[3,4]cyclopenta[1,2-d][1,3]dioxol-5-amine (1.00 g, 63.61 mmol, 1.00 eq) in H$_2$O (5.500 mL) and HCl (0.5 mL, 12 M) was stirred at 15° C. for 2 hrs. TLC (EtOAc:MeOH=10:1) showed the starting material was consumed completely. The mixture was concentrated to give (1R,2R,3S,4R,5S)-4-aminobicyclo[3.1.0]hexane-2,3-diol*HCl (780 mg g, yield: 79.9%) as a yellow solid.

Example 6: Synthesis of (1S,2S,4S)-2-amino-4-fluorocyclopentan-1-ol (Relative Stereochemistry)

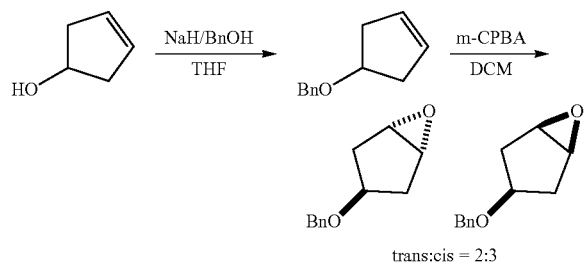

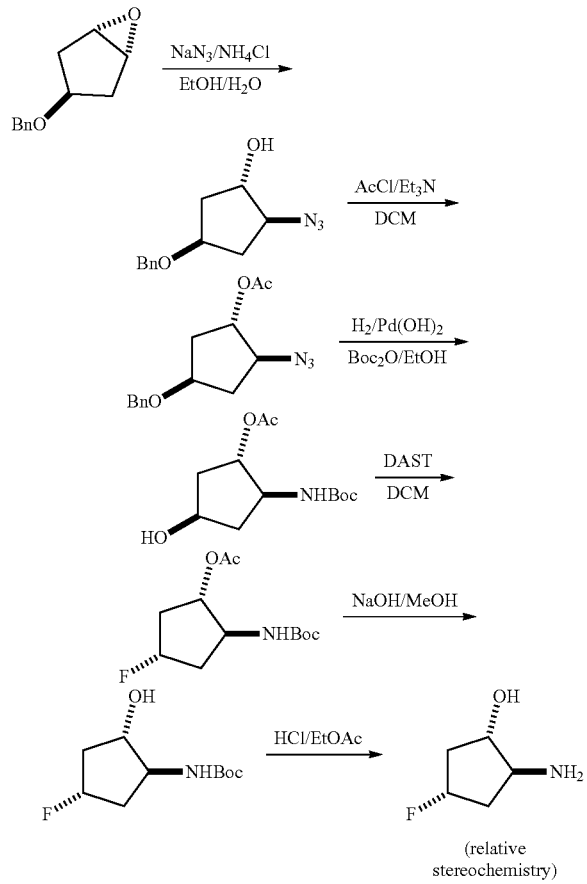

(relative stereochemistry)

Step 1: ((Cyclopent-3-en-1-yloxy)methyl)benzene

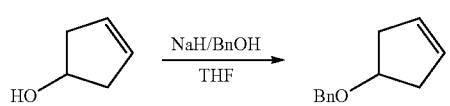 [SMILES: OC1CC=CC1 ; "NaH/BnOH" ; C1=CCC(OCc2ccccc2)C1 ; "THF"]

To a mixture of cyclopent-3-en-1-ol (60.00 g, 713.27 mmol) in THF (600.00 mL) was added NaH (37.09 g, 927.25 mmol) in portions at 0° C. After effervescence had ceased, bromomethylbenzene (158.59 g, 927.25 mmol) was added dropwise at 0° C. over 45 min period, then warmed to 25° C. and stirred for 16 hrs. TLC (PE/EtOAc=50/1) showed the reaction was complete. Excess NaH was quenched with MeOH (120 mL) at a temperature below 5° C. The mixture was warmed to 25° C., diluted with H$_2$O (600.00 mL), and the two layers were separated. The aqueous phase was extracted with ethyl acetate (200 mL*3). The combined organic phase was washed with brine (200 mL), dried over Na$_2$SO$_4$, filtered and concentrated in vacuum. The residue was purified by silica gel chromatography (PE/EtOAc=1/0) to afford ((cyclopent-3-en-1-yloxy)methyl)benzene (120.00 g, yield: 96.56%) as yellow oil. $^1$H-NMR (400 MHz, CDCl$_3$) δ ppm 7.38-7.28 (m, 5H), 5.72 (s, 2H), 4.52 (s, 2H), 4.35-4.30 (m, 1H), 2.64-2.59 (m, 2H), 2.50-2.46 (m, 2H).

Step 2: (1R,3S,5S)-3-(benzyloxy)-6-oxabicyclo[3.1.0]hexane and (1R,3r,5S)-3-(benzyloxy)-6-oxabicyclo[3.1.0]hexane

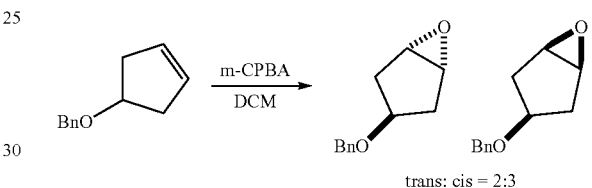

trans: cis = 2:3

To a mixture of ((cyclopent-3-en-1-yloxy)methyl)benzene (120.00 g, 688.71 mmol) in DCM (600.00 mL), was added m-CPBA (297.68 g, 1.38 mol) in one portion at 0° C. The mixture was stirred at 25° C. for 16 hrs. TLC (PE:EtOAc=20:1) showed the reaction was complete. The mixture was filtered and excess m-CPBA was reduced by the addition of saturated aq. Na$_2$SO$_3$ until a negative starch iodide test was observed. The mixture was filtered and concentrated in vacuum. The residue was purified by silica gel chromatography (PE:EtOAc=1:0, 20:1) to afford (1R,3R,5S)-3-(benzyloxy)-6-oxabicyclo[3.1.0]hexane (56.00 g, yield: 42.74%) and (1R,3S,5S)-3-(benzyloxy)-6-oxabicyclo[3.1.0]hexane (37.00 g, yield: 28.24%) as yellow oil. Spectra analysis of (1R,3S,5S)-3-(benzyloxy)-6-oxabicyclo[3.1.0]hexane. $^1$H-NMR (400 MHz, CDCl$_3$) δ ppm 7.31-7.20 (m, 5H), 4.36 (s, 2H), 3.84-3.74 (m, 1H), 3.43 (s, 2H), 2.51-2.35 (m, 2H), 1.66-1.57 (m, 2H). Spectra analysis of (1R,3R,5S)-3-(benzyloxy)-6-oxabicyclo[3.1.0]hexane $^1$H-NMR (400 MHz, CDCl$_3$) δ ppm 7.31-7.15 (m, 5H), 4.36 (s, 2H), 3.85-3.74 (m, 1H), 3.43 (s, 2H), 2.51-2.35 (m, 2H), 1.66-1.60 (m, 2H).

Step 3: (1S,2S,4R)-2-Azido-4-(benzyloxy)cyclopentan-1-ol

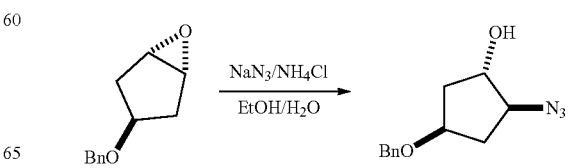

To a mixture of (1R,3S,5S)-3-(benzyloxy)-6-oxabicyclo[3.1.0]hexane (20.00 g, 105.13 mmol) in EtOH (760.00 mL) and H$_2$O (230.00 mL) was added NH$_4$Cl (20.98 g, 392.13 mmol), NaN$_3$ (24.00 g, 369.17 mmol) in one portion at 25° C. The mixture was heated to 80° C. and stirred for 16 hrs. TLC (PE:EtOAc=10:1) showed the reaction was complete. The mixture was cooled to 25° C. and EtOH was removed by N$_2$, and the aqueous phase was extracted with DCM (100 mL*3). The combined organic phase was washed with H$_2$O (30 mL*3), dried over Na$_2$SO$_4$, filtered and concentrated in vacuum to afford (1S,2S,4R)-2-azido-4-(benzyloxy)cyclopentan-1-ol (23.00 g, yield: 93.79%) as a yellow oil. $^1$H-NMR (400 MHz, CDCl$_3$) δ ppm 7.43-7.28 (m, 5H), 4.58-4.47 (m, 2H), 4.27-4.25 (m, 1H), 4.11-4.08 (m, 1H), 3.66-3.61 (m, 1H), 2.49-2.44 (m, 2H), 2.16-2.13 (m, 1H), 1.89 (br.s, 1H), 1.87-1.80 (m, 2H).

Step 4: (1S,2S,4R)-2-Azido-4-(benzyloxy)cyclopentyl Acetate

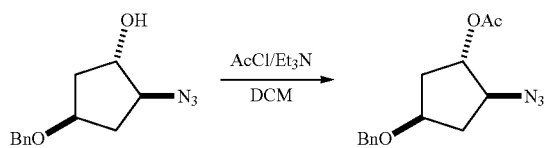

To a solution of (1S,2S,4R)-2-azido-4-(benzyloxy)cyclopentan-1-ol (22.90 g, 98.17 mmol), Et$_3$N (59.60 g, 589.02 mmol) in DCM (550 mL) was added a solution of acetylchloride (38.53 g, 490.85 mmol) in DCM (50 mL) dropwise at 0° C. over a period of 30 mins under N$_2$, during which the temperature was maintained below 5° C. The reaction mixture was then warmed to 25° C. and stirred for 16 hrs. TLC (PE:tOAc=10:1) showed the starting material was consumed completely. The reaction was quenched by the slow addition of H$_2$O (100 mL). The organic phase was washed with saturated brine (50 mL), dried over Na$_2$SO$_4$, filtered and concentrated in vacuo. The residue was purified by column chromatography on silica gel (PE:EtOAc=100:1, 50:1) to afford (1S,2S,4R)-2-azido-4-(benzyloxy)cyclopentyl acetate (17.00 g, yield: 62.90%) as yellow oil. $^1$H-NMR (400 MHz, CDCl$_3$) δ ppm 7.37-7.28 (m, 5H), 5.24-5.12 (m, 1H), 4.51 (s, 2H), 4.14-4.11 (m, 1H), 3.88-3.85 (m, 1H), 2.45-2.40 (m, 1H), 2.36-2.32 (m, 1H), 2.07 (s, 3H), 1.95-1.88 (m, 2H).

Step 5: (1S,2S,4R)-2-((tert-butoxycarbonyl)amino)-4-Hydroxycyclopentyl Acetate

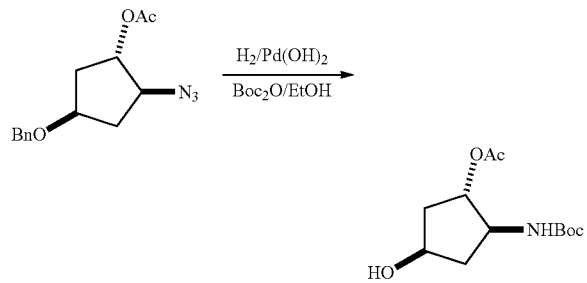

To a solution of (1S,2S,4R)-2-azido-4-(benzyloxy)cyclopentyl acetate (8.80 g, 31.97 mmol) in EtOH (100.00 mL) was added Pd(OH)$_2$ (4.42 g, 31.97 mmol) under N$_2$. The suspension was degassed under vacuum and purged with H$_2$ several times. The mixture was stirred under H$_2$ (50 psi) at 70° C. for 32 hrs. TLC (PE:EtOAc=2:1) showed the starting material was consumed completely. The reaction mixture was filtered and the filtrate was concentrated. The crude product was purified by silica gel chromatography (PE:EtOAc=10:1, 2:1) to give (1S,2S,4R)-2-((tert-butoxycarbonyl)amino)-4-hydroxycyclopentyl acetate (3.80 g, yield: 45.84%) as a yellow solid.

Step 6: (1S,2S,4S)-2-((tert-butoxycarbonyl)amino)-4-Fluorocyclopentyl Acetate

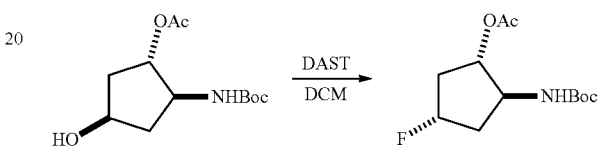

To a mixture of (1S,2S,4R)-2-((tert-butoxycarbonyl)amino)-4-hydroxycyclopentyl acetate (2.57 g, 9.91 mmol) in DCM (150.00 mL) was added DAST (2.40 g, 14.87 mmol) dropwise at −70° C. under N$_2$. The mixture was stirred at −70° C. for 30 min. TLC (PE:EtOAc=2:1) showed the reaction was complete. The mixture was cooled to 0° C. and aq. NaHCO$_3$ (5 mL, 10%) was added and allowed to stir for 10 min. The aqueous phase was extracted with EtOAc (15 mL*2), and the combined organic phase was washed with brine (10 mL), dried over Na$_2$SO$_4$, filtered, and concentrated in vacuum. The crude product was purified by silica gel chromatography (PE:AtOAc=20:1, 10:1) to give (1S,2S,4S)-2-((tert-butoxycarbonyl)amino)-4-fluorocyclopentyl acetate (700.00 mg, yield: 27.03%) as a yellow oil. $^1$H-NMR (400 MHz, CDCl$_3$) δ ppm 5.14 (s, 0.5H), 5.00 (br.s, 1H), 4.71 (s, 0.5H), 4.14-4.13 (m, 1H), 2.49-2.47 (m, 2H), 2.07-1.94 (m, 3H), 1.81-1.74 (m, 2H), 1.43-1.41 (m, 9H).

Step 7: tert-butyl ((1S,2S,4S)-4-Fluoro-2-hydroxycyclopentyl)carbamate

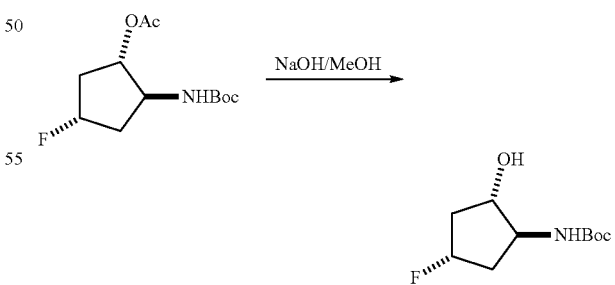

To a mixture of (1S,2S,4S)-2-((tert-butoxycarbonyl)amino)-4-fluorocyclopentyl acetate (700.00 mg, 2.68 mmol) in MeOH (20.00 mL) was added NaOH (160.80 mg, 4.02 mmol) in one portion. The mixture was stirred at 25° C. for 1 hr. TLC (PE:EtOAc=3:1) showed the reaction was complete. The mixture was concentrated under reduced pressure at 30° C. to afford tert-butyl ((1S,2S,4S)-4-fluoro-2-hydroxycyclopentyl)carbamate (650.00 mg, crude) as a white solid.

Step 8: (1S,2S,4S)-2-Amino-4-fluorocyclopentan-1-ol (Relative Stereochemistry)

The mixture of tert-butyl ((1S,2S,4S)-4-fluoro-2-hydroxycyclopentyl)carbamate (650.00 mg, 2.96 mmol) in MeOH/HCl (20.00 mL, 4 M) was stirred for 1 hr at 25° C. TLC (PE:EtOAc=2:1) showed the reaction was complete. The mixture was concentrated under reduced pressure at 30° C. to afford (1S,2S,4S)-2-amino-4-fluorocyclopentan-1-ol (relative stereochemistry) (400.00 mg, yield: 86.85%) as a white solid. $^1$H-NMR (400 MHz, DMSO-$d_6$) δ ppm 8.38 (br.s, 3H), 5.09 (d, 1H, J=53.6 Hz), 4.09-4.03 (m, 1H), 3.34-3.30 (m, 1H), 2.44-2.39 (m, 1H), 2.21-2.16 (m, 1H), 1.95-1.87 (m, 1H), 1.75-1.66 (m, 1H).

Example 7: Synthesis (1R,2R,4R)-2-amino-4-(methylsulfonyl)cyclopentan-1-ol (Relative Stereochemistry)

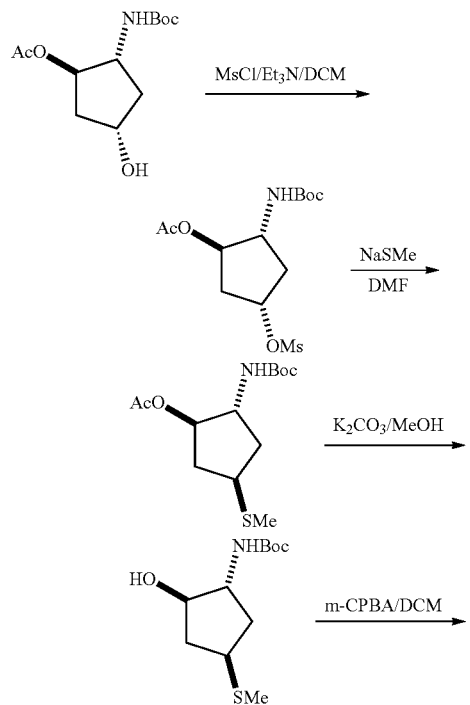

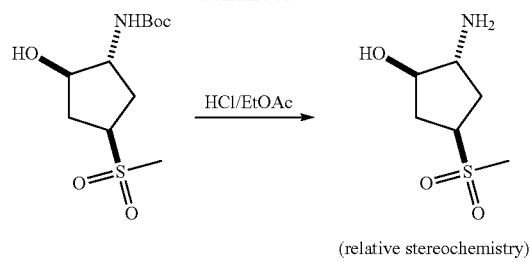

(relative stereochemistry)

Step 1: Preparation of (1R,2R,4S)-2-((tert-butoxycarbonyl)Amino)-4-((methylsulfonyl)oxy)cyclopentyl Acetate

To a mixture of (1R,2R,4S)-2-((tert-butoxycarbonyl)amino)-4-hydroxycyclopentyl acetate (3.00 g, 11.57 mmol) and Et$_3$N (4.68 g, 46.28 mmol) in DCM (50.00 mL) was added dropwise MsCl (3.98 g, 34.71 mmol) at 0° C., then the mixture was stirred at 20° C. for 3 hrs. TLC (PE:EtOAc=1:1) showed the reaction was complete. The mixture was washed with water (100 mL*3), then the organic layer was dried over Na$_2$SO$_4$ and concentrated to give (1R,2R,4S)-2-((tert-butoxycarbonyl)amino)-4-((methylsulfonyl)oxy)cyclopentyl acetate (3.5 g, crude: 100%) as a yellow solid.

Step 2: (1R,2R,4R)-2-((tert-butoxycarbonyl)amino)-4-(Methylthio)cyclopentyl Acetate

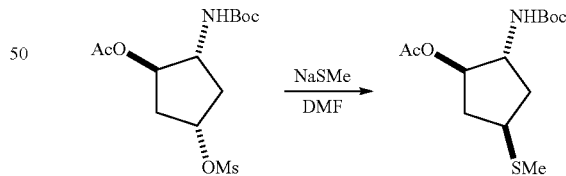

To a mixture of (1R,2R,4S)-2-((tert-butoxycarbonyl)amino)-4-((methylsulfonyl)oxy)cyclopentyl acetate (3.50 g, 10.37 mmol) in DMF (30.00 mL) was added NaSMe (4.36 g, 12.45 mmol). The mixture was then stirred at 90° C. for 2 hrs, and TLC (PE:EtOAc=2:1) showed the reaction was complete. The mixture was concentrated to give the crude (1R,2R,4R)-2-((tert-butoxycarbonyl)amino)-4-(methylthio)cyclopentyl acetate (3.00 g, crude 100%) as a yellow solid.

Step 3: tert-butyl ((1R,2R,4R)-2-Hydroxy-4-(methylthio)cyclopentyl)carbamate

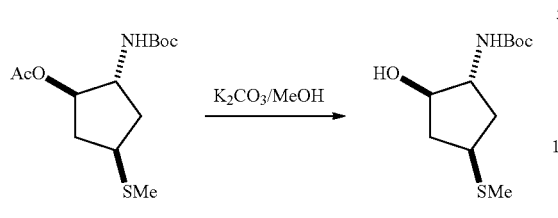

To a mixture of (1R,2R,4R)-2-((tert-butoxycarbonyl)amino)-4-(methylthio)cyclopentyl acetate (3.00 g, 10.37 mmol) in MeOH (100.00 mL) was added $K_2CO_3$ (2.87 g, 20.74 mmol). The mixture was stirred at 25° C. for 16 hrs. TLC (PE:EtOAc=2:1) showed the reaction was complete. The mixture was concentrated and purified by column chromatography on silica gel (PE:EtOAc=5:1-1:1) to give tert-butyl ((1R,2R,4R)-2-hydroxy-4-(methylthio)-cyclopentyl)carbamate (1.60 g, yield: 62.38%) as a white solid. $^1$H-NMR (400 MHz, $CDCl_3$) δ ppm 4.10-3.99 (m, 2H), 3.85 (br.s, 1H), 3.14-3.11 (m, 1H), 2.50-2.46 (m, 1H), 2.17-2.10 (m, 4H), 1.86-1.82 (m, 1H), 1.81-1.67 (m, 1H), 1.45 (s, 9H).

Step 4: tert-butyl ((1R,2R,4R)-2-Hydroxy-4-(methylsulfonyl)cyclopentyl)carbamate

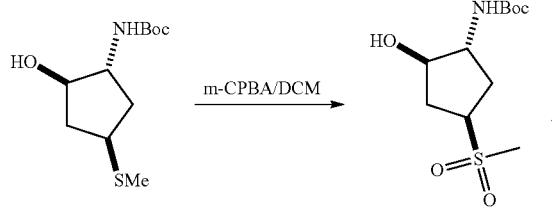

To a mixture of tert-butyl ((1R,2R,4R)-2-hydroxy-4-(methylthio)cyclopentyl)carbamate (1.60 g, 6.47 mmol) in DCM (100.00 mL) was added m-CPBA (3.49 g, 16.18 mmol). The mixture was stirred at 25° C. for 16 hrs. After TLC (PE:EtOAc=2:1) showed the starting material was consumed completely, the mixture was washed with saturated $Na_2SO_3$ (aq. 20 mL) and saturated $NaHCO_3$ (aq. 20 mL*3). The organic layer was then dried over $Na_2SO_4$, concentrated, washed with PE (10 mL), filtered, and the filter cake was dried under vacuum to give tert-butyl ((1R,2R,4R)-2-hydroxy-4-(methylsulfonyl)cyclopentyl)carbamate (1.70 g, yield: 94.06%) as a white solid. $^1$H-NMR (400 MHz, $CDCl_3$) δ ppm 4.62 (br.s, 1H), 4.07-4.04 (m, 1H), 3.81-3.79 (m, 1H), 3.48-3.45 (m, 1H), 2.82 (s, 3H), 2.57-2.40 (m, 2H), 2.11-2.07 (m, 1H), 1.90-1.87 (m, 2H), 1.38 (s, 9H).

Step 5: (1R,2R,4R)-2-Amino-4-(methylsulfonyl)cyclopentan-1-ol (Relative Stereochemistry)

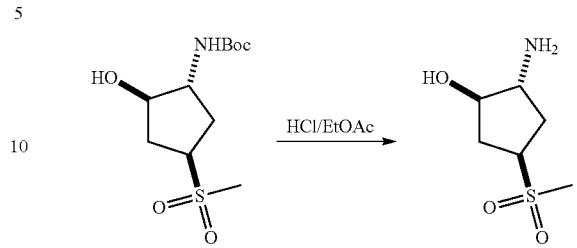

The mixture of tert-butyl ((1R,2R,4R)-2-hydroxy-4-(methylsulfonyl)cyclopentyl)carbamate (1.2 g, 4.30 mmol) in HCl/MeOH (10.00 mL) was stirred at 25° C. for 16 hrs, after which LCMS showed the reaction was complete, and the mixture was concentrated to give (1R,2R,4R)-2-amino-4-(methylsulfonyl)cyclopentan-1-ol (1.0 g, crude: 100%) as a yellow solid. $^1$H-NMR (400 MHz, $CD_3OD$) δ ppm 4.11-4.07 (m, 2H), 3.76 (br.s, 1H), 2.94 (s, 3H), 2.53 (br.s, 2H), 1.99 (br.s, 2H).

Example 8: Synthesis of (1S,2R,5R)-2-Amino-5-fluorocyclopentan-1-ol Hydrochloride (Relative Stereochemistry)

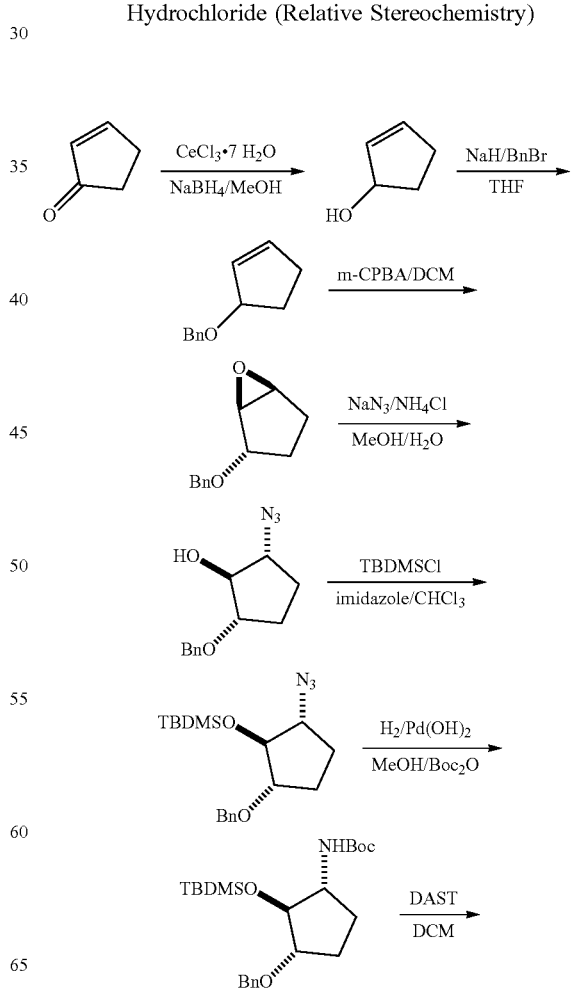

-continued

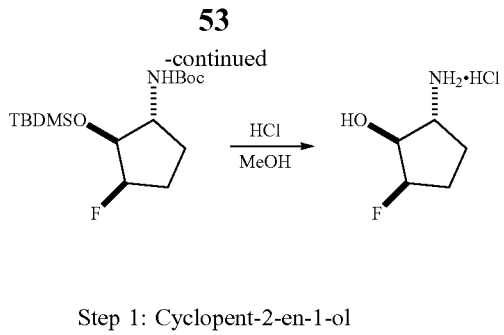

Step 1: Cyclopent-2-en-1-ol

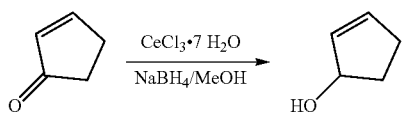 [SMILES: O=C1C=CCC1 ; "CeCl3·7 H2O" ; "NaBH4/MeOH" ; OC1C=CCC1]

To a mixture of CeCl₃·7H₂O (24.00 g, 64.42 mmol) in MeOH (120.00 mL) was added cyclopent-2-en-1-one (5.00 g, 60.90 mmol) at 15° C. After 5 min, NaBH₄ (4.61 g, 121.80 mmol) was added into the mixture in portions at 0° C. The resulting mixture was stirred at 25° C. for 1 hr, after which TLC (PE:EtOAc=5:1) showed several spots were generated and a part of the starting material was remained. The reaction was quenched by H₂O (100 mL) and the organic solvent was concentrated in vacuum. To the residue was added H₂O (300 mL), followed by extraction with MTBE (200 mL*3). The combined organic layers were dried over Na₂SO₄ and concentrated under vacuum to give the crude product cyclopent-2-en-1-ol (3.00 g, crude) as a brown oil. It was used directly to the next step without further purification. $^1$H-NMR (400 MHz, CDCl₃) δ ppm 5.91 (d, 1H, J=4.8 Hz), 5.77-5.76 (m, 1H), 4.79 (d, 1H, J=3.6 Hz), 2.47-2.42 (m, 1H), 2.21-2.15 (m, 2H), 1.64-1.59 (m, 1H).

Step 2: ((Cyclopent-2-en-1-yloxy)methyl)benzene

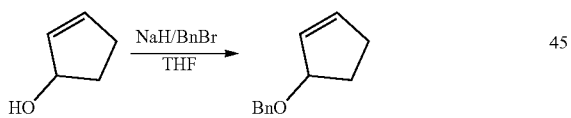

To a mixture of cyclopent-2-en-1-ol (9.00 g, 106.99 mmol) in THF (200.00 mL) was added NaH (6.80 g, 170.11 mmol) in portions at 0° C. After addition, the mixture was stirred at 20° C. for 0.5 hr, then BnBr (20.00 g, 116.94 mmol) was added into the mixture dropwise at 0° C. The resulting mixture was stirred at 20° C. for 2 hrs. TLC (PE:EtOAc=20:1) showed formation of a new species (R$_f$=0.6, 254 nm). At this point, H₂O (20 mL) was added, followed by extraction with EtOAc (20 mL*3). The combined organics were dried over Na₂SO₄ and concentrated to give the crude product, which was purified by column chromatography on silica gel (PE:EtOAc=1:0/100:1/80:1) to give ((cyclopent-2-en-1-yloxy)methyl)benzene (8.00 g, yield: 42.91%) as a yellow oil. $^1$H-NMR (400 MHz, CDCl₃) δ ppm 7.34-7.25 (m, 5H), 6.02 (br.s, 1H), 5.88 (br.s, 1H), 4.66 (br.s, 1H), 4.55-4.47 (m, 2H), 2.52-4.48 (m, 1H), 2.27-2.24 (m, 1H), 2.16-2.13 (m, 1H), 1.87-1.84 (m, 1H).

Step 3: (1S,2S,5S)-2-(Benzyloxy)-6-oxabicyclo[3.1.0]hexane

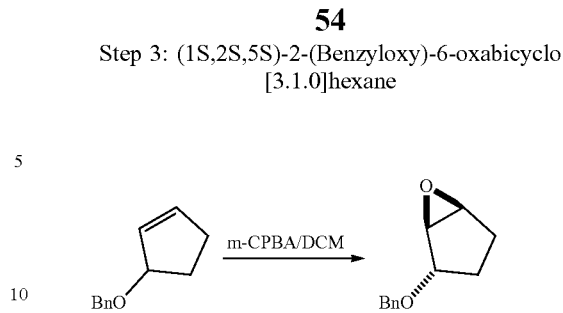

To a mixture of ((cyclopent-2-en-1-yloxy)methyl)benzene (8.50 g, 29.27 mmol) in DCM (50.00 mL) was added m-CPBA (13.50 g, 58.67 mmol) in portions at 0° C. The mixture was stirred at 25° C. for 4 hrs. Once TLC (PE:EtOAc=10:1) showed the starting material was consumed completely, the mixture was filtered, the filtrate was concentrated and purified by column chromatography on silica gel (PE:EtOAc=1:0/100:1/80:1/50:1) to give the crude product. DCM (20 mL) was then added, the mixture filtered, and H₂O (20 mL) and Na₂CO₃ (500 mg) were added to the filtrate, followed by stirring of the mixture at 25° C. for 0.5 hr. The mixture was then extracted with DCM (20 mL*3), dried over Na₂SO₄, and concentrated to give (1S,2S,5S)-2-(benzyloxy)-6-oxabicyclo[3.1.0]hexane (2.40 g, yield: 43.10%) as a colorless oil, which was confirmed by NOE. $^1$H-NMR (400 MHz, CDCl₃) δ ppm 7.37-7.26 (m, 5H), 4.61-4.51 (m, 2H), 4.09 (d, 1H, J=5.2 Hz), 3.55 (br.s, 1H), 3.49 (br.s, 1H), 1.99-1.95 (m, 1H), 1.87-1.75 (m, 2H), 1.54-1.52 (m, 1H).

Step 4: (1S,2R,5S)-2-Azido-5-(benzyloxy)cyclopentan-1-ol

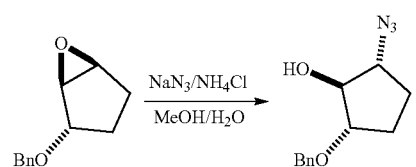

To a mixture of (1S,2S,5S)-2-(benzyloxy)-6-oxabicyclo[3.1.0]hexane (2.40 g, 12.62 mmol) and NH₄Cl (1.55 g, 29.03 mmol) in H₂O (3.00 mL) and MeOH (24.00 mL) was added NaN₃ (4.10 g, 63.10 mmol), which was stirred at 80° C. for 16 hrs. After TLC (PE:EtOAc=10:1) showed the starting material was consumed, the organic solvent was dried by N₂ and the residue was diluted with H₂O (20 mL), extracted with DCM (20 mL*3). The combined organic phases were washed with H₂O (10 mL*3), dried over Na₂SO₄, and concentrated to give (1S,2R,5S)-2-azido-5-(benzyloxy)cyclopentan-1-ol (2.60 g, yield: 88.32%) as a brown oil. $^1$H-NMR (400 MHz, CDCl₃) δ ppm 7.42-7.31 (m, 5H), 4.64-4.55 (m, 2H), 4.02-3.99 (m, 1H), 3.82-3.80 (m, 1H), 3.66-3.63 (m, 1H), 2.25 (br.s, 1H), 2.07-2.01 (m, 2H), 1.80-1.77 (m, 2H).

Step 5: (((1S,2R,5S)-2-Azido-5-(benzyloxy)cyclopentyl)oxy)(tert-butyl)dimethylsilane

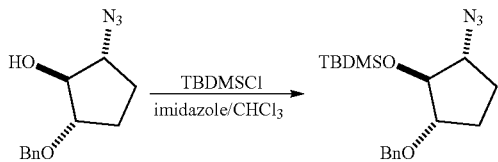

A mixture of (1S,2R,5S)-2-azido-5-(benzyloxy)cyclopentan-1-ol (2.50 g, 10.72 mmol), imidazole (1.61 g, 23.69 mmol) and TBDMSCl (2.42 g, 16.08 mmol) in CHCl$_3$ (5.00 mL) was stirred at 80° C. for 16 hrs. Once TLC (PE:EtOAc=10:1) showed the starting material was consumed completely, the mixture was concentrated and purified by column chromatography on silica gel (PE:EtOAc=1:0/100:1/80:1) to give (((1S,2R,5S)-2-azido-5-(benzyloxy)cyclopentyl)oxy)(tert-butyl)dimethylsilane (3.00 g, yield: 80.52%) as a colorless oil. $^1$H-NMR (400 MHz, CDCl$_3$) δ ppm 7.24-7.15 (m, 5H), 4.40 (d, 2H, J=2.4 Hz), 3.88-3.86 (m, 1H), 3.63-3.61 (m, 1H), 3.47-3.43 (m, 1H), 1.94-1.82 (m, 2H), 1.70-1.65 (m, 2H), 0.79 (s, 9H), 0.03 (s, 3H), 0.00 (s, 3H).

Step 6: tert-butyl ((1R,2S,3S)-2-((tert-butyldimethylsilyl)oxy)-3-Hydroxycyclopentyl)carbamate

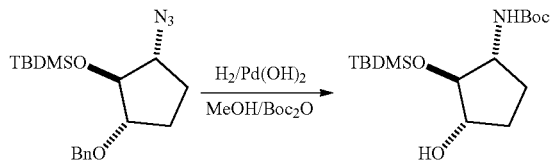 [SMILES: CC(C)(C)[Si](C)(C)O[C@@H]1[C@@H](OCc2ccccc2)CC[C@H]1N=[N+]=[N-] ; CC(C)(C)OC(=O)N[C@@H]1CC[C@H](O)[C@H]1O[Si](C)(C)C(C)(C)C]

To a mixture of (((1S,2R,5S)-2-azido-5-(benzyloxy)cyclopentyl)oxy)(tert-butyl)dimethylsilane (2.90 g, 8.34 mmol) and Boc$_2$O (2.20 g, 10.10 mmol) in MeOH (50.00 mL) was added Pd(OH)$_2$ (1.50 g, 5.42 mmol), which was stirred at 50° C. under H$_2$ (50 psi) for 20 hrs. After TLC (PE:EtOAc=3:1) showed the starting material was consumed completely, the mixture was filtered, and the filtrate was concentrated and purified by column chromatography on silica gel (PE:EtOAc=10:1/8:1/5:1) to give tert-butyl ((1R,2S,3S)-2-((tert-butyldimethylsilyl)oxy)-3-hydroxycyclopentyl)carbamate (2.10 g, yield: 75.95%) as a white solid. $^1$H-NMR (400 MHz, CDCl$_3$) δ ppm 4.81 (br.s, 1H), 3.89-3.88 (m, 1H), 3.70-3.67 (m, 2H), 2.06-1.89 (m, 2H), 1.58-1.56 (m, 2H), 1.35 (s, 9H), 0.79 (s, 9H), 0.02 (s, 3H), 0.00 (s, 3H).

Step 7: tert-butyl ((1R,2S,3R)-2-((tert-butyldimethylsilyl)oxy)-3-Fluorocyclopentyl)carbamate

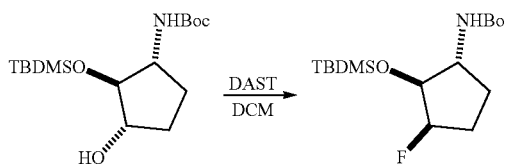

To a mixture of tert-butyl ((1R,2S,3S)-2-((tert-butyldimethylsilyl)oxy)-3-hydroxycyclopentyl)carbamate (1.10 g, 3.32 mmol) in DCM (50.00 mL) was added DAST (1.61 g, 9.96 mmol) at −70° C. The reaction mixture was stirred at −70° C. for 1 hr and 25° C. for 1 hr. After TLC (PE:EtOAc=5:1, R$_f$=0.6) showed the reaction was complete, ice water (5 mL) was added to the reaction. The solution was extracted with DCM (20 mL*3) and washed with brine (30 mL). The organic layer was dried over Na$_2$SO$_4$ and concentrated. The residue was purified by column chromatography on silica gel (PE:EtOAc=100:1) to give tert-butyl ((1R,2S,3R)-2-((tert-butyldimethylsilyl)oxy)-3-fluorocyclopentyl)carbamate (100.00 mg, yield: 9.03%) as a white solid. $^1$H-NMR (400 MHz, CDCl$_3$) δ ppm 4.64 (d, 1H, J=54.4 Hz), 4.26 (br.s, 1H), 3.90-3.86 (m, 1H), 3.76-3.68 (m, 1H), 2.11-1.79 (m, 4H), 1.34 (s, 9H), 0.81 (s, 9H), 0.00 (s, 6H).

Step 8: (1S,2R,5R)-2-Amino-5-fluorocyclopentan-1-ol Hydrochloride (Relative Stereochemistry)

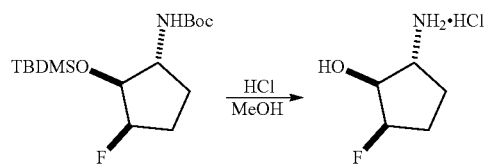

A solution of tert-butyl 1R,2S,3R)-2-((tert-butyldimethylsilyl)oxy)-3-fluorocyclopentyl)carbamate (100.00 mg, 299.84 umol) in HCl/MeOH (20.00 mL, 4 M) was stirred at 25° C. for 16 hrs. TLC (PE:EtOAc=5:1, R$_f$=0) showed the reaction was complete. The solution was dried by N$_2$, and (1S,2R,5R)-2-amino-5-fluorocyclopentan-1-ol hydrochloride (relative stereochemistry)(45.00 mg, yield: 96.45%) was obtained as a yellow solid. $^1$H-NMR (400 MHz, CD$_3$OD) δ ppm 4.93-4.89 (m, 1H), 3.98-3.88 (m, 1H), 3.52-3.47 (m, 1H), 2.30-2.00 (m, 3H), 1.66-1.62 (m, 1H).

Example 9: Synthesis of (1S,2R,5S)-2-amino-5-fluorocyclopentan-1-ol (Relative Stereochemistry)

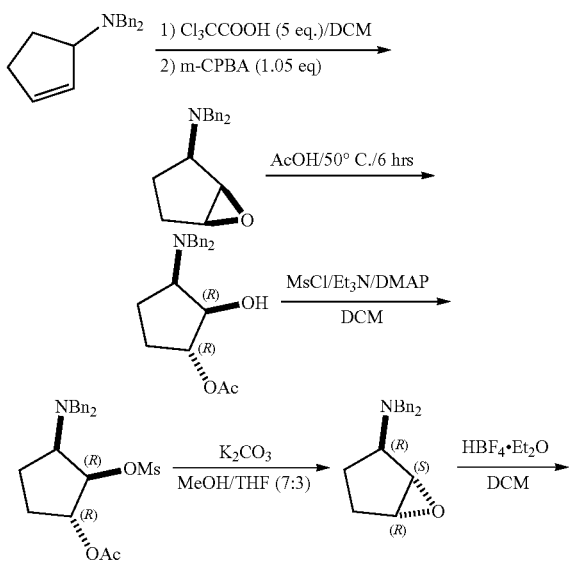

-continued

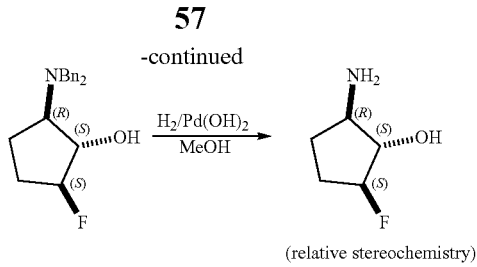

(relative stereochemistry)

Step 1: (1R,2R,5S)—N,N-Dibenzyl-6-oxabicyclo[3.1.0]hexan-2-amine

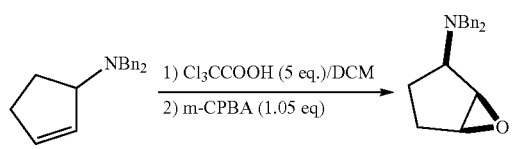

Cl₃CCOOH (154.72 g, 949.20 mmol) was added to a stirring solution of N,N-dibenzylcyclopent-2-en-1-amine (50.00 g, 189.84 mmol) in DCM (640 mL), and the resulting mixture was stirred at 20° C. for 0.1 hr. m-CPBA (43.00 g, 199.33 mmol) was added in one portion and the reaction mixture was allowed to continue to stir at 20° C. for 16 hrs. After TLC (PE:EtOAc=10:1) showed the reaction was complete, the mixture was diluted with DCM (500 mL) and sat. aq. Na₂SO₃ was added until starch-iodide paper indicated no remaining m-CPBA. Sat. aq. NaHCO₃ (500 mL) was added and the layers were separated. The organic layer was washed with aq. NaHCO₃ (200 mL*2) then dried, concentrated, and purified by column chromatography on silica gel (PE:EtOAc=100:1-50:1) to give (1R,2R,5S)—N,N-dibenzyl-6-oxabicyclo[3.1.0]hexan-2-amine (30.00 g, yield: 56.56%) as a white solid. ¹H-NMR (400 MHz, CDCl₃) δ ppm 7.41 (d, 4H, J=7.2 Hz), 7.31 (t, 4H, J=7.6 Hz), 7.25-7.22 (m, 2H), 3.86-3.70 (m, 4H), 3.44 (s, 1H), 3.32 (s, 1H), 3.28-3.24 (m, 1H), 2.04-2.01 (m, 1H), 1.54-1.45 (m, 3H).

Step 2: (1R,2R,3R)-3-(Dibenzylamino)-2-hydroxycyclopentyl Acetate

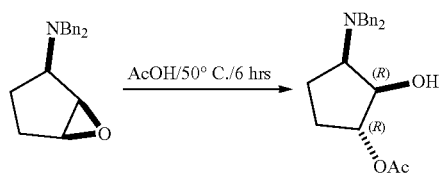

The solution of (1R,2R,5S)—N,N-dibenzyl-6-oxabicyclo[3.1.0]hexan-2-amine (30.00 g, 107.38 mmol, 1.00 Eq) in AcOH (200 mL) was stirred at 50° C. for 16 hrs. After TLC (PE:EtOAc=10:1) showed the reaction was complete, the mixture was concentrated to remove AcOH, the residue was dissolved in DCM (100 mL), and the organic layer was washed with aq. NaHCO₃ (100 mL*3), and dried over Na₂SO₄ and concentrated. The residue was purified by silica gel column chromatography (PE:EtOAc=100:1-50:1) to give (1R,2R,3R)-3-(dibenzylamino)-2-hydroxycyclopentyl acetate (20.00 g, yield: 54.87%) as a white solid. ¹H-NMR (400 MHz, CDCl₃) δ ppm 7.36-7.28 (m, 10H), 5.05-5.02 (m, 1H), 4.05 (d, 1H, J=4.0 Hz), 3.81-3.69 (m, 4H), 3.27-3.24 (m, 1H), 2.40-2.36 (m, 1H), 2.07 (s, 3H), 1.97-1.94 (m, 1H), 1.78-1.73 (m, 1H), 1.60-1.54 (m, 1H).

Step 3: (1R,2R,3R)-3-(Dibenzylamino)-2-((methylsulfonyl)oxy)cyclopentyl Acetate

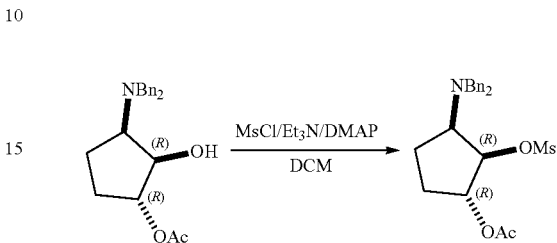

MSCl (8.10 g, 70.71 mmol) was added dropwise to a mixture of (1R,2R,3R)-3-(dibenzylamino)-2-hydroxycyclopentyl acetate (20.00 g, 58.92 mmol), Et₃N (18.48 g, 182.66 mmol) and DMAP (719.83 mg, 5.89 mmol) in DCM (200 mL). After addition, the mixture was stirred at 20° C. for 16 hrs. After TLC (PE:EtOAc=10:1) showed the reaction was complete, the mixture was washed with water (100 mL*2), the organic layer was dried over Na₂SO₄, and purified by column chromatography on silica gel (PE:EtOAc=80:1-60:1) to give (1R,2R,3R)-3-(dibenzylamino)-2-((methylsulfonyl)oxy)cyclopentyl acetate (15.00 g, yield: 60.97%) as a white solid. ¹H-NMR (400 MHz, CDCl₃) δ ppm 7.41 (d, 4H, J=7.6 Hz), 7.33 (t, 4H, J=6.8 Hz), 7.31-7.25 (m, 2H), 5.16-5.13 (m, 1H), 5.01-5.00 (m, 1H), 3.92-3.81 (m, 4H), 3.37-3.32 (m, 1H), 3.15 (s, 3H), 2.33-2.30 (m, 1H), 2.01 (s, 3H), 1.98-1.91 (m, 2H), 1.56-1.53 (m, 1H).

Step 4: (1S,2R,5R)—N,N-Dibenzyl-6-oxabicyclo[3.1.0]hexan-2-amine

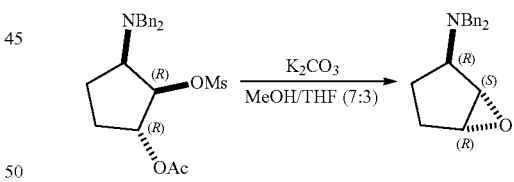

K₂CO₃ (5.96 g, 43.11 mmol) was added to a mixture of (1R,2R,3R)-3-(dibenzylamino)-2-((methylsulfonyl)oxy)cyclopentyl acetate (15.00 g, 35.93 mmol) in MeOH (70 mL)/THF (30 mL). The mixture was stirred at 20° C. for 16 hrs. After TLC (PE:EtOAc=10:1) showed the reaction was complete, the mixture was concentrated to remove MeOH and THF. The mixture was then dissolved in DCM (20 mL), the organic layer was washed with water (10 mL*2), dried over Na₂SO₄, and concentrated to give (1S,2R,5R)—N,N-dibenzyl-6-oxabicyclo[3.1.0]hexan-2-amine (10.00 g, yield: 99.62%) as a white solid. ¹H-NMR (400 MHz, CDCl₃) δ ppm 7.37 (d, 4H, J=7.6 Hz), 7.32 (d, 4H, J=7.2 Hz), 7.29-7.23 (m, 2H), 3.73-3.69 (m, 2H), 3.53-3.41 (m, 5H), 2.06-2.00 (m, 1H), 1.91-1.90 (m, 1H), 1.87-1.76 (m, 1H), 1.51-1.48 (m, 1H).

Step 5: (1S,2R,5S)-2-(Dibenzylamino)-5-fluorocyclopentan-1-ol

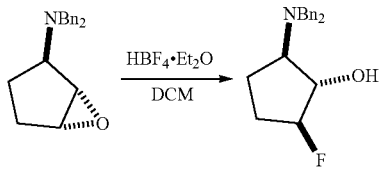

To a mixture of (1S,2R,5R)—N,N-dibenzyl-6-oxabicyclo[3.1.0]hexan-2-amine (6.50 g, 23.27 mmol) in DCM (200 mL) was added HBF$_4$/Et$_2$O (7.54 g, 46.53 mmol), and the mixture was allowed to stir at 30° C. for 0.2 hr. After TLC showed the reaction was complete, the mixture was added to Na$_2$CO$_3$ (100 mL) and extracted with DCM (200 mL*2). The organic layer was dried over Na$_2$SO$_4$, concentrated, and purified by column chromatography on silica gel (PE:EtOAc=60:1 to 20:1) to give (1S,2R,5S)-2-(dibenzylamino)-5-fluorocyclopentan-1-ol (1.80 g, yield: 25.84%) as a white solid. $^1$H-NMR (400 MHz, CDCl$_3$) δ ppm 7.38-7.22 (m, 10H), 4.81-4.67 (m, 1H), 4.23-4.15 (m, 1H), 3.83-3.55 (m, 4H), 3.04-2.98 (m, 1H), 1.93-1.79 (m, 4H).

Step 6: (1S,2R,5S)-2-Amino-5-fluorocyclopentan-1-ol (Relative Stereochemistry)

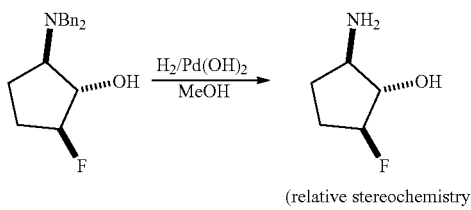

(relative stereochemistry)

To a mixture of (1S,2R,5S)-2-(dibenzylamino)-5-fluorocyclopentan-1-ol (1.60 g, 5.34 mmol) in MeOH (10 mL) was added Pd(OH)$_2$ (500.00 mg, 3.61 mmol), and the mixture was allowed to stir at 30° C. for 16 hrs under H$_2$ (30 psi). After TLC showed the reaction was complete, the mixture was filtered by celite and the filtrate was concentrated to give (1S,2R,5S)-2-amino-5-fluorocyclopentan-1-ol (600.00 mg, yield: 94.31%) as a white solid. $^1$H-NMR (400 MHz, CDCl$_3$) δ ppm 4.93-4.77 (m, 1H), 3.92-3.84 (m, 1H), 3.10-3.04 (m, 1H), 2.07-1.98 (m, 3H), 1.64-1.61 (m, 1H).

Example 10: Synthesis of 3-Fluoro-5-((2R,4S)-4-fluoropyrrolidin-2-yl)pyridine

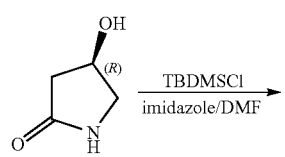

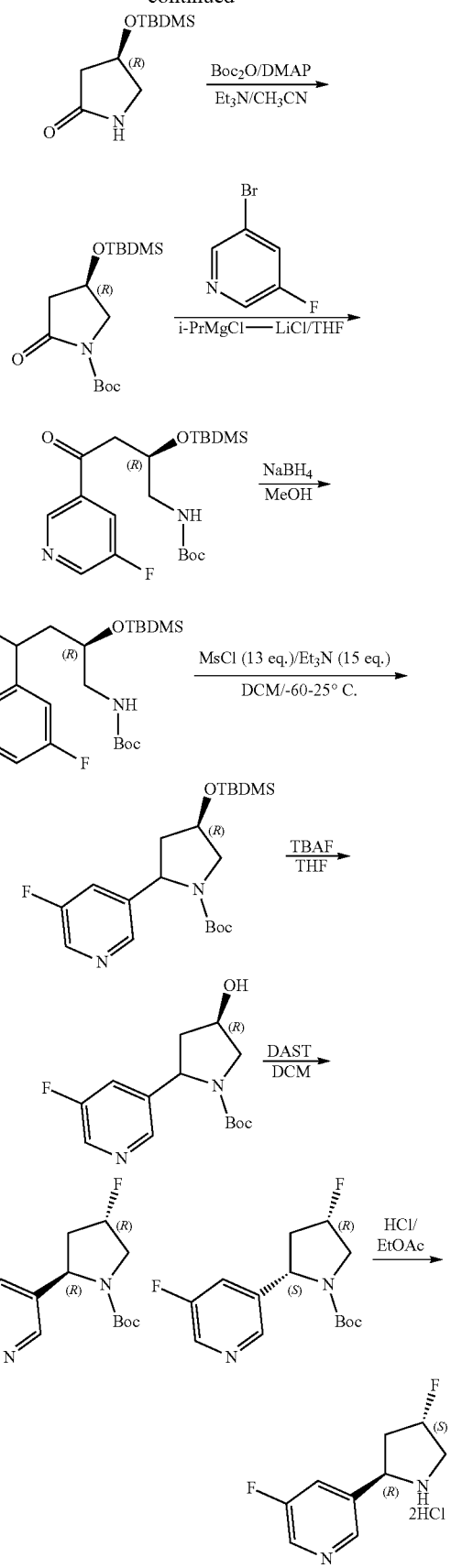

Step 1: (R)-4-((tert-butyldimethylsilyl)oxy)pyrrolidin-2-one

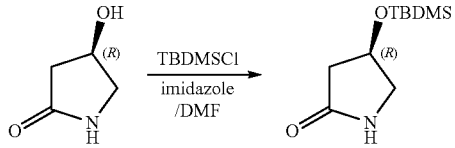

To the mixture of (R)-4-hydroxypyrrolidin-2-one (9.0 g, 89.1 mmol) in DMF (50 mL) was added imidazole (9.09 g, 134 mmol) and TBDMSCl (14.1 g, 93.6 mmol) in one portion at 0° C. The reaction mixture was stirred at 25° C. for 3 hrs. TLC (DCM/MeOH=10/1, $R_f$=0.8) showed the reaction was complete, then water (200 mL) was added the resulting precipitate was collected by filtration and dried in vacuo to give (R)-4-((tert-butyldimethylsilyl)oxy)pyrrolidin-2-one (15.5 g, yield: 80.7%) as a white solid. $^1$H-NMR (400 MHz, CDCl$_3$) δ ppm 5.90 (br.s, 1H), 4.55-4.53 (m, 1H), 3.60-3.56 (m, 1H), 3.24-3.21 (m, 1H), 2.56-2.50 (m, 1H), 2.28-2.23 (m, 1H), 0.87-0.85 (m, 9H), 0.06-0.00 (m, 6H).

Step 2: Preparation of tert-butyl (R)-4-((tert-butyldimethylsilyl)oxy)-2-oxopyrrolidine-1-carboxylate

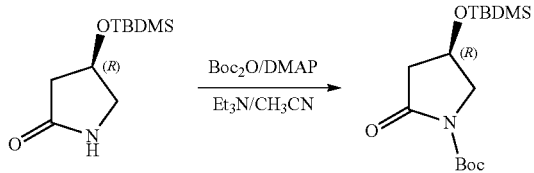

To the mixture of (R)-4-((tert-butyldimethylsilyl)oxy)pyrrolidin-2-one (15.5 g, 72.0 mmol) in CH$_3$CN (150 mL) was added Et$_3$N (8.72 g, 86.4 mmol), DMAP (4.39 g, 36 mmol), and Boc$_2$O (20.4 g, 93.7 mmol) in one portion at 0° C. The reaction mixture was stirred at 25° C. for 10 hrs. TLC (PE/EtOAc=3/1) showed the reaction was complete, then water (600 mL) was added, the resulting precipitate was collected by filtration and dried in vacuo to give tert-butyl (R)-4-((tert-butyldimethylsilyl)oxy)-2-oxopyrrolidine-1-carboxylate (19.2 g, yield: 84.6%) as a pink solid. $^1$H-NMR (400 MHz, CDCl$_3$) δ ppm 4.33-4.30 (m, 1H), 3.81-3.77 (m, 1H), 3.56-3.54 (m, 1H), 2.67-2.61 (m, 1H), 2.41-2.37 (m, 1H), 1.46 (s, 9H), 0.80 (s, 9H), 0.00 (s, 6H).

Step 3: tert-butyl ((2R)-2-((tert-butyldimethylsilyl)oxy)-4-(5-fluoropyridin-3-yl)-4-hydroxybutyl)carbamate

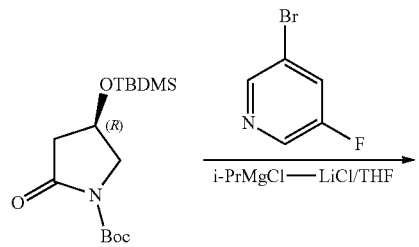

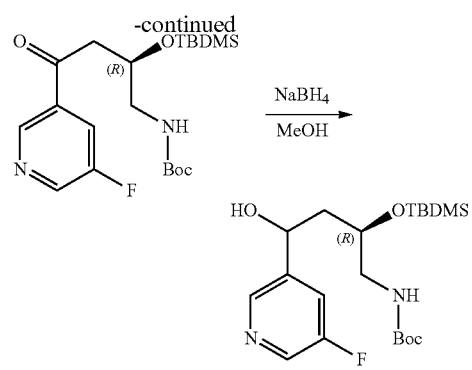

To the mixture of 3-bromo-5-fluoro-pyridine (3.35 g, 19.02 mmol, 1.20 eq) in THF (40.00 mL) was added i-PrMgCl—LiCl (1.3 M, 17.56 mL, 1.44 eq) dropwise at 0° C. over 30 mins (exothermic). After addition, the temperature was raised to 25° C. over 1 hr and stirred at 25° C. for 30 mins. TLC (PE/EtOAc=10/1) showed a new spot was generated indicating that the Mg reagent was prepared successfully. Tert-butyl (R)-4-((tert-butyldimethylsilyl)oxy)-2-oxopyrrolidine-1-carboxylate (5.00 g, 15.85 mmol, 1.00 eq) in THF (50 mL) was then added dropwise to the solution at −78° C. over 30 mins. The mixture was allowed to warm to 25° C. over 1 hr, then stirred at 25° C. for 16 hrs. TLC (PE/EtOAc=3/1) showed the starting material was consumed completely and the desired product tert-butyl (R)-(2-((tert-butyldimethylsilyl)oxy)-4-(5-fluoropyridin-3-yl)-4-oxobutyl)carbamate was detected. The reaction was quenched by addition of MeOH (50 mL) at 0° C. NaBH$_4$ (1.20 g, 31.70 mmol, 2.00 eq) was added at 0° C., then the mixture was stirred at 25° C. for 4 hrs. TLC (PE/EtOAc=2/1) and LCMS showed the reaction was complete. The combined reaction mixture (4 parallel reactions) was quenched by aqueous NH$_4$Cl (400 mL) and extracted with EtOAc (600 mL*3). The combined organics were dried over Na$_2$SO$_4$ and concentrated in vacuo, and the residue was purified by HPLC to give tert-butyl ((2R)-2-((tert-butyldimethylsilyl)oxy)-4-(5-fluoropyridin-3-yl)-4-hydroxybutyl)carbamate (1.24 g, yield: 18.91%) as a yellow oil. $^1$H-NMR (400 MHz, CDCl$_3$) δ ppm 8.26-8.22 (m, 2H), 7.37 (d, 1H, J=8.8 Hz), 4.95-4.88 (m, 2H), 4.69 (br.s, 1H), 4.00-3.98 (m, 2H), 3.23-3.10 (m, 2H), 1.73 (br.s, 2H), 1.32 (s, 9H), 0.80-0.79 (m, 9H), 0.00 (s, 6H).

Step 4: tert-butyl (4R)-4-((tert-butyldimethylsilyl)oxy)-2-(5-fluoropyridin-3-yl)pyrrolidine-1-carboxylate

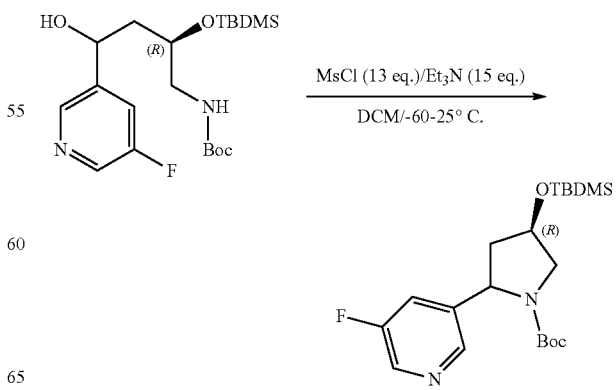

To the mixture of tert-butyl ((2R)-2-((tert-butyldimethylsilyl)oxy)-4-(5-fluoropyridin-3-yl)-4-hydroxybutyl)carbamate (8.70 g, 20.98 mmol, 1.00 eq) and Et₃N (31.84 g, 314.70 mmol, 15.00 eq) in DCM (500.00 mL) was added dropwise MsCl (31.24 g, 272.74 mmol, 13.00 eq) at −60° C. over 0.5 hr. The mixture was then stirred at −60° C. for 1 hr, and the reaction mixture was allowed to warm to 25° C. and stirred for 18 hrs. LCMS showed the starting material was consumed completely. The mixture was then washed with H₂O (200 mL*3), and the aqueous phase was extracted with DCM (200 mL*4). The combined organic layers were dried over Na₂SO₄ and concentrated in vacuo to give crude product tert-butyl (4R)-4-((tert-butyldimethylsilyl)oxy)-2-(5-fluoropyridin-3-yl)pyrrolidine-1-carboxylate (8.30 g, crude) as a black/brown oil, which was used directly without purification.

Step 5: tert-butyl (4R)-2-(5-fluoropyridin-3-yl)-4-hydroxypyrrolidine-1-carboxylate

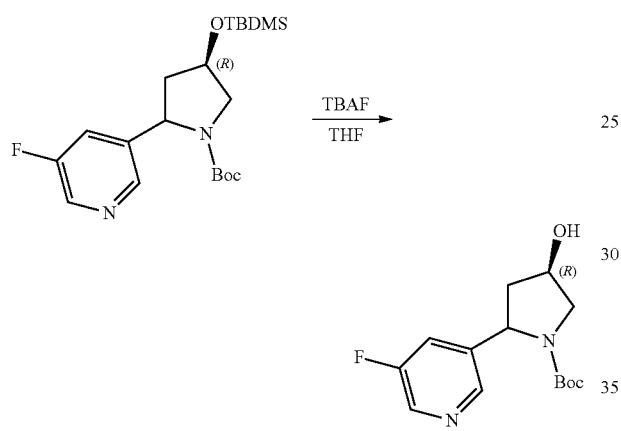

To the mixture of tert-butyl (4R)-4-((tert-butyldimethylsilyl)oxy)-2-(5-fluoropyridin-3-yl)pyrrolidine-1-carboxylate (8.30 g, 20.93 mmol, 1.00 eq) in THF (250.00 mL) was added TBAF (9.43 g, 41.86 mmol, 2.00 eq) at 25° C. The mixture was stirred at 25° C. for 16 hrs. After TLC (PE/EtOAc=1/1) showed the reaction was complete, the mixture was concentrated and the residue was dissolved in EtOAc (600 mL), washed with water (200 mL*5), dried over Na₂SO₄, and concentrated. The crude product was purified by PLC to give tert-butyl (4R)-2-(5-fluoropyridin-3-yl)-4-hydroxypyrrolidine-1-carboxylate (4.70 g, 16.65 mmol, yield: 79.54%) as a brown black oil. ¹H-NMR (400 MHz, CDCl₃) δ ppm 8.37-8.33 (m, 2H), 7.48 (br.s, 1H), 5.09-4.89 (m, 1H), 4.56-4.54 (m, 1H), 3.80-3.65 (m, 2H), 2.63-2.43 (m, 1H), 2.03-1.96 (m, 1H), 1.56-1.20 (m, 9H).

Step 6: tert-butyl (2R,4S)-4-fluoro-2-(5-fluoropyridin-3-yl)pyrrolidine-1-carboxylate

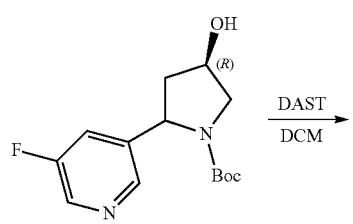

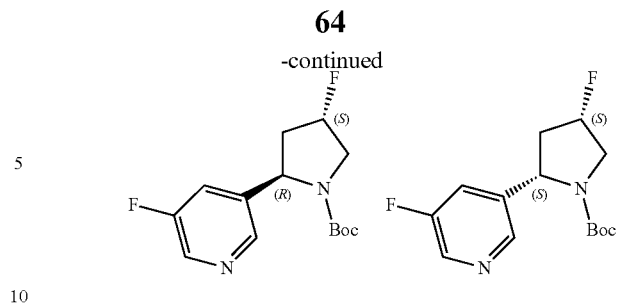

To the mixture of tert-butyl (4R)-2-(5-fluoropyridin-3-yl)-4-hydroxypyrrolidine-1-carboxylate (4.70 g, 16.65 mmol, 1.00 eq) in DCM (150.00 mL) was added DAST dropwise (29.52 g, 183.15 mmol, 11.00 eq) at −78° C. over 0.5 hr. The reaction mixture was stirred at −78° C. for 2 hrs, then allowed to warm to 25° C. and stirred for 20 hrs. After TLC (PE/EtOAc=0/1) showed the starting material was consumed completely, the mixture was cooled to 0° C. and quenched by saturated NaHCO₃ solution (100 mL) dropwise. The organic phase was separated and dried over Na₂SO₄, concentrated to give the residue, then purified by column chromatography on silica gel (PE:EtOAc from 10:1, 8:1 to 5:1, then 3:1) to give tert-butyl (2R,4S)-4-fluoro-2-(5-fluoropyridin-3-yl)pyrrolidine-1-carboxylate (1.38 g, 4.85 mmol, yield: 29.15%, R^f=0.53) as a white solid and tert-butyl (2S,4S)-4-fluoro-2-(5-fluoropyridin-3-yl)pyrrolidine-1-carboxylate (1.36 g, 4.78 mmol, yield: 28.73%, R_f=0.43) as a yellow oil. ¹H-NMR (400 MHz, CDCl₃) δ ppm 8.31-8.27 (m, 2H), 7.20-7.18 (m, 1H), 5.18 (d, 1H, J=51.6 Hz), 4.97-4.88 (m, 1H), 4.04-4.00 (m, 1H), 3.64 (dd, 1H, J=38.8, 12.8 Hz), 2.67 (dd, 1H, J=15.6, 6.8 Hz), 1.97-1.67 (m, 1H), 1.56-1.12 (m, 9H).

Step 7: 3-Fluoro-5-((2R,4S)-4-fluoropyrrolidin-2-yl)pyridine

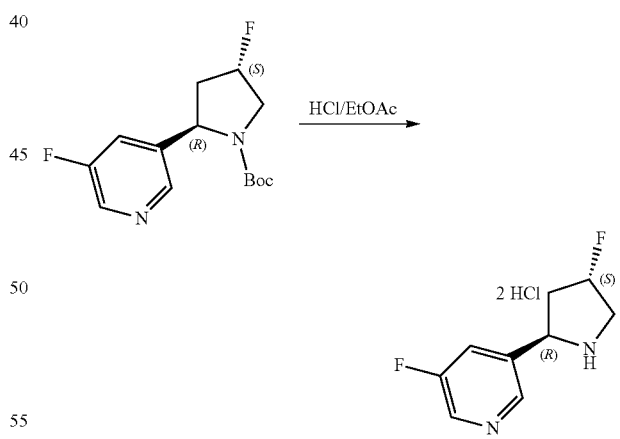

To the mixture of tert-butyl (2R,4S)-4-fluoro-2-(5-fluoropyridin-3-yl)pyrrolidine-1-carboxylate (1.38 g, 4.85 mmol, 1.00 eq) in EtOAc (10 mL) was added dropwise HCl/EtOAc (40.00 mL, 4 M) at 0° C. The mixture was allowed to warm to 25° C. and stirred 3 hrs. After TLC (PE:EtOAc=1:1) showed the reaction was complete, the solvent was evaporated to give 3-fluoro-5-((2R,4S)-4-fluoropyrrolidin-2-yl)pyridine (1.25 g, 4.86 mmol, yield: 100.00%) as a brown solid. ¹H-NMR (400 MHz, CD₃OD) δ ppm 8.84-8.81 (m, 2H), 8.31 (d, 1H, J=9.2 Hz), 5.62 (dt, 1H, J=52.0, 2.4 Hz), 5.23-5.18 (m, 1H), 4.00-3.95 (m, 1H), 3.88-3.71 (m, 1H), 2.67 (td, 1H, J=16.0, 6.0 Hz), 1.69-1.59 (m, 1H).

Example 11: Synthesis of (3R,4S,5R)-5-aminotetrahydro-2H-pyran-3,4-diol

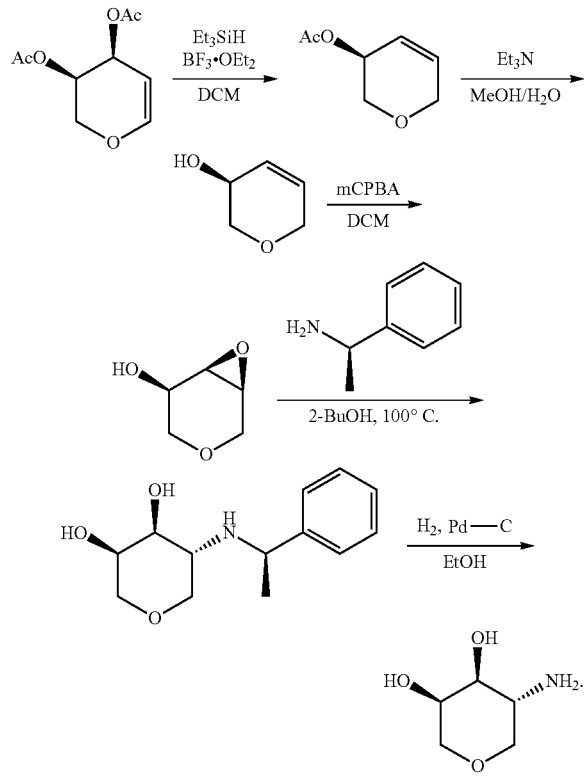

Step 1: (S)-3,6-dihydro-2H-pyran-3-yl Acetate (3R,4S)-3,4-dihydro-2H-pyran-3,4-diyl diacetate (2.9 g, 14.49 mmol) was taken up in DCM (15 ml), and stirred under N₂ at room temperature. Triethylsilane (2.55 ml, 15.93 mmol) was added and stirred for 5 minutes. BF₃.OEt₂ (1.836 ml, 14.49 mmol) was added dropwise and stirring was continued for 30 minutes. The reaction mixture was quenched with 30 ml of saturated bicarbonate and the layers were separated. The combined organic layers were dried over sodium sulfate and the solvent was removed. The residue was purified via flash chromatography (0-30% Hex/EtOAc). (S)-3,6-dihydro-2H-pyran-3-yl acetate (1.9 g, 92% yield) was recovered as clear oil. ¹H NMR (400 MHz, DMSO-d6) δ 6.10 (dddt, J=10.2, 3.2, 2.1, 1.0 Hz, 1H), 5.84 (ddt, J=10.1, 4.3, 2.1 Hz, 1H), 4.96 (dtd, J=4.3, 2.7, 1.5 Hz, 1H), 4.16-3.89 (m, 2H), 3.73 (t, J=2.9 Hz, 2H), 2.01 (d, J=0.9 Hz, 3H).

Step 2: (S)-3,6-dihydro-2H-pyran-3-ol (S)-3,6-dihydro-2H-pyran-3-yl acetate (1.9 g, 13.37 mmol) was taken up in MeOH (30 ml) and Water (20 ml). Triethylamine (7 ml, 50.2 mmol) was added and stirred at room temperature for 30 min. The solvent was removed under reduced pressure. The residual water was then extracted with EtOAc three times. The organic layers were combined, dried over sodium sulfate and the solvent was removed. (S)-3,6-dihydro-2H-pyran-3-ol (1.1 g, 10.99 mmol, 82% yield) was recovered as a clear oil. The crude product was carried on without further purification.

Step 3: (1S,5R,6R)-3,7-dioxabicyclo[4.1.0]heptan-5-ol (S)-3,6-dihydro-2H-pyran-3-ol (1.1 g, 10.99 mmol) was taken up in CH₂Cl₂ (20 ml) and cooled to 0° C. mCPBA (4.55 g, 13.18 mmol) was added portion wise. The reaction mixture was stirred while warming to room temperature, overnight. The white precipitate of the reaction mixture was filtered off, the eluant was retained, the solvent was removed and triturated with diethyl ether. This step was repeated. The residue, (1S,5R,6R)-3,7-dioxabicyclo[4.1.0]heptan-5-ol (1.2 g, 100% yield) was carried on without further purification.

Step 4: (3R,4S,5R)-5-(((R)-1-phenylethyl)amino)tetrahydro-2H-pyran-3,4-diol (1S,5R,6R)-3,7-dioxabicyclo[4.1.0]heptan-5-ol (1.26 g, 10.85 mmol), (R)-1-phenylethanamine (1.658 ml, 13.02 mmol) were taken up in 2-BuOH (15 ml). The reaction mixture was heated to 100° C. for 18 hours. The reaction mixture was cooled to room temperature, the solvent was removed, and the residue was then purified on ISCO 0-100% EtOAc. The fractions were combined, the solvent removed, and then the residue was treated with MTBE and stirred overnight. The white precipitate of the organic mixture was filtered off. Recovered (3R,4S,5R)-5-(((R)-1-phenylethyl)amino)tetrahydro-2H-pyran-3,4-diol (0.350 g, 14% yield). ¹H NMR (400 MHz, DMSO-d₆) δ 7.38-7.24 (m, 4H), 7.22-7.12 (m, 1H), 4.61 (d, J=5.6 Hz, 1H), 4.46 (d, J=4.8 Hz, 1H), 3.88 (q, J=6.5 Hz, 1H), 3.64 (tt, J=5.0, 2.8 Hz, 1H), 3.47 (dd, J=11.4, 4.7 Hz, 1H), 3.39 (ddd, J=8.4, 5.6, 3.1 Hz, 1H), 3.31 (s, 2H), 3.29 (t, J=3.0 Hz, 1H), 3.25 (d, J=2.5 Hz, 0H), 2.79 (dd, J=11.1, 7.8 Hz, 1H), 2.57 (td, J=7.8, 3.9 Hz, 1H), 1.86 (s, 1H), 1.21 (d, J=6.6 Hz, 3H).

Step 5: (3R,4S,5R)-5-aminotetrahydro-2H-pyran-3,4-diol (3R,4S,5R)-5-(((R)-1-phenylethyl)amino)tetrahydro-2H-pyran-3,4-diol (0.350 g, 1.475 mmol) was taken up in EtOH (3 ml) and Pd—C (0.031 g, 0.295 mmol) was added. The reaction mixture was stirred under H₂ balloon overnight. The reaction mixture was filtered through Celite and the solvent was removed to give (3R,4S,5R)-5-aminotetrahydro-2H-pyran-3,4-diol (0.190 g, 1.427 mmol, 97% yield) as an off white solid. The crude product was carried on without further purification. LCMS (M+H) 134.

Example 12. (R)-3-(4,4-difluoropyrrolidin-2-yl)-5-fluoropyridine

Step 1: tert-butyl (2R,4R)-4-((tert-butyldimethylsilyl)oxy)-2-(5-fluoropyridin-3-yl)pyrrolidine-1-carboxylate

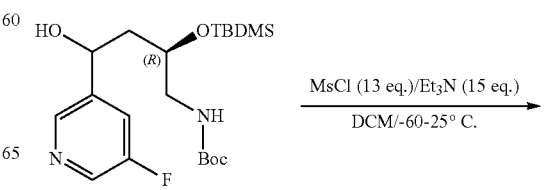

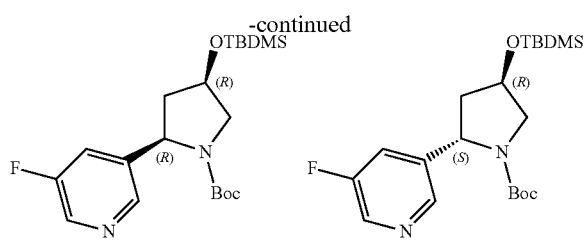

To a mixture of tert-butyl ((2R)-2-((tert-butyldimethylsilyl)oxy)-4-(5-fluoropyridin-3-yl)-4-hydroxybutyl)carbamate (6.80 g, 16.40 mmol) and Et$_3$N (24.89 g, 246.00 mmol) in DCM (500.00 mL) was added MSCl (24.42 g, 213.20 mmol) dropwise at −60° C. over 30 minutes. The mixture was stirred at −60° C. for 1 hr. The reaction mixture was allowed to warm to 25° C. and stirred for an additional 18 hrs. The mixture was washed with H$_2$O (200 mL*3). The aqueous phase was extracted with DCM (200 mL*4). The combined organic layers were dried over Na$_2$SO$_4$ and concentrated in vacuo. The residue was purified by silica gel chromatography (PE:EtOAc=50/1, 20/1, 10/1) to afford tert-butyl (2S,4R)-4-((tert-butyldimethylsilyl)oxy)-2-(5-fluoropyridin-3-yl)pyrrolidine-1-carboxylate (2.70 g, yield: 41.52%) and tert-butyl (2R,4R)-4-((tert-butyldimethylsilyl)oxy)-2-(5-fluoropyridin-3-yl)pyrrolidine-1-carboxylate (2.40 g, yield: 36.89%) as brown oil. 1H-NMR (400 MHz, CDCl3) δ ppm 8.40 (br.s, 2H), 7.56-7.45 (m, 1H), 5.11-4.94 (m, 2H), 4.53 (br.s, 1H), 3.85-3.79 (m, 1H), 3.66-3.53 (m, 1H), 2.62-2.58 (m, 1H), 2.04-2.01 (m, 1H), 1.56 (s, 3H), 1.32 (s, 6H), 0.99-0.88 (m, 9H), 0.18-0.00 (m, 6H).

Step 2: tert-butyl (2R,4R)-2-(5-fluoropyridin-3-yl)-4-hydroxypyrrolidine-1-carboxylate

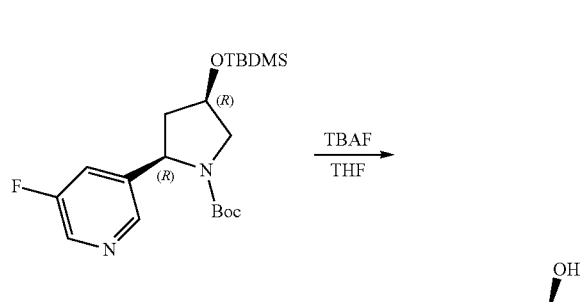

To a mixture of tert-butyl (2R,4R)-4-((tert-butyldimethylsilyl)oxy)-2-(5-fluoropyridin-3-yl)pyrrolidine-1-carboxylate (2.40 g, 6.05 mmol) in THF (60.00 mL) was added TBAF (3.16 g, 12.10 mmol) in one portion at 25° C. The mixture was concentrated under reduced pressure at 50° C. The residue was added to water (20 mL). The aqueous phase was extracted with ethyl acetate (30 mL*3). The combined organic phase was washed with saturated brine (20 mL*2), dried over Na$_2$SO$_4$, filtered and concentrated in vacuo. The residue was purified by silica gel chromatography (PE:EtOAc=20/1, 10/1, 1/3) to afford tert-butyl (2R,4R)-2-(5-fluoropyridin-3-yl)-4-hydroxypyrrolidine-1-carboxylate (1.30 g, yield: 76.11%) as a yellow solid. 1H-NMR (400 MHz, CDCl3) δ ppm 8.26 (d, 2H, J=12.8 Hz), 7.39 (br.s, 1H), 4.95-4.81 (m, 1H), 4.48-4.47 (m, 1H), 3.73 (br.s, 1H), 3.56-3.53 (m, 1H), 2.55 (br.s, 1H), 1.97-1.98 (m, 1H), 1.65-1.16 (m, 9H).

Step 3: tert-butyl (R)-2-(5-fluoropyridin-3-yl)-4-oxopyrrolidine-1-carboxylate

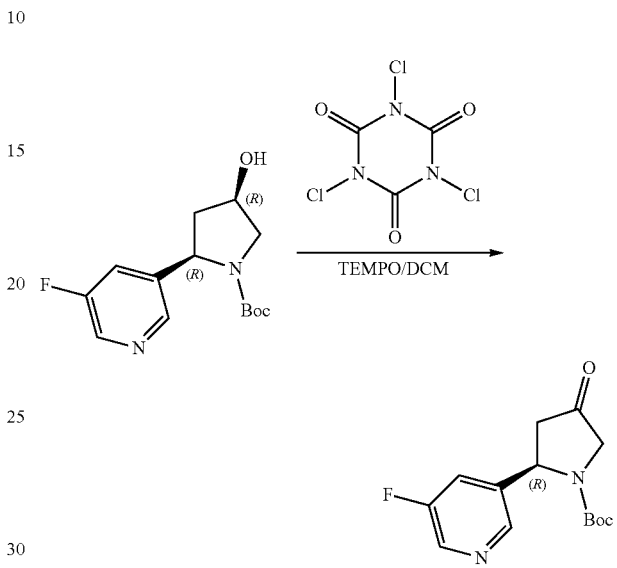

To a mixture of tert-butyl (2R,4R)-2-(5-fluoropyridin-3-yl)-4-hydroxypyrrolidine-1-carboxylate (1.30 g, 4.60 mmol) and trichloroisocyanuric acid (1.10 g, 4.60 mmol) was added TEMPO (72.41 mg, 460.49 umol) at −10° C. The mixture was stirred at −10° C. for 15 min, then warmed to 25° C. and stirred for 1 hr. TLC (EtOAc) showed the reaction was complete. The organic phase was washed with NaHCO$_3$ (20 mL*2), dried over Na$_2$SO$_4$, filtered and concentrated in vacuum. The residue was purified by silica gel chromatography (petroleum ether/ethyl acetate=50/1, 10/1) to afford tert-butyl (R)-2-(5-fluoropyridin-3-yl)-4-oxopyrrolidine-1-carboxylate (1.10 g, yield: 85.32%) as a brown oil.

Step 4: tert-butyl (R)-4,4-difluoro-2-(5-fluoropyridin-3-yl)pyrrolidine-1-carboxylate

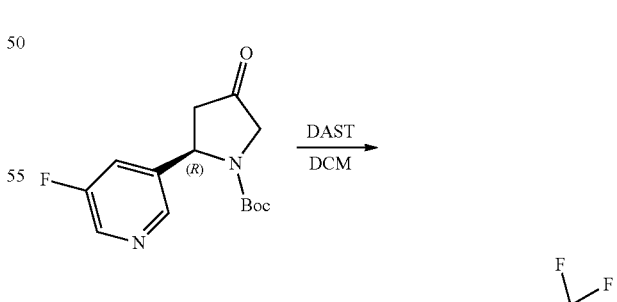

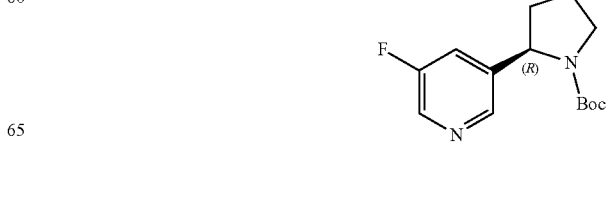

To a mixture of tert-butyl (R)-2-(5-fluoropyridin-3-yl)-4-oxopyrrolidine-1-carboxylate (1.00 g, 3.57 mmol) in DCM (100.00 mL) was added DAST (14.39 g, 89.25 mmol) dropwise at −70° C. under N₂. The mixture was stirred at −70° C. for 30 min. Then the mixture was stirred at 25° C. for 16 hrs. The reaction mixture was quenched by saturated aq. NaHCO₃ slowly at 0° C. and the aqueous phase was extracted with DCM (50 mL*4). The combined organic phase was washed with saturated brine (30 mL), dried over Na₂SO₄, filtered and concentrated in vacuo. The residue was purified by silica gel chromatography (petroleum ether/ethyl acetate=100/1, 30/1) to afford tert-butyl (R)-4,4-difluoro-2-(5-fluoropyridin-3-yl)pyrrolidine-1-carboxylate (1.00 g, yield: 92.66%) as a brown oil. 1H-NMR (400 MHz, CDCl3) δ ppm 8.40 (s, 1H), 8.34 (s, 1H), 7.30-7.21 (m, 1H), 5.06 (br.s, 1H), 4.14-3.85 (m, 2H), 2.91-2.84 (m, 1H), 2.39-2.32 (m, 1H), 1.43-1.14 (m, 9H).

Step 5: (R)-3-(4,4-difluoropyrrolidin-2-yl)-5-fluoropyridine

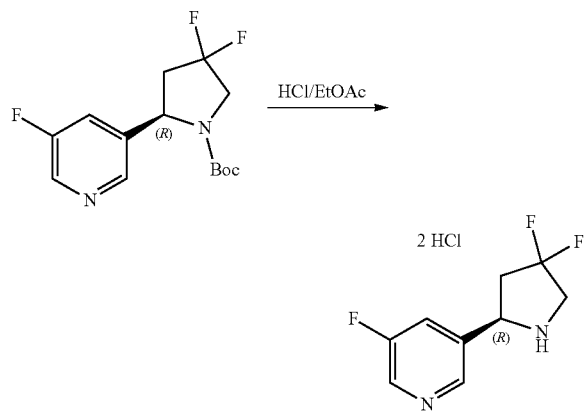

A mixture of tert-butyl (R)-4,4-difluoro-2-(5-fluoropyridin-3-yl)pyrrolidine-1-carboxylate (1.00 g, 3.31 mmol) in HCl/EtOAc (50.00 mL, 4 M) was stirred for 2 hrs at 25° C. The mixture was concentrated under reduced pressure at 30° C. to afford (R)-3-(4,4-difluoropyrrolidin-2-yl)-5-fluoropyridine (840.00 mg, yield: 92.25%) as a white solid as bis HCl salt. 1H-NMR (400 MHz, MeOD) δ ppm 8.68-8.63 (m, 1H), 7.97 (d, 1H, J=9.2 Hz), 5.26-5.21 (m, 1H), 4.03-3.90 (m, 2H), 3.13-2.92 (m, 2H).

Example 13. (3S,5R)-5-(2,5-difluorophenyl)pyrrolidine-3-carbonitrile

Step 1: tert-butyl ((2R)-2-((tert-butyldimethylsilyl)oxy)-4-(2,5-difluorophenyl)-4-hydroxybutyl)carbamate

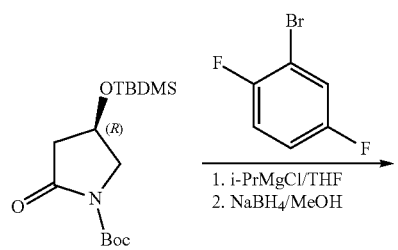

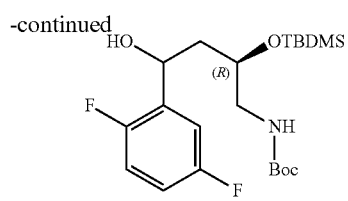

To a solution of 2-bromo-1,4-difluoro-benzene (3.01 g, 15.60 mmol, 1.20 Eq) in THF (15 mL) was added isopropylmagnesium chloride complex (2.27 g, 15.60 mmol, 1.20 Eq) at 0° C. dropwise under N₂. The reaction was stirred at 15° C. for 1 hr to prepare (2, 5-difluorophenyl) magnesium bromide (23 mL). To a solution of tert-butyl (R)-4-((tert-butyldimethylsilyl)oxy)-2-oxopyrrolidine-1-carboxylate (4.10 g, 13.00 mmol, 1.00 Eq) in THF (50 mL) was added (2,5-difluorophenyl) magnesium bromide (23 mL) dropwise at 0° C. over 30 mins. The reaction mixture was stirred at 0° C. for 1 hr. Methanol (20 mL) was added to the mixture followed by NaBH₄ (738 mg, 19.50 mmol, 1.50 Eq) at 0° C. The mixture was stirred at 0° C. for 1 hr then poured into 10% aqueous NH₄Cl. The mixture was extracted with EtOAc (20 mL*2), the combined organic layers were washed with brine, dried over Na₂SO₄, filtered and concentrated. The crude product was purified by medium pressure liquid chromatography (MPLC) to give tert-butyl ((2R)-2-((tert-butyldimethylsilyl)oxy)-4-(2,5-difluorophenyl)-4-hydroxybutyl)carbamate (2.22 g, 5.14 mmol, 39.6% yield). ¹H-NMR (400 MHz, CDCl₃) δ ppm 7.17-7.15 (m, 1H), 6.86-6.79 (m, 2H), 5.11-5.06 (m, 1H), 4.70 (br.s, 1H), 4.02-3.98 (m, 1H), 3.69 (br.s, 0.5H), 3.46 (br.s, 0.5H), 3.33-3.14 (m, 2H), 1.80-1.69 (m, 2H), 1.35 (s, 9H), 0.84-0.82 (9H, m), 0.04-0.03 (6H, m).

Step 2: tert-butyl (4R)-4-((tert-butyldimethylsilyl)oxy)-2-(2,5-difluorophenyl)pyrrolidine-1-carboxylate

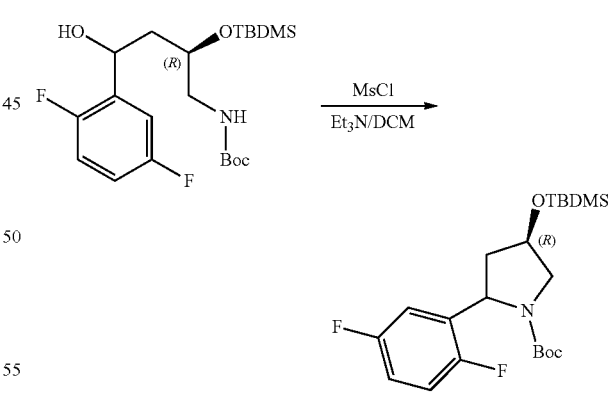

To a solution of tert-butyl ((2R)-2-((tert-butyldimethylsilyl)oxy)-4-(2,5-difluorophenyl)-4-hydroxybutyl)carbamate (13.40 g, 31.05 mmol, 1.00 Eq) and Et₃N (9.43 g, 93.14 mmol, 3.00 Eq) in DCM (50 mL) was added dropwise methanesulfonyl chloride (5.33 g, 46.57 mmol, 1.50 Eq) at −60° C. by under N₂. The mixture was stirred at −60° C. for 2 hrs and 15° C. for 16 hrs. LCMS showed the starting material was consumed completely. The reaction mixture was extracted with DCM (30 mL*2) and the combined organics were washed with brine (50 mL), dried over Na₂SO₄ and filtered, concentrated to give tert-butyl (4R)-4-((tert-butyldimethylsilyl)oxy)-2-(2,5-difluorophenyl)pyrrolidine-1-carboxylate (12.00 g, 26.11 mmol, yield: 84.10%, 90% purity) which was used directly without further purification.

Step 3: tert-butyl (2R,4R)-2-(2,5-difluorophenyl)-4-hydroxypyrrolidine-1-carboxylate

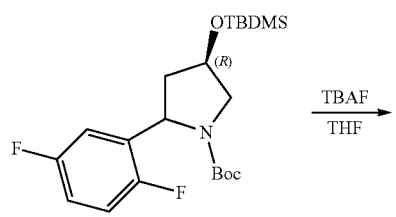

To a solution of tert-butyl (4R)-4-((tert-butyldimethylsilyl)oxy)-2-(2,5-difluorophenyl)pyrrolidine-1-carboxylate (4.50 g, 10.88 mmol, 1.00 Eq) in THF (30 mL) was added TBAF/THF (1 M, 14.15 mL, 1.30 Eq) at 15° C. The mixture was stirred at 15° C. for 16 hrs. TLC (PE:EtOAc=3:1) showed the starting material was consumed completely. The reaction mixture was quenched by H₂O (50 mL), extracted with EtOAc (30 mL*2) and the combined organics were washed with brine (10 mL), dried over Na₂SO₄, filtered and concentrated in vacuo. The residue was purified by neutral prep-HPLC to afford tert-butyl (2R,4R)-2-(2,5-difluorophenyl)-4-hydroxypyrrolidine-1-carboxylate (1.00 g, 3.34 mmol, yield: 30.70%) as a white solid. ¹H-NMR (400 MHz, CDCl₃) δ ppm 7.04-6.80 (m, 3H), 5.10-5.00 (m, 1H), 4.43 (s, 1H), 3.75 (br.s, 1H), 3.53-3.49 (m, 1H), 2.53 (br.s, 1H), 1.93-1.90 (m, 1H), 1.40-1.16 (m, 9H).

Step 4: tert-butyl (2R,4R)-2-(2,5-difluorophenyl)-4-((methylsulfonyl)oxy)pyrrolidine-1-carboxylate

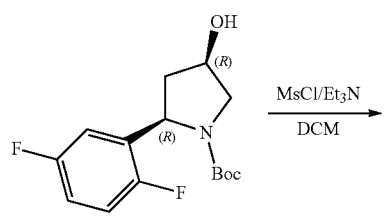

To a mixture of tert-butyl (2R,4R)-2-(2,5-difluorophenyl)-4-hydroxypyrrolidine-1-carboxylate (3.00 g, 10.02 mmol, 1.00 eq) and Et₃N (2.03 g, 20.04 mmol, 2.00 eq) in DCM (80.00 mL) was added MsCl (1.61 g, 14.03 mmol, 1.40 eq) dropwise at 0° C. The mixture was stirred at 18° C. for 2 hrs. The mixture was quenched by H₂O (30 mL). The aqueous phase was extracted by DCM (50 mL*3). The combined organic layer was dried over Na₂SO₄ and concentrated under reduced pressure. tert-Butyl (2R,4R)-2-(2,5-difluorophenyl)-4-((methylsulfonyl)oxy)pyrrolidine-1-carboxylate (3.60 g, 9.54 mmol, yield: 95.20%) was obtained as a brown solid.

Step 5: tert-butyl (2R,4S)-4-cyano-2-(2,5-difluorophenyl)pyrrolidine-1-carboxylate

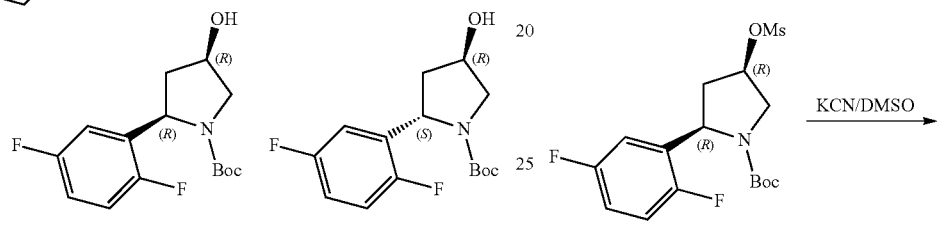

To a mixture of tert-Butyl (2R,4R)-2-(2,5-difluorophenyl)-4-((methylsulfonyl)oxy)pyrrolidine-1-carboxylate (3.60 g, 9.54 mmol, 1.00 eq) in DMSO (20.00 mL) was added KCN (745.49 mg, 11.45 mmol, 1.20 eq) in one portion. The mixture was stirred at 90° C. for 3 hrs. 80 mL of H₂O was added to the mixture, and the mixture was extracted by EtOAc (80 mL*4). The combined organic layer was concentrated under reduced pressure. The residue was purified by silica gel chromatography (PE/EtOAc=40:1, 30:1, 10:1). tert-Butyl (2R,4S)-4-cyano-2-(2,5-difluorophenyl)pyrrolidine-1-carboxylate (1.60 g, 5.19 mmol, yield: 54.40%) was obtained as light green liquid.

Step 6: (3S,5R)-5-(2,5-difluorophenyl)pyrrolidine-3-carbonitrile

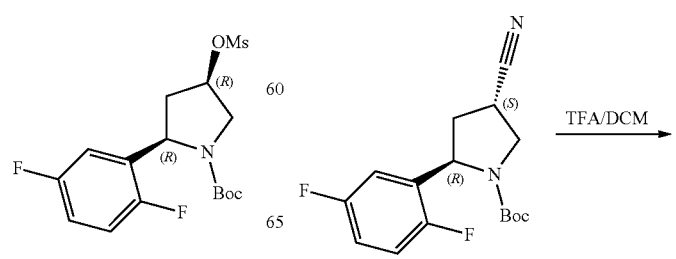

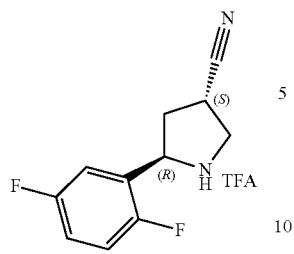

A mixture of tert-Butyl (2R,4S)-4-cyano-2-(2,5-difluorophenyl)pyrrolidine-1-carboxylate (800.00 mg, 2.59 mmol, 1.00 eq) in TFA (4.00 mL)/DCM (20.00 mL) was stirred at 18° C. for 3 hrs. The mixture was dried under N₂. (3S,5R)-5-(2,5-difluorophenyl)pyrrolidine-3-carbonitrile (780.00 mg, 2.42 mmol, yield: 93.44%) was obtained as a light yellow solid.

Example 14. 3-fluoro-5-((2R,4S)-4-fluoropyrrolidin-2-yl)benzamide

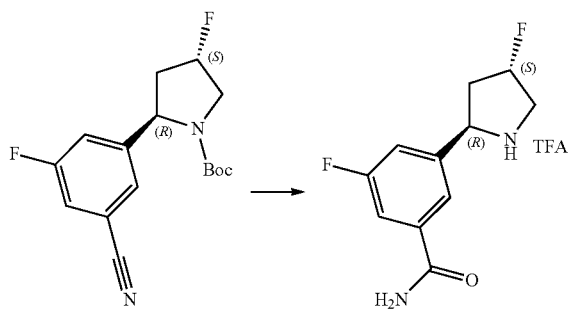

3-Fluoro-5-((2R,4S)-4-fluoropyrrolidin-2-yl)benzonitrile (0.050 g, 0.240 mmol) (Prepared as in WO 2012/034095) was taken up in TFA (0.800 ml, 10.38 mmol) and H₂SO₄ (0.200 ml, 3.75 mmol) and stirred overnight at room temperature. The reaction mixture was diluted with ice water (3 ml) and the solid was isolated by filtration, and used directly.

Example 15. 2-chloro-5-fluoro-3-((2R,4S)-4-fluoropyrrolidin-2-yl)pyridine

Step 1: (S,Z)—N-((2-chloro-5-fluoropyridin-3-yl)methylene)-2-methylpropane-2-sulfinamide

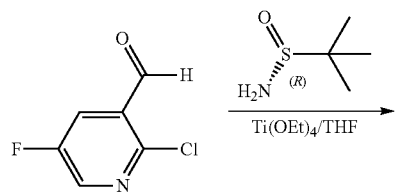

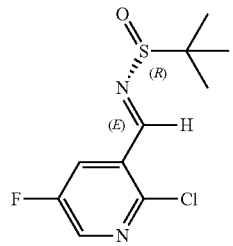

2-chloro-5-fluoronicotinaldehyde (20 g, 125 mmol) was taken up in THF (150 ml) at 0° C. (R)-2-Methylpropane-2-sulfinamide (16.71 g, 138 mmol) was added followed by dropwise addition of titaniumtetraethanolate (22.88 ml, 150 mmol). The reaction mixture was stirred while warming to RT. After 3 hours the reaction mixture was cooled to 0° C., and 150 ml of brine was added and stirred for 20 minutes. The mixture was filtered through Celite. The aqueous layer was separated and discarded. The organic layer with dried over Na₂SO₄ and the solvent was removed to give (S,Z)—N-((2-chloro-5-fluoropyridin-3-yl)methylene)-2-methylpropane-2-sulfinamide (32 g, 122 mmol, 97% yield), which was carried on without further purification. LCMS: 263 M+H.

Step 2: (R)—N—((R)-1-(2-chloro-5-fluoropyridin-3-yl)but-3-en-1-yl)-2-methylpropane-2-sulfinamide

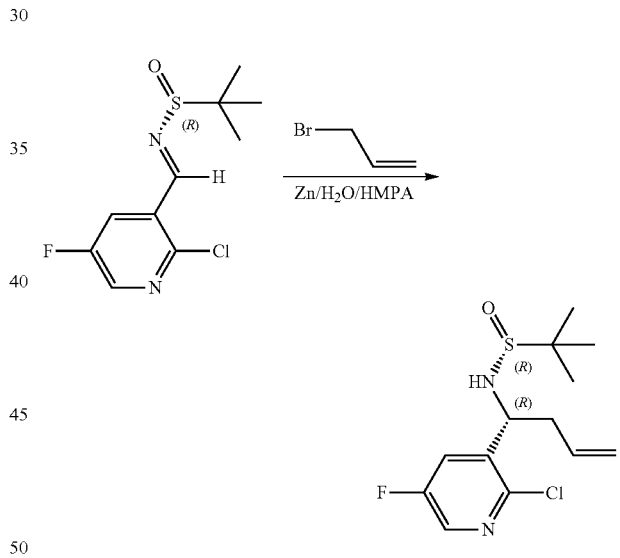

(R,E)-N-((2-chloro-5-fluoropyridin-3-yl)methylene)-2-methylpropane-2-sulfinamide (32.9 g, 125 mmol) was dissolved in HMPA (100 ml) and cooled to 0° C. Zinc (16.37 g, 250 mmol), allyl bromide (21.67 ml, 250 mmol) and water (2.256 ml, 125 mmol) were added at 0° C. and the reaction mixture was allowed to warm to RT overnight. LCMS showed complete conversion to desired product. 100 ml of water was added at RT and stirred for 30 minutes. 30 ml of MBTE was added followed by 60 ml of 10% citric acid and the reaction mixture was stirred for 30 minutes. The mixture was filtered through Celite and washed with MTBE. The organic layer was washed with 10% citric acid, water and brine. The solvent was removed under vacuum to give (R)—N—((R)-1-(2-chloro-5-fluoropyridin-3-yl)but-3-en-1-yl)-2-methylpropane-2-sulfinamide (14.5 g, 47.6 mmol, 38.0% yield) as an orange oil. LCMS: 305 M+H.

Step 3: (R)-1-(2-chloro-5-fluoropyridin-3-yl)but-3-en-1-amine, HCl

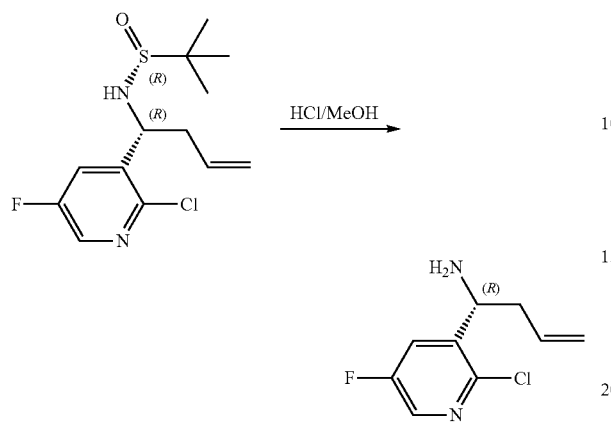

(R)—N—((R)-1-(2-chloro-5-fluoropyridin-3-yl)but-3-en-1-yl)-2-methylpropane-2-sulfinamide (7.5 g, 24.61 mmol) was taken up in 10 ml MeOH. HCl (4M in dioxane) (30.8 ml, 123 mmol) was added and stirred at RT for 1 h. The solvent was removed under vacuum and the residue was diluted in DCM and washed with saturated aqueous NaHCO$_3$. The layers were separated and the organic layer was dried with Na$_2$SO$_4$ and the solvent was removed under vacuum. Recovered (R)-1-(2-chloro-5-fluoropyridin-3-yl)but-3-en-1-amine, HCl (5.83 g, 24.59 mmol, 100% yield) as a solid. LCMS: 201 M+H.

Step 4: (R)—N-(1-(2-chloro-5-fluoropyridin-3-yl)but-3-en-1-yl)acetamide

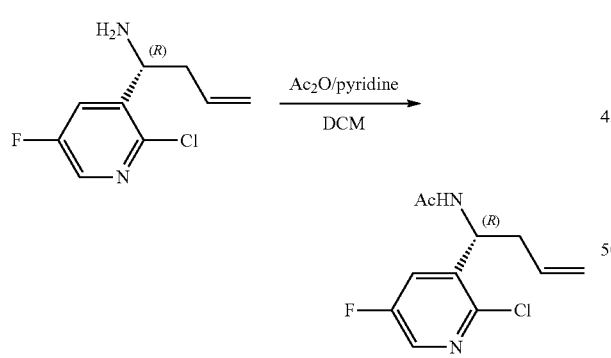

To (R)-1-(2-chloro-5-fluoropyridin-3-yl)but-3-en-1-amine.HCl (5.83 g, 24.59 mmol) in DCM (70.3 ml) at 0° C. was added TEA (4.11 ml, 29.5 mmol) and acetic anhydride (2.320 ml, 24.59 mmol). The mixture was stirred for 2 hours. The reaction mixture was poured into saturated aqueous NaHCO$_3$ and extracted with DCM. The organic layer was washed with brine, dried over MgSO$_4$, and evaporated under reduced pressure. Recovered (R)—N-(1-(2-chloro-5-fluoropyridin-3-yl)but-3-en-1-yl)acetamide (5.97 g, 24.60 mmol, 100% yield) and was carried on without further purification. LCMS: 243 M+H.

Step 5: (5R)-5-(2-chloro-5-fluoropyridin-3-yl)pyrrolidin-3-yl acetate

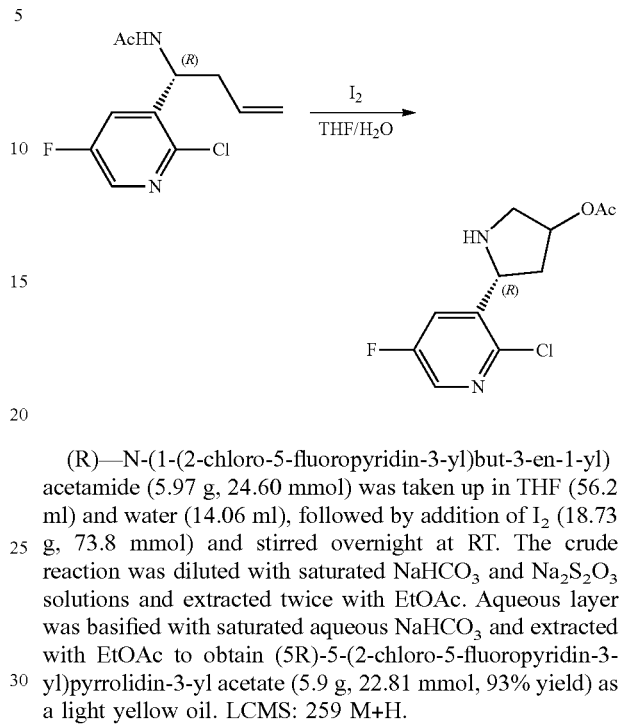

(R)—N-(1-(2-chloro-5-fluoropyridin-3-yl)but-3-en-1-yl)acetamide (5.97 g, 24.60 mmol) was taken up in THF (56.2 ml) and water (14.06 ml), followed by addition of I$_2$ (18.73 g, 73.8 mmol) and stirred overnight at RT. The crude reaction was diluted with saturated NaHCO$_3$ and Na$_2$S$_2$O$_3$ solutions and extracted twice with EtOAc. Aqueous layer was basified with saturated aqueous NaHCO$_3$ and extracted with EtOAc to obtain (5R)-5-(2-chloro-5-fluoropyridin-3-yl)pyrrolidin-3-yl acetate (5.9 g, 22.81 mmol, 93% yield) as a light yellow oil. LCMS: 259 M+H.

Step 6: (2R)-tert-butyl 4-acetoxy-2-(2-chloro-5-fluoropyridin-3-yl)pyrrolidine-1-carboxylate

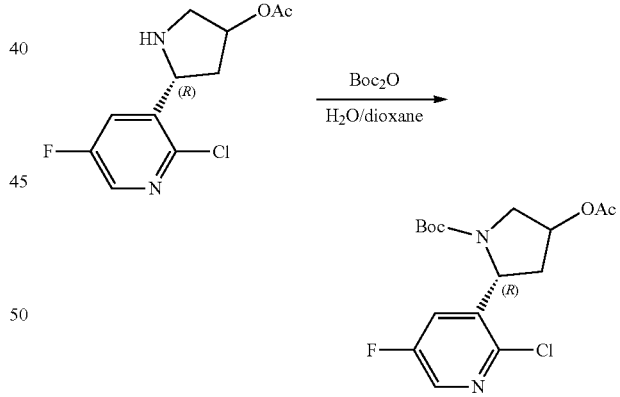

To a solution of (5R)-5-(2-chloro-5-fluoropyridin-3-yl)pyrrolidin-3-yl acetate (5.9 g, 22.81 mmol) in dioxane (76 ml) and water (76 ml) was added BOC-anhydride (7.94 ml, 34.2 mmol) followed by careful addition of 2N NaOH (7 ml) to achieve pH ~9. The reaction mixture was stirred for 1 hour at RT. The reaction mixture was diluted with water and extracted with EtOAc three times. The organic layer was dried over Na$_2$SO$_4$ and the solvent was removed under vacuum to give (2R)-tert-butyl 4-acetoxy-2-(2-chloro-5-fluoropyridin-3-yl)pyrrolidine-1-carboxylate (3.5 g, 9.75 mmol, 42.8% yield), which was carried on without further purification. LCMS: 359 M+H.

Step 7: (2R)-tert-butyl 2-(2-chloro-5-fluoropyridin-3-yl)-4-hydroxypyrrolidine-1-carboxylate

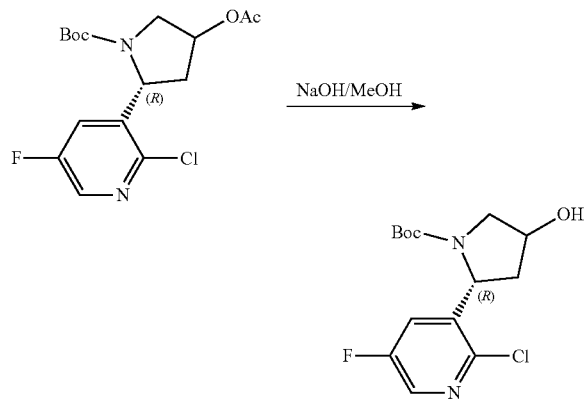

(2R)-tert-butyl 4-acetoxy-2-(2-chloro-5-fluoropyridin-3-yl)pyrrolidine-1-carboxylate (3.5 g, 9.75 mmol) was taken up in MeOH (48.8 ml) followed by addition of 2M NaOH (5.37 ml, 10.73 mmol) and the reaction mixture was stirred at RT for 2 hours. The solvent was removed under vacuum and the aqueous layer was neutralized with 1N HCl, and extracted with EtOAc three times. The combined organic layers were dried over $Na_2SO_4$. The solvent was removed under vacuum and the residue was purified via silica gel chromatography (0-70% Hex/EtOAc) to give (2R)-tert-butyl 2-(2-chloro-5-fluoropyridin-3-yl)-4-hydroxypyrrolidine-1-carboxylate (2.1 g, 6.63 mmol, 68.0% yield). LCMS: 317 M+H.

Step 8: (R)-tert-butyl 2-(2-chloro-5-fluoropyridin-3-yl)-4-oxopyrrolidine-1-carboxylate

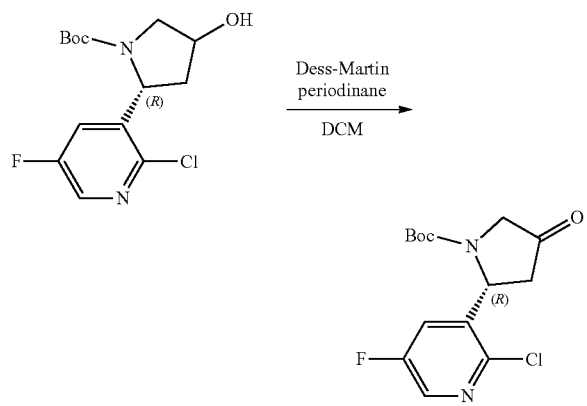

(2R)-tert-butyl 2-(2-chloro-5-fluoropyridin-3-yl)-4-hydroxypyrrolidine-1-carboxylate (2.1 g, 6.63 mmol) was taken up in DCM (66.3 ml) and $NaHCO_3$ (0.557 g, 6.63 mmol) was added followed by Dess-Martin periodinane (8.44 g, 19.89 mmol). The reaction mixture was stirred overnight. Water was added (0.119 ml, 6.63 mmol) followed by Dess-Martin periodinane (8.44 g, 19.89 mmol) and stirred for 18 hours. The pH was adjusted to ~7 with saturated aqueous $NaHCO_3$ and extracted with DCM×3. The organic layers were combined, dried over $Na_2SO_4$ and the solvent was removed under vacuum. The residue was purified via flash chromatography (0-70% Hex/EtOAc) to give (R)-tert-butyl 2-(2-chloro-5-fluoropyridin-3-yl)-4-oxopyrrolidine-1-carboxylate (1.6 g, 5.08 mmol, 77% yield). LCMS: 315 M+H.

Step 9: (2R,4R)-tert-butyl 2-(2-chloro-5-fluoropyridin-3-yl)-4-hydroxypyrrolidine-1-carboxylate

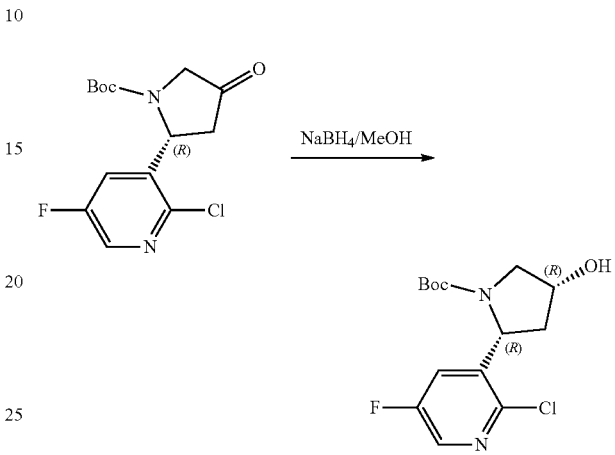

(R)-tert-butyl 2-(2-chloro-5-fluoropyridin-3-yl)-4-oxopyrrolidine-1-carboxylate (1.6 g, 5.08 mmol) was suspended in ethanol (33.9 ml) and cooled to 0° C. $NaBH_4$ was added portionwise (0.096 g, 2.54 mmol) and stirred for 45 minutes at 0° C. The reaction was quenched slowly with saturated $NH_4Cl$ and allowed to warm to RT, and the solution was extracted with DCM×3. The organic layers were combined and dried over $Na_2SO_4$. The residue was purified via flash chromatography (0-70% Hex/EtOAc) to give (2R,4R)-tert-butyl 2-(2-chloro-5-fluoropyridin-3-yl)-4-hydroxypyrrolidine-1-carboxylate (1.446 g, 4.57 mmol, 90% yield). LCMS: 317 M+H.

Step 10: (2R,4S)-tert-butyl 2-(2-chloro-5-fluoropyridin-3-yl)-4-fluoropyrrolidine-1-carboxylate

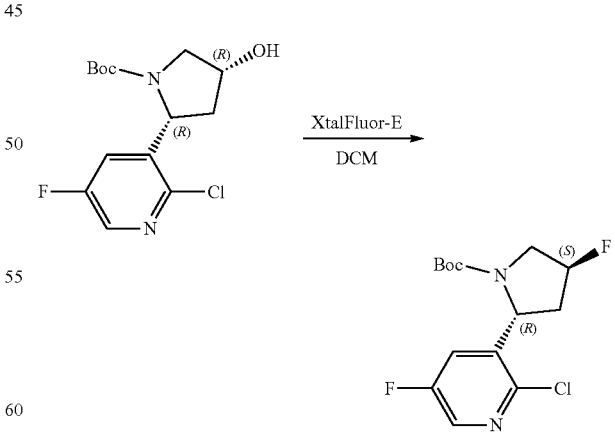

(2R,4R)-tert-butyl 2-(2-chloro-5-fluoropyridin-3-yl)-4-hydroxypyrrolidine-1-carboxylate (1.0 g, 3.16 mmol) was taken up in DCM (25 ml) and cooled to −78° C. TEA-HF (1.098 ml, 9.47 mmol) was added and stirred for 10 minutes. XtalFluor-E (1.446 g, 6.31 mmol) was added and after 10 minutes the reaction mixture was transferred to an ice bath and allowed to warm to 0° C. After 2 hours the reaction mixture was diluted with DCM and quenched with saturated aqueous NaHCO₃. The organic layers were separated, and the solvent was removed under vacuum. The residue was purified via ISCO (0-50% Hex/EtOAc; 12 g column) to give (2R,4S)-tert-butyl 2-(2-chloro-5-fluoropyridin-3-yl)-4-fluoropyrrolidine-1-carboxylate (0.805 g, 2.53 mmol, 80% yield) as a white solid. LCMS: 319 M+H.

Step 11: 2-chloro-5-fluoro-3-((2R,4S)-4-fluoropyrrolidin-2-yl)pyridine, HCl

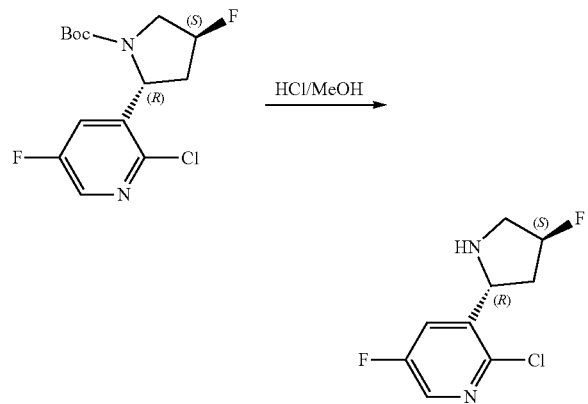

(2R,4S)-tert-butyl 2-(2-chloro-5-fluoropyridin-3-yl)-4-fluoropyrrolidine-1-carboxylate (0.805 g, 2.53 mmol, 80% yield) was taken up in EtOAc (5 ml) and 4N HCl/dioxane (3 ml) was added. The reaction mixture was stirred at RT for 1 hour. The precipitate was filtered off, washed with ether, and dried under high vacuum overnight to give 2-chloro-5-fluoro-3-((2R,4S)-4-fluoropyrrolidin-2-yl)pyridine, HCl (0.612 g, 2.399 mmol, 76% yield) as an off white solid. LCMS: 219 M+H.

Example 16. 5-fluoro-3-((2R,4S)-4-fluoropyrrolidin-2-yl)-2-methoxypyridine

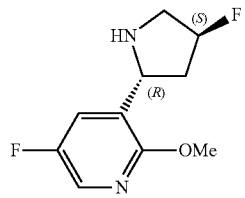

5-Fluoro-3-((2R,4S)-4-fluoropyrrolidin-2-yl)-2-methoxypyridine was prepared in the same way as 3-fluoro-5-((2R,4S)-4-fluoropyrrolidin-2-yl)benzamide, substituting for 5-fluoro-2-methoxynicotinaldehyde for 2-chloro-5-fluoronicotinaldehyde.

Example 17. Methyl (1R,3R,4R)-3-amino-4-hydroxycyclopentane-1-carboxylate

Step 1: (1S,2R,4S,5R)-3-oxa-6-azatricyclo[3.2.1.02,4]octan-7-one

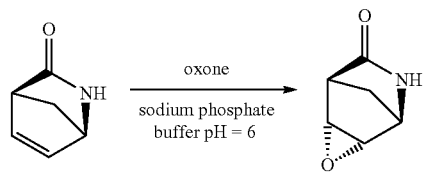

To a solution of (1R,4S)-2-azabicyclo[2.2.1]hept-5-en-3-one (30.00 g, 274.90 mmol, 1.00 eq) in NaH₂PO₄ (395.00 mL, 0.2M) and Na₂HPO₄ (55.00 mL, 0.2 M) was added H₂O (450.00 mL) and oxone (669.31 g, 4.40 mol, 16.00 eq) at 0° C. portion-wise over 5 hrs, and maintaining the pH=6 by addition of aq. NaOH (12 M) and keeping the temperature at 0° C. After addition, the mixture was stirred at 0° C. for further 2 hrs, TLC (PE:EtOAc=1:1) showed the starting material was consumed completely, the mixture was filtered and aqueous phase was extracted with DCM (400 mL*5), the combined organic layers were dried over Na₂SO₄, concentrated in vacuum to get (1S,2R,4S,5R)-3-oxa-6-azatricyclo[3.2.1.02,4]octan-7-one (9.00 g, 71.93 mmol, yield: 26.16%) as a yellow solid. ¹H-NMR (400 MHz, CDCl₃) δ ppm 5.96 (br.s, 1H), 3.86 (s, 1H), 3.62 (1H, d, J=3.2 Hz), 3.53 (1H, d, J=2.8 Hz), 2.86 (s, 1H), 1.82 (d, 1H, J=9.6 Hz), 1.64 (d, 1H, J=10.0 Hz).

Step 2: tert-butyl (1S,2R,4S,5R)-7-oxo-3-oxa-6-azatricyclo[3.2.1.02,4]octane-6-carboxylate

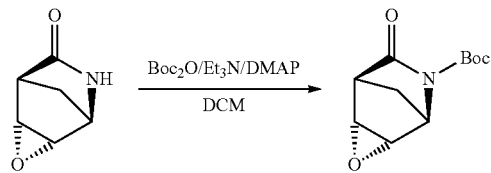

To a solution of (1S,2R,4S,5R)-3-oxa-6-azatricyclo[3.2.1.02,4]octan-7-one (9.00 g, 71.93 mmol, 1.00 eq) in DCM (100.00 mL) was added Boc₂O (17.27 g, 79.12 mmol, 1.10 eq), Et₃N (8.73 g, 86.32 mmol, 1.20 eq) and DMAP (878.71 mg, 7.19 mmol, 0.10 eq), the mixture was stirred at 25° C. for 16 hrs, LCMS showed the starting material was consumed completely, the mixture was washed with NH₄Cl aq. (100 mL*3), the combined organic layers were dried over Na₂SO₄, concentrated in vacuum, the crude product was purified with column chromatography on silica gel (PE:EtOAc=5:1~1:1) to get tert-butyl (1S,2R,4S,5R)-7-oxo-3-oxa-6-azatricyclo[3.2.1.02,4]octane-6-carboxylate (12.00 g, 53.28 mmol, yield: 74.07%) as a yellow solid. ¹H-NMR (400 MHz, CDCl₃) δ ppm 4.56 (s, 1H), 3.71 (d, 1H, J=2.8 Hz), 3.54 (d, 1H, J=2.8 Hz), 3.00 (s, 1H), 1.75 (d, 1H, J=10.0 Hz), 1.57 (d, 1H, J=10.8 Hz), 1.46 (s, 9H).

Step 3: methyl (3R,4R)-4-((tert-butoxycarbonyl)amino)-3-hydroxycyclopent-1-ene-1-carboxylate

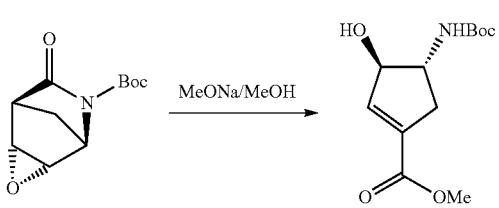

Na (3.37 mg, 146.50 umol, 0.01 eq) was added to MeOH (10.00 mL) at 0° C., then the solution was stirred at 0° C. for 0.5 hr, the solution was added to tert-butyl (1S,2R,4S,5R)-7-oxo-3-oxa-6-azatricyclo[3.2.1.02,4]octane-6-carboxylate (3.30 g, 14.65 mmol, 1.00 eq) in MeOH (30.00 mL), and then mixture was stirred at 16° C. for 13.5 hrs, LCMS showed the starting material was consumed completely, the reaction was quenched with acetic acid (5 mL), and then washed with NaHCO$_3$ (20 mL*3), the organic layer was dried over Na$_2$SO$_4$, and concentrated in vacuum, the crude product was washed with PE (20 mL) to get methyl (3R, 4R)-4-((tert-butoxycarbonyl)amino)-3-hydroxycyclopent-1-ene-1-carboxylate (2.10 g, 8.16 mmol, yield: 55.72%) as a white solid. $^1$H-NMR (400 MHz, CDCl$_3$) δ ppm 6.65 (s, 1H), 4.98 (s, 1H), 4.81 (d, 1H, J=2.8 Hz), 4.46 (s, 1H), 3.98-3.92 (m, 1H), 3.75 (s, 3H), 3.07-3.01 (m, 1H), 2.36-2.29 (m, 1H), 1.45 (s, 9H).

Step 4: methyl (1R,3R,4R)-3-((tert-butoxycarbonyl)amino)-4-hydroxycyclopentane-1-carboxylate

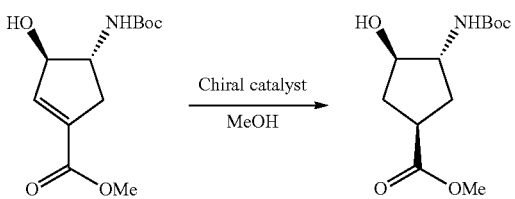 [SMILES: "MeOH" ; COC(=O)C1=C[C@@H](O)[C@H](NC(=O)OC(C)(C)C)C1 ; COC(=O)[C@H]1C[C@@H](O)[C@H](NC(=O)OC(C)(C)C)C1]

A mixture of methyl (3R,4R)-4-((tert-butoxycarbonyl)amino)-3-hydroxycyclopent-1-ene-1-carboxylate (2.00 g, 7.77 mmol, 1.00 eq), (1Z,5Z)-cycloocta-1,5-diene; (2S,5S)-1-[2-[(2S,5S)-2,5-dimethylphospholan-1-yl]ethyl]-2,5-dimethyl-phospholane; rhodium(1+); trifluoromethanesulfonate (48.08 mg, 77.74 umol, 0.01 eq) in MeOH (50.00 mL) was degassed and purged with H$_2$ for 3 times, and then the mixture was stirred at 55° C. for 16 hrs under H$_2$ (40 psi) atmosphere, TLC (PE:EtOAc=1:1) showed the starting material was consumed, the mixture was concentrated in vacuum, and then dissolved in EtOAc (5 mL), then to the mixture was added PE (20 mL), white solid was formed, the precipitate was collected, dried in vacuum, the solid was dissolved in MeOH (7 mL), and purified with acidic prep-HPLC (HCl) to get methyl (1R,3R,4R)-3-((tert-butoxycarbonyl)amino)-4-hydroxycyclopentane-1-carboxylate (750.00 mg, 2.89 mmol, yield: 37.23%) as a yellow oil, the structure was confirmed by chiral HPLC and $^1$H-NMR. $^1$H-NMR (400 MHz, CDCl$_3$) δ ppm 4.04-3.99 (m, 1H), 3.80-3.77 (m, 1H), 3.70 (s, 3H), 2.93-2.91 (m, 1H), 2.48-2.44 (m, 1H), 2.43-2.35 (m, 1H), 1.92-1.89 (m, 1H), 1.87-1.69 (m, 1H), 1.45 (s, 9H).

Example 18. Synthesis of methyl (1R,3R,4R)-3-amino-4-hydroxycyclopentane-1-carboxylate

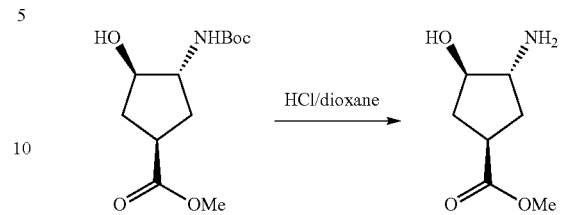

Methyl (1R,3R,4R)-3-((tert-butoxycarbonyl)amino)-4-hydroxycyclopentane-1-carboxylate (700.00 mg, 2.70 mmol, 1.00 eq) in HCl/dioxane (10.00 mL, 4 M) was stirred at 19° C. for 5 hrs, LCMS showed the starting material was consumed, the mixture was concentrated in vacuum to get methyl (1R,3R,4R)-3-amino-4-hydroxycyclopentane-1-carboxylate (500.00 mg, 2.56 mmol, yield: 94.66%) as yellow oil. $^1$H-NMR (400 MHz, CD$_3$OD) δ ppm 4.09-4.05 (m, 1H), 3.75-3.66 (m, 3H), 3.37-3.33 (m, 1H), 3.06-3.04 (m, 1H), 2.45-2.37 (m, 2H), 1.87-1.81 (m, 2H). LC-MS (mobile phase: from 95% [water+0.375‰ v/v TFA] and 5% [CH$_3$CN+0.188‰ v/v TFA], under this condition for 0.25 min, then changed to 15% [CH$_3$CN+0.188‰ v/v TFA] in 10.0 min, under this condition for 5 min, finally changed to 95% [water+0.375‰ v/v TFA] and 5% [CH$_3$CN+0.188‰ v/v TFA] in 0.01 min, then under this condition for 5 min. The flow is 1.0 mL·min$^{-1}$ all along) purity is 98.803%, Rt=0.893 min, MS Calcd.: 159.2, MS Found: 160.1 ([M+1]$^+$).

Example 19. (3aS,4R,6aR)-2,2-dimethyl-3a,6a-dihydro-4H-cyclopenta[d][1,3]dioxol-4-amine

Step 1: (3aS,4S,6aR)-2,2-dimethyl-3a,6a-dihydro-4H-cyclopenta[d][1,3]dioxol-4-ol

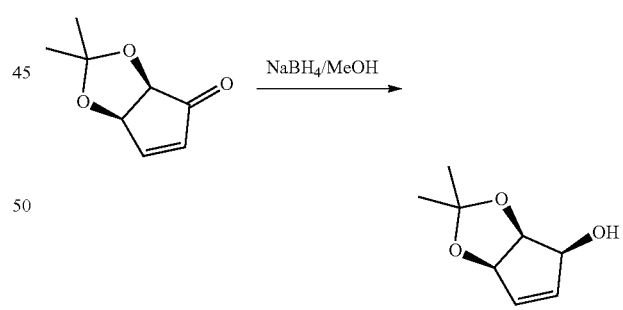

(3aR,6aR)-2,2-dimethyl-3a,6a-dihydro-4H-cyclopenta[d][1,3]dioxol-4-one (50.00 g, 324.34 mmol, 1.00 eq) was taken up to MeOH (1.00 L), then CeCl$_3$.7H$_2$O (120.84 g, 324.34 mmol, 30.83 mL, 1.00 eq) was added. The mixture was cooled to 0° C. Then NaBH$_4$ (24.54 g, 648.68 mmol, 2.00 eq) was added portion-wise at 0° C. among 1.5 hrs. After addition, the reaction was complete checked by TLC (PE/EtOAc=5/1). The reaction was quenched by saturated NH$_4$Cl (1000 mL), extracted with DCM (500 mL*5). The combined organic layers were dried over Na$_2$SO$_4$ and concentrated in vacuo at 45° C. (3aS,4S,6aR)-2,2-dimethyl-3a, 6a-dihydro-4H-cyclopenta[d][1,3]dioxol-4-ol (50.66 g, 324.37 mmol, yield: 100.00%) was obtained as a yellow liquid, which was used directly without purification.

Step 2: 2-((3aS,4R,6aR)-2,2-dimethyl-3a,6a-dihydro-4H-cyclopenta[d][1,3]dioxol-4-yl)isoindoline-1,3-dione

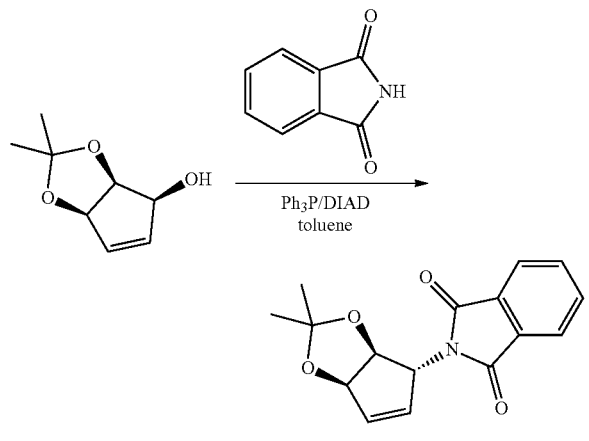

To the mixture of (3aS,4S,6aR)-2,2-dimethyl-3a,6a-dihydro-4H-cyclopenta[d][1,3]dioxol-4-ol (8.00 g, 51.22 mmol, 1.00 eq) and isoindoline-1,3-dione (9.04 g, 61.46 mmol, 1.20 eq) in toluene (250.00 mL) was added PPh$_3$ (20.15 g, 76.83 mmol, 1.50 eq) at 20° C. Then DIAD (15.54 g, 76.83 mmol, 1.50 eq) was added dropwise to the mixture at 0° C. After addition, the mixture was allowed to 80° C. and stirred for 16 hrs. TLC (PE/EtOAc=5/1) showed the reaction was complete. The mixture was concentrated. The residue was purified by column chromatography on silica gel (PE/EtOAc=25/1 to 15/1). The obtained product was crude as yellow oil with some polar spots on TLC. So 80 mL of MeOH was added and the white precipitate was generated and collected by filtration. 2-((3aS,4R,6aR)-2,2-dimethyl-3a,6a-dihydro-4H-cyclopenta[d][1,3]dioxol-4-yl)isoindoline-1,3-dione (9.60 g, 33.65 mmol, yield: 65.70%) was obtained as a white solid.

Step 3: (3aS,4R,6aR)-2,2-dimethyl-3a,6a-dihydro-4H-cyclopenta[d][1,3]dioxol-4-amine

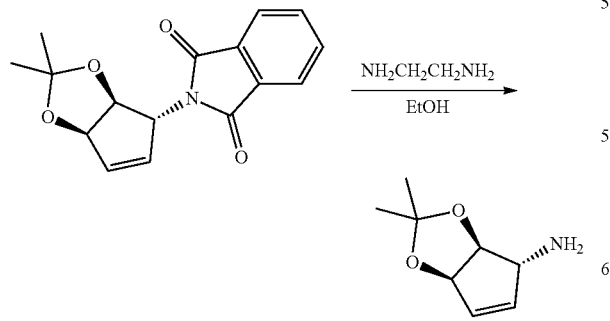

To the mixture of 2-((3aS,4R,6aR)-2,2-dimethyl-3a,6a-dihydro-4H-cyclopenta[d][1,3]dioxol-4-yl)isoindoline-1,3-dione (9.52 g, 33.37 mmol, 1.00 eq) in EtOH (300.00 mL) was added ethane-1,2-diamine (4.01 g, 66.74 mmol, 2.00 eq). The resulting mixture was stirred at 80° C. for 16 hrs. Lots of white precipitate was generated. TLC (PE/EtOAc=5/1) showed the starting material was consumed completely. The precipitate was filtered. To the filtrate was added 300 mL of NaOH (0.5 M). The mixture was extracted with DCM (200 mL*5), dried over Na$_2$SO$_4$ and concentrated. (3aS,4R,6aR)-2,2-dimethyl-3a,6a-dihydro-4H-cyclopenta[d][1,3]dioxol-4-amine (4.90 g, 31.57 mmol, yield: 94.62%) was obtained as a yellow oil.

Example 20. (1R,3R,4R)-3-amino-4-hydroxycyclopentane-1-carbonitrile

Step 1: (1R,3R,4R)-3-((tert-butoxycarbonyl)amino)-4-hydroxycyclopentane-1-carboxylic Acid

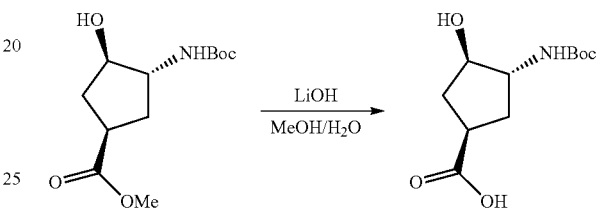

A mixture of methyl (1R,3R,4R)-3-((tert-butoxycarbonyl)amino)-4-hydroxycyclopentane-1-carboxylate (5.00 g, 19.28 mmol, 1.00 eq), LiOH.H$_2$O (2.43 g, 57.85 mmol, 3.00 eq) in MeOH (10.00 mL) and H$_2$O (10.00 mL) was stirred at 15° C. for 16 hrs, TLC (PE:EtOAc=1:1) showed the reaction was complete, to the mixture was added diluted HCl (1 M) until pH=6, and concentrated in vacuum, then the mixture was the dissolved in DCM (15 mL) and EtOAc (5 mL), the mixture was filtered, and the filtrate was concentrated in vacuum to get the product (1R,3R,4R)-3-((tert-butoxycarbonyl)amino)-4-hydroxycyclopentane-1-carboxylic acid (6.50 g, crude) as a white solid. $^1$H-NMR (400 MHz, CD$_3$OD) δ ppm 3.95-3.90 (m, 1H), 3.74-3.69 (m, 1H), 2.91-2.87 (m, 1H), 2.32-2.22 (m, 2H), 1.82-1.72 (m, 2H), 1.45 (s, 9H).

Step 2: tert-butyl ((1R,2R,4R)-4-carbamoyl-2-hydroxycyclopentyl)carbamate

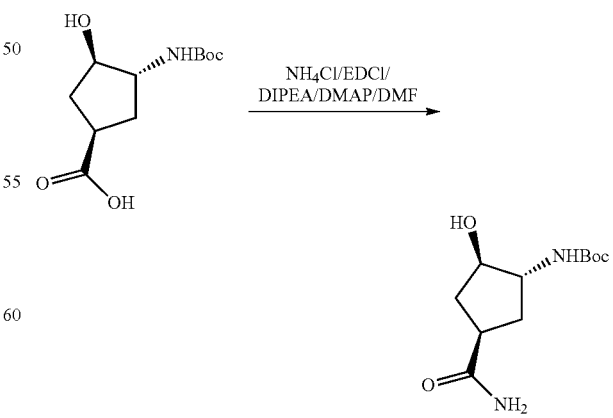

To a mixture of (1R,3R,4R)-3-((tert-butoxycarbonyl)amino)-4-hydroxycyclopentane-1-carboxylic acid (3.00 g, 12.23 mmol, 1.00 eq) in DMF (40.00 mL) was added HATU (6.05 g, 15.90 mmol, 1.30 eq), DIPEA (4.74 g, 36.69 mmol, 3.00 eq) and NH₄Cl (1.96 g, 36.69 mmol, 3.00 eq), and then the mixture was stirred at 15° C. for 32 hrs, LCMS showed the reaction was complete, the mixture was concentrated in vacuum to get tert-butyl ((1R,2R,4R)-4-carbamoyl-2-hydroxycyclopentyl)carbamate (11 g, crude) (2 batches were set up and purified together). ¹H-NMR (400 MHz, CD₃OD) δ ppm 4.58 (br.s, 1H), 3.96-3.94 (m, 1H), 3.77-3.75 (m, 1H), 2.25-2.20 (m, 2H), 1.79-1.75 (m, 2H), 1.44 (s, 9H).

Step 3: tert-butyl ((1R,2R,4R)-4-cyano-2-hydroxycyclopentyl)carbamate

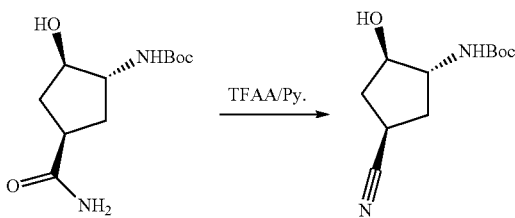 [SMILES: CC(C)(C)OC(=O)N[C@@H]1C[C@@H](C(N)=O)C[C@H]1O ; "TFAA/Py." ; CC(C)(C)OC(=O)N[C@@H]1C[C@@H](C#N)C[C@H]1O]

To a mixture of tert-butyl ((1R,2R,4R)-4-carbamoyl-2-hydroxycyclopentyl)carbamate (2.00 g, 8.19 mmol, 1.00 eq), pyridine (1.94 g, 24.56 mmol, 3.00 eq) in THF (3.00 mL) was added TFAA (2.58 g, 12.28 mmol, 1.50 eq) dropwise at 0° C., then the mixture was stirred at 0° C. for 0.5 hr, then to the mixture was added Et₃N (2.49 g, 24.56 mmol, 3.00 eq) at 15° C., and the mixture was stirred at 15° C. for 0.5 hr, and to the mixture was added TFAA (2.58 g, 12.28 mmol, 1.50 eq), and the mixture was stirred at 15° C. for 0.5 hr, LCMS showed the reaction was complete, the mixture was concentrated in vacuum, purified by prep-HPLC (TFA, MS) to get tert-butyl ((1R,2R,4R)-4-cyano-2-hydroxycyclopentyl)carbamate (380.00 mg, 1.68 mmol, yield: 20.51%) as a colorless oil. ¹H-NMR (400 MHz, CD₃OD) (5 ppm 4.07-3.97 (m, 1H), 3.79-3.78 (m, 0.5H), 3.51-3.49 (m, 0.5H), 3.19-3.05 (m, 1H), 2.44-2.35 (m, 0.5H), 2.33-2.28 (m, 1.5H), 1.97-1.94 (m, 1H), 1.92-1.82 (m, 1H), 1.41 (s, 9H).

Step 4: (1R,3R,4R)-3-amino-4-hydroxycyclopentane-1-carbonitrile

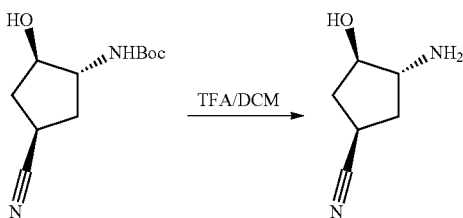

A mixture of tert-butyl ((1R,2R,4R)-4-cyano-2-hydroxycyclopentyl)carbamate (800.00 mg, 3.54 mmol, 1.00 eq) in TFA (5.00 mL) and DCM (5.00 mL) was stirred at 20° C. for 2 hrs, LCMS showed the reaction was complete, the mixture was concentrated in vacuum to get (1R,3R,4R)-3-amino-4-hydroxycyclopentane-1-carbonitrile (545.00 mg, 2.27 mmol, yield: 64.10%) as a colorless oil. ¹H-NMR (400 MHz, CD₃OD) δ ppm 4.12-4.06 (m, 1H), 3.51-3.47 (m, 1H), 3.23-3.20 (m, 1H), 2.48-2.42 (m, 2H), 2.11-2.10 (m, 1H), 1.94-1.90 (m, 1H).

Example 21. (3aS,4R,6aS)-6,6-difluoro-2,2-dimethyltetrahydro-4H-cyclopenta[d][1,3]dioxol-4-amine Step 1: 2-((3aS,4R,6S,6aR)-6-hydroxy-2,2-dimethyltetrahydro-4H-cyclopenta[d][1,3]dioxol-4-yl)isoindoline-1,3-dione

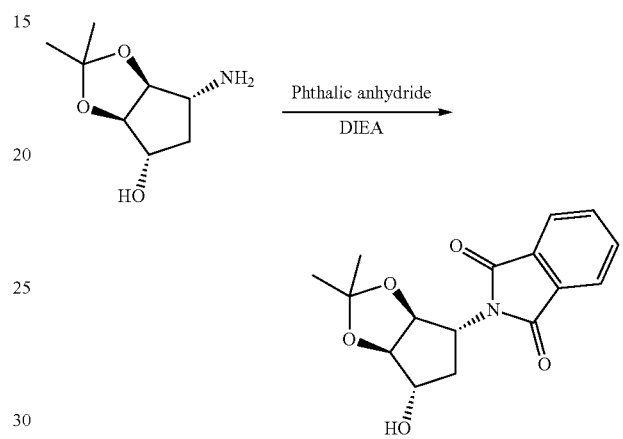

A mixture of (3aR,4S,6R,6aS)-6-amino-2,2-dimethyltetrahydro-4H-cyclopenta[d][1,3]dioxol-4-ol (0.43 g, 2.46 mmol, 1.00 eq), Phthalic anhydride (0.36 g, 2.46 mmol, 1 eq) and DIEA (0.65 mL, 3.7 mmol, 1.5 eq) in Toluene (6.2 mL) was stirred at 100° C. for 9 hrs. LCMS showed the reaction was complete. EtOAc was added to the reaction mixture and then washed with aqueous saturated sodium bicarbonate solution (15 mL). The combined organic layers were washed with saturated brine solution, dried over Na₂SO₄ and concentrated in vacuo. The residue was purified by column chromatography on silica gel (Hexanes/EtOAc) to get the product 2-((3aS,4R,6S,6aR)-6-hydroxy-2,2-dimethyltetrahydro-4H-cyclopenta[d][1,3]dioxol-4-yl)isoindoline-1,3-dione (0.62 g, 83%) as a white solid.

Step 2: 2-((3aS,4R,6aS)-2,2-dimethyl-6-oxotetrahydro-4H-cyclopenta[d][1,3]dioxol-4-yl)isoindoline-1,3-dione

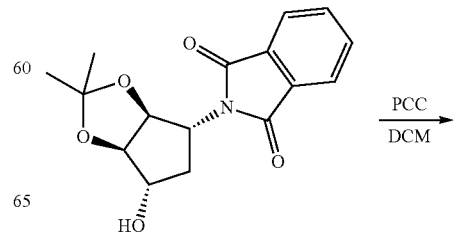

-continued

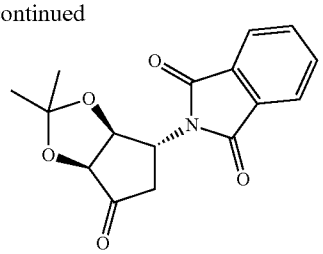

To a solution of 2-((3aS,4R,6S,6aR)-6-hydroxy-2,2-dimethyltetrahydro-4H-cyclopenta[d][1,3]dioxol-4-yl)isoindoline-1,3-dione (0.20 g, 0.68 mmol, 1.00 eq) in DCM (4.5 mL) was added PCC (0.29 g, 1.35 mmol, 2 eq) and the solution was stirred at 23° C. for 16 hrs. Another aliquot of PCC (0.15 g, 0.67 mmol) was added and the reaction continued for another 16 hours. LCMS showed the reaction was complete. EtOAc was added to the reaction mixture and then filtered through a celite pad. The residue was concentrated and then purified by column chromatography on silica gel (Hexanes/EtOAc) to get the product 2-((3aS,4R,6aS)-2,2-dimethyl-6-oxotetrahydro-4H-cyclopenta[d][1,3]dioxol-4-yl)isoindoline-1,3-dione (0.19 g, 94%) as an off-white solid.

Step 3: 2-((3aS,4R,6aS)-6,6-difluoro-2,2-dimethyltetrahydro-4H-cyclopenta[d][1,3]dioxol-4-yl)isoindoline-1,3-dione

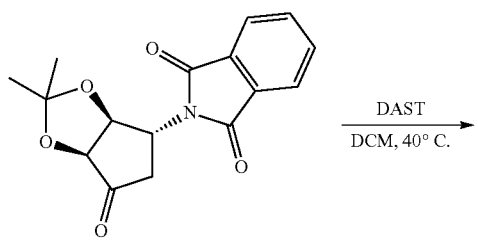

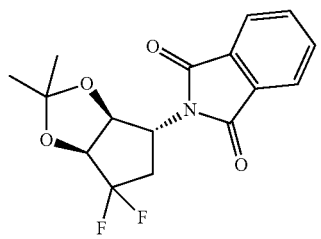

To a solution of 2-((3aS,4R,6aS)-2,2-dimethyl-6-oxotetrahydro-4H-cyclopenta[d][1,3]dioxol-4-yl)isoindoline-1,3-dione (0.16 g, 0.53 mmol, 1.00 eq) in DCM (3.5 mL) was added DAST (0.42 g, 2.64 mmol, 5 eq) and the solution was stirred at reflux for 16 hrs. Another aliquot of DAST (0.42 g, 2.64 mmol, 5 eq) was added and the reaction continued for another 16 hours at 23° C. The reaction mixture was diluted with DCM and then washed with aqueous saturated sodium bicarbonate solution. The combined organic layers were washed with saturated brine solution, dried over Na$_2$SO$_4$ and concentrated in vacuo. The residue was purified by column chromatography on silica gel (Hexanes/EtOAc) to get the product 2-((3aS,4R,6aS)-6,6-difluoro-2,2-dimethyltetrahydro-4H-cyclopenta[d][1,3]dioxol-4-yl)isoindoline-1,3-dione (0.065 g, 38%).

Step 4: (3 aS,4R,6aS)-6,6-difluoro-2,2-dimethyltetrahydro-4H-cyclopenta[d][1,3]dioxol-4-amine

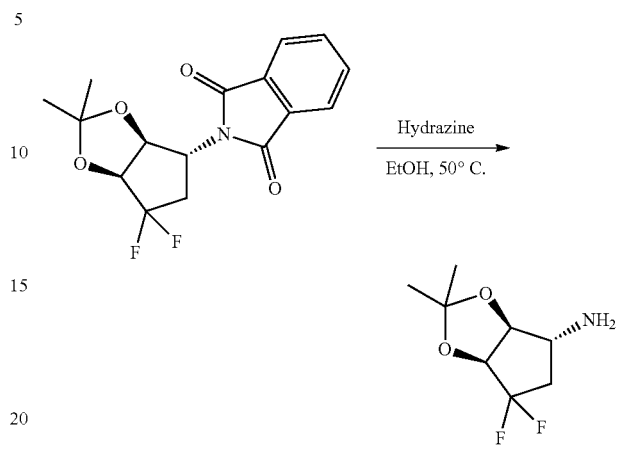

To a solution of 2-((3aS,4R,6aS)-6,6-difluoro-2,2-dimethyltetrahydro-4H-cyclopenta[d][1,3]dioxol-4-yl)isoindoline-1,3-dione (0.065 g, 0.2 mmol, 1.00 eq) in Ethanol (1.8 mL) was added Hydrazine monohydrate (0.015 mL, 0.3 mmol, 1.5 eq) and the solution was stirred at 50° C. for 2 hrs and then at 70° C. for another 2 hours. The heterogeneous reaction mixture was filtered using minimum volume of Ethanol. The filtrate was then concentrated and the isolated crude product (3aS,4R,6aS)-6,6-difluoro-2,2-dimethyltetrahydro-4H-cyclopenta[d][1,3]dioxol-4-amine was used without further purification in the next step.

Example 22. Synthesis of (1R,3R,4R)-4-aminocyclohexane-1,3-diol

Step 1: (1r,4r)-4-(benzyloxy)cyclohexanol and (1s,4s)-4-(benzyloxy)cyclohexanol

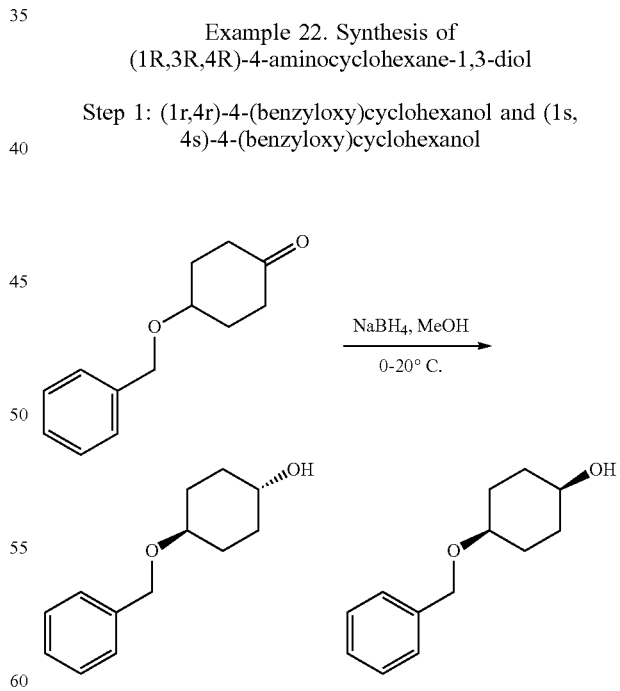

To an ice-bath cooled solution of 4-(benzyloxy)cyclohexanone (31.0 g, 152 mmol) in 500 mL methanol, sodium borohydride (5.78 g, 153 mmol) was added in several portion during a period of 10 min, then the solution was stirred at 20° C. for 2 h. Then the mixture was quenched by saturated aqueous solution of ammonium chloride (50 mL), concentrated and the residue was dissolved in 200 mL water and extracted with ethyl acetate (200 mL×3), the combined organic phase was dried over sodium sulfate, then concentrated under vacuo to give title product (1r,4r)-4-(benzyloxy) cyclohexanol and (1s,4s)-4-(benzyloxy)cyclohexanol as a pale yellow oil (31.0 g, crude) which was used to next step directly without further purification. MS (ES+) $C_{13}H_{18}O_2$ requires: 206, found: 207[M+H]$^+$.

Step 2: ((Cyclohex-3-enyloxy)methyl)benzene

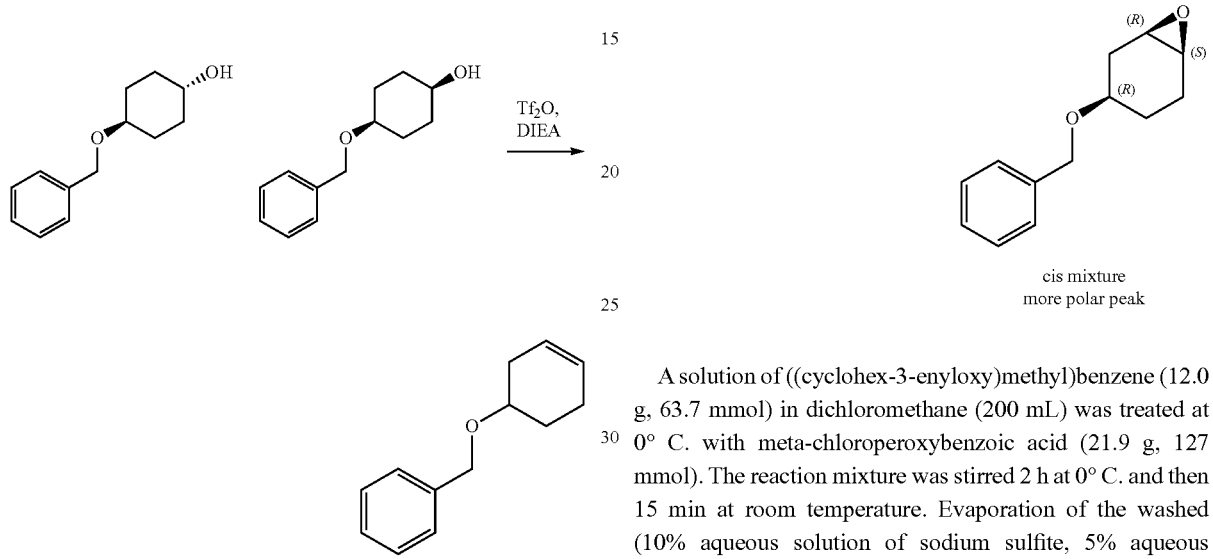

To an ice-bath cooled solution of (1r,4r)-4-(benzyloxy) cyclohexanol and (1s,4s)-4-(benzyloxy)cyclohexanol (30.0 g, 145 mmol) and N,N-Diisopropylethylamine (28.1 g, 218 mmol) in 1200 mL dichloromethane, trifluoromethanesulfonic anhydride (30.7 g, 109 mmol) was added dropwise during a period of 30 min, then the solution was stirred at 25° C. for 18 h. Then the mixture was concentrated under vacuo and the residue was purified with silica gel column chromatography, eluting with petroleum ether:ethyl acetate=12:1 to give the title compound (28.0 g, yield 100%) as a yellow oil. MS (ES+) $C_{13}H_{16}O$ requires: 188, found: 189 [M+H]$^+$.

Step 3: (1R,3R,6S)-3-(benzyloxy)-7-oxa-bicyclo[4.1.0]heptane

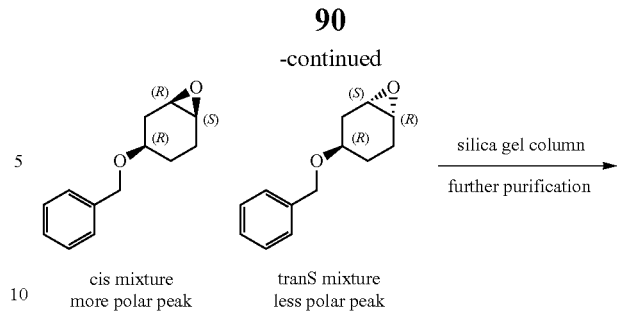

A solution of ((cyclohex-3-enyloxy)methyl)benzene (12.0 g, 63.7 mmol) in dichloromethane (200 mL) was treated at 0° C. with meta-chloroperoxybenzoic acid (21.9 g, 127 mmol). The reaction mixture was stirred 2 h at 0° C. and then 15 min at room temperature. Evaporation of the washed (10% aqueous solution of sodium sulfite, 5% aqueous sodium hydroxide solution and then water) organic solution afforded a liquid residue, which was separated with silica gel column chromatography, eluting with hexane:isopropyl ether:ethyl acetate=65:28:7 to give the title compound (4.18 g, yield 32%) as a yellow oil. The trans-(1S,3R,6R)-3-(benzyloxy)-7-oxa-bicyclo[4.1.0]heptane showed a little less polarity on TLC and eluted firstly. The cis-(1R,3R,6S)-3-(benzyloxy)-7-oxa-bicyclo[4.1.0]heptane eluted secondly. MS (ES+) $C_{13}H_{16}O_2$ requires: 204, found: 205 [M+H]$^+$.

Step 4: (1R,2R,5R)-5-(benzyloxy)-2-((S)-1-phenylethylamino)cyclohexanol

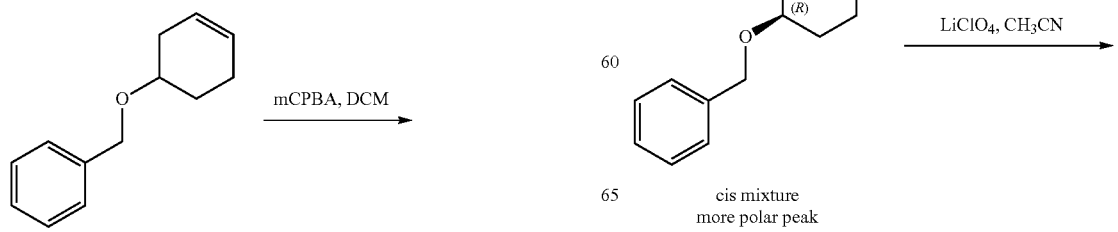

-continued

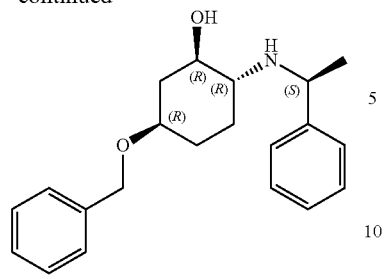

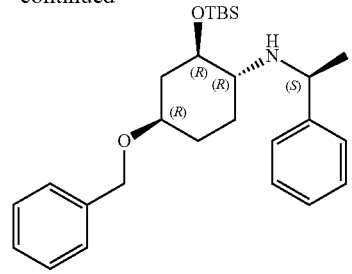

Lithium perchlorate (7.27 g, 68.4 mmol) was added to an ice-bath cooled stirred solution of (1R,3R,6S)-3-(benzyloxy)-7-oxa-bicyclo[4.1.0]heptane (7.0 g, 34.2 mmol) in 120 mL 4 A-MS dried acetonitrile, the bath was removed and (S)-1-phenylethanamine (5.58 g, 46.1 mmol) was added dropwise during a period of 15 min, then the solution was stirred at 25° C. for 18 h. Then the mixture was diluted in 200 mL water and extracted with ethyl acetate (200 mL×3), the combined organic phase was dried over sodium sulfate, then concentrated and the residue was purified with silica gel column chromatography, eluting with petroleum ether:ethyl acetate:triethylamine=98:0:2~49:49:2 to give the title compound (3.5 g, yield 31%) as a yellow oil. The (1S,2S,5S)-5-(benzyloxy)-2-((S)-1-phenylethylamino)cyclohexanol showed a little less polarity on TLC, and eluted firstly. The (1R,2R,5R)-5-(benzyloxy)-2-((S)-1-phenylethylamino)cyclohexanol eluted secondly. MS (ES+) $C_{21}H_{27}NO_2$ requires: 325, found: 326[M+H]$^+$.

Step 5: (1R,2R,4R)-4-(benzyloxy)-2-(tert-butyldimethylsilyloxy)-N—((S)-1-phenylethyl)cyclohexanamine

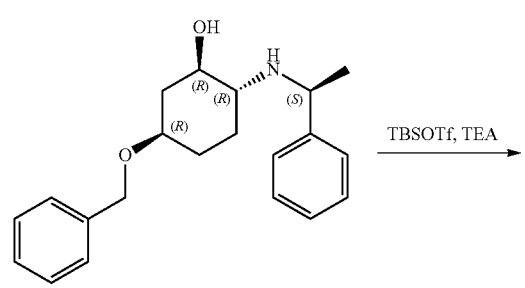

tert-Butyldimethylsilyl trifluoromethanesulfonate (13.0 g, 49.5 mmol) was added to an ice-bath cooled, stirred solution of (1R,2R,5R)-5-(benzyloxy)-2-((S)-1-phenylethylamino) cyclohexanol (5.4 g, 16.5 mmol) and triethylamine (5.0 g, 49.5 mmol) in 100 mL dried dichloromethane. After 30 min, this was washed with a saturated aqueous solution of sodium bicarbonate, dried over sodium sulfate. Removal of the solvent, and the residue was purified with silica gel column chromatography, eluting with petroleum ether:ethyl acetate=100:0~70:30 to give the title compound (5.4 g, yield 71%) as a yellow oil. MS (ES+) $C_{27}H_{41}NO_2Si$ requires: 439, found: 440 [M+H]$^+$.

Step 7: (1R,2R,5R)-5-(benzyloxy)-2-((S)-1-phenylethylamino)cyclohexanol

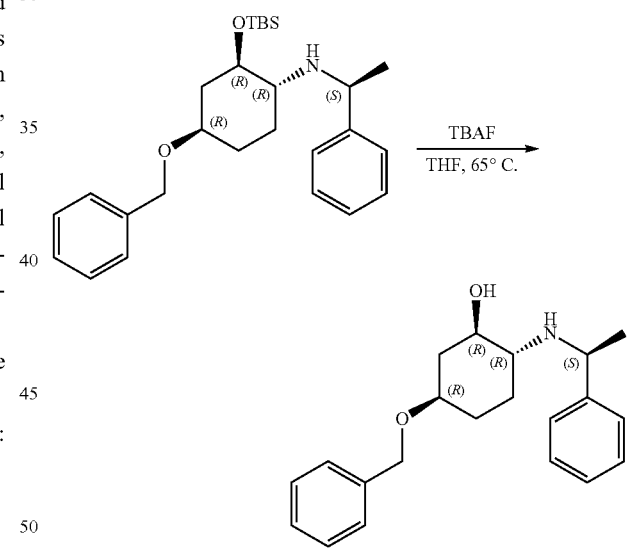

Tetrabutylammonium fluoride (2.66 g, 10.2 mmol) was added to a stirred solution of (1R,2R,4R)-4-(benzyloxy)-2-(tert-butyldimethylsilyloxy)-N—((S)-1-phenylethyl)cyclohexanamine (1.5 g, 3.41 mmol) in 50 mL dried oxolane at room temperature. Then this solution was stirred at 65° C. for 2 h. Then the mixture was concentrated under vacuo and the residue was diluted in 200 mL water and extracted with ethyl acetate (200 mL×3), the combined organic phase was washed with water and saturated aqueous solution of sodium chloride, dried over sodium sulfate. Removal of the solvent, and the residue was purified with silica gel column chromatography, eluting with petroleum ether:ethyl acetate=100:0~70:30 to give the title compound (0.75 g, yield 68%) as a colorless oil. MS (ES+) $C_{21}H_{27}NO_2$ requires: 325, found: 326[M+H]$^+$.

Step 8: (1R,3R,4R)-4-aminocyclohexane-1,3-diol

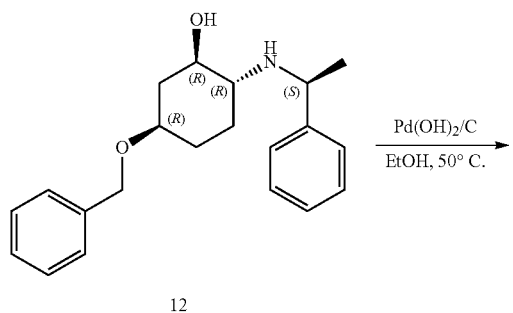

10% Palladium hydroxide in activated carbon (697 mg, catalyst) was added to a solution of (1R,2R,5R)-5-(benzyloxy)-2-((S)-1-phenylethylamino)cyclohexanol (650 mg, 1.99 mmol) in 15 mL ethanol at room temperature. Then this solution was stirred at 50° C. for 20 h under hydrogen. Then the mixture was cooled and filtered though celite, the filter-cake was washed with methanol:dichloromethane=1:10, the filtrate was concentrated under vacuo and the residue was diluted in 20 mL methanol:dichloromethane=1:10 solution and concentrated, dried under high-vacuo, then cooled at −20° C. to give the title compound (240 mg, yield 92%) as a white crystal. MS (ES+) $C_6H_{13}NO_2$ requires: 131, found: 132[M+H]$^+$. $^1$H-NMR (400 MHz, 6d-DMSO) δ ppm 4.62-4.49 (m, 2H), 3.42-3.33 (m, 2H, J=3.2 Hz), 2.93-2.86 (m, 1H), 2.25-2.18 (m, 1H), 1.98-1.92 (m, 1H), 1.72-1.59 (m, 3H), 1.13-1.03 (m, 2H), 0.97-0.90 (m, 1H).

Example 23. Synthesis of tert-butyl (1R,2R)-2-(tert-butyldimethylsilyloxy)-4-oxocyclohexylcarbamate Step 1: tert-butyl (1R,2R,4R)-2-(tert-butyldimethylsilyloxy)-4-hydroxycyclohexylcarbamate

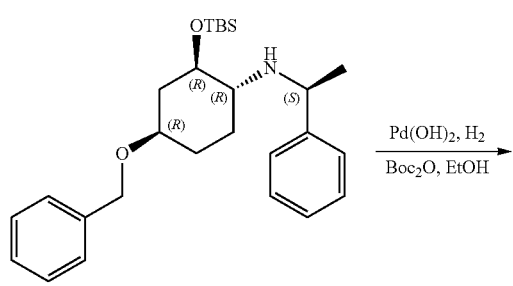

10% Palladium hydroxide in activated carbon (1.9 g, catalyst) was added to a solution of (1R,2R,4R)-4-(benzyloxy)-2-(tert-butyldimethylsilyloxy)-N—((S)-1-phenylethyl)cyclohexanamine from the previous example (2.0 g, 4.54 mmol) and di-tert-butyl dicarbonate (3.95 g, 18.1 mmol) in 60 mL ethanol at room temperature. Then this solution was stirred at 50° C. for 20 h under hydrogen. Then the mixture was cooled and filtered through celite, the filter-cake was washed with methanol:dichloromethane=1:10, the filtrate was concentrated under vacuo and the residue was diluted in 20 mL methanol:dichloromethane=1:10 solution and concentrated, dried under high-vacuo to give the title compound (1.2 g, yield 77%) as a colorless oil. MS (ES+) $C_{17}H_{35}NO_4Si$ requires: 345, found: 346 [M+H]$^+$.

Step 2: tert-butyl (1R,2R)-2-(tert-butyldimethylsilyloxy)-4-oxocyclohexylcarbamate

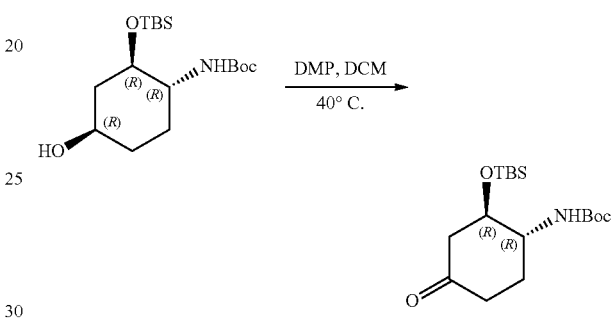

1,1,1-Triacetoxy-1,1-dihydro-1,2-benziodoxol-3(1H)-one (Dess-Martin periodinane, 4.11 g, 9.71 mmol) was added to a solution of tert-butyl (1R,2R,4R)-2-(tert-butyldimethylsilyloxy)-4-hydroxycyclohexylcarbamate (1.4 g, 4.05 mmol) in 50 mL dichloromethane at room temperature. Then this solution was stirred at 40° C. for 3 h under nitrogen. Then the mixture concentrated under vacuo and the residue was purified with silica gel column chromatography, eluting with petroleum ether:ethyl acetate=100:0~95:5 to give the title compound (1.2 g, yield 86%) as a yellow oil. MS (ES+) $C_{17}H_{33}NO_4Si$ requires: 343, found: 344[M+H]$^+$. $^1$H-NMR (400 MHz, CDCl$_3$) δ ppm 4.70-4.49 (br., 1H), 4.10-3.90 (br. s, 1H), 3.79-3.65 (br., 1H), 2.64 (dd, 1H, J=14.4, 4.0 Hz), 2.42-2.28 (m, 4H), 1.46 (s, 9H), 0.87 (s, 9H), 0.08 (d, 6H, J=6.8 Hz).

Example 23. Synthesis of tert-butyl (1R,2R)-2-(tert-butyldimethylsilyloxy)-4-oxocyclohexylcarbamate and (1R,3R,4R)-4-aminocyclohexane-1,3-diol Step 1: (1R,4R)-4-(benzyloxy)cyclohexanol and (1S,4S)-4-(benzyloxy)cyclohexanol

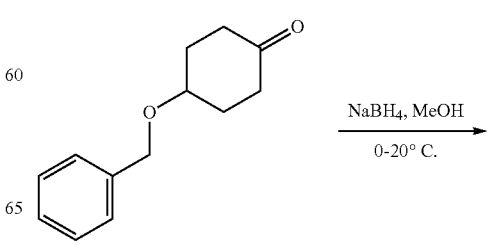

-continued

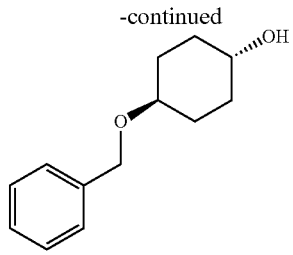

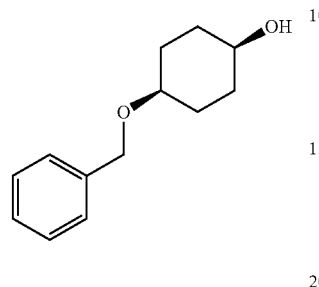

To an ice-bath cooled solution of 4-(benzyloxy)cyclohexanone (31.0 g, 152 mmol) in 500 mL methanol, sodium borohydride (5.78 g, 153 mmol) was added in several portion during a period of 10 min, then the solution was stirred at 20° C. for 2 h. Then the mixture was quenched by saturated aqueous solution of ammonium chloride (50 mL), concentrated and the residue was dissolved in 200 mL water and extracted with ethyl acetate (200 mL×3), the combined organic phase was dried over sodium sulfate, then concentrated under vacuo to give title product (1R,4R)-4-(benzyloxy)cyclohexanol and (1S,4S)-4-(benzyloxy)cyclohexanol as a pale yellow oil (31.0 g, crude) which was used to next step directly without further purification. MS (ES+) $C_{13}H_{18}O_2$ requires: 206, found: 207[M+H]$^+$.

Step 2: ((Cyclohex-3-enyloxy)methyl)benzene

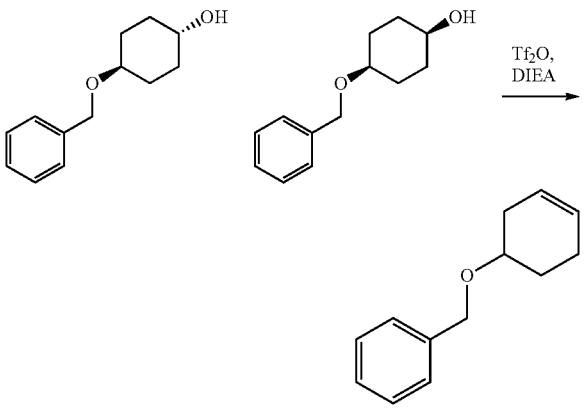

To an ice-bath cooled solution of (1R,4R)-4-(benzyloxy) cyclohexanol and (1S,4S)-4-(benzyloxy)cyclohexanol (30.0 g, 145 mmol) and N,N-Diisopropylethylamine (28.1 g, 218 mmol) in 1200 mL dichloromethane, trifluoromethanesulfonic anhydride (30.7 g, 109 mmol) was added dropwise during a period of 30 min, then the solution was stirred at 25° C. for 18 h. Then the mixture was concentrated under vacuo and the residue was purified with silica gel column chromatography, eluting with petroleum ether:ethyl acetate=12:1 to give the title compound (28.0 g, yield 100%) as a yellow oil. MS (ES+) $C_{13}H_{16}O$ requires: 188, found: 189 [M+H]$^+$.

Step 3: (1R,3R,6S)-3-(benzyloxy)-7-oxa-bicyclo[4.1.0]heptane

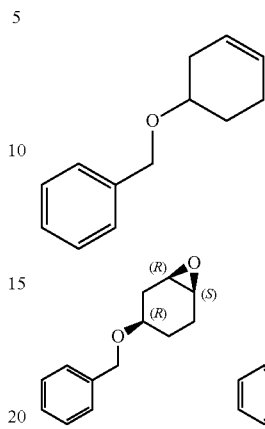

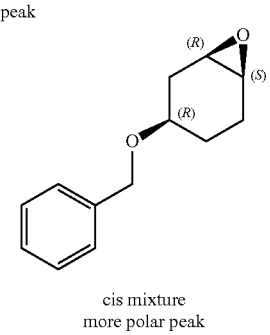

A solution of ((cyclohex-3-enyloxy)methyl)benzene (12.0 g, 63.7 mmol) in dichloromethane (200 mL) was treated at 0° C. with meta-chloroperoxybenzoic acid (21.9 g, 127 mmol). The reaction mixture was stirred 2 h at 0° C. and then 15 min at room temperature. Evaporation of the washed (10% aqueous solution of sodium sulfite, 5% aqueous sodium hydroxide solution and then water) organic solution afforded a liquid residue, which was separated with silica gel column chromatography, eluting with hexane:isopropyl ether:ethyl acetate=65:28:7 to give the title compound (4.18 g, yield 32%) as a yellow oil. The trans-(1S,3R,6R)-3-(benzyloxy)-7-oxa-bicyclo[4.1.0]heptane showed a little less polarity on TLC and eluted firstly. The cis-(1R,3R,6S)-3-(benzyloxy)-7-oxa-bicyclo[4.1.0]heptane eluted secondly. MS (ES+) $C_{13}H_{16}O_2$ requires: 204, found: 205 [M+H]$^+$.

cis-(1R,3R,6S)-3-(benzyloxy)-7-oxa-bicyclo[4.1.0]heptane $^1$H-NMR (400 MHz, CDCl$_3$) δ ppm 7.35-7.27 (m, 5H), 4.56-4.45 (m, 2H), 3.35-3.29 (m, 1H), 3.12-3.09 (m, 2H), 2.37-2.32 (m, 1H), 2.25-2.20 (m, 1H), 1.89-1.68 (m, 3H), 1.49-1.44 (m, 1H).

Trans-(1S,3R,6R)-3-(benzyloxy)-7-oxa-bicyclo[4.1.0]heptane $^1$H-NMR (400 MHz, CDCl$_3$) δ ppm 7.35-7.27 (m, 5H), 4.48 (dd, 2H, J=28.0, 12.4 Hz), 3.56-3.52 (m, 1H), 3.19-3.17 (m, 2H), 2.24-2.18 (m, 1H), 2.15-2.07 (m, 1H), 2.00-1.91 (m, 2H), 1.64-1.53 (m, 2H).

Step 3: (1R,2R,5R)-5-(benzyloxy)-2-((S)-1-phenyl-ethylamino)cyclohexanol

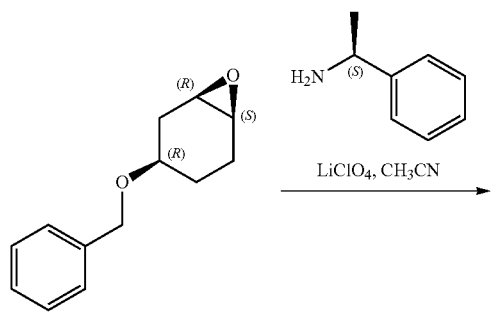

cis mixture; more polar peak

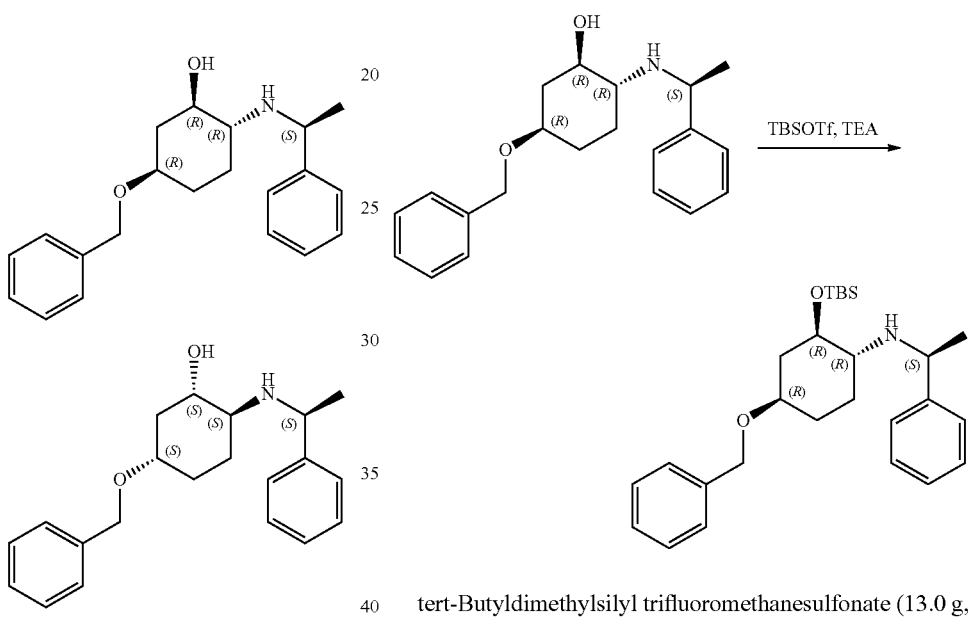

Lithium perchlorate (7.27 g, 68.4 mmol) was added to an ice-bath cooled stirred solution of (1R,3R,6S)-3-(benzyloxy)-7-oxa-bicyclo[4.1.0]heptane (7.0 g, 34.2 mmol) in 120 mL 4 A-MS dried acetonitrile, the bath was removed and (S)-1-phenylethanamine (5.58 g, 46.1 mmol) was added dropwise during a period of 15 min, then the solution was stirred at 25° C. for 18 h. Then the mixture was diluted in 200 mL water and extracted with ethyl acetate (200 mL×3), the combined organic phase was dried over sodium sulfate, then concentrated and the residue was purified with silica gel column chromatography, eluting with petroleum ether:ethyl acetate:triethylamine=98:0:2~49:49:2 to give the title compound (3.5 g, yield 31%) as a yellow oil. The (1S,2S,5S)-5-(benzyloxy)-2-((S)-1-phenylethylamino)cyclohexanol showed a little less polarity on TLC, and eluted firstly. The (1R,2R,5R)-5-(benzyloxy)-2-((S)-1-phenylethylamino)cyclohexanol eluted secondly. MS (ES+) $C_{21}H_{27}NO_2$ requires: 325, found: 326[M+H]$^+$.

(1R,2R,5R)-5-(benzyloxy)-2-((S)-1-phenylethylamino)cyclohexanol $^1$H-NMR (400 MHz, CDCl$_3$) δ ppm 7.35-7.24 (m, 10H), 4.52 (d, 2H, J=2.0 Hz), 3.97 (q, 1H, J=6.8 Hz), 3.42-3.34 (m, 1H), 3.19-3.12 (m, 1H), 2.39 (dd, 1H, J=12.0, 2.4 Hz), 2.16 (dd, 1H, J=12.0, 3.6 Hz), 2.09-2.00 (m, 2H), 1.65-1.49 (m, 1H), 1.35 (d, 3H, J=6.4 Hz), 1.28-1.15 (m, 2H), 0.90 (qd, 1H, J=13.2, 3.6 Hz).

(1S,2S,5S)-5-(benzyloxy)-2-((S)-1-phenylethylamino)cyclohexanol $^1$H-NMR (400 MHz, CDCl$_3$) δ ppm 7.36-7.22 (m, 10H), 4.54 (d, 2H, J=3.2 Hz), 3.90 (q, 1H, J=6.4 Hz), 3.44-3.35 (m, 1H), 3.15-3.09 (m, 1H), 2.51-2.45 (m, 1H), 2.43-2.36 (m, 1H), 2.04-1.99 (m, 1H), 1.95-1.90 (m, 1H), 1.47-1.29 (m, 3H), 1.34 (d, 3H, J=6.4 Hz), 0.82 (qd, 1H, J=13.2, 3.2 Hz).

Step 4: Synthesis of (1R,2R,4R)-4-(benzyloxy)-2-(tert-butyldimethylsilyloxy)-N—((S)-1-phenylethyl)cyclohexanamine tert-Butyldimethylsilyl trifluoromethanesulfonate (13.0 g, 49.5 mmol) was added to an ice-bath cooled, stirred solution of (1R,2R,5R)-5-(benzyloxy)-2-((S)-1-phenylethylamino)cyclohexanol (5.4 g, 16.5 mmol) and triethylamine (5.0 g, 49.5 mmol) in 100 mL dried dichloromethane. After 30 min, this was washed with a saturated aqueous solution of sodium bicarbonate, dried over sodium sulfate. Removal of the solvent, and the residue was purified with silica gel column chromatography, eluting with petroleum ether:ethyl acetate=100:0~70:30 to give the title compound (5.4 g, yield 71%) as a yellow oil. MS (ES+) $C_{27}H_{41}NO_2Si$ requires: 439, found: 440 [M+H]$^+$.

Step 5: (1R,2R,5R)-5-(benzyloxy)-2-((S)-1-phenylethylamino)cyclohexanol

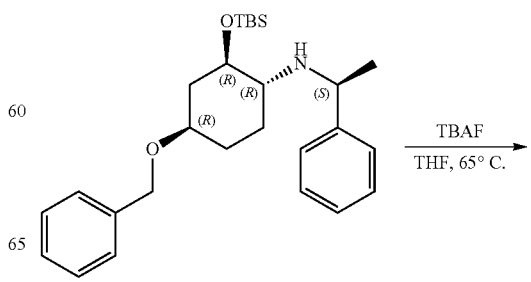

-continued

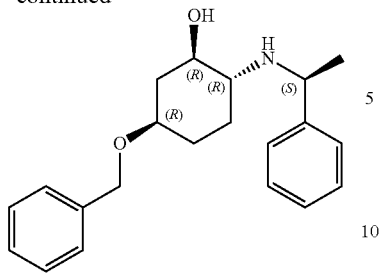

Tetrabutylammonium fluoride (2.66 g, 10.2 mmol) was added to a stirred solution of (1R,2R,4R)-4-(benzyloxy)-2-(tert-butyldimethylsilyloxy)-N—((S)-1-phenylethyl)cyclohexanamine (1.5 g, 3.41 mmol) in 50 mL dried oxolane at room temperature. Then this solution was stirred at 65° C. for 2 h. Then the mixture was concentrated under vacuo and the residue was diluted in 200 mL water and extracted with ethyl acetate (200 mL×3), the combined organic phase was washed with water and saturated aqueous solution of sodium chloride, dried over sodium sulfate. Removal of the solvent, and the residue was purified with silica gel column chromatography, eluting with petroleum ether:ethyl acetate=100:0~70:30 to give the title compound (0.75 g, yield 68%) as a colorless oil. MS (ES+) $C_{21}H_{27}NO_2$ requires: 325, found: 326[M+H]$^+$.

Step 6: (1R,3R,4R)-4-aminocyclohexane-1,3-diol

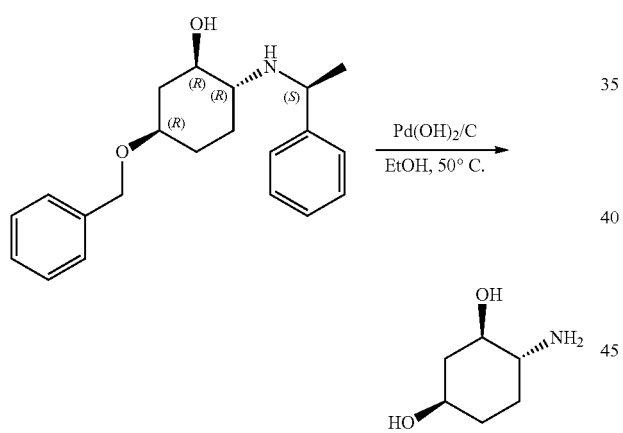

10% Palladium hydroxide in activated carbon (697 mg, catalyst) was added to a solution of (1R,2R,5R)-5-(benzyloxy)-2-((S)-1-phenylethylamino)cyclohexanol (650 mg, 1.99 mmol) in 15 mL ethanol at room temperature. Then this solution was stirred at 50° C. for 20 h under hydrogen. Then the mixture was cooled and filtered though celite, the filter-cake was washed with methanol:dichloromethane=1:10, the filtrate was concentrated under vacuo and the residue was diluted in 20 mL methanol:dichloromethane=1:10 solution and concentrated, dried under high-vacuo, then cooled at −20° C. to give the title compound (240 mg, yield 92%) as a white crystal. MS (ES+) $C_6H_{13}NO_2$ requires: 131, found: 132[M+H]$^+$.

(1R,3R,4R)-4-aminocyclohexane-1,3-diol $^1$H-NMR (400 MHz, 6d-DMSO) δ ppm 4.62-4.49 (m, 2H), 3.42-3.33 (m, 2H, J=3.2 Hz), 2.93-2.86 (m, 1H), 2.25-2.18 (m, 1H), 1.98-1.92 (m, 1H), 1.72-1.59 (m, 3H), 1.13-1.03 (m, 2H), 0.97-0.90 (m, 1H).

Example 24: Synthesis of Compound 232

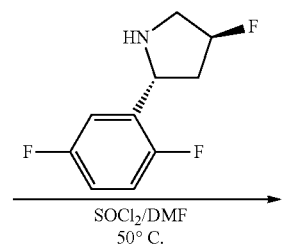

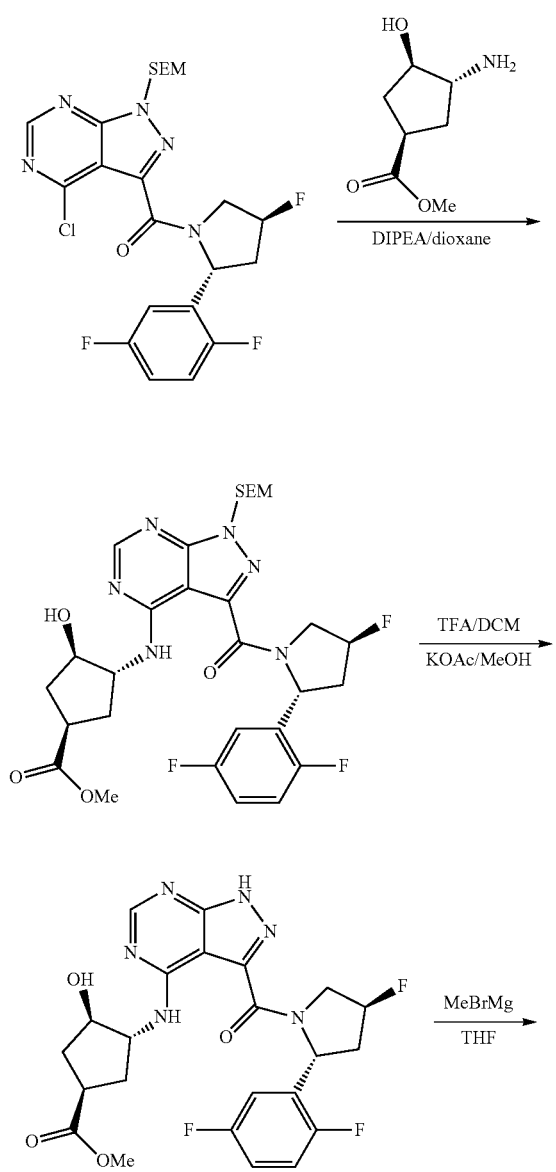

-continued

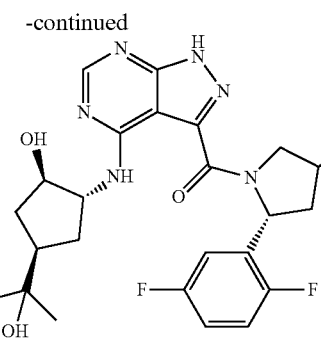

Step 1: (4-chloro-1-((2-(trimethylsilyl)ethoxy)methyl)-1H-pyrazolo[3,4-d]pyrimidin-3-yl)((2R,4S)-2-(2,5-difluorophenyl)-4-fluoropyrrolidin-1-yl)methanone

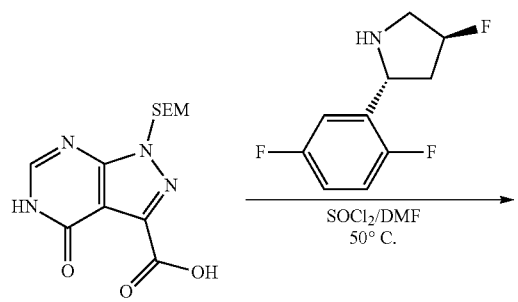

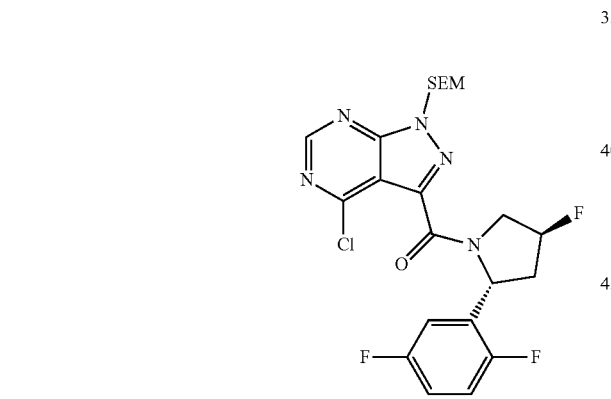

To a solution of 4-oxo-1-((2-(trimethylsilyl)ethoxy)methyl)-4,5-dihydro-1H-pyrazolo[3,4-d]pyrimidine-3-carboxylic acid (1.00 g, 3.22 mmol, 1.00 eq) in $SOCl_2$ (164.00 g, 1.38 mol, 428.11 eq) was added DMF (235.49 mg, 3.22 mmol, 1.00 eq) at 15° C. The reaction was heated at 50° C. for 16 hrs. TLC (PE:EtOAc=3:1, $R_f$=0.8 and 0.7) showed the reaction was complete. The mixture was concentrated. The residue was cooled to −10° C. and dissolved in DCM (25.00 mL). $Et_3N$ (1.63 g, 16.10 mmol, 5.00 eq) and (2R,4S)-2-(2,5-difluorophenyl)-4-fluoro-pyrrolidine (497.40 mg, 2.09 mmol, 0.65 eq, HCl) was added to the reaction. The reaction was stirred at 0° C. for 0.2 hr. TLC (PE:EtOAc=3:1, $R_f$=0.38) showed the reaction was complete. The solution was washed with brine (5 mL), dried over $Na_2SO_4$ and concentrated. The residue was purified by prep-TLC (PE:EtOAc=10:1) to give (4-chloro-1-((2-(trimethylsilyl)ethoxy)methyl)-1H-pyrazolo[3,4-d]pyrimidin-3-yl)((2R,4S)-2-(2,5-difluorophenyl)-4-fluoropyrrolidin-1-yl)methanone (400.00 mg, yield: 24.26%) as a yellow solid.

Step 2: methyl (1R,3R,4R)-3-((3-((2R,4S)-2-(2,5-difluorophenyl)-4-fluoropyrrolidine-1-carbonyl)-1-((2-(trimethylsilyl)ethoxy)methyl)-1H-pyrazolo[3,4-d]pyrimidin-4-yl)amino)-4-hydroxycyclopentane-1-carboxylate

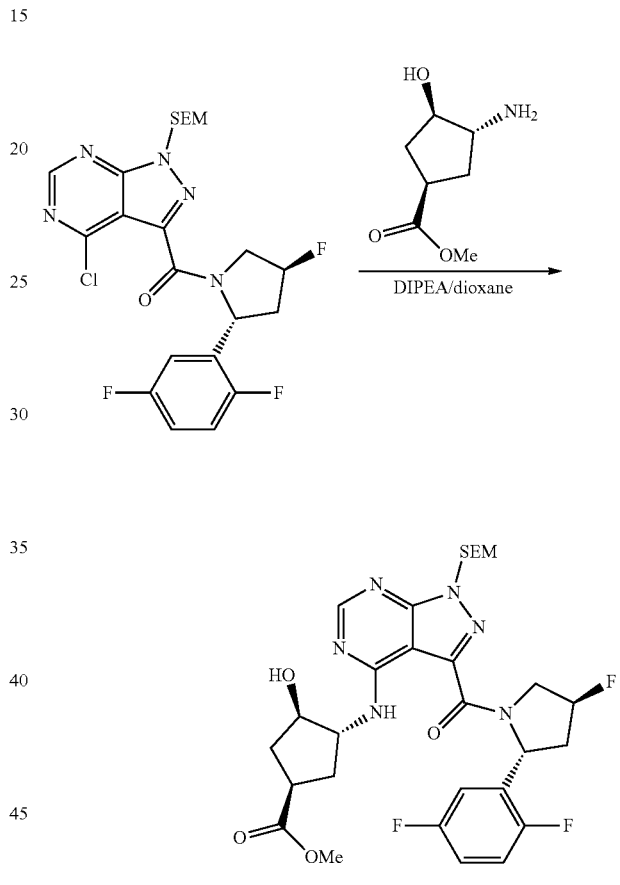

To a solution of (4-chloro-1-((2-(trimethylsilyl)ethoxy)methyl)-1H-pyrazolo[3,4-d]pyrimidin-3-yl)((2R,4S)-2-(2,5-difluorophenyl)-4-fluoropyrrolidin-1-yl)methanone (200.00 mg, 390.63 umol, 1.00 eq) and methyl (1R,3R,4R)-3-amino-4-hydroxy-cyclopentanecarboxylate (80.24 mg, 410.16 umol, 1.05 eq, HCl) in dioxane (10.00 mL) was added DIPEA (151.46 mg, 1.17 mmol, 3.00 eq). The reaction was heated at 90° C. for 5 hrs. LCMS showed the reaction was complete. The solution was concentrated. The residue was purified by prep-TLC (PE:EtOAc=2:1) to give methyl (1R,3R,4R)-3-((3-((2R,4S)-2-(2,5-difluorophenyl)-4-fluoropyrrolidine-1-carbonyl)-1-((2-(trimethylsilyl)ethoxy)methyl)-1H-pyrazolo[3,4-d]pyrimidin-4-yl)amino)-4-hydroxycyclopentane-1-carboxylate (120.00 mg, yield: 48.40%) as a yellow solid.

Step 3: methyl (1R,3R,4R)-3-((3-((2R,4S)-2-(2,5-difluorophenyl)-4-fluoropyrrolidine-1-carbonyl)-1H-pyrazolo[3,4-d]pyrimidin-4-yl)amino)-4-hydroxycyclopentane-1-carboxylate

Step 4: ((2R,4S)-2-(2,5-difluorophenyl)-4-fluoropyrrolidin-1-yl)(4-(((1R,2R,4R)-2-hydroxy-4-(2-hydroxypropan-2-yl)cyclopentyl)amino)-1H-pyrazolo[3,4-d]pyrimidin-3-yl)methanone

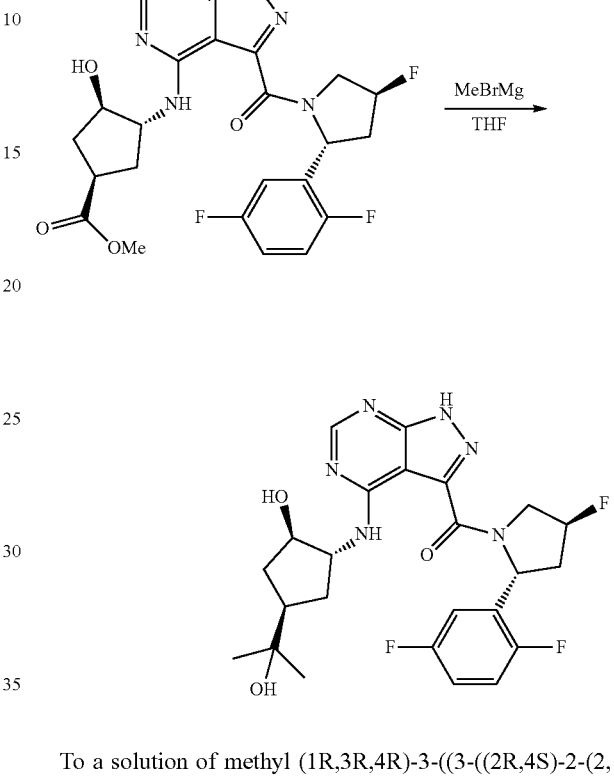

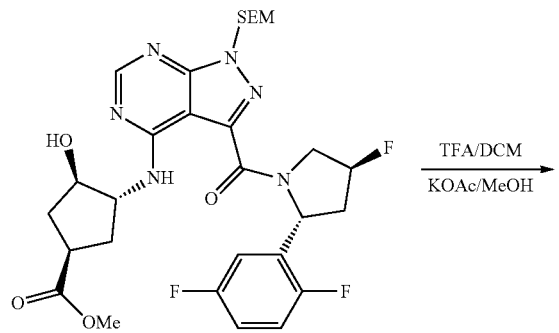

To a solution of methyl (1R,3R,4R)-3-((3-((2R,4S)-2-(2,5-difluorophenyl)-4-fluoropyrrolidine-1-carbonyl)-1-((2-(trimethylsilyl)ethoxy)methyl)-1H-pyrazolo[3,4-d]pyrimidin-4-yl)amino)-4-hydroxycyclopentane-1-carboxylate (120.00 mg, 189.06 umol, 1.00 eq) in DCM (3.00 mL) was added TFA (3.00 mL) at 15° C. The reaction was stirred at 15° C. for 16 hrs. LCMS showed the starting material was consumed. Little of (1R,3R,4R)-methyl 3-((3-((2R,4S)-2-(2,5-difluorophenyl)-4-fluoropyrrolidine-1-carbonyl)-1-(hydroxymethyl)-1H-pyrazolo[3,4-d]pyrimidin-4-yl)amino)-4-hydroxycyclopentanecarboxylate was detected. The reaction was concentrated. The residue was dissolved in MeOH (20.00 mL). KOAc (185.54 mg, 1.89 mmol, 10.00 eq) was added to the reaction. The reaction was heated at 50° C. for 16 hrs. LCMS showed the reaction was complete. The solution was concentrated. The residue was dissolved in EtOAc (20 mL) and washed with brine (10 mL), dried over $Na_2SO_4$ and concentrated to give methyl (1R,3R,4R)-3-((3-((2R,4S)-2-(2,5-difluorophenyl)-4-fluoropyrrolidine-1-carbonyl)-1H-pyrazolo[3,4-d]pyrimidin-4-yl)amino)-4-hydroxycyclopentane-1-carboxylate (80.00 mg, crude) as a red solid which was used in the next step without purification.

To a solution of methyl (1R,3R,4R)-3-((3-((2R,4S)-2-(2,5-difluorophenyl)-4-fluoropyrrolidine-1-carbonyl)-1H-pyrazolo[3,4-d]pyrimidin-4-yl)amino)-4-hydroxycyclopentane-1-carboxylate (80.00 mg, 158.59 umol, 1.00 eq) in THF (20.00 mL) was added MeMgBr (3 M, 1.59 mL, 30.00 eq) at −70° C. The reaction was slowly warmed to 15° C. and stirred for 2 hrs. TLC (EtOAc, $R_f$=0.24) and LCMS showed the reaction was complete. The solution was neutralized with 1N aq. HCl to pH=7. The reaction mixture was concentrated. The residue was purified by neutral prep-HPLC. to give ((2R,4S)-2-(2,5-difluorophenyl)-4-fluoropyrrolidin-1-yl)(4-(((1R,2R,4R)-2-hydroxy-4-(2-hydroxypropan-2-yl)cyclopentyl)amino)-1H-pyrazolo[3,4-d]pyrimidin-3-yl)methanone (17.40 mg, yield: 21.75%) as a yellow solid.

For this compound and compound 156, below, LC-MS conditions were as follows: (mobile phase: from 99% [water+0.375‰ v/v TFA] and 1% [$CH_3CN$+0.188‰ v/v TFA], under this condition for 0.4 min, then changed to 10% [water+0.375‰ v/v TFA] and 90% [$CH_3CN$+0.188‰ v/v TFA] in 3.0 min, then changed to 100% [$CH_3CN$+0.188‰ v/v TFA] in 0.45 min, finally changed to 99% [water+0.375‰ v/v TFA] and 1% [$CH_3CN$+0.188‰ v/v TFA] in 0.01 min, then under this condition for 0.64 min. The flow is 0.8 mL·min$^{-1}$ all along.) Purity is 99.870%

Example 25. Synthesis of Compound 229

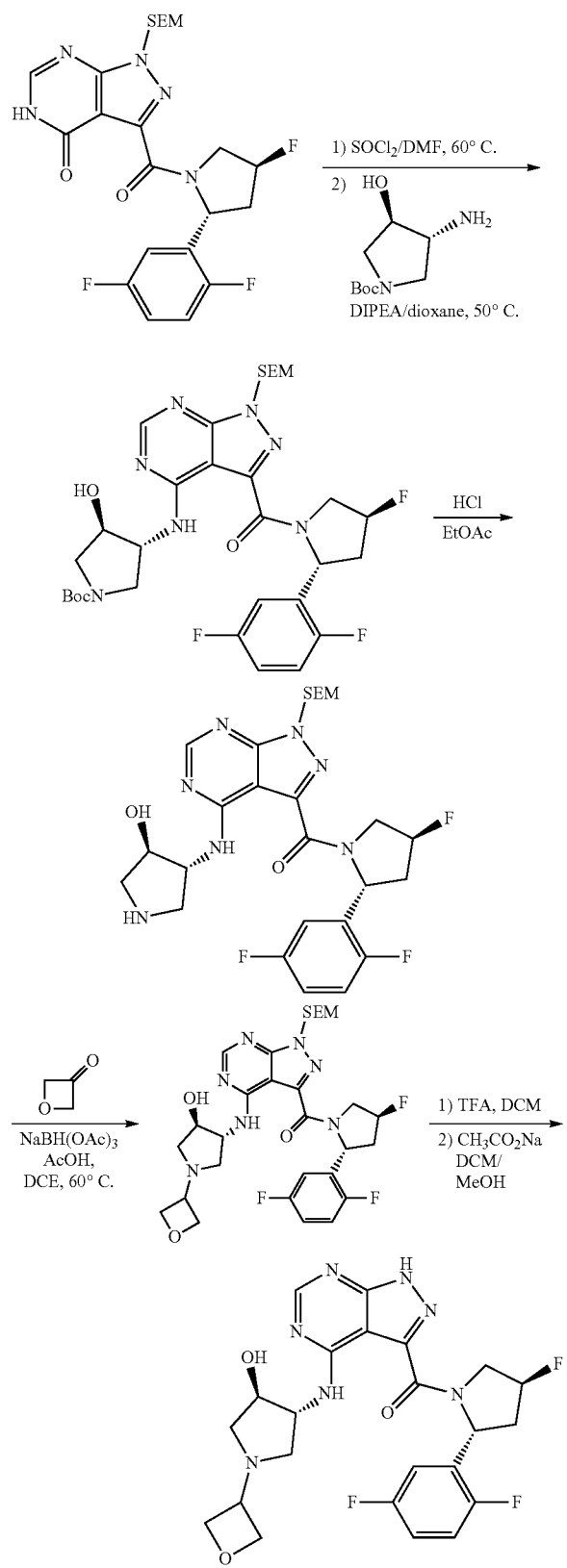

Step 1: tert-butyl (3R,4R)-3-((3-((2R,4S)-2-(2,5-difluorophenyl)-4-fluoropyrrolidine-1-carbonyl)-1-((2-(trimethylsilyl)ethoxy)methyl)-1H-pyrazolo[3,4-d]pyrimidin-4-yl)amino)-4-hydroxypyrrolidine-1-carboxylate

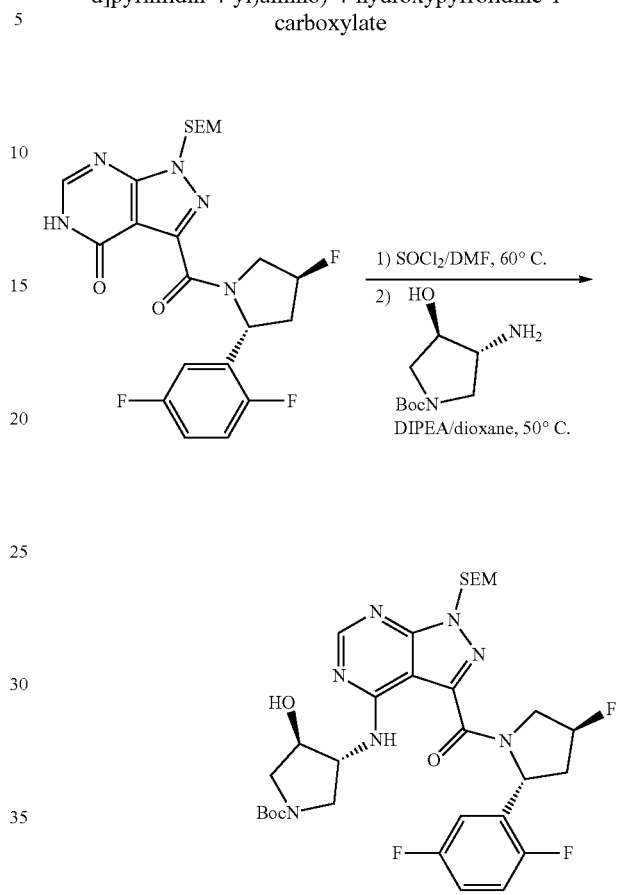

A solution of 3-((2R,4S)-2-(2,5-difluorophenyl)-4-fluoropyrrolidine-1-carbonyl)-1-((2-(trimethylsilyl)ethoxy)methyl)-1,5-dihydro-4H-pyrazolo[3,4-d]pyrimidin-4-one (0.085 g, 0.17 mmol, 1 eq) was stirred with thionyl chloride (0.031 mL, 0.43 mmol, 2.5 eq) and few drops of DMF in DCM (0.7 mL) at 50° C. for 3 hours. LCMS indicated complete consumption of SM to the chloro-heterocycle intermediate. The reaction mixture was cooled on ice and added Dioxane (0.7 mL) followed by DIEA (0.21 mL, 1.21 mmol, 7 eq) and tert-butyl (3R,4R)-3-amino-4-hydroxypyrrolidine-1-carboxylate (0.05 g, 0.26 mmol, 1.5 eq). The reaction mixture was then stirred at 70° C. for 3 hours. LCMS indicated reaction was complete. The reaction mixture was then diluted with DCM and washed with aqueous saturated sodium bicarbonate solution. The combined organic layers were washed with saturated brine solution, dried over $Na_2SO_4$ and concentrated in vacuo. The residue was purified by column chromatography on silica gel (Hexanes/EtOAc) to get the product tert-butyl (3R,4R)-3-((3-((2R,4S)-2-(2,5-difluorophenyl)-4-fluoropyrrolidine-1-carbonyl)-1-((2-(trimethylsilyl)ethoxy)methyl)-1H-pyrazolo[3,4-d]pyrimidin-4-yl)amino)-4-hydroxypyrrolidine-1-carboxylate (0.084 g, 72%).

Step 2: ((2R,4S)-2-(2,5-difluorophenyl)-4-fluoropyr-rolidin-1-yl)(4-(((3R,4R)-4-hydroxypyrrolidin-3-yl)amino)-1-((2-(trimethylsilyl)ethoxy)methyl)-1H-pyrazolo[3,4-d]pyrimidin-3-yl)methanone

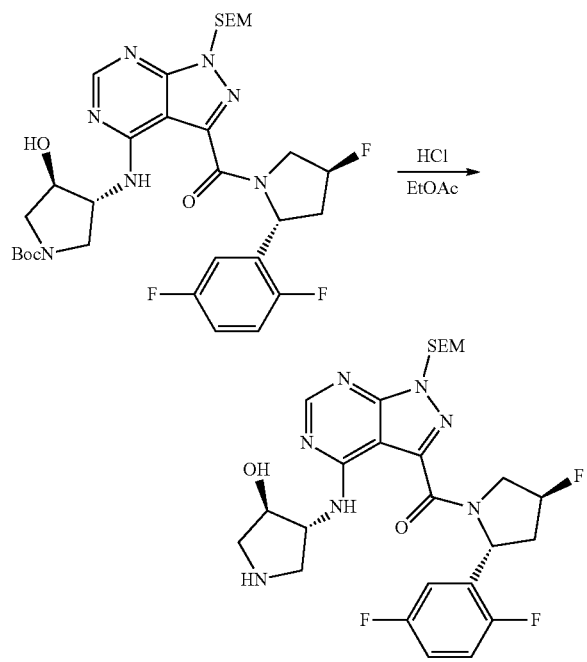

A solution of (3R,4R)-3-((3-((2R,4S)-2-(2,5-difluorophenyl)-4-fluoropyrrolidine-1-carbonyl)-1-((2-(trimethylsilyl)ethoxy)methyl)-1H-pyrazolo[3,4-d]pyrimidin-4-yl)amino)-4-hydroxypyrrolidine-1-carboxylate (0.084 g, 0.12 mmol, 1 eq) in EtOAc (1.25 mL) was treated with HCl in Dioxane (4M, 0.9 mL, 3.72 mmol, 30 eq). After stirring at 23° C. for 4 hours, LCMS indicated reaction was complete. The reaction mixture was diluted with EtOAc and washed with aqueous saturated sodium bicarbonate solution. The combined organic layers were washed with saturated brine solution, dried over Na$_2$SO$_4$ and concentrated in vacuo. The crude product ((2R,4S)-2-(2,5-difluorophenyl)-4-fluoropyr-rolidin-1-yl)(4-(((3R,4R)-4-hydroxypyrrolidin-3-yl)amino)-1-((2-(trimethylsilyl)ethoxy)methyl)-1H-pyrazolo[3,4-d]pyrimidin-3-yl)methanone was used without further purification in the next step.

Step 3: ((2R,4S)-2-(2,5-difluorophenyl)-4-fluoropyr-rolidin-1-yl)(4-(((3R,4R)-4-hydroxy-1-(oxetan-3-yl)pyrrolidin-3-yl)amino)-1-((2-(trimethylsilyl)ethoxy)methyl)-1H-pyrazolo[3,4-d]pyrimidin-3-yl)methanone

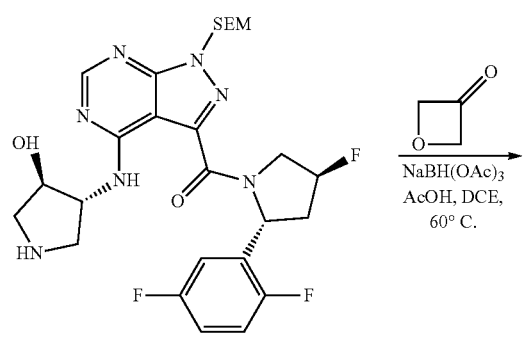

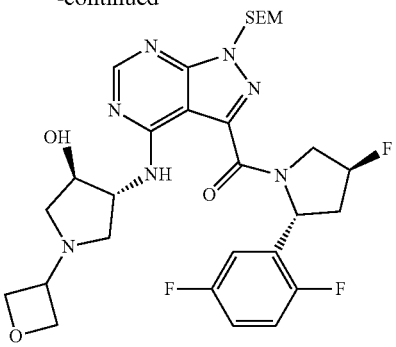

To a solution of ((2R,4S)-2-(2,5-difluorophenyl)-4-fluoropyrrolidin-1-yl)(4-(((3R,4R)-4-hydroxypyrrolidin-3-yl)amino)-1-((2-(trimethylsilyl)ethoxy)methyl)-1H-pyrazolo[3,4-d]pyrimidin-3-yl)methanone (0.036 g, 0.062 mmol, 1 eq) in DCE (0.5 mL) was added few drops of Acetic acid (2 ∞L, 0.031 mmol, 0.5 eq) followed by oxetan-3-one (0.015 mL, 0.21 mmol, 3.3 eq) and the reaction mixture was heated at 60° C. for 2 hours. Added sodium triacetoxyborohydride (0.033 g, 0.16 mmol, 2.5 eq) and the solution was stirred at 23° C. for 24 hours. LCMS indicated the reaction was complete. The reaction mixture was diluted with EtOAc and washed with aqueous saturated sodium bicarbonate solution. The combined organic layers were washed with saturated brine solution, dried over Na$_2$SO$_4$ and concentrated in vacuo. The residue was then purified by column chromatography on silica gel (DCM/MeOH) to isolate the product ((2R,4S)-2-(2,5-difluorophenyl)-4-fluoropyrrolidin-1-yl)(4-(((3R,4R)-4-hydroxy-1-(oxetan-3-yl)pyrrolidin-3-yl)amino)-1-((2-(trimethylsilyl)ethoxy)methyl)-1H-pyrazolo[3,4-d]pyrimidin-3-yl)methanone (0.030 g, 75%).

Step 4: ((2R,4S)-2-(2,5-difluorophenyl)-4-fluoropyr-rolidin-1-yl)(4-(((3R,4R)-4-hydroxy-1-(oxetan-3-yl)pyrrolidin-3-yl)amino)-1H-pyrazolo[3,4-d]pyrimi-din-3-yl)methanone

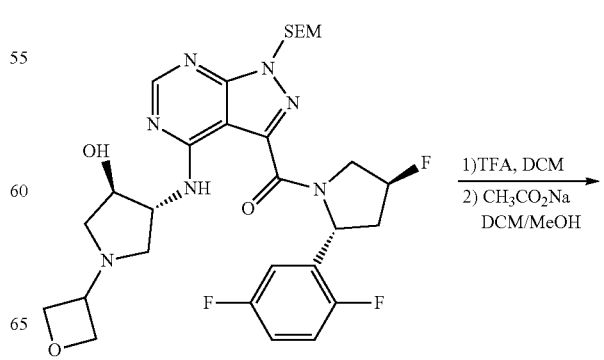

-continued

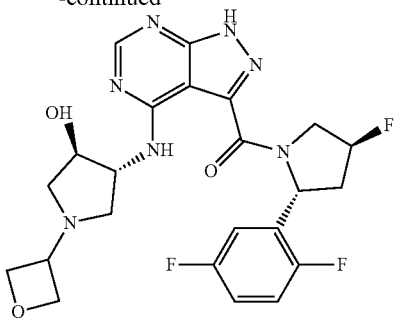

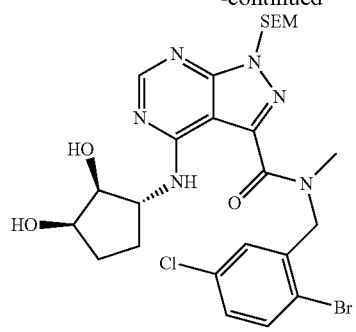

A solution of ((2R,4S)-2-(2,5-difluorophenyl)-4-fluoropyrrolidin-1-yl)(4-(((3R,4R)-4-hydroxy-1-(oxetan-3-yl)pyrrolidin-3-yl)amino)-1-((2-(trimethylsilyl)ethoxy)methyl)-1H-pyrazolo[3,4-d]pyrimidin-3-yl)methanone (0.060 g, 0.095 mmol, 1 eq) in DCM (1 mL) was treated with TFA (0.73 mL, 9.5 mmol, 100 eq) for 16 hours. The reaction mixture was diluted with DCM and washed with aqueous saturated sodium bicarbonate solution. The combined organic layers were washed with saturated brine solution, dried over Na$_2$SO$_4$ and concentrated in vacuo. To the intermediate in DCM/MeOH (1/1, 1 mL) was added sodium acetate (0.016 g, 0.19 mmol, 2 eq) and the reaction was stirred at 23° C. for 2 hours. The reaction mixture was diluted with DCM and then washed with aqueous saturated sodium bicarbonate solution. The combined organic layers were washed with saturated brine solution, dried over Na$_2$SO$_4$ and concentrated in vacuo. The residue was then purified first by column chromatography on silica gel (DCM/MeOH containing 10% NH$_4$OH) and then by preparative-TLC to isolate the product ((2R,4S)-2-(2,5-difluorophenyl)-4-fluoropyrrolidin-1-yl)(4-(((3R,4R)-4-hydroxy-1-(oxetan-3-yl)pyrrolidin-3-yl)amino)-1H-pyrazolo[3,4-d]pyrimidin-3-yl)methanone (0.034 g, 70%).

Example 26. Synthesis of Compound 156

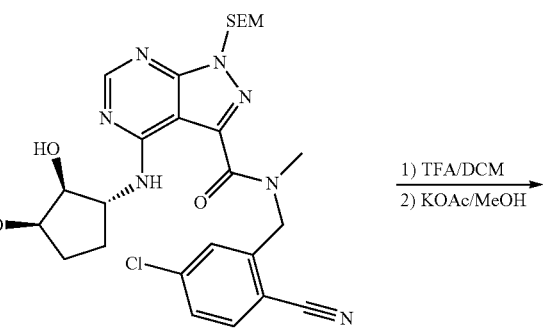

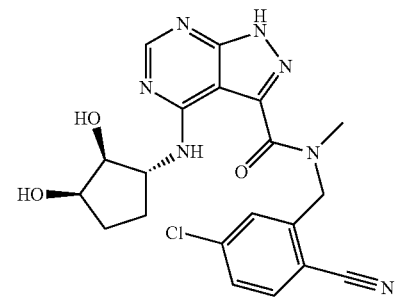

Step 1: 1-bromo-2-(bromomethyl)-4-chlorobenzene

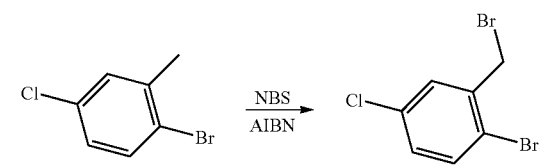

A solution of 1-bromo-4-chloro-2-methylbenzene (3.00 g, 14.60 mmol, 1.00 eq), NBS (2.34 g, 13.14 mmol, 0.90 eq) and AIBN (239.75 mg, 1.46 mmol, 0.10 eq) in CCl$_4$ (20.00 mL) was stirred at 90° C. for 12 hrs. The solution was concentrated under vacuum to give a crude product 1-bromo-2-(bromomethyl)-4-chlorobenzene (5.40 g, crude) as a yellow solid which was used directly in the next step without further purification.

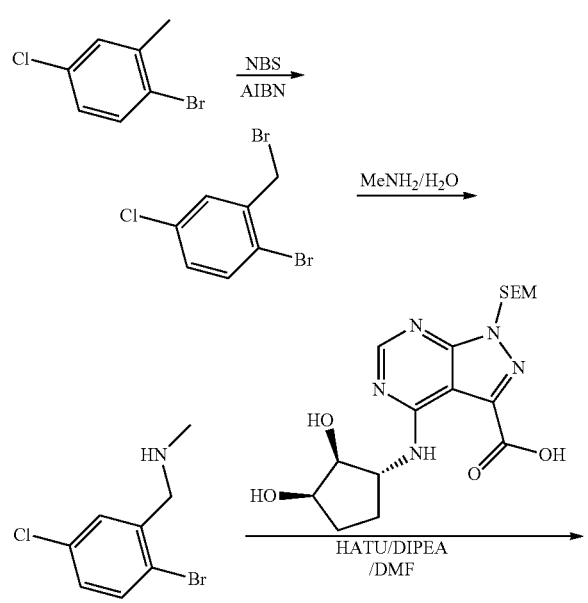

Step 2: 1-(2-bromo-5-chlorophenyl)-N-methylmethanamine

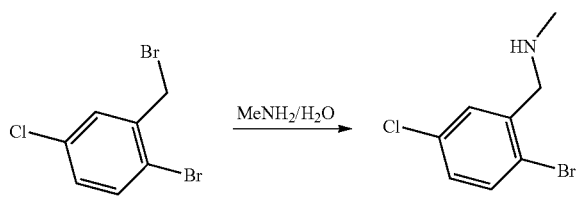

The solution of 1-bromo-2-(bromomethyl)-4-chlorobenzene (5.40 g, 18.99 mmol, 1.00 eq) in MeNH$_2$/H$_2$O (30.00 mL) was stirred at 25° C. for 15 hrs. When the reaction was complete, the product was extracted with EtOAc (50 mL*3), the combined organic layers were concentrated under vacuum to give a crude product. The crude product was purified by column chromatography on silica gel (PE:EtOAc=5:1 to 1:1) to obtain 1-(2-bromo-5-chlorophenyl)-N-methylmethanamine (1.00 g, yield: 22.45%) as a off-white solid. $^1$H-NMR (400 MHz, CDCl$_3$) δ ppm 7.45 (d, 1H, J=8.8 Hz), 7.40-7.39 (m, 1H), 7.10 (dd, 1H, J=8.4, 2.4 Hz), 3.79 (s, 2H), 2.46 (s, 3H).

Step 3: N-(2-bromo-5-chlorobenzyl)-4-(((1R,2S,3R)-2,3-dihydroxycyclopentyl)amino)-N-methyl-1-((2-(trimethylsilyl)ethoxy)methyl)-1H-pyrazolo[3,4-d]pyrimidine-3-carboxamide

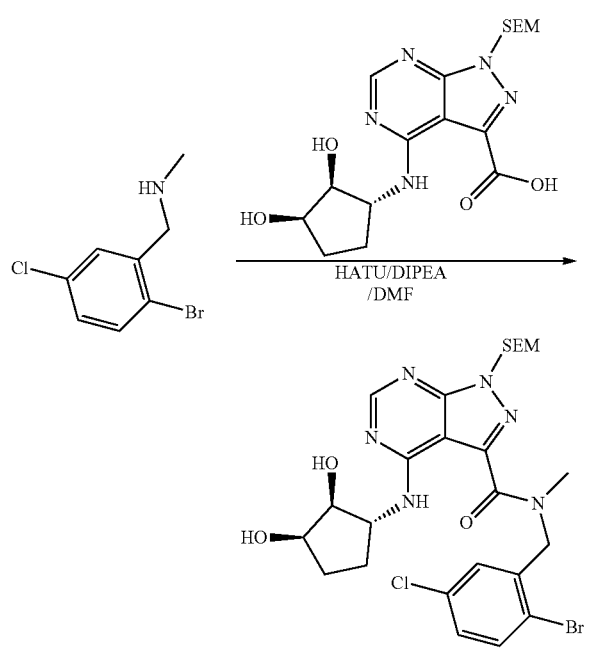

To the solution of 1-(2-bromo-5-chlorophenyl)-N-methylmethanamine (500.00 mg, 1.22 mmol, 1.00 eq) and 4-(((1R,2S,3R)-2,3-dihydroxycyclopentyl)amino)-1-((2-(trimethylsilyl)ethoxy)methyl)-1H-pyrazolo[3,4-d]pyrimidine-3-carboxylic acid (314.98 mg, 1.34 mmol, 1.10 eq) in DMF (5.00 mL) was added DIPEA (315.35 mg, 2.44 mmol, 2.00 eq) and HATU (556.66 mg, 1.46 mmol, 1.20 eq), the resulting mixture was stirred at 25° C. for 15 hrs. When the reaction was complete, H$_2$O (20 mL) was added, the product was extracted by EtOAc (20 mL*3), the combined organic layers were concentrated under vacuum to give a crude product. The crude product was purified by prep-TLC (EtOAc) to obtain N-(2-bromo-5-chlorobenzyl)-4-(((1R,2S,3R)-2,3-dihydroxycyclopentyl)amino)-N-methyl-1-((2-(trimethylsilyl)ethoxy)methyl)-1H-pyrazolo[3,4-d]pyrimidine-3-carboxamide (520.00 mg, yield: 81.20%) as a red oil. $^1$H-NMR (400 MHz, CDCl$_3$) ppm 9.77 (br.s, 0.5H), 9.49 (br.s, 0.5H), 8.45 (d, 1H, J=11.4 Hz), 7.63 (dd, 1H, J=8.4, 4.4 Hz), 7.33-7.31 (m, 1H), 7.26-7.25 (m, 1H), 5.87 (s, 1H), 5.67 (s, 1H), 5.46 (s, 1H), 4.98 (s, 1H), 4.45-4.44 (m, 1H), 4.31-4.29 (m, 1H), 4.03-4.02 (m, 1H), 3.79 (t, 1H, J=8.0 Hz), 3.71 (s, 1.5H), 3.55 (t, 1H, J=8.0 Hz), 3.29 (s, 1.5H), 3.16 (d, 1H, J=6.0 Hz), 2.65-2.61 (m, 1H), 2.05-1.83 (m, 2H), 1.05 (t, 1H, J=8.4 Hz), 0.90 (t, 1H, J=8.0 Hz), 0.07 (s, 4.5H), 0.00 (s, 4.5H).

Step 4: N-(5-chloro-2-cyanobenzyl)-4-(((1R,2S,3R)-2,3-dihydroxycyclopentyl)amino)-N-methyl-1-((2-(trimethylsilyl)ethoxy)methyl)-1H-pyrazolo[3,4-d]pyrimidine-3-carboxamide

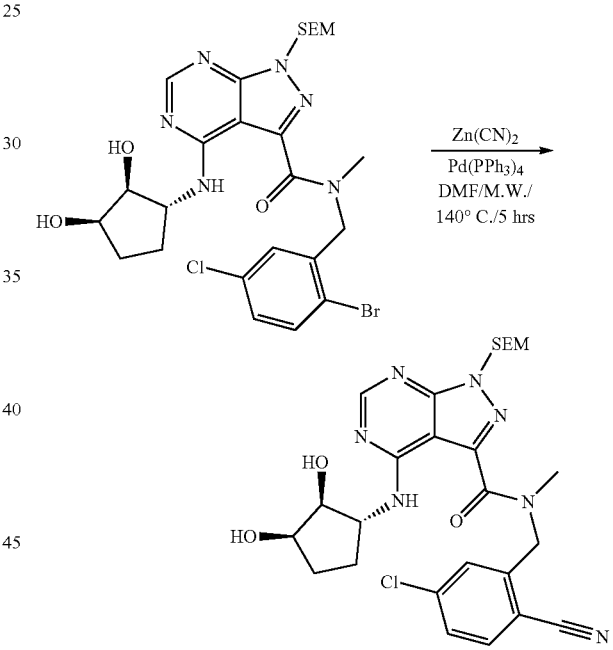

The mixture of N-(2-bromo-5-chlorobenzyl)-4-(((1R,2S,3R)-2,3-dihydroxycyclopentyl)amino)-N-methyl-1-((2-(trimethylsilyl)ethoxy)methyl)-1H-pyrazolo[3,4-d]pyrimidine-3-carboxamide (420.00 mg, 670.91 umol, 1.00 eq), Zn(CN)$_2$ (630.22 mg, 5.37 mmol, 340.66 uL, 8.00 eq) and Pd(PPh$_3$)$_4$ (77.53 mg, 67.09 umol, 0.10 eq) was dissolved in DMF (3.00 mL) in a sealed tube, it was radiated with microwave at 140° C. for 3 hrs. After 3 hrs, LCMS showed the starting material was not consumed completely, so more Zn(CN)$_2$ (2 eq) and Pd(PPh$_3$)$_4$ (0.1 eq) was added, it was radiated with microwave at 150° C. for another 2 hrs. When the reaction was complete, H$_2$O (15 mL) was added, the product was extracted by EtOAC (20 mL*3). The combined organic layers were dried over anhydrous Na/SO$_4$, concentrated to give a crude product. The crude product was purified by prep-TLC (EtOAc) to obtain N-(5-chloro-2-cyanobenzyl)-4-(((1R,2S,3R)-2,3-dihydroxycyclopentyl)

amino)-N-methyl-1-((2-(trimethylsilyl)ethoxy)methyl)-1H-pyrazolo[3,4-d]pyrimidine-3-carboxamide (520.00 mg, crude, including PPh₃O) was obtained as a yellow oil. ¹H-NMR (400 MHz, CDCl₃) δ ppm 9.72 (br.s, 0.5H), 9.44 (br.s, 0.5H), 8.45 (d, 1H, J 6.4 Hz), 7.79-7.54 (m, 3H), 5.86 (s, 1H), 5.70 (s, 1H), 5.67 (s, 1H), 5.11 (s, 1H), 4.45-4.44 (m, 1H), 4.30-4.29 (m, 1H), 4.03-4.02 (m, 1H), 3.81-3.76 (m, 2.5H), 3.59 (t, 1H, J=8.0 Hz), 3.32 (s, 1.5H), 3.18-3.16 (m, 1H), 2.19-1.86 (m, 3H), 1.04 (t, 1H, J=8.0 Hz), 0.92 (t, 1H, J=8.0 Hz), 0.06 (s, 4.5H), 0.00 (s, 4.5H).

Step 5: N-(5-chloro-2-cyanobenzyl)-4-(((1R,2S,3R)-2,3-dihydroxycyclopentyl)amino)-N-methyl-1H-pyrazolo[3,4-d]pyrimidine-3-carboxamide

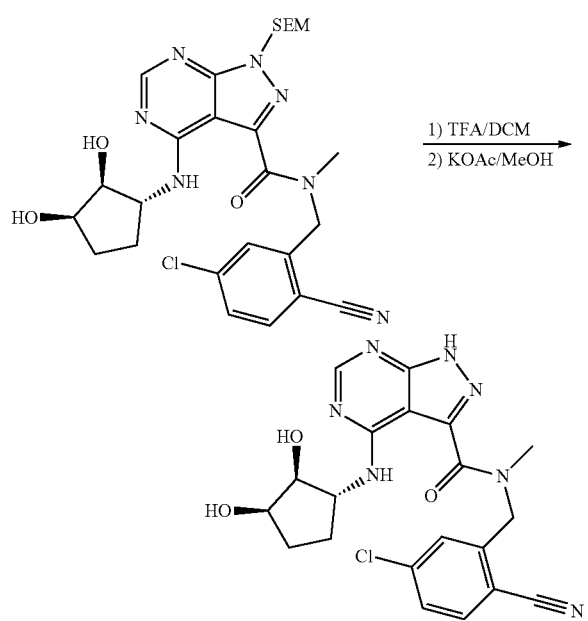

To the mixed solvents TFA (10.00 mL) and DCM (10.00 mL) was added N-(5-chloro-2-cyanobenzyl)-4-(((1R,2S,3R)-2,3-dihydroxycyclopentyl)amino)-N-methyl-1-((2-(trimethylsilyl)ethoxy)methyl)-1H-pyrazolo[3,4-d]pyrimidine-3-carboxamide (520.00 mg, 908.88 umol, 1.00 eq), the resulting mixture was stirred at 25° C. for 1 hr. The solvent was evaporated by N₂ to give a crude product. The crude product was dissolved in MeOH (15.00 mL), adjusted to pH=7-8 by NaHCO₃, and KOAc (178.39 mg, 1.82 mmol, 2.00 eq) was added, it was stirred at 50° C. for 2 hrs. When the reaction was complete, the mixture was concentrated under vacuum to give a crude product which was dissolved in EtOAc (50 mL), washed by H₂O (15 mL*3). The organic layer was concentrated under vacuum to give a crude product which was purified by acidic prep-HPLC (TFA) to obtain N-(5-chloro-2-cyanobenzyl)-4-(((1R,2S,3R)-2,3-dihydroxycyclopentyl)amino)-N-methyl-1H-pyrazolo[3,4-d]pyrimidine-3-carboxamide (171.00 mg, yield: 33.85%, TFA) as a white solid.

Example 27. Synthesis of Compound 226

Step 1: Methyl (1R,3R,4R)-3-((tert-butoxycarbonyl)amino)-4-((tert-butyldiphenylsilyl)oxy) cyclopentane-1-carboxylate

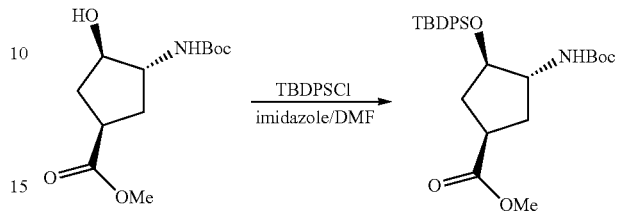

To a solution of methyl (1R,3R,4R)-3-((tert-butoxycarbonyl)amino)-4-hydroxycyclopentane-1-carboxylate (1.50 g, 5.78 mmol, 1.00 eq) and imidazole (590.74 mg, 8.67 mmol, 1.50 eq) in DMF (10.00 mL) was added TBDPSCl (1.67 g, 6.07 mmol, 1.05 eq) at 0° C. The reaction was stirred at 15° C. for 16 hrs. TLC (PE:EtOAc=5:1, R_f=0.43) showed the reaction was complete. The solution was poured into water (20 mL) and extracted with EtOAc (10 mL*3). The organic layer was dried over Na₂SO₄ and concentrated. The residue was recrystallized from PE (1 mL) to give methyl (1R,3R,4R)-3-((tert-butoxycarbonyl)amino)-4-((tert-butyldiphenylsilyl)oxy)cyclopentane-1-carboxylate (2.80 g, yield: 97.40%) as a white solid. ¹H-NMR (400 MHz, CDCl₃) δ ppm 7.69-7.64 (m, 4H), 7.43-7.37 (m, 6H), 4.10 (br.s, 1H), 3.92-3.97 (m, 2H), 3.66 (s, 3H), 2.75-2.71 (m, 1H), 2.46-2.43 (m, 1H), 2.01-1.95 (m, 2H), 1.65-1.61 (m, 1H), 1.40 (s, 9H), 1.05 (s, 9H).

Step 2: Tert-butyl ((1R,2R,4R)-2-((tert-butyldiphenylsilyl)oxy)-4-(hydroxymethyl)cyclopentyl) carbamate

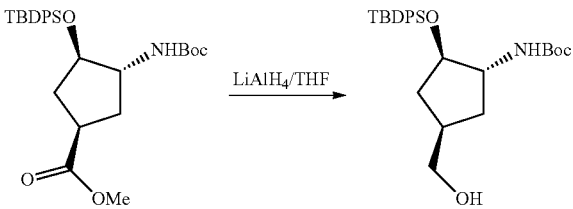

To a solution of methyl (1R,3R,4R)-3-((tert-butoxycarbonyl)amino)-4-((tert-butyldiphenylsilyl)oxy)cyclopentane-1-carboxylate (2.80 g, 5.63 mmol, 1.00 eq) in THF (30.00 mL) was added LiAlH₄ (427.32 mg, 11.26 mmol, 2.00 eq) at −30° C. The reaction was slowly warmed to 15° C. and stirred for 2 hrs. TLC (PE:EtOAc=3:1, R_f=0.24) showed the reaction was complete. The reaction was quenched with 0.43 mL of WO and 0.43 mL of 10% aq. NaOH at 0° C. The mixture was filtered and the filtrate was concentrated. The residue was washed with PE (5 mL). The solid was collected. tert-butyl ((1R,2R,4R)-2-((tert-butyldiphenylsilyl)oxy)-4-(hydroxymethyl)cyclopentyl)carbamate (2.30 g, yield: 86.98%) as a white solid was obtained. ¹H-NMR (400 MHz, CDCl₃) δ ppm 7.69-7.65 (m, 4H), 7.43-7.38 (m, 6H), 4.11-4.10 (m, 1H), 3.89 (br.s, 2H), 3.54 (br.s, 2H), 2.14-2.10 (m, 1H), 1.97-1.89 (m, 2H), 1.62-1.58 (m, 1H), 1.39 (s, 9H), 1.06 (s, 9H).

Step 3: tert-butyl ((1R,2R,4R)-2-((tert-butyldiphenylsilyl)oxy)-4-formylcyclopentyl)carbamate

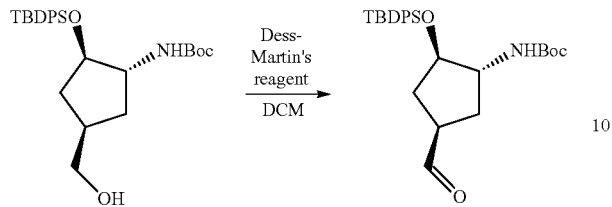

To a solution of tert-butyl ((1R,2R,4R)-2-((tert-butyldiphenylsilyl)oxy)-4-(hydroxymethyl)cyclopentyl)carbamate (2.30 g, 4.90 mmol, 1.00 eq) in DCM (50.00 mL) was added Dess-Martin periodinane reagent (3.12 g, 7.35 mmol, 1.50 eq) at 0° C. The reaction was stirred at 15° C. for 16 hrs. TLC (PE:EtOAc=3:1, $R_f$=0.7) showed the reaction was complete. The reaction was quenched with sat'd aq. NaHCO$_3$ (30 mL) at 0° C. and extracted with DCM (30 mL). The organic layer was dried over Na$_2$SO$_4$ and concentrated. The residue was purified by column chromatography on silica gel (PE:EtOAc=30:1). tert-butyl ((1R,2R,4R)-2-((tert-butyldiphenylsilyl)oxy)-4-formylcyclopentyl)carbamate (900.00 mg, yield: 39.27%) as a yellow oil was obtained. $^1$H-NMR (400 MHz, CDCl$_3$) δ ppm 9.55 (s, 1H), 7.61-7.56 (m, 4H), 7.37-7.31 (m, 6H), 4.08 (d, 1H, J=7.2 Hz), 3.93-3.89 (m, 1H), 3.79 (br.s, 1H), 2.62-2.55 (m, 1H), 2.44-2.40 (m, 1H), 1.86-1.83 (m, 2H), 1.57-1.52 (m, 1H), 1.34 (s, 9H), 0.97 (s, 9H).

Step 4: tert-butyl ((1R,2R,4R)-2-((tert-butyldiphenylsilyl)oxy)-4-(difluoromethyl)cyclopentyl)carbamate

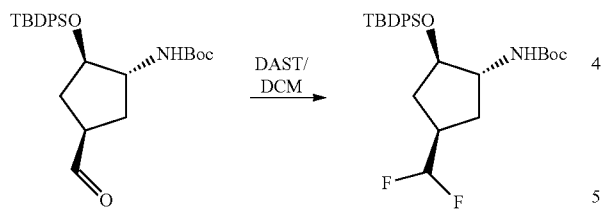

To a solution of tert-butyl ((1R,2R,4R)-2-((tert-butyldiphenylsilyl)oxy)-4-formylcyclopentyl)carbamate (900.00 mg, 1.92 mmol, 1.00 eq) in DCM (50.00 mL) was added DAST (928.45 mg, 5.76 mmol, 3.00 eq) at 0° C. The reaction was stirred at 15° C. for 5 hrs. TLC (PE:EtOAc=3:1, $R_f$=0.6) showed the reaction was complete. The solution was quenched with sat'd aq. NaHCO$_3$ (20 mL) and extracted with DCM (20 mL). The organic layer was dried over Na$_2$SO$_4$ and concentrated. The residue was purified by column chromatography on silica gel (PE:EtOAc=30:1-20:1). tert-butyl ((1R,2R,4R)-2-((tert-butyldiphenylsilyl)oxy)-4-(difluoromethyl)cyclopentyl)carbamate (250.00 mg, yield: 26.59%) as a yellow oil was obtained. $^1$H-NMR (400 MHz, CDCl$_3$) δ ppm 7.62-7.56 (m, 4H), 7.34-7.31 (m, 6H), 5.76-5.43 (m, 1H), 3.88-3.82 (m, 2H), 2.30-2.24 (m, 1H), 2.07-2.04 (m, 1H), 1.80-1.75 (m, 1H), 1.65-1.57 (m, 1H), 1.33 (s, 9H), 0.99 (s, 9H).

Step 5: (1R,2R,4R)-2-((tert-butyldiphenylsilyl)oxy)-4-(difluoromethyl)cyclopentan-1-amine

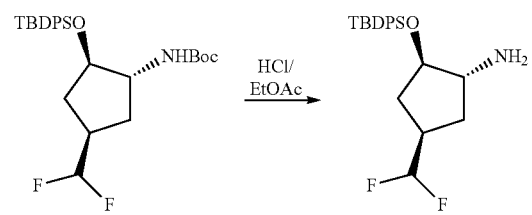

To a solution of tert-butyl ((1R,2R,4R)-2-((tert-butyldiphenylsilyl)oxy)-4-(difluoromethyl)cyclopentyl)carbamate (50.00 mg, 102.11 umol, 1.00 eq) in EtOAc (2.00 mL) was added HCl/EtOAc (10.00 Ml, 4 M) at 15° C. The reaction was stirred at 15° C. for 1 hr. TLC (PE:EtOAc=3:1, $R_f$=0.05) showed the reaction was complete. The solvent was blown to dryness by N$_2$. The residue wasn't further purified. (1R,2R,4R)-2-((tert-butyldiphenylsilyl)oxy)-4-(difluoromethyl)cyclopentan-1-amine (40.00 mg, yield: 91.95%, HCl) as a yellow oil was obtained. $^1$H-NMR (400 MHz, CDCl$_3$) δ ppm 7.70-7.68 (m, 4H), 7.49-7.43 (m, 6H), 5.81 (td, 1H, J=57.2, 4.8 Hz), 4.25 (dd, 1H, J=12.0, 5.6 Hz), 3.50 (dd, 1H, J=13.2, 6.4 Hz), 2.22-2.19 (m, 1H), 1.80-1.74 (m, 2H), 1.66-1.63 (m, 1H), 1.08 (s, 9H).

Step 6: (4-(((1R,2R,4R)-2-((tert-butyldiphenylsilyl)oxy)-4-(difluoromethyl)cyclopentyl)amino)-1-((2-(trimethylsilyl)ethoxy)methyl)-1H-pyrazolo[3,4-d]pyrimidin-3-yl)((2R,4S)-2-(2,5-difluorophenyl)-4-fluoropyrrolidin-1-yl)methanone

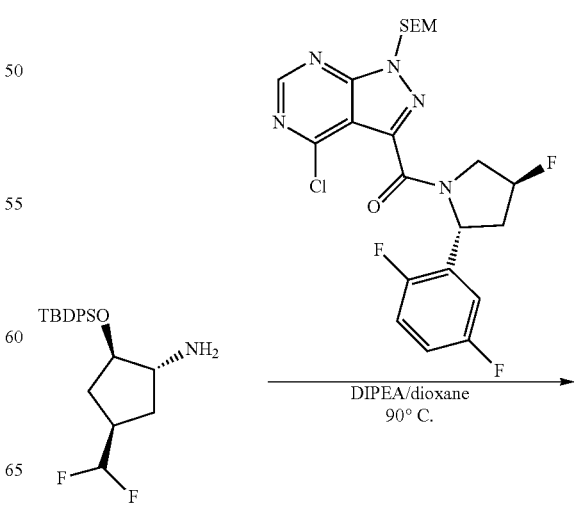

117
-continued

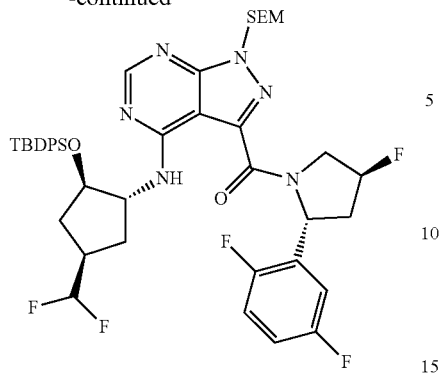

To a solution of (1R,2R,4R)-2-((tert-butyldiphenylsilyl)oxy)-4-(difluoromethyl)cyclopentan-1-amine (40.00 mg, 93.89 umol, 1.00 eq, HCl) and (4-chloro-1-((2-(trimethylsilyl)ethoxy)methyl)-1H-pyrazolo[3,4-d]pyrimidin-3-yl)((2R,4S)-2-(2,5-difluorophenyl)-4-fluoropyrrolidin-1-yl)methanone (48.07 mg, 93.89 umol, 1.00 eq) in dioxane (10.00 mL) was added DIPEA (60.67 mg, 469.45 umol, 5.00 eq). The reaction was heated at 90° C. for 0.5 hr. LCMS showed the reaction was complete. The solution was concentrated. The residue was purified by prep-TLC (PE:EtOAc=3:1). (4-(((1R,2R,4R)-2-((tert-butyldiphenylsilyl)oxy)-4-(difluoromethyl)cyclopentyl)amino)-1-((2-(trimethylsilyl)ethoxy)methyl)-1H-pyrazolo[3,4-d]pyrimidin-3-yl)((2R,4S)-2-(2,5-difluorophenyl)-4-fluoropyrrolidin-1-yl)methanone (38.00 mg, yield: 46.78%) as a yellow oil was obtained.

Step 7: (4-(((1R,2R,4R)-4-(difluoromethyl)-2-hydroxycyclopentyl)amino)-1H-pyrazolo[3,4-d]pyrimidin-3-yl)((2R,4S)-2-(2,5-difluorophenyl)-4-fluoropyrrolidin-1-yl)methanone (Compound 226)

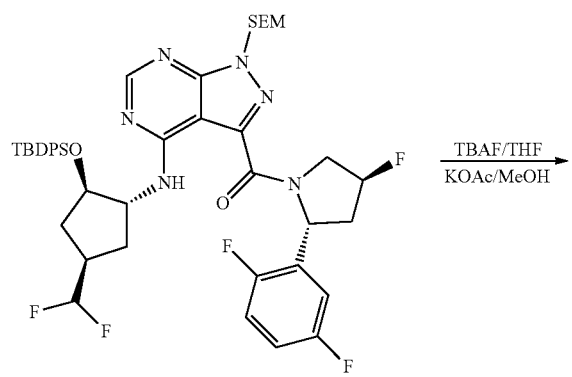

118
-continued

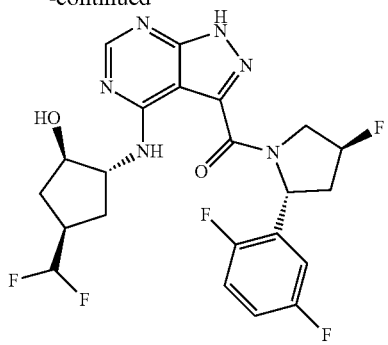

A solution of (4-(((1R,2R,4R)-2-((tert-butyldiphenylsilyl)oxy)-4-(difluoromethyl)cyclopentyl)amino)-1-((2-(trimethylsilyl)ethoxy)methyl)-1H-pyrazolo[3,4-d]pyrimidin-3-yl)((2R,4S)-2-(2,5-difluorophenyl)-4-fluoropyrrolidin-1-yl)methanone (38.00 mg, 43.93 umol, 1.00 eq) in TBAF/THF (5.00 mL) was heated at 50° C. for 2 hrs. LCMS showed (4-(((1R,2R,4R)-4-(difluoromethyl)-2-hydroxycyclopentyl)amino)-1-(hydroxymethyl)-1H-pyrazolo[3,4-d]pyrimidin-3-yl)((2R,4S)-2-(2,5-difluorophenyl)-4-fluoropyrrolidin-1-yl)methanone was remained. The reaction mixture was concentrated. The residue was dissolved in EtOAc (20 mL) and washed with brine (10 mL*2). The organic layer was concentrated and dissolved in MeOH (20.00 mL). KOAc (21.56 mg, 219.65 umol, 5.00 eq) was added to the reaction. The reaction was heated at 50° C. for 16 hrs. LCMS showed the reaction was complete. The solution was concentrated. The residue was purified by prep-HPLC (MeOH/TFA system). (13.50 mg, yield: 50.34%, TFA) of (4-(((1R,2R,4R)-4-(difluoromethyl)-2-hydroxycyclopentyl)amino)-1H-pyrazolo[3,4-d]pyrimidin-3-yl)((2R,4S)-2-(2,5-difluorophenyl)-4-fluoropyrrolidin-1-yl)methanone as a yellow solid was obtained.

Example 28. Synthesis of Other Compounds

Additional compounds of the invention were synthesized using similar techniques to those set forth in the above examples. The table below indicates the specific example ("Example") upon which the synthesis of each compound ("Cmpd") was based, as well as the appropriate amino alcohol and amine that were used to synthesize each specific compound.

TABLE 1

Protocol and Intermediates Used for Synthesizing Exemplary Compounds.

| Cmpd | Amino Alcohol | Amine | Example |
|---|---|---|---|
| 1 | | | 1 |

TABLE 1-continued

*Protocol and Intermediates Used for Synthesizing Exemplary Compounds.*

| Cmpd | Amino Alcohol | Amine | Example |
|---|---|---|---|
| 2 | (1S,2R,3S)-3-amino-1,2-cyclopentanediol | 5-fluoro-2-methylbenzylamine | 1 |
| 3 | (1S,2R,5R,6R)-2-amino-6,1-epoxybicyclic cyclopentanol | 2,5-difluorobenzylamine | 1 |
| 4 | bicyclic hydroxy amine | 2,5-difluorobenzylamine | 1 |
| 5 | (1S,2R,3S)-3-amino-1,2-cyclopentanediol | N-methyl-(5-fluoropyridin-3-yl)methanamine | 1 |
| 6 | (1S,2R)-2-aminocyclopentanol | N-methyl-2,5-difluorobenzylamine | 1 |
| 7 | (1S,2R)-2-aminocyclopentanol | (S)-1-(2,5-difluorophenyl)ethanamine | 1 |
| 8 | (3R,4R)-3-amino-tetrahydropyran-4-ol | 2,5-difluorobenzylamine | 1 |

TABLE 1-continued

*Protocol and Intermediates Used for Synthesizing Exemplary Compounds.*

| Cmpd | Amino Alcohol | Amine | Example |
|---|---|---|---|
| 9 | (1S,2R,3S)-3-aminocyclopentane-1,2-diol | 2,5-difluorobenzylamine | 2 |
| 10 | (1R,2S,3R)-3-aminocyclopentane-1,2-diol | 2,5-difluorobenzylamine | 2 |
| 11 | (3R,4R)-4-aminotetrahydro-2H-pyran-3-ol | 2,5-difluorobenzylamine | 1 |
| 12 | (1S,2R,4S)-2-amino-4-hydroxycyclopentan-1-ol | 2,5-difluorobenzylamine | 2 |
| 13 | (1R,2S,4R)-2-amino-4-hydroxycyclopentan-1-ol | 2,5-difluorobenzylamine | 2 |
| 14 | (1S,2R,4S)-2-amino-4-fluorocyclopentan-1-ol | 2,5-difluorobenzylamine | 3 |
| 15 | (1R,2S,4R)-2-amino-4-fluorocyclopentan-1-ol | 2,5-difluorobenzylamine | 3 |

TABLE 1-continued

Protocol and Intermediates Used for Synthesizing Exemplary Compounds.

| Cmpd | Amino Alcohol | Amine | Example |
|---|---|---|---|
| 16 | (1S,2R,4S)-4-fluoro-2-aminocyclopentanol | 2,5-difluorobenzylamine | 3 |
| 17 | (1R,2S,4S)-4-fluoro-2-aminocyclopentanol | 2,5-difluorobenzylamine | 3 |
| 18 | (1S,2R,5R)-5-fluoro-2-aminocyclopentanol | 2,5-difluorobenzylamine | 3 |
| 19 | (1R,2S,5S)-5-fluoro-2-aminocyclopentanol | 2,5-difluorobenzylamine | 3 |
| 20 | (1R,2S,5R)-5-fluoro-2-aminocyclopentanol | 2,5-difluorobenzylamine | 3 |
| 21 | (1S,2R,5S)-5-fluoro-2-aminocyclopentanol | 2,5-difluorobenzylamine | 3 |
| 22 | 2-amino-cyclopentane-1,3-diol | 3-fluoro-5-cyanobenzylamine | 1 |

TABLE 1-continued

Protocol and Intermediates Used for Synthesizing Exemplary Compounds.

| Cmpd | Amino Alcohol | Amine | Example |
|---|---|---|---|
| 23 | (1R,2S,3S)-3-amino-1,2-cyclopentanediol | N-methyl-(5-fluoro-2-methylbenzyl)amine | 1 |
| 24 | (3R,4R)-3-amino-tetrahydropyran-4-ol | (5-fluoro-2-methoxybenzyl)amine | 1 |
| 25 | bicyclic amino diol | (2,5-difluorobenzyl)amine | 1 |
| 26 | (1S,2R)-2-aminocyclopentanol | N-ethyl-(2,5-difluorobenzyl)amine | 1 |
| 27 | (1S,2R)-2-aminocyclopentanol | (R)-2-amino-2-(2,5-difluorophenyl)ethanol | 1 |
| 28 | (1R,2S,3S)-3-amino-1,2-cyclopentanediol | N-methyl-(2,5-difluorobenzyl)amine | 1 |
| 29 | (3R,4R)-3-amino-tetrahydropyran-4-ol | N-methyl-(2,5-difluorobenzyl)amine | 1 |
| 30 | (3R,4R)-3-amino-tetrahydropyran-4-ol | (S)-1-(2,5-difluorophenyl)ethylamine | 1 |

TABLE 1-continued

*Protocol and Intermediates Used for Synthesizing Exemplary Compounds.*

| Cmpd | Amino Alcohol | Amine | Example |
|------|---------------|-------|---------|
| 31 | 3-amino-tetrahydropyran-4-ol | (S)-1-(2,5-difluorophenyl)ethylamine | 1 |
| 32 | 2-amino-cyclohexane-1,3-diol | 2,5-difluorobenzylamine | 1 |
| 33 | 2-amino-cyclopentane-1,3-diol | N-methyl-3,5-difluorobenzylamine | 1 |
| 34 | 2-amino-cyclopentane-1,3-diol | (S)-1-(2,5-difluorophenyl)ethylamine | 2 |
| 35 | 2-amino-cyclopentane-1,3-diol | (S)-1-(2,5-difluorophenyl)ethylamine | 2 |
| 36 | 2-amino-cyclopentane-1,3-diol | 2-chloro-5-fluorobenzylamine | 1 |
| 37 | 3-amino-tetrahydropyran-4-ol | 2-chloro-5-fluorobenzylamine | 1 |

TABLE 1-continued

Protocol and Intermediates Used for Synthesizing Exemplary Compounds.

| Cmpd | Amino Alcohol | Amine | Example |
|---|---|---|---|
| 38 | (1S,2S,3R)-3-amino-cyclopentane-1,2-diol | 3-chloro-5-fluorobenzylamine | 1 |
| 39 | (3R,4R)-3-amino-tetrahydro-2H-pyran-4-ol with N-CD₃ | N-(2,5-difluorobenzyl)methan-d3-amine | 1 |
| 40 | (3R,4R)-3-amino-tetrahydro-2H-pyran-4-ol | 2,3,5-trifluorobenzylamine | 1 |
| 41 | (1S,2S,3R)-3-amino-cyclopentane-1,2-diol | 2,3,5-trifluorobenzylamine | 1 |
| 42 | 4,4-difluoro-cyclopentane amino alcohol | 2,5-difluorobenzylamine | 1 |
| 43 | 4,4-difluoro-cyclopentane amino alcohol | 2,6-difluorobenzylamine | 1 |
| 44 | (1S,2S,3R)-3-amino-cyclopentane-1,2-diol | N-methyl-3-fluoro-5-cyanobenzylamine | 1 |

TABLE 1-continued

Protocol and Intermediates Used for Synthesizing Exemplary Compounds.

| Cmpd | Amino Alcohol | Amine | Example |
|------|---------------|-------|---------|
| 45 | (1S,2R)-2-aminocyclopentan-1-ol | (S)-2-(2,5-difluorophenyl)pyrrolidine | 1 |
| 46 | (1S,2R)-2-aminocyclopentan-1-ol | (2S,4S)-2-(5-fluoropyridin-3-yl)-4-fluoropyrrolidine | 1 |
| 47 | (3R,4R)-3-amino-tetrahydro-2H-pyran-4-ol | 1-(2,5-difluorophenyl)cyclopropan-1-amine | 1 |
| 48 | (1S,2R,3S)-3-aminocyclopentane-1,2-diol | N-methyl-(3-fluoro-5-methoxybenzyl)amine | 1 |
| 49 | (1S,2R,3S)-3-aminocyclopentane-1,2-diol | N-methyl-(5-fluoro-2-methoxybenzyl)amine | 1 |
| 50 | (3S,4R)-3-amino-tetrahydrofuran-4-ol | (2S,4S)-2-(5-fluoropyridin-3-yl)-4-fluoropyrrolidine | 1 |
| 51 | tert-butyl (3R,4R)-3-amino-4-hydroxypyrrolidine-1-carboxylate | (S)-1-(2,5-difluorophenyl)ethan-1-amine | 23 |

TABLE 1-continued

Protocol and Intermediates Used for Synthesizing Exemplary Compounds.

| Cmpd | Amino Alcohol | Amine | Example |
|---|---|---|---|
| 52 | (1R,2S,3S)-3-amino-1,2-dihydroxycyclopentane | N-methyl-(5-fluoro-2-methoxypyridin-3-yl)methanamine | 1 |
| 53 | (3R,4R)-3-amino-4-hydroxytetrahydropyran | N-ethyl-(2,5-difluorophenyl)methanamine | 1 |
| 54 | (3R,4R)-3-amino-4-hydroxytetrahydropyran | (3,5-difluoro-2-methoxyphenyl)methanamine | 1 |
| 55 | (3R,4R,5S)-3-amino-4,5-dihydroxytetrahydropyran | N-methyl-(2,5-difluorophenyl)methanamine | 1 |
| 56 | (3R,4R)-3-amino-4-hydroxytetrahydropyran | (R)-2-amino-2-(2,5-difluorophenyl)ethanol | 1 |
| 57 | (1R,2S,3S)-3-amino-1,2-dihydroxycyclopentane | N-methyl-(2-chloro-5-fluoropyridin-3-yl)methanamine | 1 |
| 58 | (1R,2S,3S)-3-amino-1,2-dihydroxycyclopentane | N-methyl-(3-chloro-5-fluorophenyl)methanamine | 1 |

TABLE 1-continued

Protocol and Intermediates Used for Synthesizing Exemplary Compounds.

| Cmpd | Amino Alcohol | Amine | Example |
|---|---|---|---|
| 59 | (1S,2R,3R)-3-amino-1,2-dihydroxycyclopentane | 3,5-difluoro-2-methoxybenzylamine | 1 |
| 60 | (1S,2R,3R)-3-amino-1,2-dihydroxycyclopentane | (2-chloro-5-fluoropyridin-3-yl)-N-methylmethanamine | 1 |
| 61 | (1S,2R,4S)-2-amino-4-fluorocyclopentanol | (S)-2-amino-2-(2,5-difluorophenyl)ethanol | 3 |
| 62 | (1S,2R,4S)-2-amino-4-fluorocyclopentanol | (R)-2-amino-2-(2,5-difluorophenyl)ethanol | 3 |
| 63 | (1S,2R,3R)-3-amino-1,2-dihydroxycyclopentane | N-methyl-(2,3,5-trifluorobenzyl)amine | 1 |
| 64 | (1R,2S)-2-amino-6,6-difluorocyclohexanol | 2,5-difluorobenzylamine | 1 |
| 65 | (1S,2R)-2-amino-6,6-difluorocyclohexanol | 2,5-difluorobenzylamine | 1 |
| 66 | (1S,2R)-2-aminocyclopentanol | (S)-2,2,2-trifluoro-1-(3-fluorophenyl)ethylamine | 2 |

TABLE 1-continued

*Protocol and Intermediates Used for Synthesizing Exemplary Compounds.*

| Cmpd | Amino Alcohol | Amine | Example |
|------|---------------|-------|---------|
| 67 | | | 2 |
| 68 | | | 1 |
| 69 | | | 1 |
| 70 | | | 2 |
| 71 | | | 2 |
| 72 | | | 1 |

TABLE 1-continued

*Protocol and Intermediates Used for Synthesizing Exemplary Compounds.*

| Cmpd | Amino Alcohol | Amine | Example |
|------|---------------|-------|---------|
| 73 | | | 1 |
| 74 | | | 1 |
| 75 | | | 3 |
| 76 | | | 3 |
| 77 | | | 1 |
| 78 | | | 1 |

TABLE 1-continued

Protocol and Intermediates Used for Synthesizing Exemplary Compounds.

| Cmpd | Amino Alcohol | Amine | Example |
|---|---|---|---|
| 79 | (1R,2S)-2-aminocyclopentan-1-ol | (3S,5R)-5-(2,5-difluorophenyl)pyrrolidine-3-carbonitrile | 1 |
| 80 | (3R,4R)-3-aminotetrahydro-2H-pyran-4-ol | (5-fluoro-2-(trifluoromethyl)phenyl)methanamine | 1 |
| 81 | (1S,2R,3S)-3-aminocyclopentane-1,2-diol | (5-fluoro-2-(trifluoromethyl)phenyl)methanamine | 1 |
| 82 | (3S,4R)-4-aminotetrahydrofuran-3-ol | (3S,5R)-5-(2,5-difluorophenyl)pyrrolidine-3-carbonitrile | 1 |
| 83 | (3R,4R)-3-aminotetrahydro-2H-pyran-4-ol | (2,3-dichloro-5-fluorophenyl)methanamine | 1 |
| 84 | (1S,3R,4S)-3-amino-4-hydroxy-N,N-dimethylcyclopentane-1-carboxamide | (2,6-difluorophenyl)methanamine | 22 |
| 85 | (2S,3R,4S)-3-aminotetrahydro-2H-pyran-2,4-diol | (R)-3-((S)-4-fluoropyrrolidin-2-yl)-5-fluoropyridine | 1 |

TABLE 1-continued

Protocol and Intermediates Used for Synthesizing Exemplary Compounds.

| Cmpd | Amino Alcohol | Amine | Example |
|---|---|---|---|
| 86 | (1S,3R,4S)-3-amino-4-hydroxycyclopentan-1-ol (HO⟋⟍NH₂, OH) | 2-(2,5-difluorophenyl)-4-fluoropyrrolidine | 2 |
| 87 | (1S,3R,4S)-3-amino-4-hydroxycyclopentan-1-ol stereoisomer | 2-(2,5-difluorophenyl)-4-fluoropyrrolidine | 2 |
| 88 | (1R,2S,3S)-3-aminocyclopentane-1,2-diol | 2-(2,5-difluorophenyl)-4-fluoropyrrolidine | 1 |
| 89 | (1R,2S,3S)-3-aminocyclopentane-1,2-diol | 2-(2,3,5-trifluorophenyl)pyrrolidine | 1 |
| 90 | methyl (1S,2R,3S,4R,5S)-4-amino-2,3-dihydroxy-5-... cyclopentanecarboxylate | (2,5-difluorophenyl)methanamine | 2 |
| 91 | methyl (1S,2R,3S,4R,5S)-4-amino-2,3-dihydroxy-5-... cyclopentanecarboxylate stereoisomer | (2,5-difluorophenyl)methanamine | 2 |

TABLE 1-continued

Protocol and Intermediates Used for Synthesizing Exemplary Compounds.

| Cmpd | Amino Alcohol | Amine | Example |
|------|---------------|-------|---------|
| 92 | (3-amino-4-hydroxy tetrahydropyran) | 2-(2,5-difluorophenyl)-4-fluoropyrrolidine | 1 |
| 93 | (3-amino-4-hydroxy tetrahydropyran, other stereoisomer) | 2-(2,5-difluorophenyl)-4-fluoropyrrolidine | 1 |
| 94 | (2-amino-cyclopentane-1,3-diol) | 2-(5-fluoropyridin-3-yl)-4,4-difluoropyrrolidine | 1 |
| 95 | (2-amino-4-fluorocyclopentan-1-ol) | 2-(2,5-difluorophenyl)-4-fluoropyrrolidine | 3 |
| 96 | (2-amino-4-fluorocyclopentan-1-ol, other stereoisomer) | 2-(2,5-difluorophenyl)-4-fluoropyrrolidine | 3 |
| 97 | (2-amino-4-methylsulfonyl-cyclopentan-1-ol) | 2,5-difluorobenzylamine | 2 |

TABLE 1-continued

*Protocol and Intermediates Used for Synthesizing Exemplary Compounds.*

| Cmpd | Amino Alcohol | Amine | Example |
|---|---|---|---|
| 98 | (1S,3R,4S)-3-(methylsulfonyl)-4-aminocyclopentan-1-ol | 2,5-difluorobenzylamine | 2 |
| 99 | (1R,2S,3S)-3-aminocyclopentane-1,2-diol | N-methyl-1-(5-fluoro-2-(trifluoromethyl)phenyl)methanamine | 1 |
| 100 | (3R,4R)-3-aminotetrahydro-2H-pyran-4-ol | (3R,5S)-5-(2,5-difluorophenyl)pyrrolidine-3-carbonitrile | 1 |
| 101 | (1R,2S,3S)-3-aminocyclopentane-1,2-diol | 5-fluoro-2-(trifluoromethoxy)benzylamine | 1 |
| 102 | tert-butyl (3S,4R)-3-amino-4-hydroxypyrrolidine-1-carboxylate | 2,5-difluorobenzylamine | 23 |
| 103 | (3R,4R)-3-aminotetrahydro-2H-pyran-4-ol | (S)-1-(2,5-difluorophenyl)-2,2,2-trifluoroethan-1-amine | 1 |
| 104 | (1S,2R,3S,5R)-3-aminobicyclo-pentane-1,2-diol | (3S,5S)-5-(2,5-difluorophenyl)-3-fluoropyrrolidine | 1 |

TABLE 1-continued

Protocol and Intermediates Used for Synthesizing Exemplary Compounds.

| Cmpd | Amino Alcohol | Amine | Example |
|---|---|---|---|
| 105 | (1R,2S,3S)-3-amino-1,2-cyclohexanediol | 2-(2,5-difluorophenyl)pyrrolidine | 1 |
| 106 | (1R,2S,3S)-3-amino-1,2-cyclohexanediol | 2-(2,5-difluorophenyl)-4-fluoropyrrolidine | 1 |
| 107 | 3-amino-tetrahydropyran-4,5-diol | 2-(2,5-difluorophenyl)-5-fluoropyrrolidine | 1 |
| 108 | 3-amino-1,2-cyclopentanediol | 2-(3,5-difluorophenyl)-4,4-difluoropyrrolidine | 1 |
| 109 | N-Boc-3-amino-4-hydroxypyrrolidine | 2-(5-fluoro-2-methoxyphenyl)methanamine | 23 |
| 110 | 3-amino-1,2-cyclopentanediol | N-methyl-[5-fluoro-2-(trifluoromethoxy)phenyl]methanamine | 1 |
| 111 | N-Boc-3-amino-4-hydroxypyrrolidine | 1-(2,5-difluorophenyl)ethanamine | 23 |

TABLE 1-continued

Protocol and Intermediates Used for Synthesizing Exemplary Compounds.

| Cmpd | Amino Alcohol | Amine | Example |
|---|---|---|---|
| 112 | | | 1 |
| 113 | | | 23 |
| 114 | | | 1 |
| 115 | | | 2 |
| 116 | | | 2 |
| 117 | | | 1 |
| 118 | | | 1 |

TABLE 1-continued

Protocol and Intermediates Used for Synthesizing Exemplary Compounds.

| Cmpd | Amino Alcohol | Amine | Example |
|---|---|---|---|
| 119 | (1R,2S)-2-aminocyclopentan-1-ol | (2S,4R)-2-(2,5-difluorophenyl)-4-fluoropyrrolidine | 1 |
| 120 | (1S,2R,3S)-3-aminocyclopentane-1,2-diol | N-methyl-1-(3-chloro-2,5-difluorophenyl)methanamine | 1 |
| 121 | (1R,2S)-2-aminocyclopentan-1-ol | 3-((2S,4R)-4-fluoropyrrolidin-2-yl)-5-fluorobenzonitrile | 1 |
| 122 | (1S,2R,3S,4R,5S)-3-aminobicyclo[3.1.0]hexane-1,2-diol | (2S,4R)-2-(3-fluorophenyl)-4-fluoropyrrolidine | 1 |
| 123 | (1S,2R,4S)-2-amino-4-fluorocyclopentan-1-ol | 3-((2S,4R)-4-fluoropyrrolidin-2-yl)-5-fluorobenzonitrile | 3 |
| 124 | (1S,2R,4S)-2-amino-4-methoxycyclopentan-1-ol | (2S,4R)-2-(2,5-difluorophenyl)-4-fluoropyrrolidine | 2 |

TABLE 1-continued

Protocol and Intermediates Used for Synthesizing Exemplary Compounds.

| Cmpd | Amino Alcohol | Amine | Example |
|------|---------------|-------|---------|
| 125 | | | 2 |
| 126 | | | 1 |
| 127 | | | 1 |
| 128 | | | 1 |
| 129 | | | 1 |
| 130 | | | 1 |

TABLE 1-continued

Protocol and Intermediates Used for Synthesizing Exemplary Compounds.

| Cmpd | Amino Alcohol | Amine | Example |
|---|---|---|---|
| 131 | (1S,2R,3S)-3-amino-1,2-cyclopentanediol | N-methylbenzylamine | 1 |
| 132 | (1S,2R,3S)-3-amino-1,2-cyclopentanediol | N-methyl-3-fluorobenzylamine | 1 |
| 133 | (1S,2R,3S)-3-amino-1,2-cyclopentanediol | N-methyl-(2-fluoropyridin-3-yl)methylamine | 1 |
| 134 | (1S,2R,3S)-3-amino-1,2-cyclopentanediol | N-methyl-3-cyanobenzylamine | 1 |
| 135 | (1S,2R)-2-aminocyclopentanol | N-methyl-(2-bromo-5-fluorobenzyl)amine | 24 |
| 136 | (1S,2R)-2-aminocyclopentanol | N-methyl-(5-fluoro-1-methyl-2-oxo-1,2-dihydropyridin-3-yl)methylamine | 1 |
| 137 | (1S,2R,3S)-3-amino-1,2-cyclopentanediol | N-methyl-3-chlorobenzylamine | 1 |
| 138 | (1S,2R,3S)-3-amino-1,2-cyclopentanediol | N-methyl-(2-chloropyridin-3-yl)methylamine | 1 |

TABLE 1-continued

Protocol and Intermediates Used for Synthesizing Exemplary Compounds.

| Cmpd | Amino Alcohol | Amine | Example |
|---|---|---|---|
| 139 | cyclopentane with NH₂, OH, HO substituents | HN(CH₃)CH₂-(2,3-difluorophenyl) | 1 |
| 140 | cyclopentene fused with 2,2-dimethyl-1,3-dioxolane, NH₂ | HN(CH₃)CH₂-(2-bromo-5-fluorophenyl) | 24 |
| 141 | cyclopentane with NH₂, OH, HO substituents | HN(CH₃)CH₂-(2-bromo-5-fluorophenyl) | 24 |
| 142 | cyclopentane with NH₂, OH, HO substituents | HN(CH₃)CH₂-(2-fluoro-3-cyanophenyl) | 1 |
| 143 | tetrahydropyran with NH₂, OH | HN(CH₃)CH₂-(2-bromo-5-fluorophenyl) | 24 |
| 144 | cyclopentane with NH₂, OH, HO substituents | (2-phenyl-4-fluoro)pyrrolidine | 1 |
| 145 | tetrahydropyran with NH₂, OH | (2-phenyl-4-fluoro)pyrrolidine | 1 |

TABLE 1-continued

*Protocol and Intermediates Used for Synthesizing Exemplary Compounds.*

| Cmpd | Amino Alcohol | Amine | Example |
|---|---|---|---|
| 146 | (4-fluoro-2-amino-cyclopentan-1-ol, trans) | N-methyl-(2-bromo-5-fluorobenzyl)amine | 24 |
| 147 | (2-amino-3-hydroxy-cyclopentan-1-ol) | 3-(methylaminomethyl)-1-methyl-5-fluoropyridin-2(1H)-one | 1 |
| 148 | (2-amino-3-hydroxy-cyclopentan-1-ol) | N-methyl-(2-fluoro-5-chlorobenzyl)amine | 1 |
| 149 | (3-amino-tetrahydropyran-4-ol) | N-methyl-(2-chloro-5-fluoropyridin-3-yl)methanamine | 1 |
| 150 | (3-amino-tetrahydropyran-4-ol) | N-methyl-(2-chloro-5-fluoropyridin-3-yl)methanamine | 1 |
| 151 | (4-fluoro-2-amino-cyclopentan-1-ol) | N-methyl-(2-chloro-5-fluoropyridin-3-yl)methanamine | 3 |
| 152 | (bicyclic amino diol) | N-methyl-(2-bromo-4-fluorobenzyl)amine | 24 |

TABLE 1-continued

*Protocol and Intermediates Used for Synthesizing Exemplary Compounds.*

| Cmpd | Amino Alcohol | Amine | Example |
|------|---------------|-------|---------|
| 153 | | | 1 |
| 154 | | | 24 |
| 155 | | | 1 |
| 156 | | | 24 |
| 157 | | | 1 |
| 158 | | | 1 |

TABLE 1-continued

*Protocol and Intermediates Used for Synthesizing Exemplary Compounds.*

| Cmpd | Amino Alcohol | Amine | Example |
|---|---|---|---|
| 159 | | | 1 |
| 160 | | | 1 |
| 161 | | | 1 |
| 162 | | | 1 |
| 163 | | | 1 |
| 164 | | | 1 |
| 165 | | | 24 |

TABLE 1-continued

Protocol and Intermediates Used for Synthesizing Exemplary Compounds.

| Cmpd | Amino Alcohol | Amine | Example |
|---|---|---|---|
| 166 | | | 1 |
| 167 | | | 24 |
| 168 | | | 1 |
| 169 | | | 1 |
| 170 | | | 1 |
| 171 | | | 1 |

TABLE 1-continued

Protocol and Intermediates Used for Synthesizing Exemplary Compounds.

| Cmpd | Amino Alcohol | Amine | Example |
|---|---|---|---|
| 172 | | | 1 |
| 173 | | | 1 |
| 174 | | | 1 |
| 175 | | | 1 |
| 176 | | | 1 |
| 177 | | | 1 |

TABLE 1-continued

*Protocol and Intermediates Used for Synthesizing Exemplary Compounds.*

| Cmpd | Amino Alcohol | Amine | Example |
|---|---|---|---|
| 178 | (1S,2R,4S)-4-fluoro-2-aminocyclopentan-1-ol | (2S,4S)-2-(3,5-difluorophenyl)-4-fluoropyrrolidine | 3 |
| 179 | (1R,2S,3S)-3-aminocyclopentane-1,2-diol | N-[(3-(difluoromethoxy)-5-fluorophenyl)methyl]-N-methylamine | 1 |
| 180 | (1S,2R,4S)-4-(difluoromethyl)-2-aminocyclopentan-1-ol | (1S)-1-(2,5-difluorophenyl)-2-hydroxy-N-methylethan-1-amine | 1 |
| 181 | (3R,4S)-3-amino-tetrahydro-2H-pyran-4-ol | 3-[(2S,4S)-4-fluoropyrrolidin-2-yl]-5-fluorobenzonitrile | 1 |
| 182 | (3S,4R)-3-amino-tetrahydro-2H-pyran-4-ol | 3-[(2S,4S)-4-fluoropyrrolidin-2-yl]-5-fluorobenzonitrile | 1 |
| 183 | (3S,4R)-3-amino-tetrahydro-2H-pyran-4-ol | (2S,4S)-2-(2-bromo-5-fluorophenyl)-4-fluoropyrrolidine | 24 |

TABLE 1-continued

Protocol and Intermediates Used for Synthesizing Exemplary Compounds.

| Cmpd | Amino Alcohol | Amine | Example |
|---|---|---|---|
| 184 | (cyano/amino/hydroxy cyclopentane) | 2-(2,5-difluorophenyl)-4-fluoropyrrolidine | 1 |
| 185 | (cyano/amino/hydroxy cyclopentane) | 2-(3,5-difluorophenyl)-4-fluoropyrrolidine | 1 |
| 186 | (fluoro/amino/hydroxy cyclopentane) | 2-(2-bromo-5-fluorophenyl)-4-fluoropyrrolidine | 3 |
| 187 | (fluoro/amino/hydroxy cyclopentane) | 2-(2-bromo-5-fluorophenyl)-4-fluoropyrrolidine | 3 |
| 188 | (bicyclic amino diol) | 2-(3,5-difluorophenyl)-4-fluoropyrrolidine | 1 |
| 189 | (bicyclic amino diol) | 2-(2,3-difluorophenyl)-4-fluoropyrrolidine | 1 |

TABLE 1-continued

Protocol and Intermediates Used for Synthesizing Exemplary Compounds.

| Cmpd | Amino Alcohol | Amine | Example |
|---|---|---|---|
| 190 | | | 1 |
| 191 | | | 1 |
| 192 | | | 1 |
| 193 | | | 1 |
| 194 | | | 1 |
| 195 | | | 1 |

TABLE 1-continued

Protocol and Intermediates Used for Synthesizing Exemplary Compounds.

| Cmpd | Amino Alcohol | Amine | Example |
|------|---------------|-------|---------|
| 196 | 4-aminotetrahydro-2H-pyran-3-ol | 2-(2-chloro-5-fluorophenyl)-4-fluoropyrrolidine | 1 |
| 197 | 3-aminotetrahydro-2H-pyran-4,5-diol | 2-(3,5-difluorophenyl)-4-fluoropyrrolidine | 1 |
| 198 | 4-aminotetrahydro-2H-pyran-3-ol | 2-(3-chloro-5-fluorophenyl)-4-fluoropyrrolidine | 1 |
| 199 | amino-cyclopentenyl acetonide | 4-fluoro-2-(3,4,5-trifluorophenyl)pyrrolidine | 1 |
| 200 | 4-aminotetrahydro-2H-pyran-3-ol | 2-(5-chloro-2-fluorophenyl)-4-fluoropyrrolidine | 1 |
| 201 | 3-aminocyclopentane-1,2-diol | 2-(5-chloro-2-fluorophenyl)-4-fluoropyrrolidine | 1 |

TABLE 1-continued

Protocol and Intermediates Used for Synthesizing Exemplary Compounds.

| Cmpd | Amino Alcohol | Amine | Example |
|------|---------------|-------|---------|
| 202 | | | 1 |
| 203 | | | 1 |
| 204 | | | 1 |
| 205 | | | 1 |
| 206 | | | 1 |
| 207 | | | 3 |

TABLE 1-continued

*Protocol and Intermediates Used for Synthesizing Exemplary Compounds.*

| Cmpd | Amino Alcohol | Amine | Example |
|------|---------------|-------|---------|
| 208 | | | 3 |
| 209 | | | 1 |
| 210 | | | 22 |
| 211 | | | 1 |
| 212 | | | 1 |
| 213 | | | 1 |

TABLE 1-continued

Protocol and Intermediates Used for Synthesizing Exemplary Compounds.

| Cmpd | Amino Alcohol | Amine | Example |
|---|---|---|---|
| 214 | bicyclic amino diol with NH2 | 3-fluoro-5-chlorophenyl (3S,5S)-5-fluoropyrrolidin-2-yl | 1 |
| 215 | bicyclic amino diol with NH2 | 5-chloro-2-fluorophenyl (3S,5S)-5-fluoropyrrolidin-2-yl | 1 |
| 216 | bicyclic amino diol with NH2 | 2,5-difluoropyridin-3-yl (3S,5S)-5-fluoropyrrolidin-2-yl | 1 |
| 217 | cyclohexane amino diol with NH2 | 5-fluoro-2-chlorophenyl (3S,5S)-5-fluoropyrrolidin-2-yl | 1 |
| 218 | tetrahydropyran amino alcohol | 3,5-difluoro-2-methoxyphenyl (3S,5S)-5-fluoropyrrolidin-2-yl | 1 |
| 219 | cyclopentane amino diol | 3,5-difluoro-2-methoxyphenyl (3S,5S)-5-fluoropyrrolidin-2-yl | 1 |

TABLE 1-continued
Protocol and Intermediates Used for Synthesizing Exemplary Compounds.
| Cmpd | Amino Alcohol | Amine | Example |
|---|---|---|---|
| 220 | 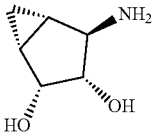 | 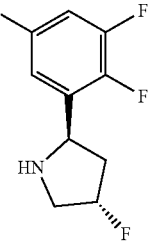 | 1 |
| 221 | 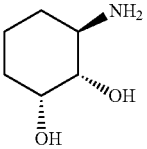 | 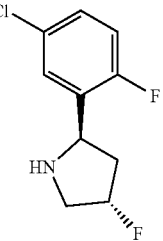 [SMILES: Fc1ccc(F)c([C@H]2C[C@H](F)CN2)c1] | 1 |
| 222 | 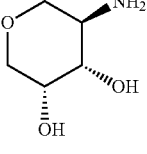 | 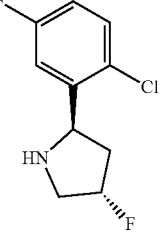 | 1 |
| 223 | 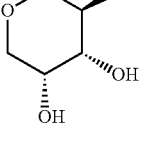 | 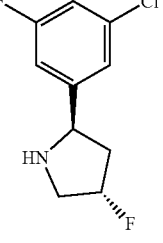 | 1 |
| 224 | 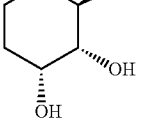 | 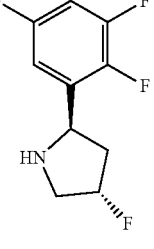 | 1 |
| 225 | 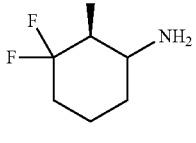 | 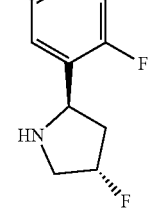 | 1 |

TABLE 1-continued

*Protocol and Intermediates Used for Synthesizing Exemplary Compounds.*

| Cmpd | Amino Alcohol | Amine | Example |
|---|---|---|---|
| 226 | | | 27 |
| 227 | | | 1 |
| 228 | | | 1 |
| 229 | | | 23 |
| 230 | | | 1 |
| 231 | | | 1 |

TABLE 1-continued

Protocol and Intermediates Used for Synthesizing Exemplary Compounds.

| Cmpd | Amino Alcohol | Amine | Example |
|------|---------------|-------|---------|
| 232 | | | 22 |
| 233 | | | 1 |
| 234 | | | 1 |
| 235 | | | 1 |
| 236 | | | 1 |
| 237 | | | 1 |

TABLE 1-continued

Protocol and Intermediates Used for Synthesizing Exemplary Compounds.

| Cmpd | Amino Alcohol | Amine | Example |
|---|---|---|---|
| 238 | (tetrahydropyran with NH₂ and ⋯OH) | 5-fluoro-2-(difluoromethoxy)phenyl-(4-fluoropyrrolidin-2-yl) | 1 |
| 239 | (bicyclic cyclopentane with NH₂, ⋯OH, HO) | 5-fluoro-2-(difluoromethoxy)phenyl-(4-fluoropyrrolidin-2-yl) | 1 |
| 240 | (cyclopentane with NH₂, ⋯OH, HO) | 5-fluoro-2-(trifluoromethoxy)phenyl-(4-fluoropyrrolidin-2-yl) | 1 |
| 241 | (tetrahydropyran with NH₂ and ⋯OH) | 5-fluoro-2-(trifluoromethoxy)phenyl-(4-fluoropyrrolidin-2-yl) | 1 |
| 242 | (bicyclic cyclopentane with NH₂, ⋯OH, HO) | 5-fluoro-2-(trifluoromethoxy)phenyl-(4-fluoropyrrolidin-2-yl) | 1 |
| 243 | (cyclohexane with NH₂, ⋯OH, OH) | 5-fluoro-2-(trifluoromethoxy)phenyl-(4-fluoropyrrolidin-2-yl) | 1 |

TABLE 1-continued

Protocol and Intermediates Used for Synthesizing Exemplary Compounds.

| Cmpd | Amino Alcohol | Amine | Example |
|---|---|---|---|
| 244 | (tetrahydropyran with NH2 and two OH groups) | 5-fluoro-2-(trifluoromethoxy)phenyl substituted 4-fluoropyrrolidine | 1 |

The NMR and LC MS data obtained for compounds disclosed herein are shown in FIG. 1.

Example 29. Assays

NTRK1 Wild Type Assay at 1 mM ATP

In each well of a 384-well plate, 1 nM-1.5 nM of wild type NTRK1 enzyme (BPS Bioscience; 40280) was incubated in a total of 12.5 μL of buffer (100 mM HEPES pH 7.5, 0.015% Brij 35, 10 mM $MgCl_2$, 1 mM DTT) with 1-2 μM CSKtide (Tuft's University or Anaspec; FITC-AHA-KKKKD DIYFFFG-NH2) and 1 mM ATP at 25° C. for 60 minutes in the presence or absence of a dosed concentration series of compound (1% DMSO final concentration). The reaction was stopped by the addition of 70 μL of Stop buffer (100 mM HEPES pH 7.5, 0.015% Brij 35, 35 mM EDTA and 0.2% of Coating Reagent 3 (Caliper Lifesciences)). The plate was then read on a Caliper EZReader 2 (protocol settings: −1.7 psi, upstream voltage −500, downstream voltage −3000, post sample sip 35s). Data was normalized to 0% and 100% inhibition controls and the $IC_{50}$ calculated using a 4-parameter fit in the CORE LIMS.

NTRK Wild Type and G595R Mutant Cellular Assays Protocol

KM12 wild type colon carcinoma cell line harboring the TPM3-NTRK1 fusion protein was obtained from the National Cancer Institute (NCI). This line has been previously shown to be dependent upon the NTRK activity derived from the NTRK fusion protein for growth and survival. The KM12 Cliff (G595R) cell line was generated by mutagenizing the wild type KM12 line with a DNA methylating agent and subsequently selecting for clones that were resistant to chronic exposure to high concentration of a known NTRK inhibitor (Crizotinib). Cells were first plated in 384-well plates at 1000 cells/well in complete media (10% FBS and 1% pen/strep) and incubated overnight at 37° C. Cells were then dosed with test articles at varying concentrations using the Bravo liquid handling system. Concentrations ranged from 25 uM down to 9.5 pM (4-fold dilutions, 10 concentrations total). Each compound was run in duplicate per plate. DMSO and staurosporine (25 uM) were included on each plate as negative and positive controls for growth inhibition. 72 hr after dosing, assay plates were developed using CellTiter-Glo (Promega) and resultant luminescence was read on the Envision plate reader. $IC_{50}$ determinations were calculated using a 4-parameter curve fitting algorithm The table below summarizes the results from the biological assays described above. The following designations are used to indicate $IC_{50}$ in each assay: A<10.00 nM; B=10.01-100.0 nM; C=100.01-1000.0 nM; and D>1000.1 nM; "ND"=not determined.

| Compound Number | Enz NTRK1 | KM12 (WT) | KM12 (G595R) |
|---|---|---|---|
| 1 | B | B | B |
| 2 | C | C | C |
| 3 | D | D | D |
| 4 | C | D | D |
| 5 | C | C | C |
| 6 | A | B | B |
| 7 | B | B | B |
| 8 | B | B | C |
| 9 | B | B | C |
| 10 | C | C | D |
| 11 | C | C | C |
| 12 | C | C | D |
| 13 | B | B | C |
| 14 | C | C | C |
| 15 | C | C | D |
| 16 | C | D | D |
| 17 | B | B | C |
| 18 | C | C | D |
| 19 | D | D | D |
| 20 | B | B | C |
| 21 | C | C | D |
| 22 | C | D | D |
| 23 | A | B | B |
| 24 | B | C | C |
| 25 | B | B | C |
| 26 | B | B | C |
| 27 | A | B | B |
| 28 | A | B | B |
| 29 | A | B | B |
| 30 | C | B | C |
| 31 | C | C | C |
| 32 | B | C | C |
| 33 | B | B | B |
| 34 | B | B | C |
| 35 | C | C | D |
| 36 | B | C | C |
| 37 | B | C | C |
| 38 | C | C | C |
| 39 | A | B | B |
| 40 | B | C | C |
| 41 | B | C | C |
| 42 | C | D | D |
| 43 | B | B | C |
| 44 | B | B | C |
| 45 | A | A | A |
| 46 | A | A | A |
| 47 | C | C | C |
| 48 | B | B | C |
| 49 | A | B | B |
| 50 | B | B | C |
| 51 | C | C | C |
| 52 | B | B | B |

-continued

| Compound Number | Enz NTRK1 | KM12 (WT) | KM12 (G595R) |
|---|---|---|---|
| 53 | B | B | C |
| 54 | B | C | C |
| 55 | B | B | B |
| 56 | B | C | C |
| 57 | A | A | B |
| 58 | A | B | B |
| 59 | C | C | C |
| 60 | B | B | B |
| 61 | C | C | D |
| 62 | B | B | C |
| 63 | A | B | B |
| 64 | C | C | C |
| 65 | C | ND | ND |
| 66 | D | D | D |
| 67 | D | D | D |
| 68 | A | A | A |
| 69 | A | B | B |
| 70 | A | B | B |
| 71 | B | B | C |
| 72 | A | B | B |
| 73 | A | A | B |
| 74 | A | B | B |
| 75 | B | C | D |
| 76 | A | B | B |
| 77 | A | B | B |
| 78 | A | A | B |
| 79 | A | A | B |
| 80 | B | C | C |
| 81 | B | C | C |
| 82 | B | C | C |
| 83 | B | C | C |
| 84 | A | B | B |
| 85 | A | B | B |
| 86 | A | A | A |
| 87 | A | B | B |
| 88 | A | A | A |
| 89 | A | B | A |
| 90 | D | D | D |
| 91 | B | B | C |
| 92 | A | A | A |
| 93 | A | A | A |
| 94 | C | C | D |
| 95 | A | A | A |
| 96 | B | B | C |
| 97 | A | B | C |
| 98 | C | D | D |
| 99 | A | A | A |
| 100 | B | B | C |
| 101 | C | C | C |
| 102 | A | B | B |
| 103 | D | D | D |
| 104 | A | A | A |
| 105 | A | B | B |
| 106 | A | A | A |
| 107 | A | B | B |
| 108 | B | C | C |
| 109 | A | B | C |
| 110 | A | B | B |
| 111 | A | B | B |
| 112 | B | B | C |
| 113 | A | B | B |
| 114 | A | A | A |
| 115 | A | B | B |
| 116 | A | A | A |
| 117 | C | C | D |
| 118 | A | A | A |
| 119 | A | A | A |
| 120 | B | B | B |
| 121 | A | A | A |
| 122 | A | A | A |
| 123 | A | B | B |
| 124 | A | ND | ND |
| 125 | A | ND | ND |
| 126 | A | A | A |
| 127 | A | A | A |
| 128 | A | A | A |
| 129 | A | B | B |
| 130 | A | A | A |
| 131 | C | C | C |
| 132 | B | B | C |
| 133 | C | C | C |
| 134 | C | C | C |
| 135 | A | A | A |
| 136 | A | B | B |
| 137 | B | B | B |
| 138 | C | C | C |
| 139 | B | B | B |
| 140 | A | B | A |
| 141 | A | B | A |
| 142 | B | B | C |
| 143 | B | B | B |
| 144 | B | B | C |
| 145 | C | B | C |
| 146 | A | B | B |
| 147 | B | C | C |
| 148 | A | A | A |
| 149 | A | B | B |
| 150 | B | B | B |
| 151 | B | B | B |
| 152 | A | B | A |
| 153 | B | B | B |
| 154 | A | B | B |
| 155 | B | B | B |
| 156 | B | B | A |
| 157 | A | B | B |
| 158 | A | B | B |
| 159 | A | B | B |
| 160 | A | B | B |
| 161 | B | B | B |
| 162 | A | B | B |
| 163 | A | B | B |
| 164 | B | B | B |
| 165 | A | A | A |
| 166 | A | C | C |
| 167 | A | A | A |
| 168 | A | A | A |
| 169 | B | B | B |
| 170 | A | A | A |
| 171 | B | B | B |
| 172 | A | B | B |
| 173 | A | A | A |
| 174 | A | A | A |
| 175 | A | B | B |
| 176 | A | B | B |
| 177 | A | A | A |
| 178 | A | B | B |
| 179 | B | B | C |
| 180 | A | A | A |
| 181 | A | B | B |
| 182 | A | A | B |
| 183 | A | A | A |
| 184 | A | A | A |
| 185 | A | A | A |
| 186 | A | A | A |
| 187 | A | B | B |
| 188 | A | A | A |
| 189 | A | A | B |
| 190 | A | B | B |
| 191 | A | B | B |
| 192 | A | B | B |
| 193 | A | B | B |
| 194 | B | B | B |
| 195 | A | A | A |
| 196 | A | A | A |
| 197 | A | B | B |
| 198 | A | A | A |
| 199 | B | A | A |
| 200 | A | B | B |
| 201 | A | A | A |
| 202 | A | B | B |
| 203 | A | A | A |
| 204 | A | A | A |

-continued

| Compound Number | Enz NTRK1 | KM12 (WT) | KM12 (G595R) |
| --- | --- | --- | --- |
| 205 | A | A | A |
| 206 | A | A | A |
| 207 | B | B | B |
| 208 | A | A | A |
| 209 | A | B | B |
| 210 | A | A | A |
| 211 | A | A | A |
| 212 | A | A | A |
| 213 | A | A | A |
| 214 | A | A | A |
| 215 | A | A | A |
| 216 | A | A | A |
| 217 | A | A | A |
| 218 | A | A | A |
| 219 | A | A | A |
| 220 | A | A | A |
| 221 | A | A | A |
| 222 | A | B | B |
| 223 | A | B | B |
| 224 | A | A | A |
| 225 | A | B | B |
| 226 | A | A | A |
| 227 | A | A | A |
| 228 | B | B | B |
| 229 | A | A | A |
| 230 | A | B | B |
| 231 | B | B | C |
| 232 | A | A | A |
| 233 | A | A | A |
| 234 | A | A | A |
| 235 | A | B | B |
| 236 | A | A | B |
| 237 | A | B | B |
| 238 | ND | B | B |
| 239 | A | A | B |
| 240 | A | A | A |
| 241 | A | A | A |
| 242 | A | A | A |
| 243 | A | A | A |
| 244 | A | A | A |

INCORPORATION BY REFERENCE

All publications and patents mentioned herein are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method for treating a patient suffering from a tumor by inhibiting neurotrophic tyrosine receptor kinase (NTRK) activity, the method comprising administering to the patient a compound of Formula (I):

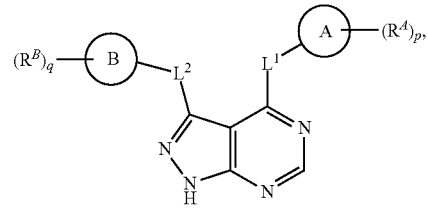

or a pharmaceutically acceptable salt thereof, wherein:
Ring A is selected from aryl, heteroaryl, cycloalkyl, cycloalkenyl, and heterocyclyl;
Ring B is selected from aryl, heteroaryl, cycloalkyl, and heterocyclyl;
$L^1$ is selected from —C(O)—, —N($R^1$)—, —N($R^1$)—C(O)-†, —C(O)—N($R^1$)-†, -($C_1$-$C_6$ alkylene)-N($R^1$)-†, —N($R^1$)—($C_1$-$C_6$ alkylene)-†, —N($R^1$)—C(O)-($C_1$-$C_6$ alkylene)-†, and —C(O)—N($R^1$)—($C_1$-$C_6$ alkylene)-†, wherein "†" represents a portion of $L^1$ bound to ring A and each alkylene portion of $L^1$ is independently substituted with 0-5 occurrences of R';
$L^2$ is selected from —C(O)—, —C(O)—N($R^1$)-*, —N($R^1$)—C(O)-($C_1$-$C_6$ alkylene)-*, and —C(O)—N($R^1$)—($C_1$-$C_6$ alkylene)-*, wherein "*" represents a portion of $L^2$ bound to ring B and each alkylene portion of $L^2$ is independently substituted with 0-5 occurrences of R';
each $R^A$ is independently selected from hydroxyl, $C_1$-$C_6$ alkyl, $C_2$-$C_6$ alkenyl, $C_2$-$C_6$ alkynyl, $C_1$-$C_6$ alkoxyl, halo, $C_1$-$C_6$ heteroalkyl, $C_1$-$C_6$ haloalkyl, $C_1$-$C_6$ haloalkoxyl, $C_1$-$C_6$ hydroxyalkyl, cycloalkyl, aryl, heteroaryl, aryloxy, aralkyl, heterocyclyl, heterocyclylalkyl, nitro, cyano, —C(O)$R^1$, —OC(O)$R^1$, —C(O)O$R^1$, -($C_1$-$C_6$ alkylene)-C(O)$R^1$, —S$R^1$, —S(O)$_2R^1$, —S(O)$_2$-N($R^1$)($R^1$), -($C_1$-$C_6$ alkylene)-S(O)$_2R^1$, —($C_1$-$C_6$ alkylene)-S(O)$_2$-N($R^1$)($R^1$), —N($R^1$)($R^1$), —C(O)—N($R^1$)($R^1$), —N($R^1$)—C(O)$R^1$, —N($R^1$)—C(O)O$R^1$, —($C_1$-$C_6$ alkylene)-N($R^1$)—C(O)$R^1$, —N($R^1$)S(O)$_2R^1$, and —P(O)($R^1$)($R^1$), wherein each alkyl, alkenyl, alkynyl, alkoxyl, heteroalkyl, haloalkyl, haloalkoxyl, hydroxyalkyl, cycloalkyl, aryl, heteroaryl, aryloxy, aralkyl, heterocyclyl, and heterocyclylalkyl portion of each $R^A$ is independently substituted with 0-5 occurrences of $R^a$, or 2 $R^A$ together with the carbon atom(s) to which they are attached form a cycloalkyl or heterocyclyl ring independently substituted with 0-5 occurrences of $R^a$;
each $R^B$ is independently selected from oxo, hydroxyl, $C_1$-$C_6$ alkyl, $C_2$-$C_6$ alkenyl, $C_2$-$C_6$ alkynyl, $C_1$-$C_6$ alkoxyl, halo, $C_1$-$C_6$ heteroalkyl, $C_1$-$C_6$ haloalkyl, $C_1$-$C_6$ haloalkoxyl, $C_1$-$C_6$ hydroxyalkyl, cycloalkyl, aryl, heteroaryl, aryloxy, aralkyl, heterocyclyl, heterocyclylalkyl, nitro, cyano, —C(O)$R^1$, —OC(O)$R^1$, —C(O)O$R^1$, —($C_1$-$C_6$ alkylene)-C(O)$R^1$, —S$R^1$, —S(O)$_2R^1$, —S(O)$_2$-N($R^1$)($R^1$), —($C_1$-$C_6$ alkylene)-S(O)$_2R^1$, —($C_1$-$C_6$ alkylene)-S(O)$_2$-N($R^1$)($R^1$), —N($R^1$)($R^1$), —C(O)—N($R^1$)($R^1$), —N($R^1$)—C(O)$R^1$, —N($R^1$)—C(O)O$R^1$, —($C_1$-$C_6$ alkylene)-N($R^1$)—C(O)$R^1$, —N($R^1$)S(O)$_2R^1$, and —P(O)($R^1$)($R^1$), wherein each alkyl, alkenyl, alkynyl, alkoxyl, heteroalkyl, haloalkyl, haloalkoxyl, hydroxyalkyl, cycloalkyl, aryl, heteroaryl, aryloxy, aralkyl, heterocyclyl, and heterocyclylalkyl portion of each $R^B$ is independently substituted with 0-5 occurrences of $R^a$, or 2 $R^B$ together with the carbon atom(s) to which they are attached form a cycloalkyl or heterocyclyl ring independently substituted with 0-5 occurrences of $R^a$;

- each $R^1$ is independently selected from hydrogen, hydroxyl, halo, thiol, $C_1$-$C_6$ alkyl, $C_1$-$C_6$ thioalkyl, $C_1$-$C_6$ alkoxyl, $C_1$-$C_6$ haloalkyl, $C_1$-$C_6$ hydroxyalkyl, $C_1$-$C_6$ heteroalkyl, cycloalkyl, cycloalkylalkyl, heteroarylalkyl, heterocyclyl, and heterocyclylalkyl, wherein each alkyl, thioalkyl, alkoxyl, haloalkyl, hydroxyalkyl, heteroalkyl, cycloalkyl, cycloalkylalkyl, heteroarylalkyl, heterocyclyl, and heterocyclylalkyl portion of $R^1$ is independently substituted with 0-5 occurrences of $R^b$, or 2 $R^1$ together with the atom(s) to which they are attached form a cycloalkyl or heterocyclyl ring independently substituted with 0-5 occurrences of $R^b$;

- each $R^a$ and $R^b$ is independently selected from $C_1$-$C_6$ alkyl, halo, hydroxyl, $C_1$-$C_6$ haloalkyl, $C_1$-$C_6$ heteroalkyl, $C_1$-$C_6$ hydroxyalkyl, $C_1$-$C_6$ alkoxyl, cycloalkyl, heterocyclyl, and cyano, wherein each alkyl, haloalkyl, heterocyclyl, hydroxyalkyl, alkoxyl, cycloalkyl, and heterocyclyl portion of $R^a$ and $R^b$ is independently substituted with 0-5 occurrences of R';

- each R' is independently selected from $C_1$-$C_6$ alkyl, $C_1$-$C_6$ heteroalkyl, halo, hydroxyl, $C_1$-$C_6$ haloalkyl, $C_1$-$C_6$ hydroxyalkyl, cycloalkyl and cyano; or 2 R' together with the atom(s) to which they are attached form a cycloalkyl or heterocyclyl ring; and

- p is 0, 1, 2, 3, 4, or 5; and
- q is 0, 1, 2, 3, or 4.

2. The method of claim 1, wherein the compound is a compound of Formula (Ia):

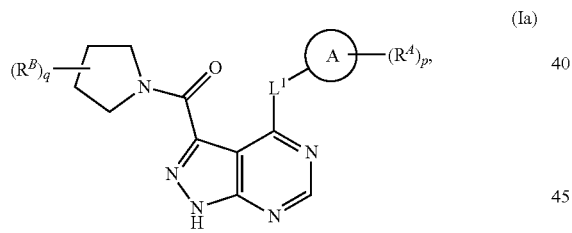

or a pharmaceutically acceptable salt thereof.

3. A method for treating a patient suffering from a tumor by inhibiting neurotrophic tyrosine receptor kinase (NTRK) activity, the method comprising administering to the patient a compound selected from:

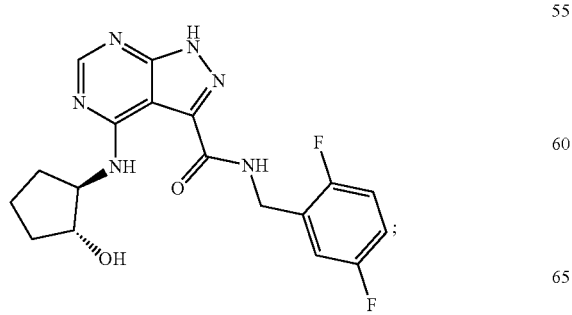

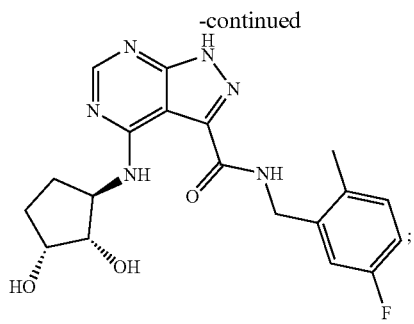

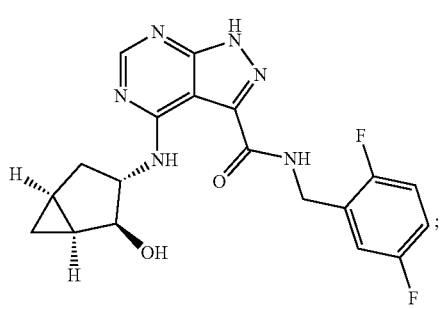

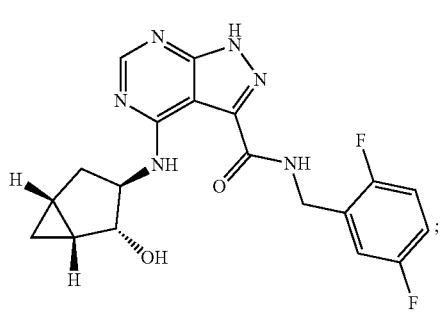

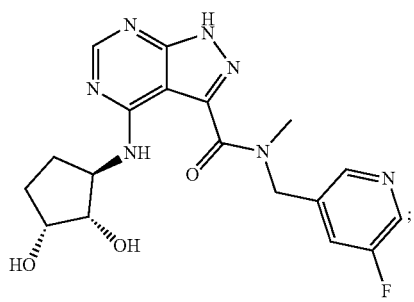

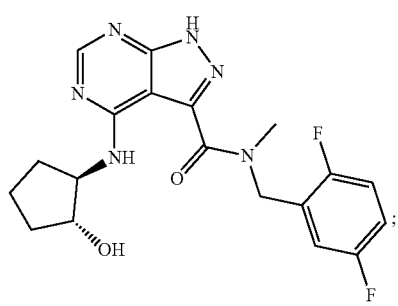

201
-continued
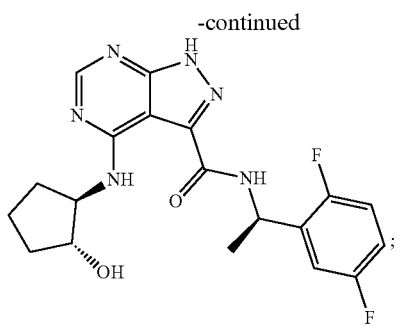
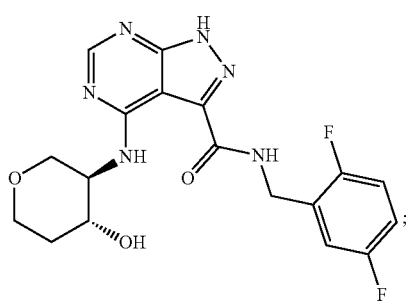
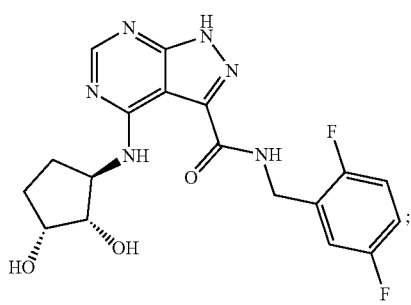
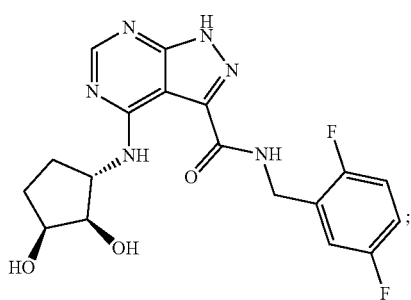
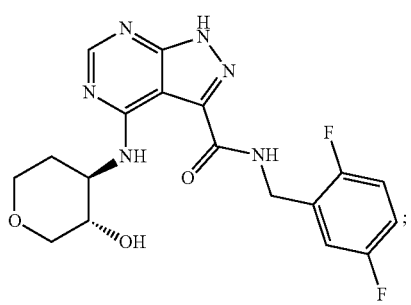
202
-continued
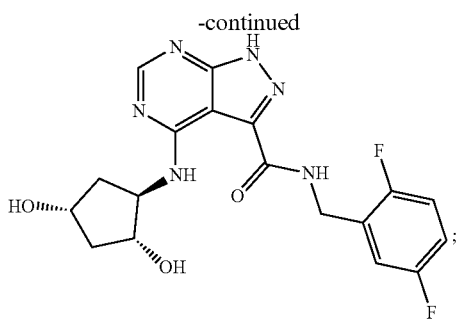
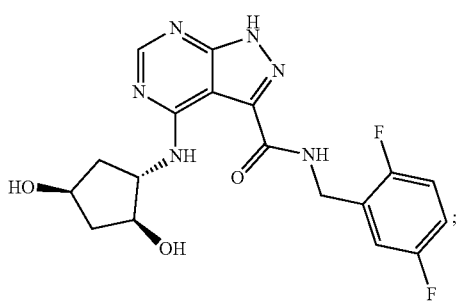
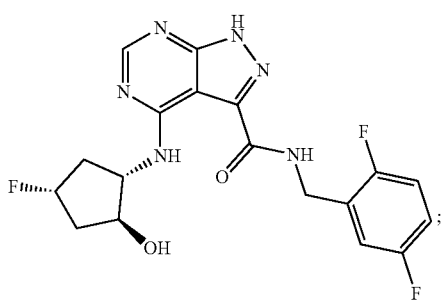
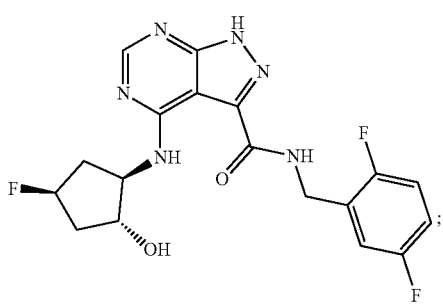
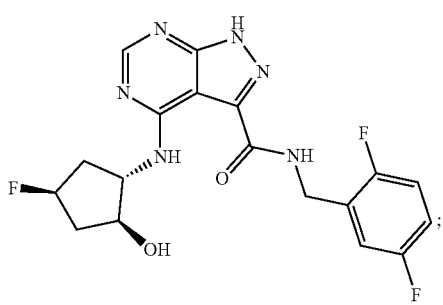

| 203 | 204 |
|---|---|
| -continued | -continued |
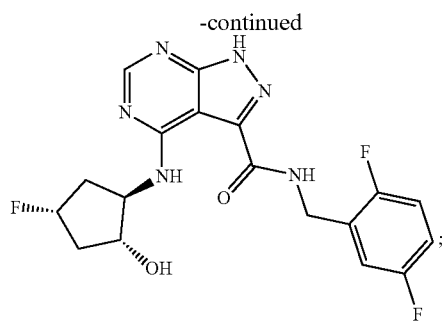
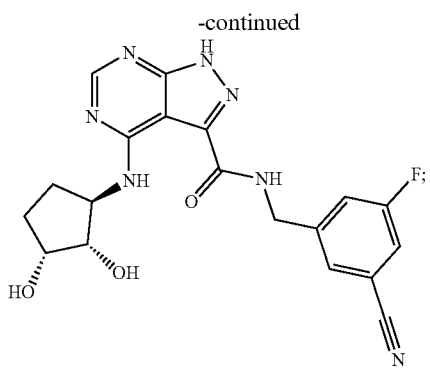
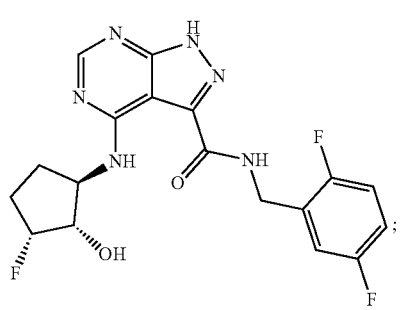
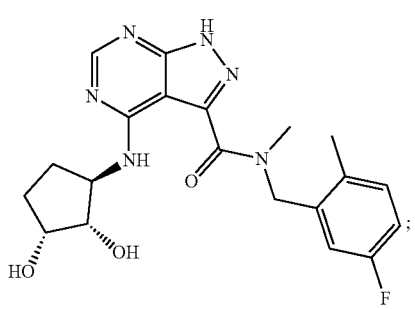
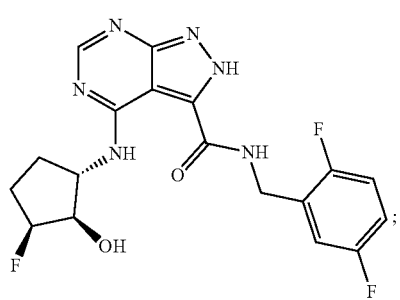
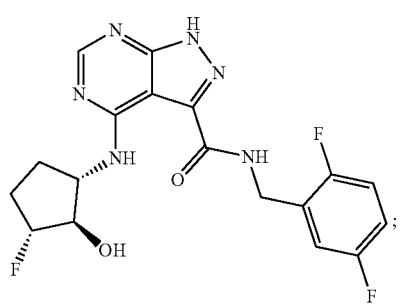
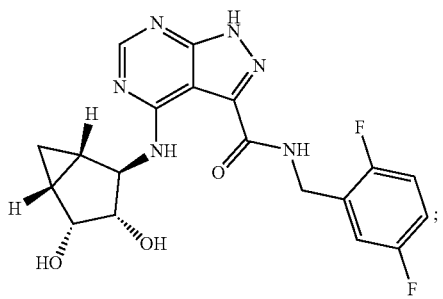
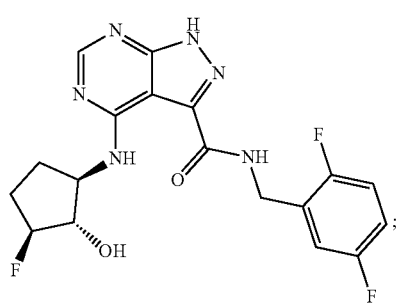
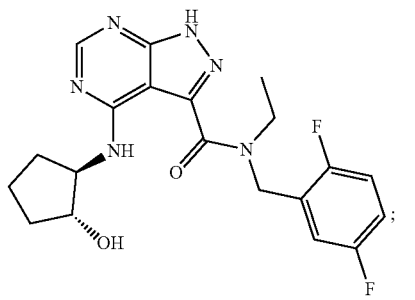

205
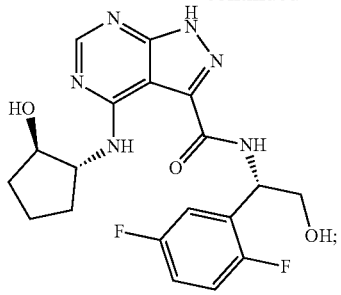
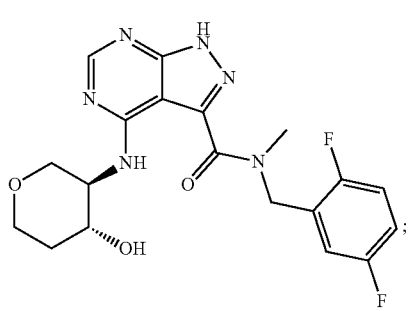
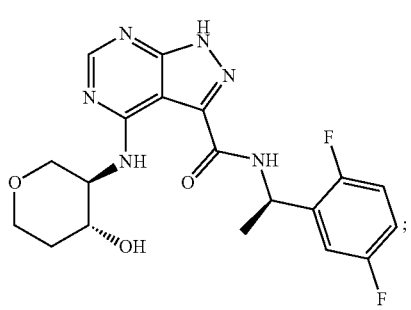
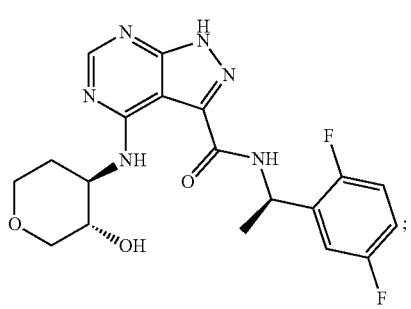
206
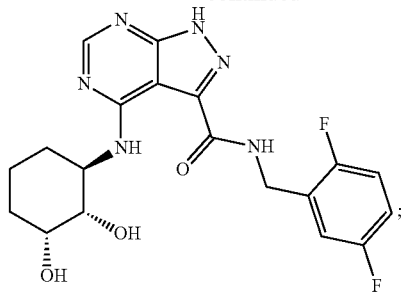
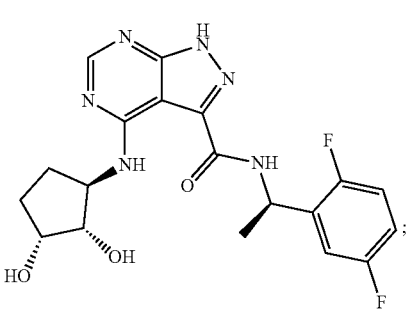
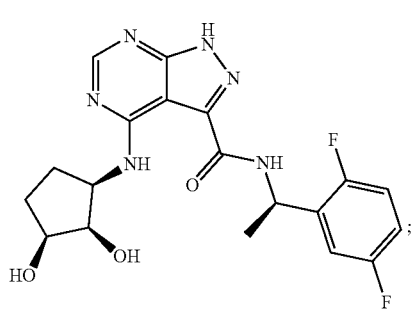
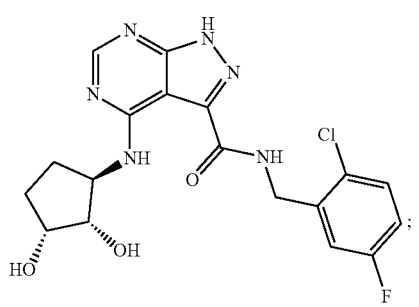

207
-continued
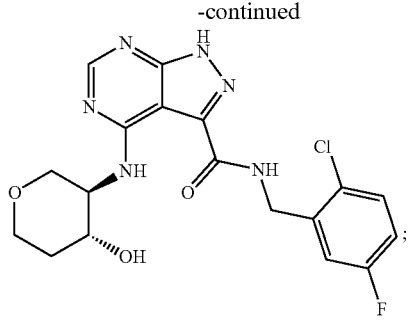
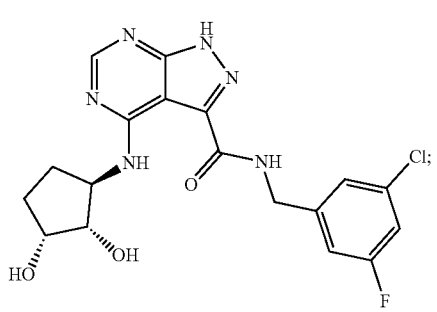
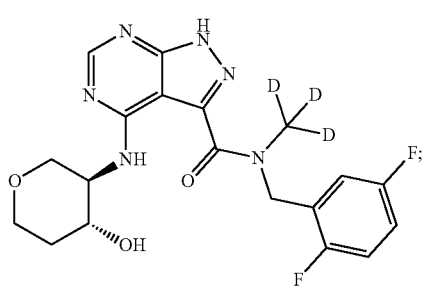
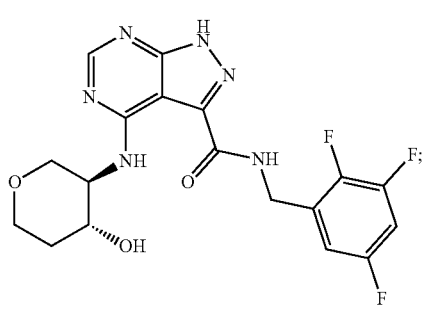
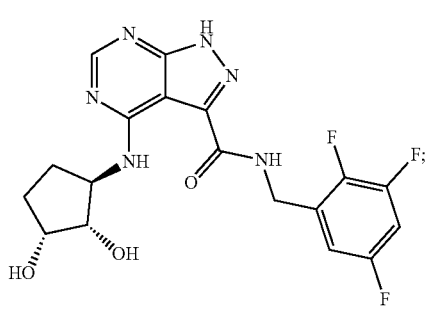
208
-continued
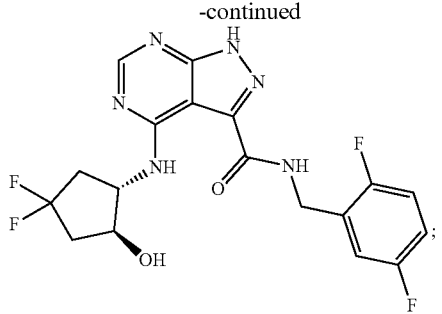
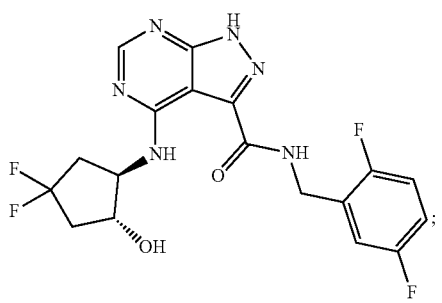
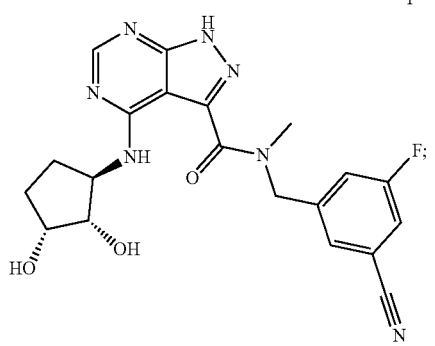
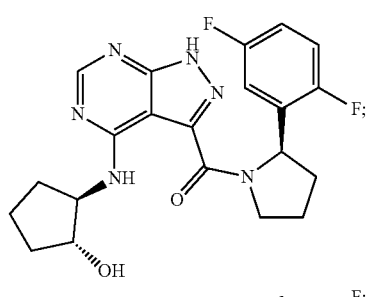
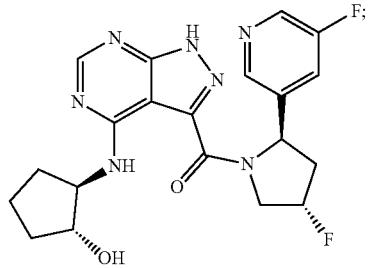
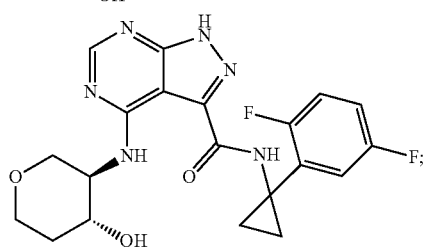

209
-continued
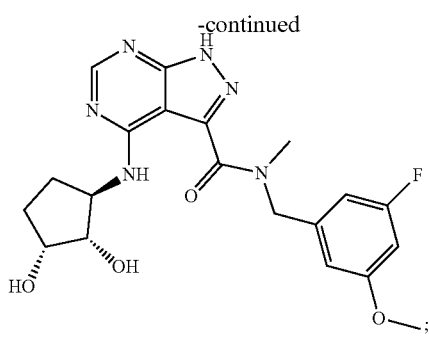
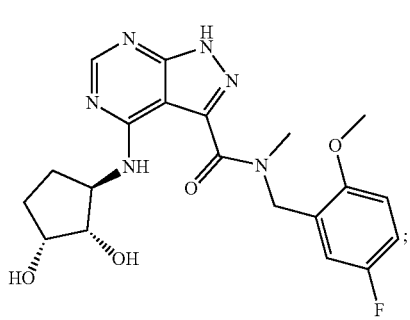
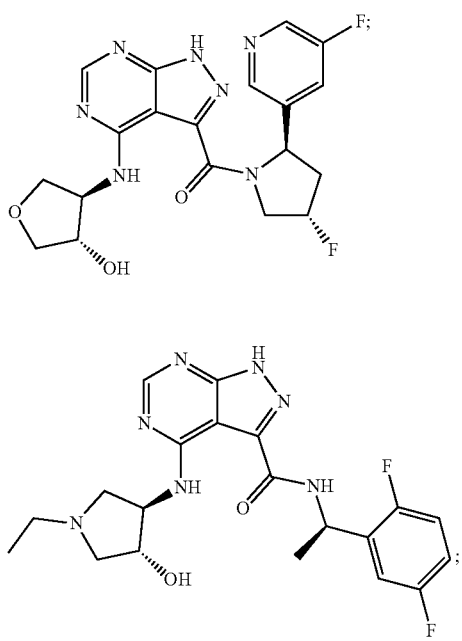
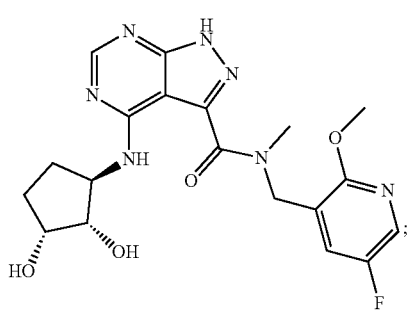
210
-continued
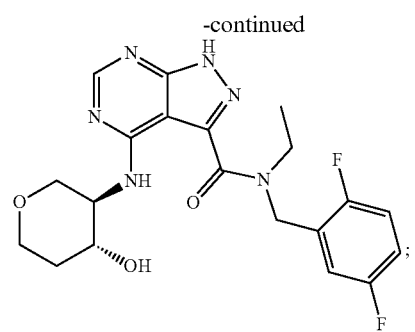
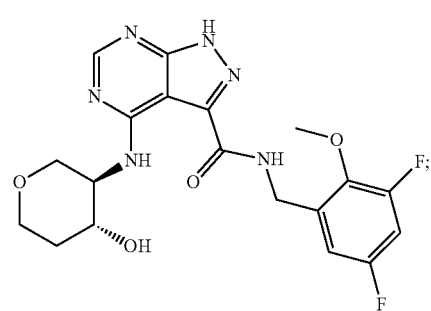
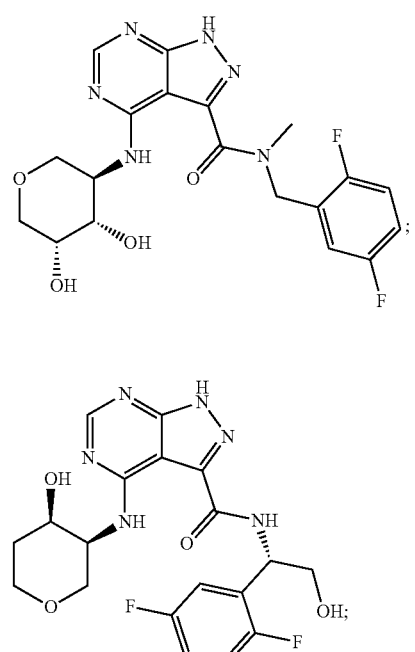
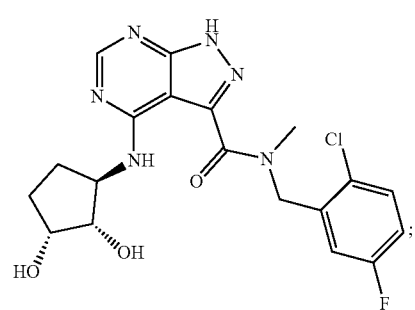

211
-continued
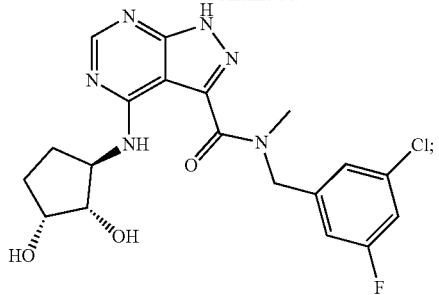
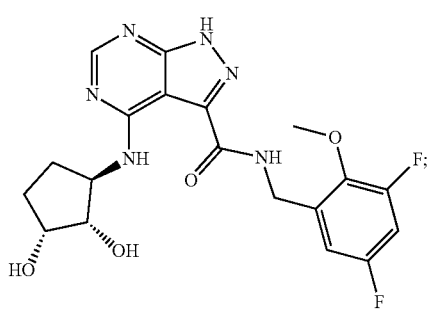
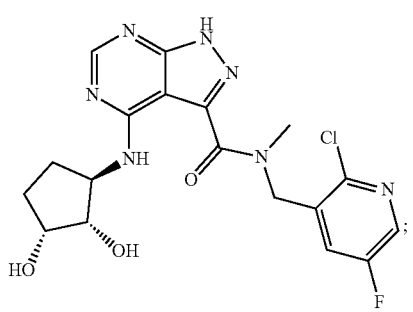
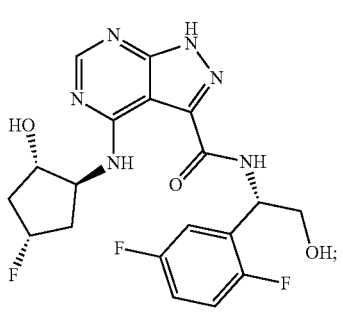
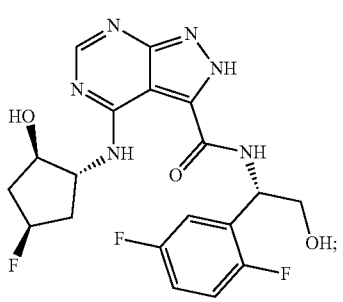
212
-continued
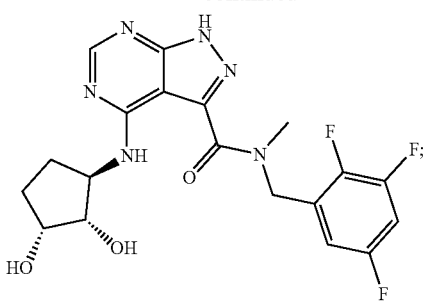
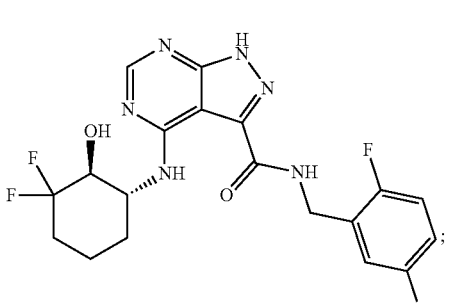
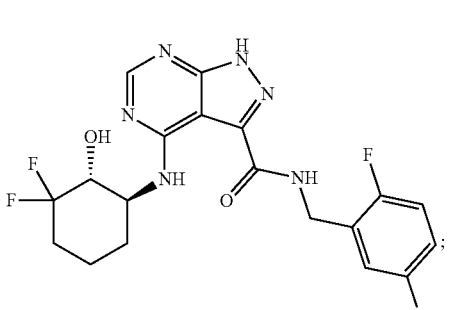
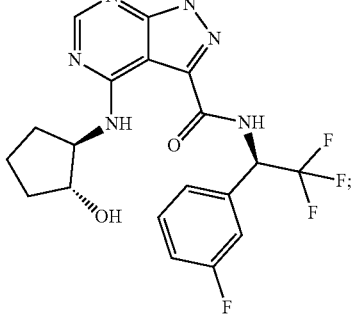
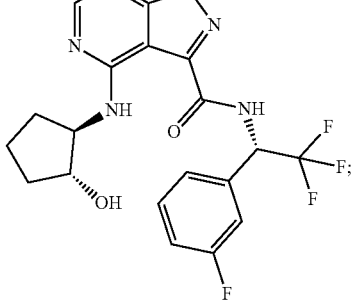

213
-continued
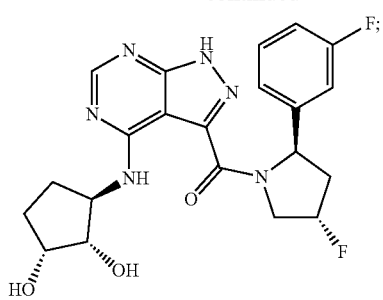
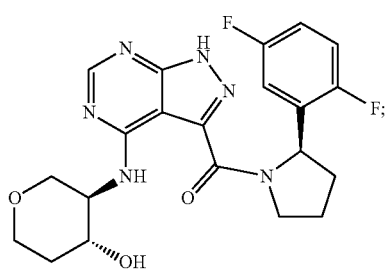
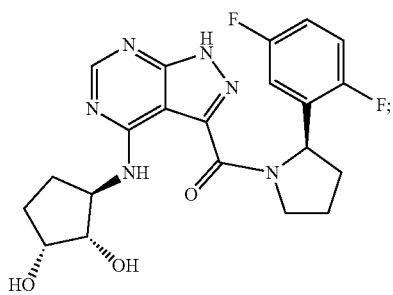
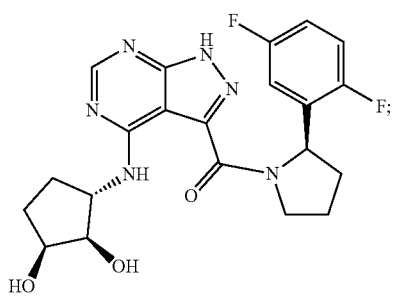
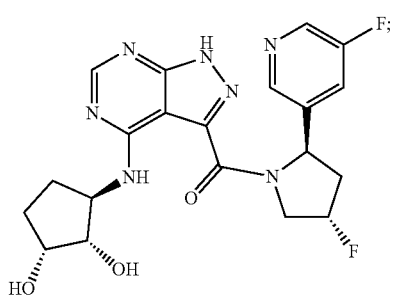
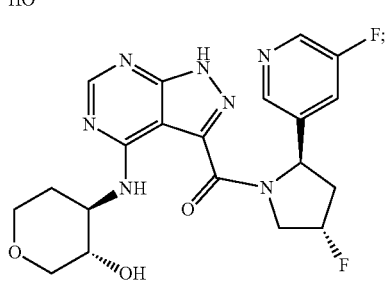
214
-continued
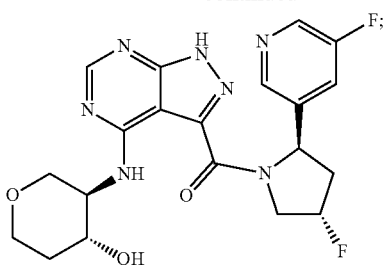
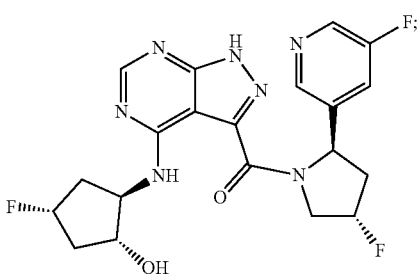
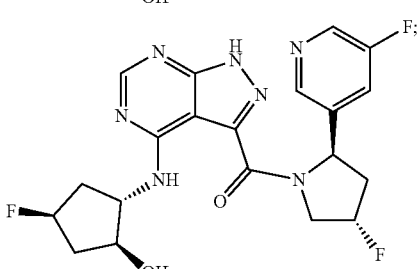
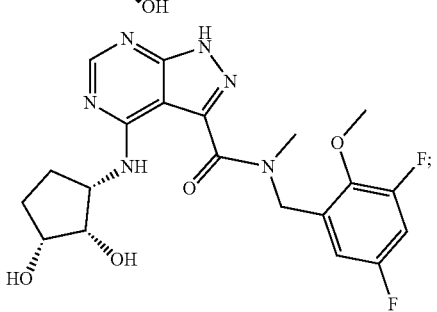
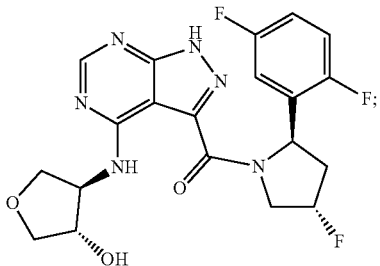
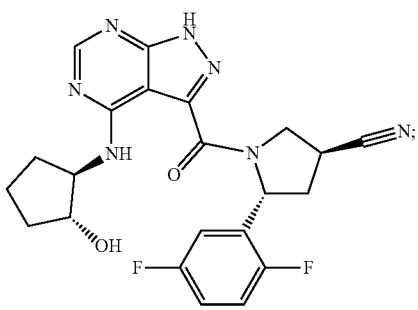

215
-continued
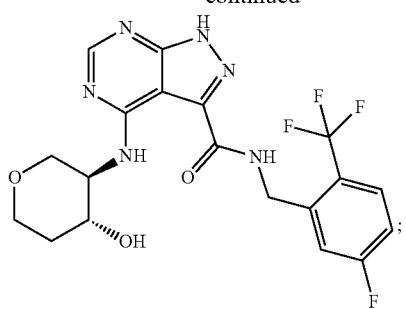
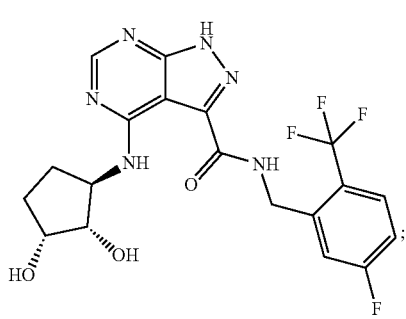
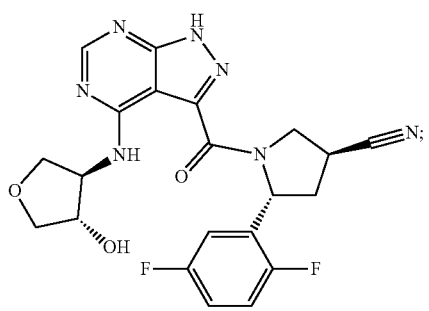
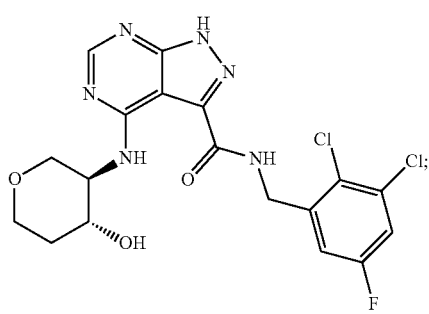
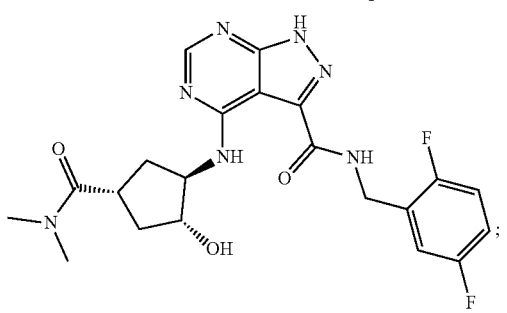
216
-continued
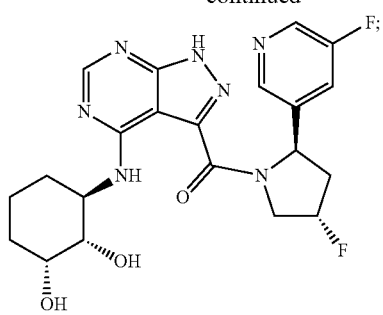
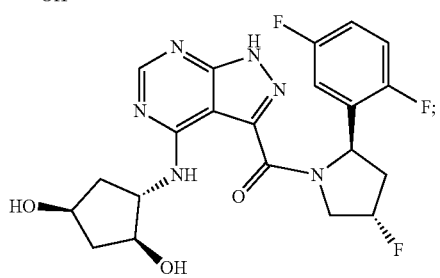
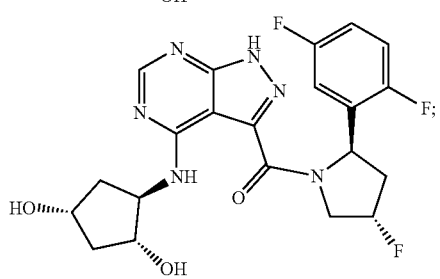
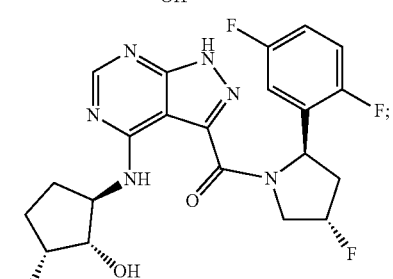
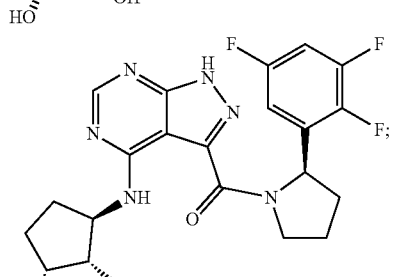
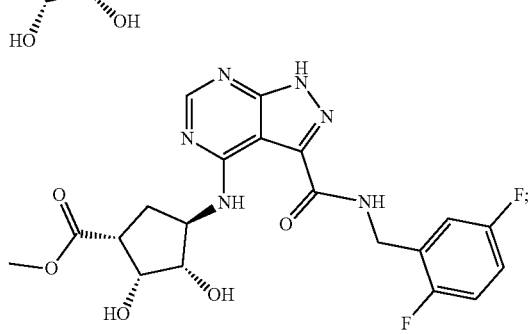

217
-continued
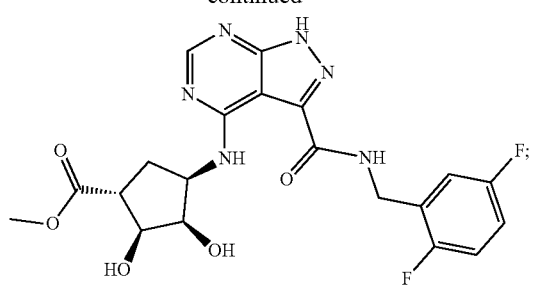
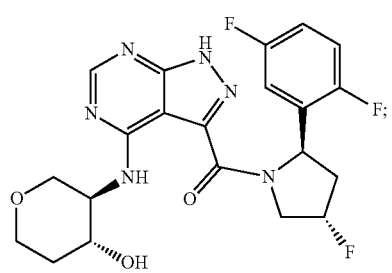
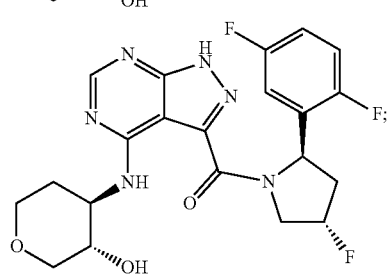
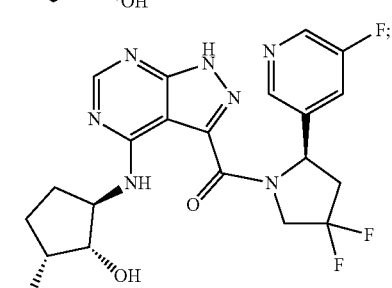
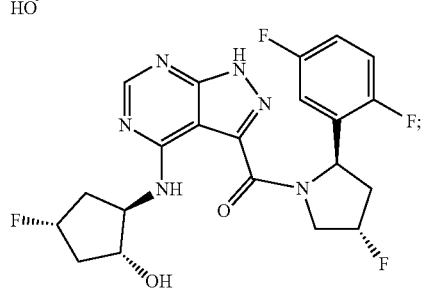
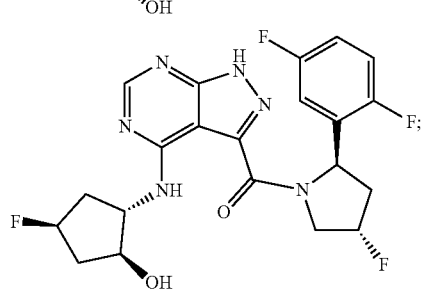
218
-continued
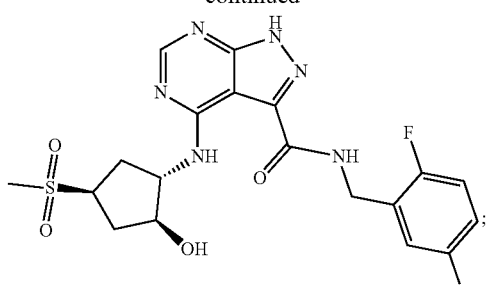
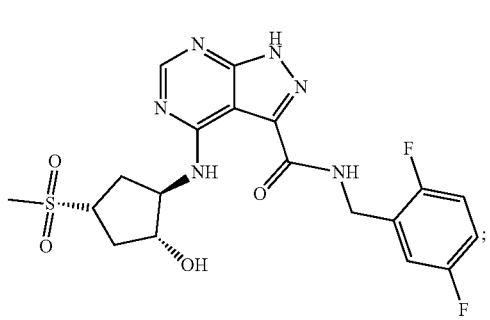
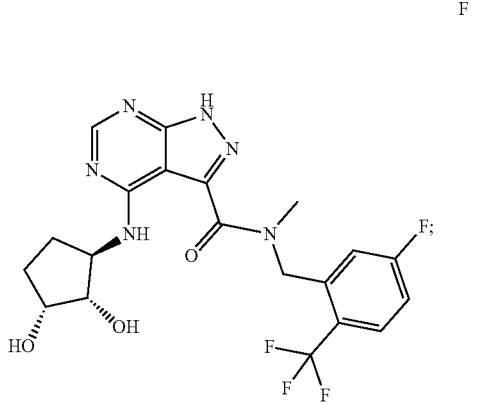
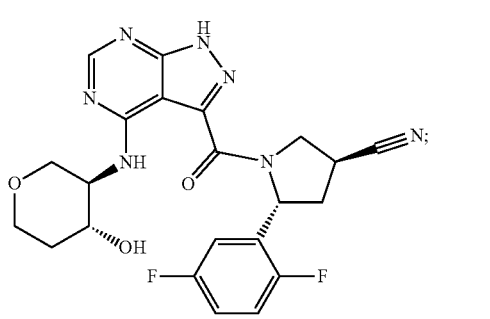
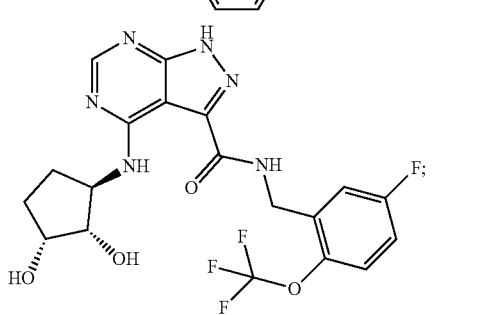

-continued
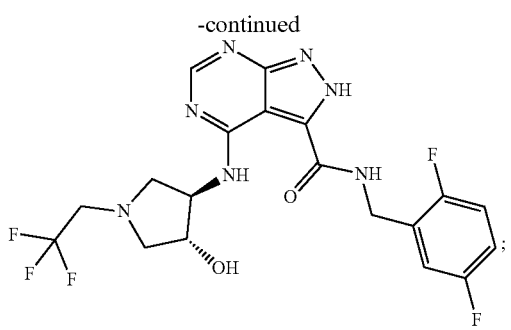
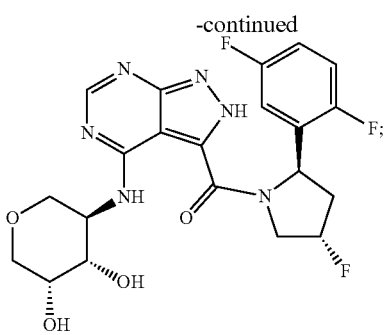

221
-continued
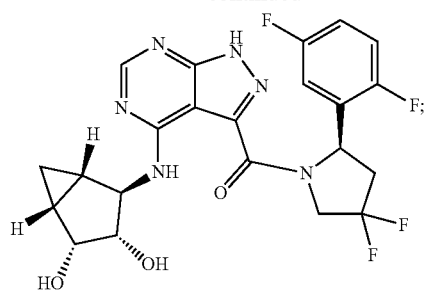
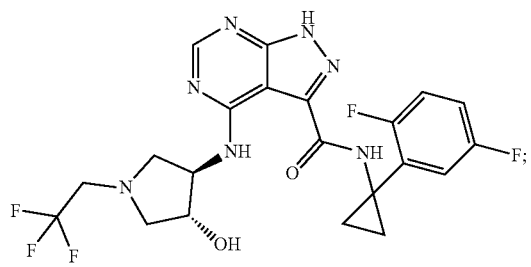
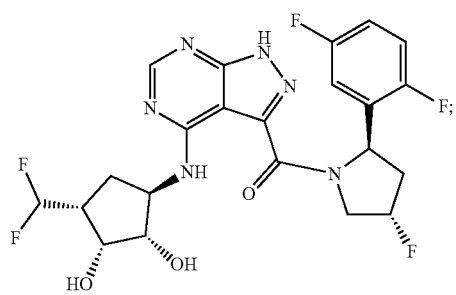
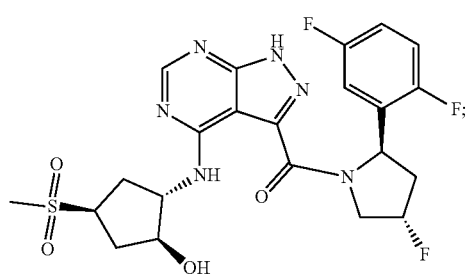
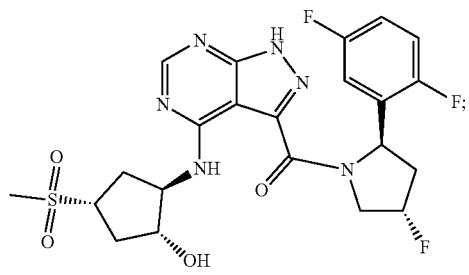
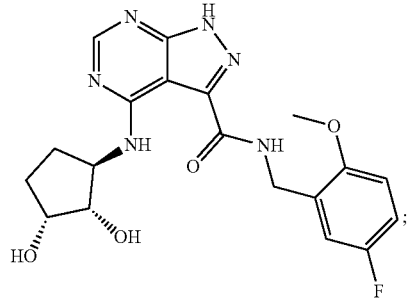
222
-continued
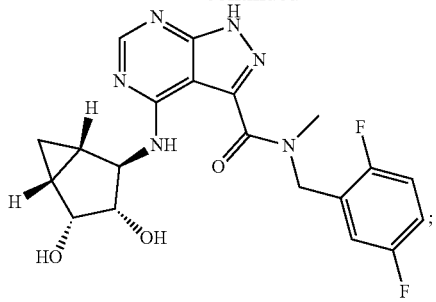
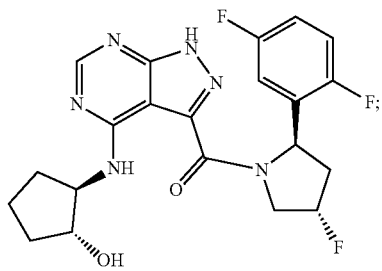
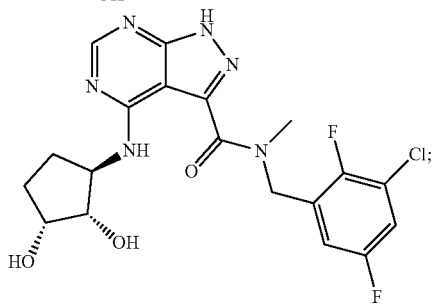
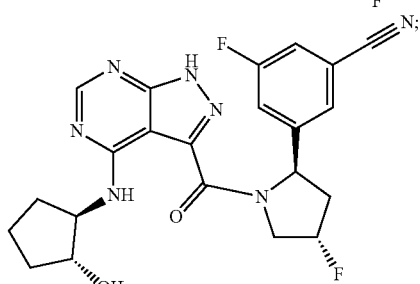
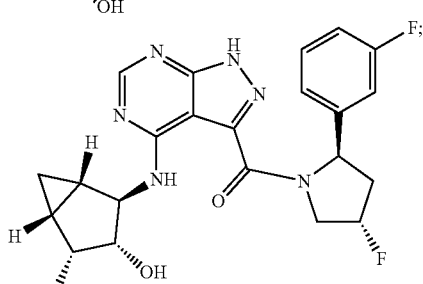
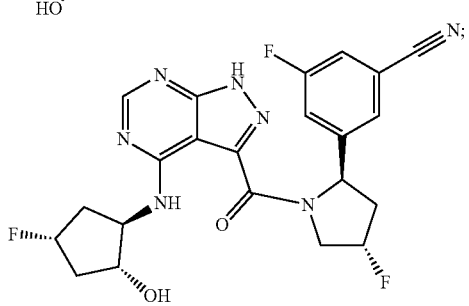

223
-continued
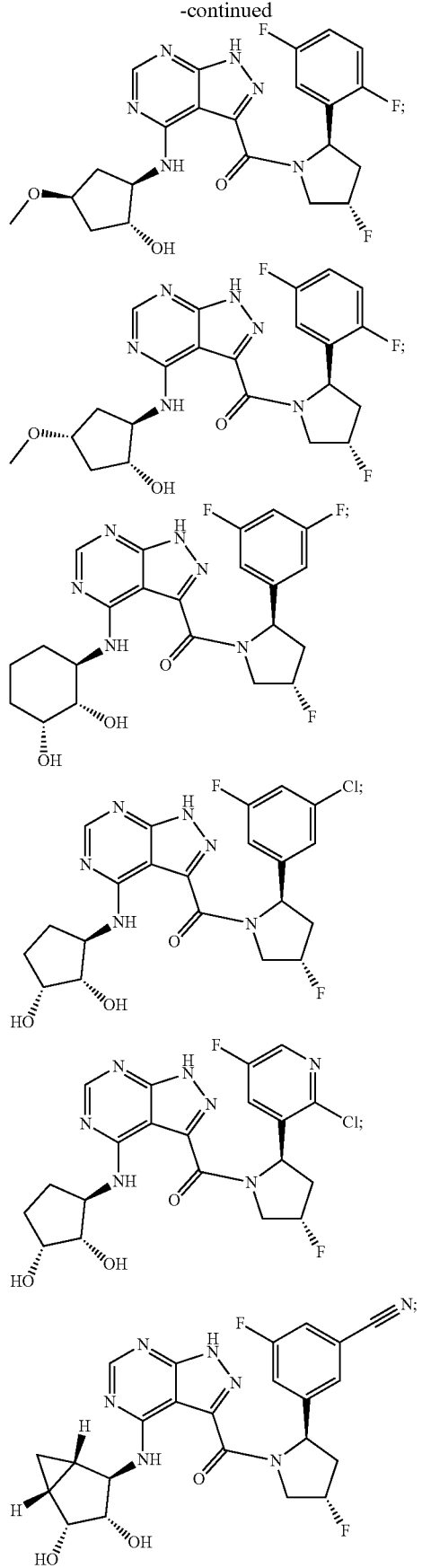
224
-continued
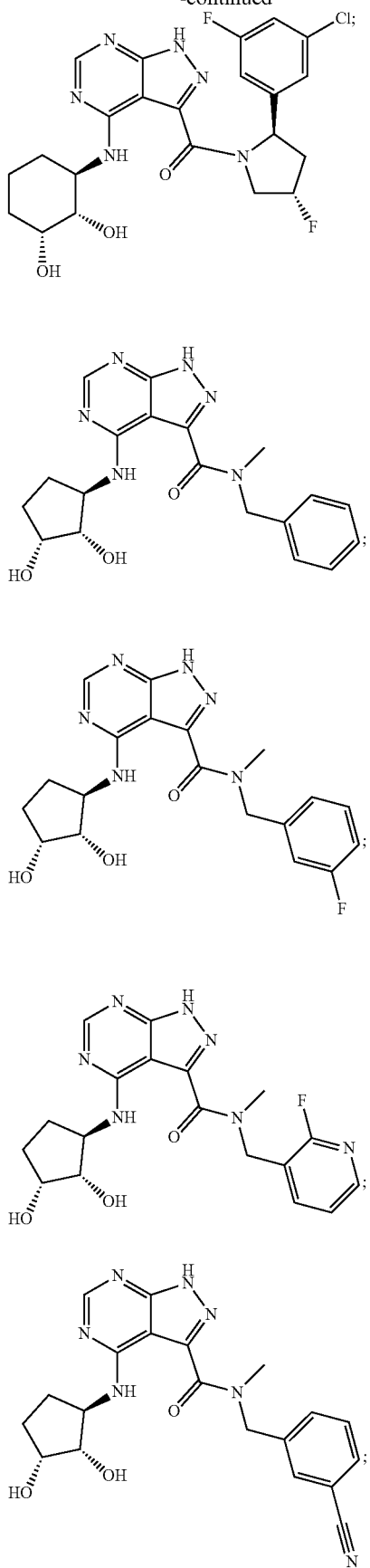

225
-continued
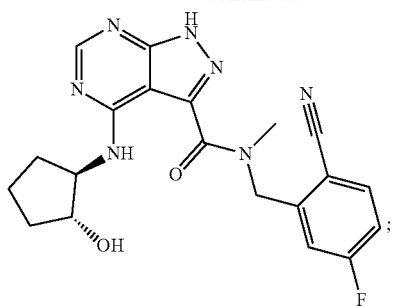
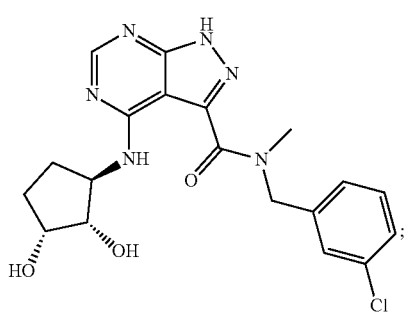
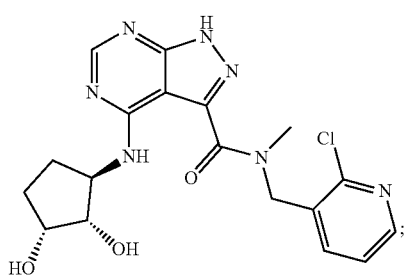
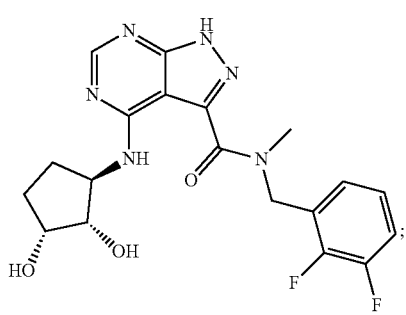
226
-continued
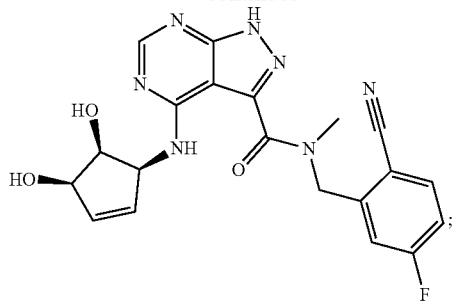
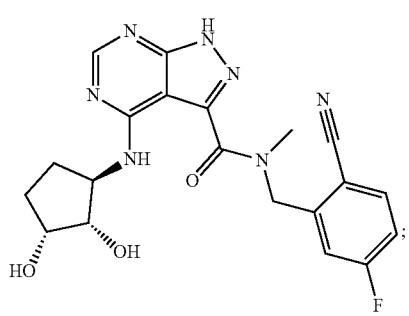
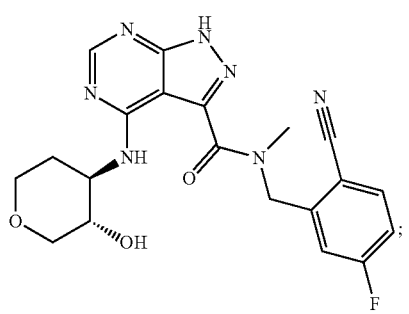
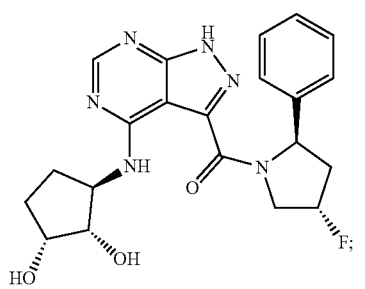

227
-continued
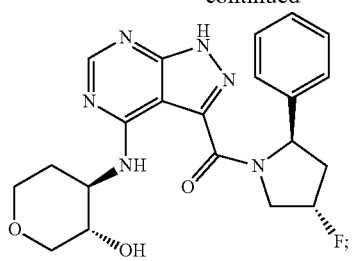
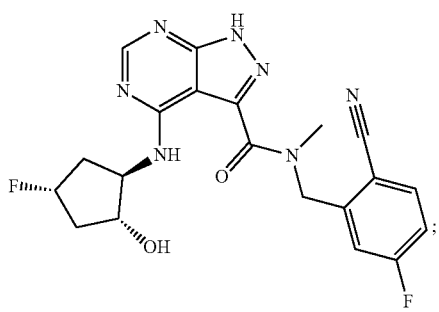
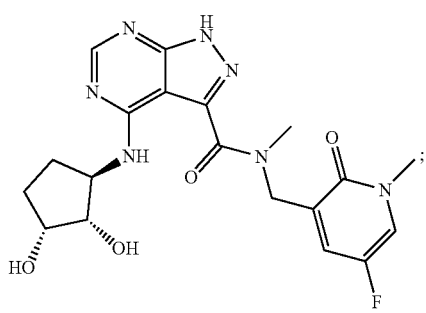
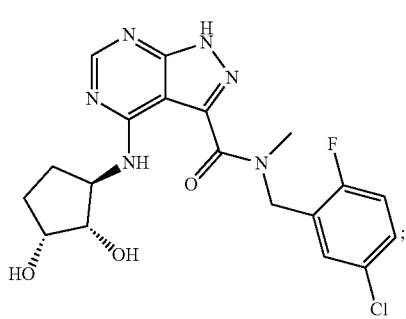
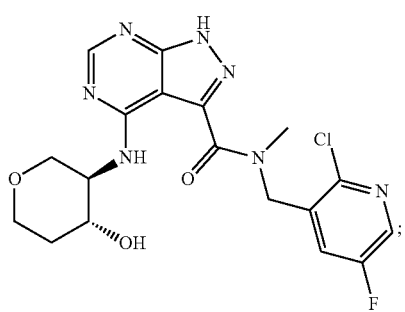
228
-continued
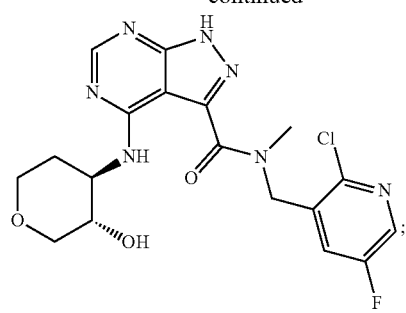
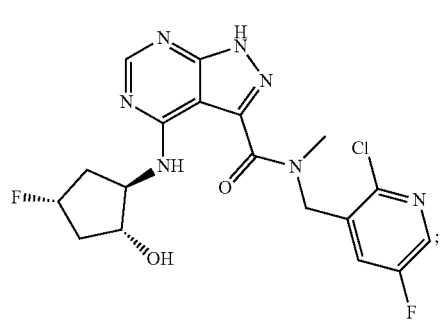
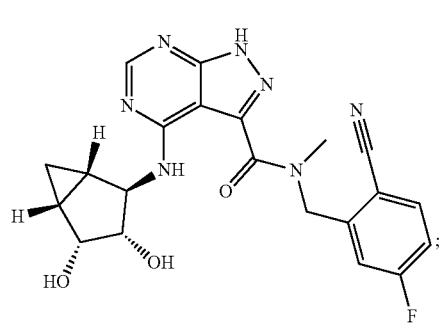
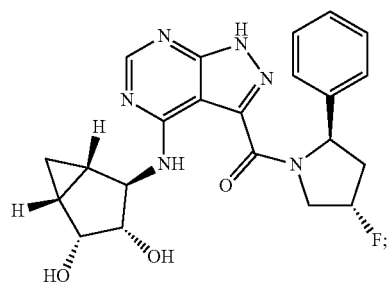
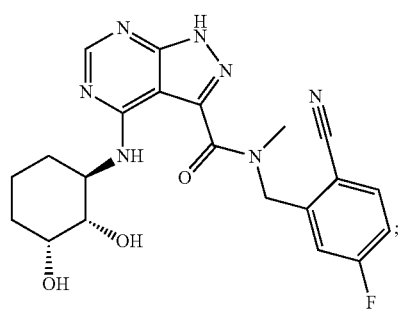

229
-continued
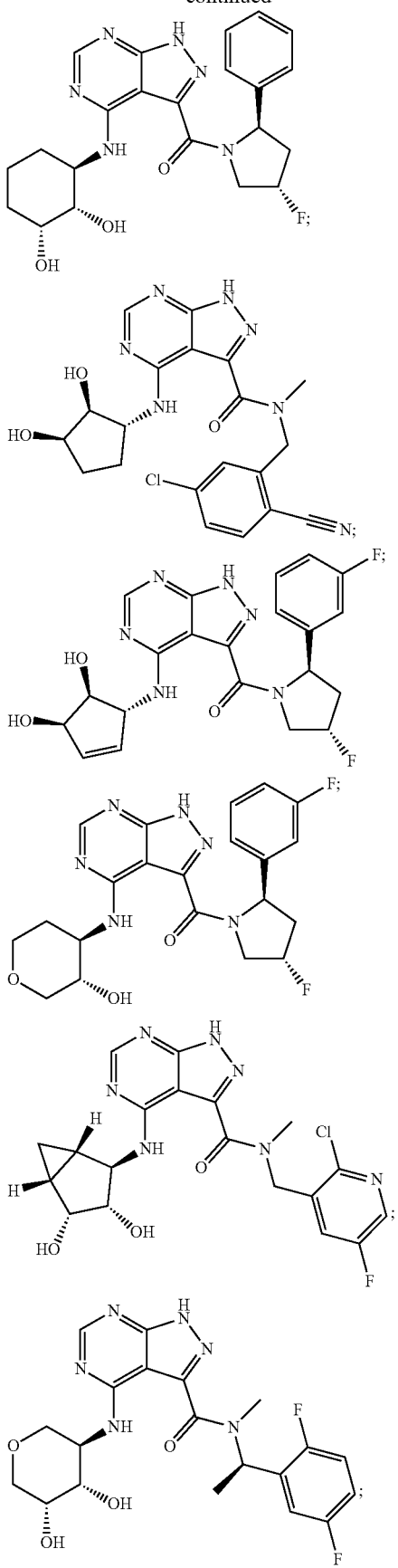
230
-continued
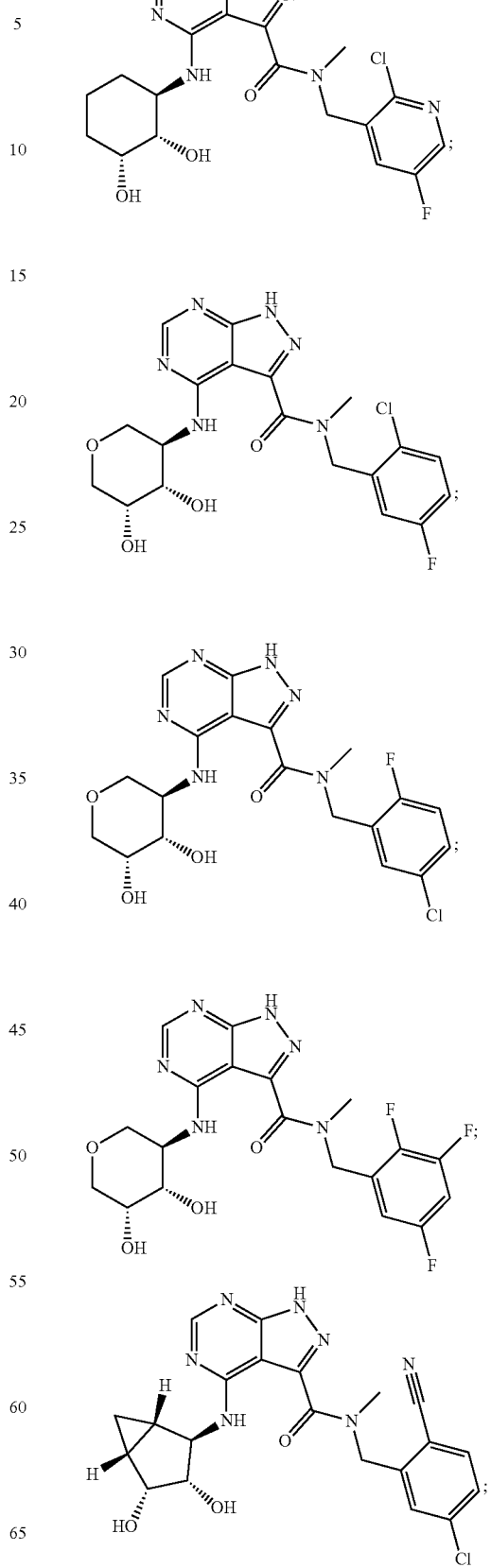

231
-continued
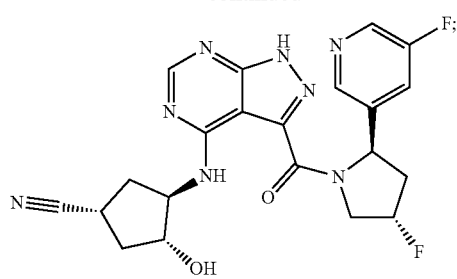
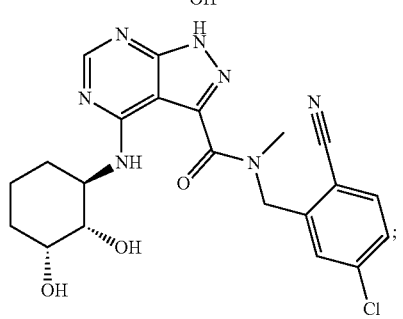
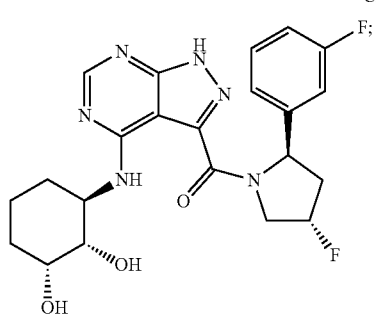
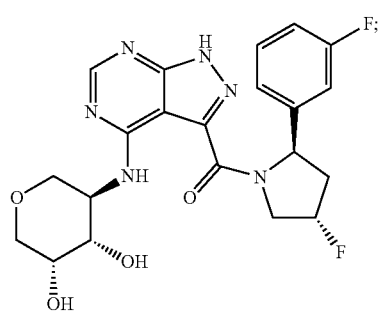
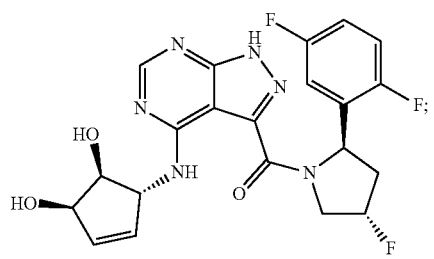
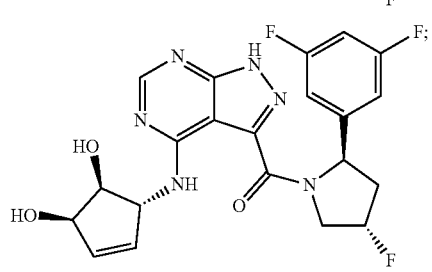
232
-continued
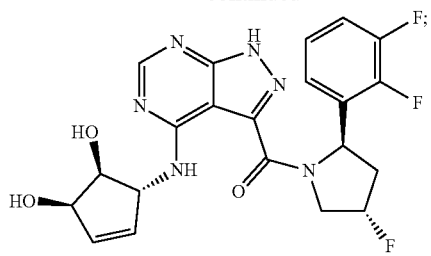
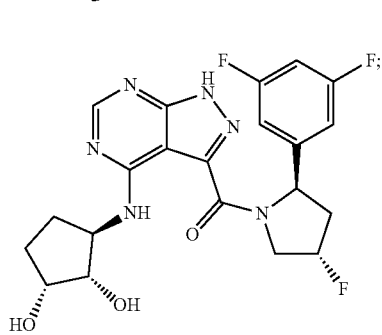
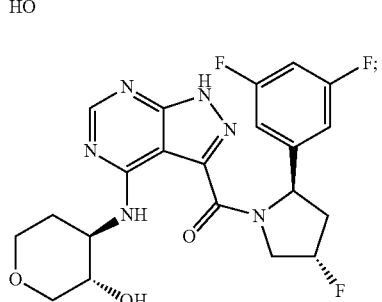
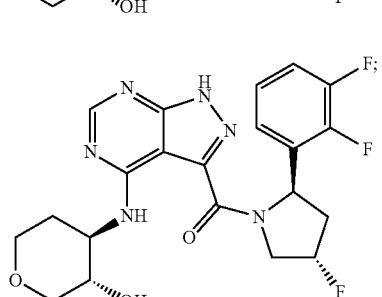
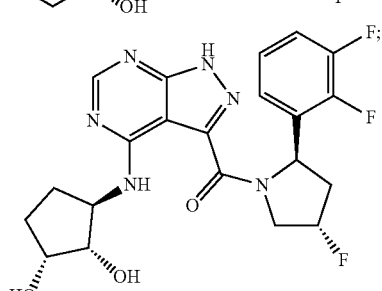
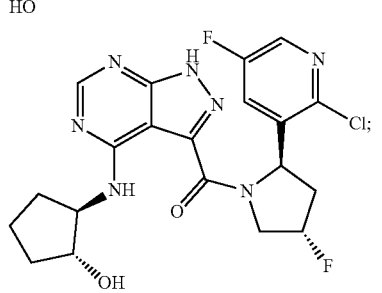

233
-continued
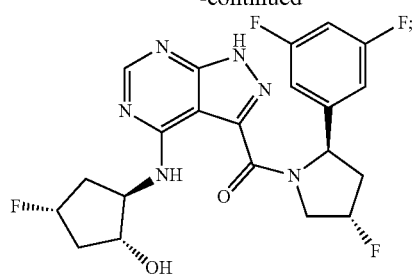
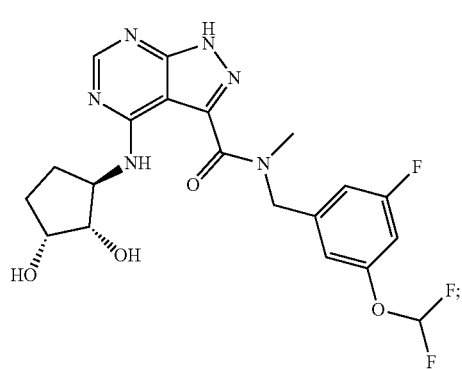
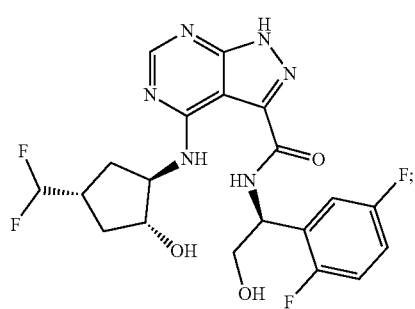
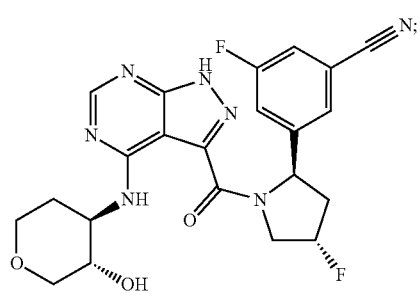
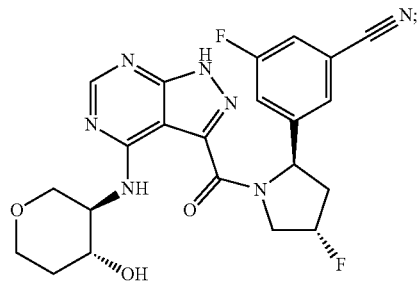
234
-continued
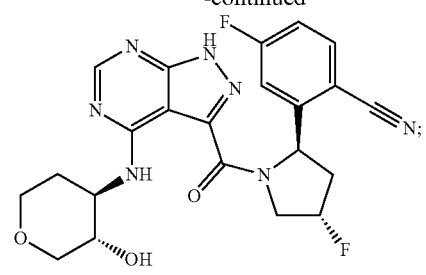
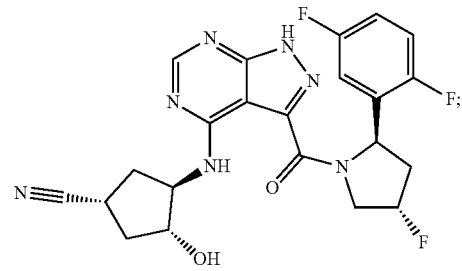
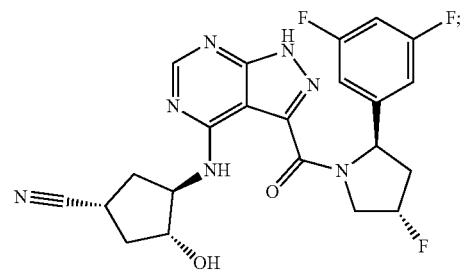
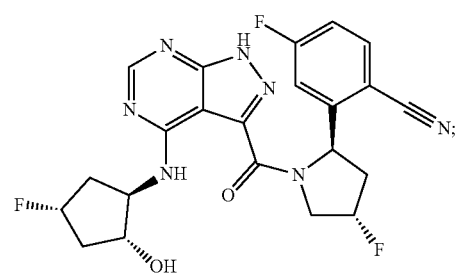
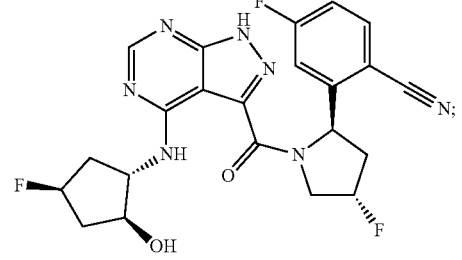
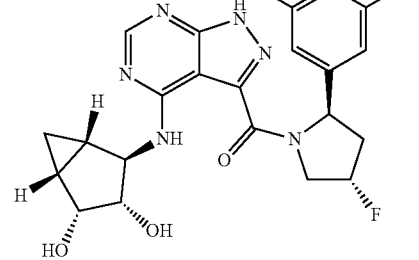

235
-continued
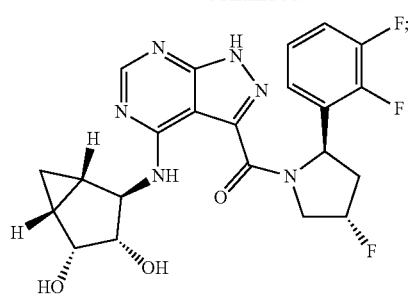
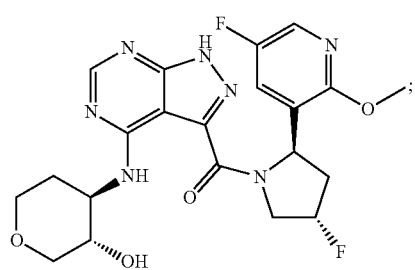
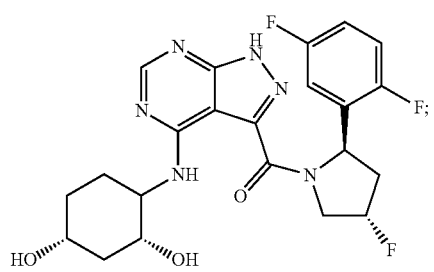
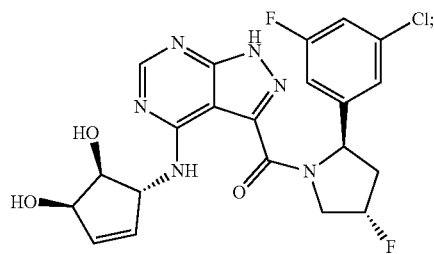
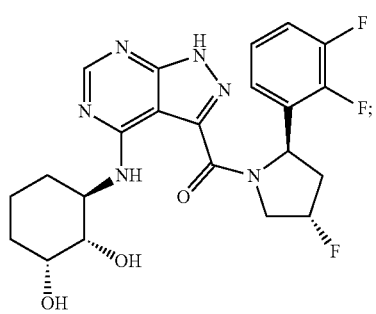
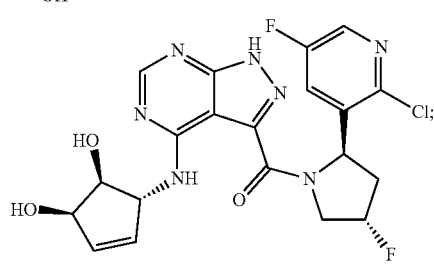
236
-continued
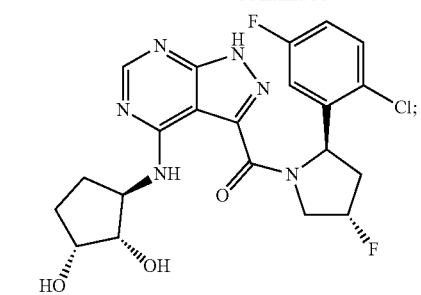
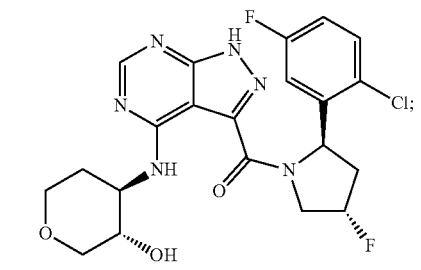
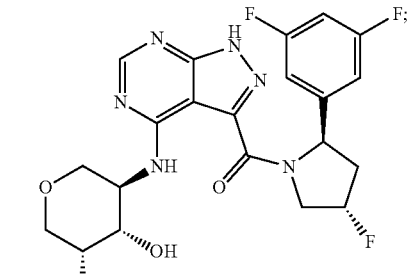
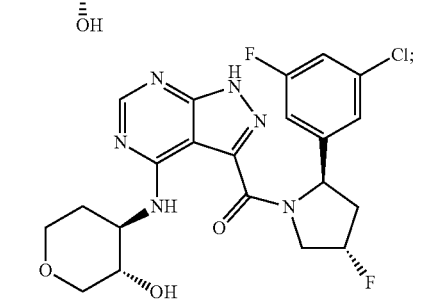
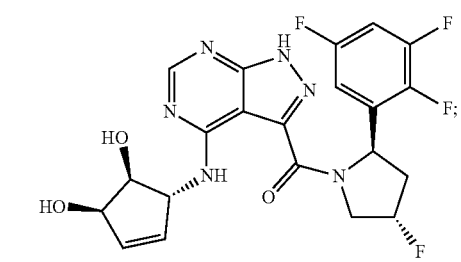
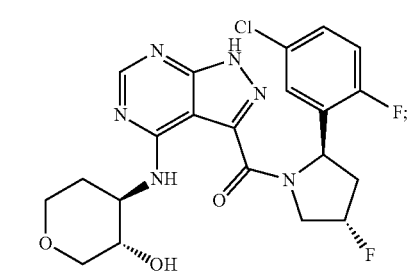

237
-continued
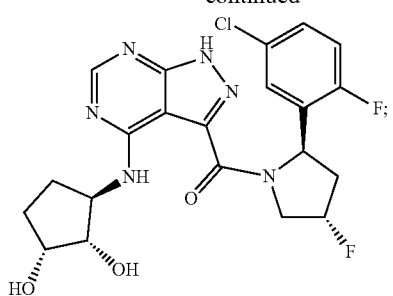
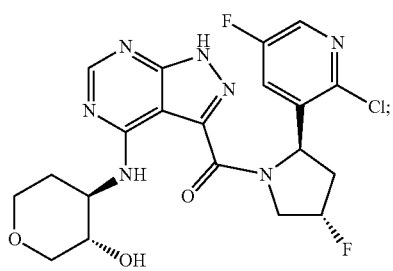
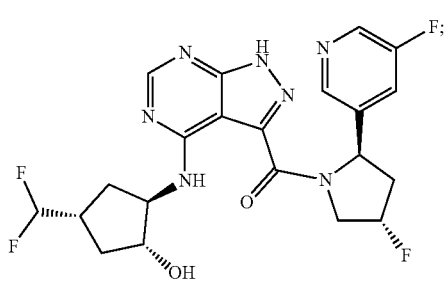
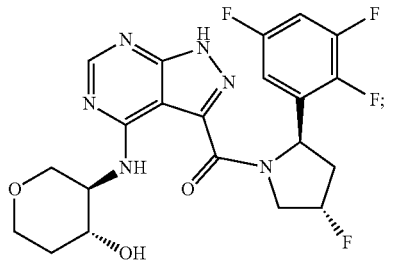
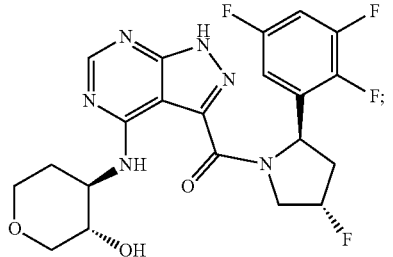
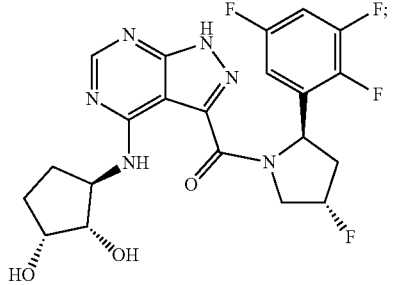
238
-continued
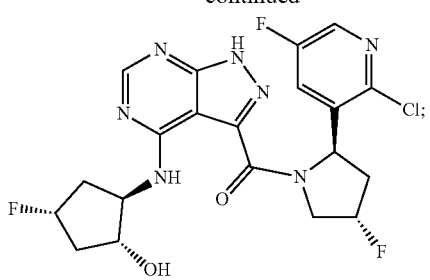
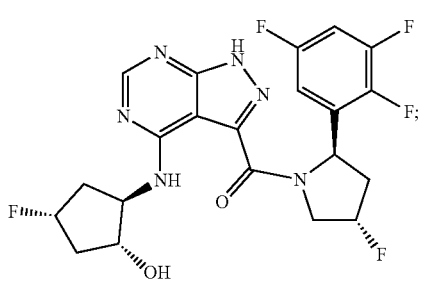
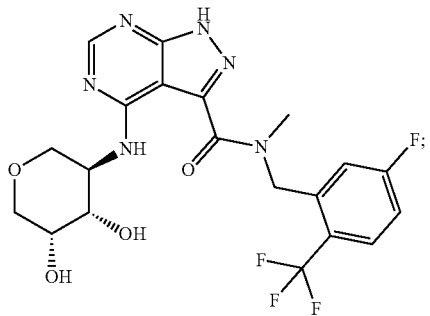
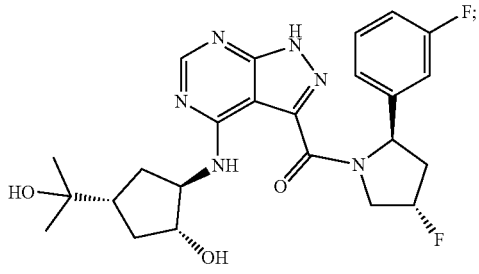
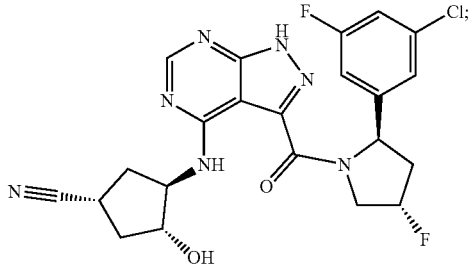
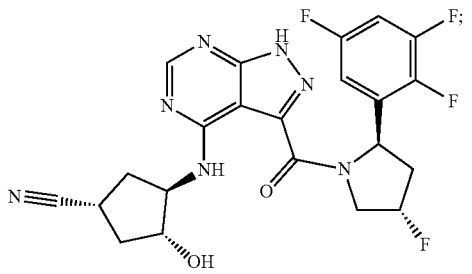

239
-continued
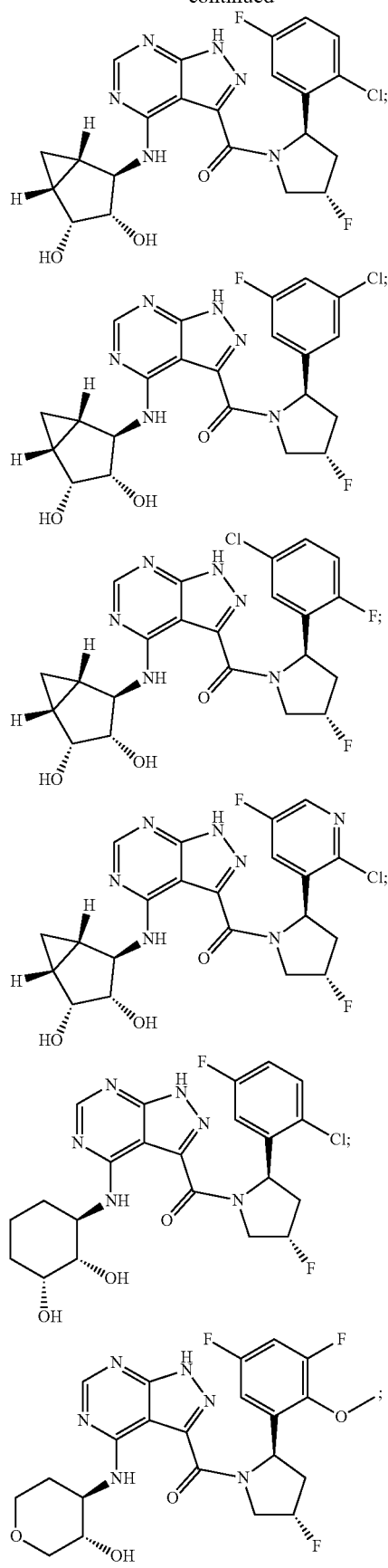
240
-continued
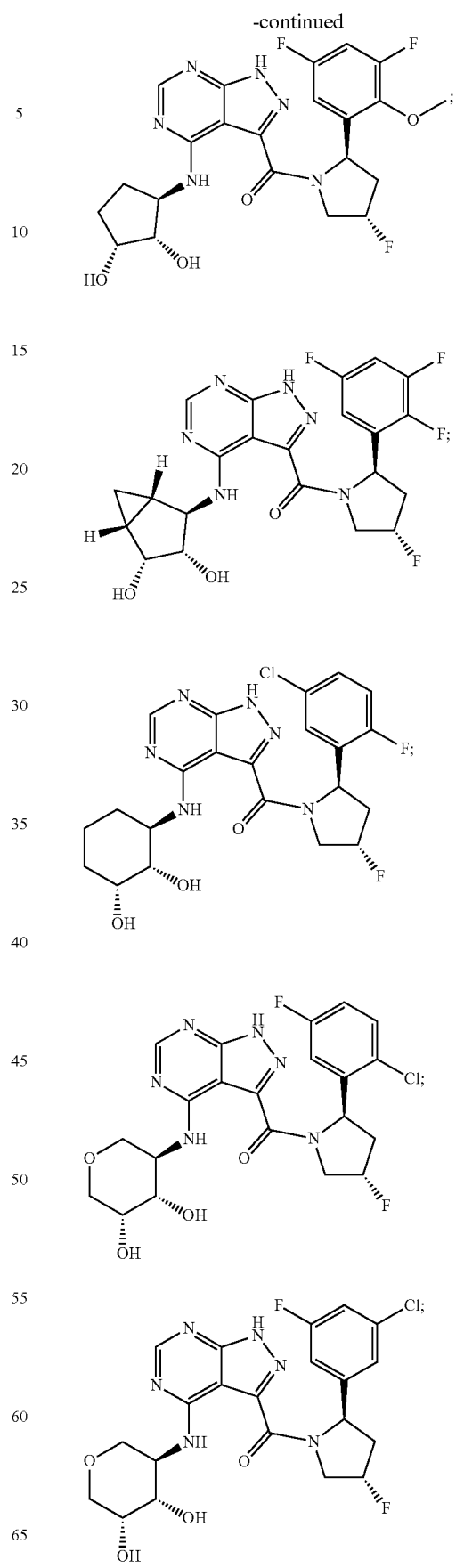

241
-continued
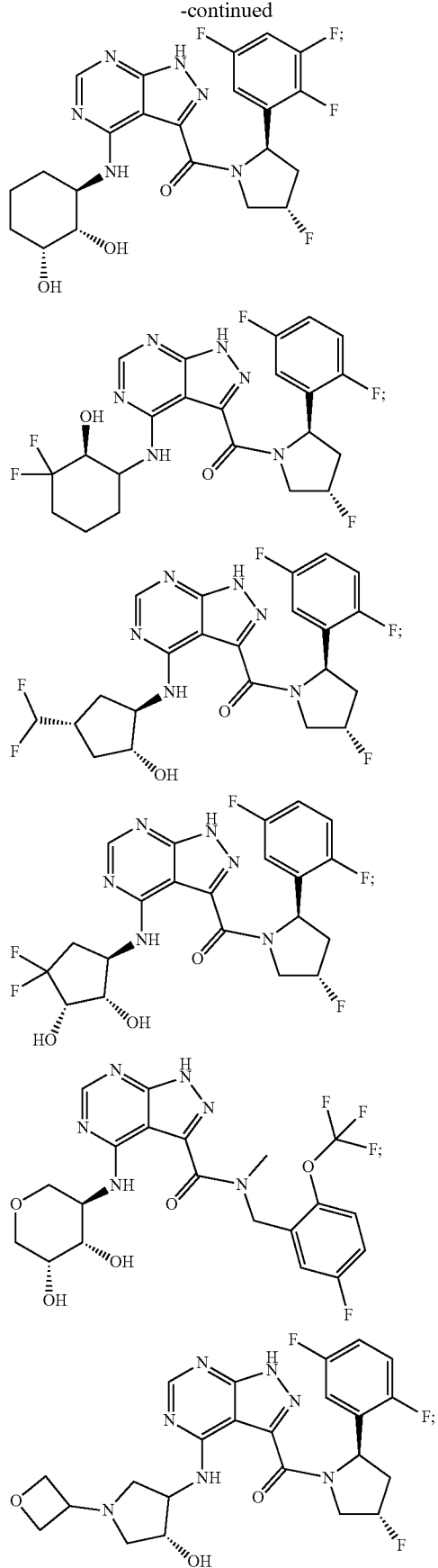
242
-continued
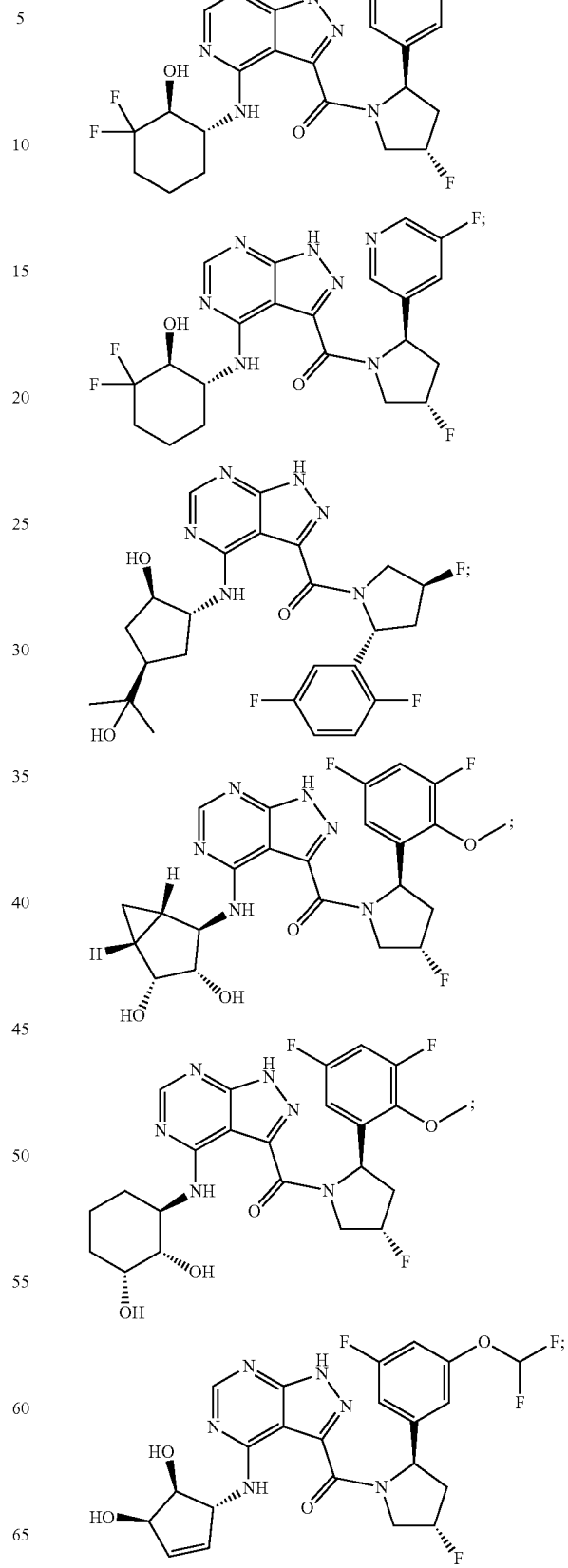

-continued
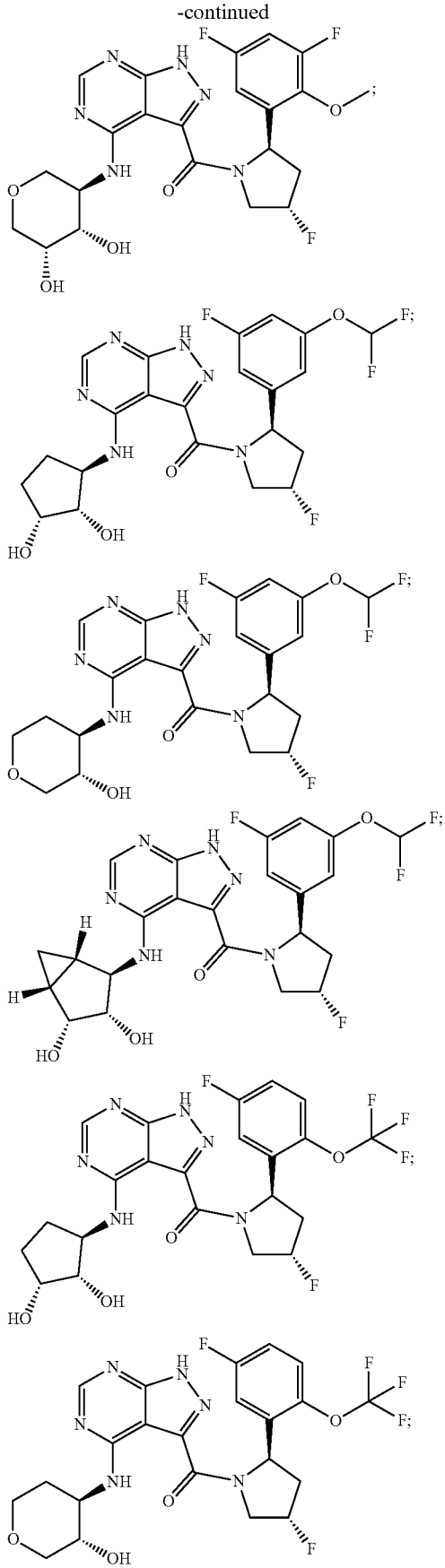
-continued
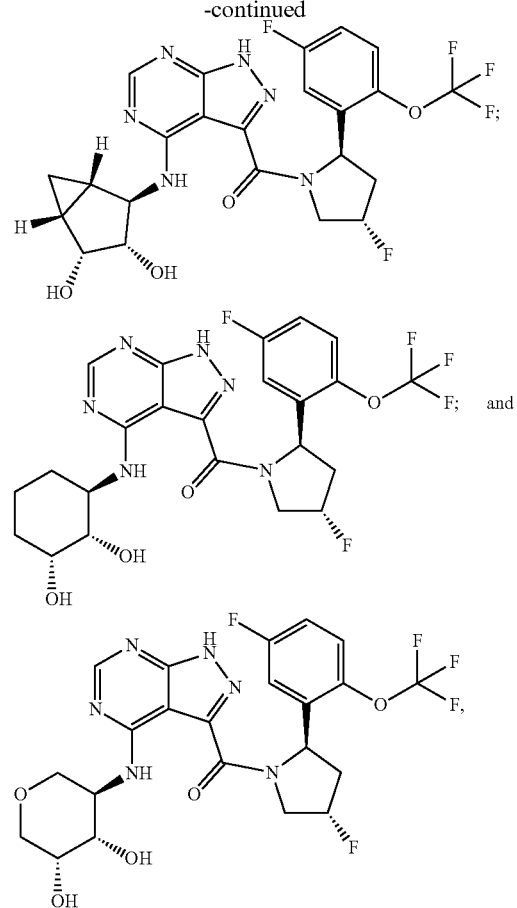
or a pharmaceutically acceptable salt thereof.
4. The method of claim 3, wherein the compound is
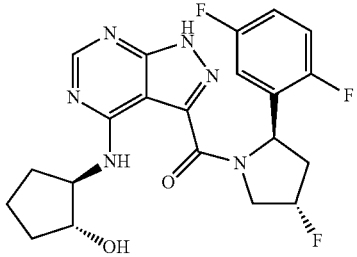 [SMILES: O=C(c1n[nH]c2ncnc(N[C@@H]3CCC[C@H]3O)c12)N1C[C@@H](F)C[C@@H]1c1cc(F)ccc1F]
or a pharmaceutically acceptable salt thereof.
5. The method of claim 3, wherein the compound is
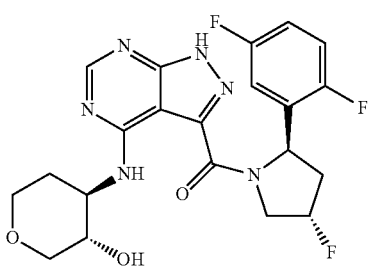 [SMILES: O=C(c1n[nH]c2ncnc(N[C@@H]3CCOC[C@H]3O)c12)N1C[C@@H](F)C[C@@H]1c1cc(F)ccc1F]
or a pharmaceutically acceptable salt thereof.

6. The method of claim 3, wherein the compound is

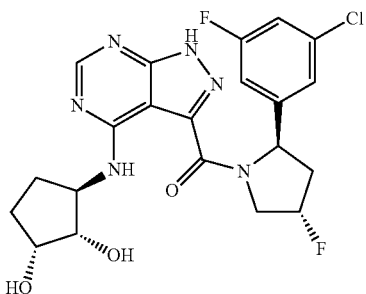 [SMILES: O=C(c1n[nH]c2ncnc(N[C@@H]3CC[C@@H](O)[C@H]3O)c12)N1C[C@@H](F)C[C@@H]1c1cc(F)cc(Cl)c1]

or a pharmaceutically acceptable salt thereof.

7. The method of claim 3, wherein the compound is

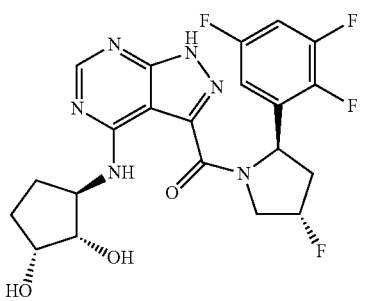 [SMILES: O=C(c1n[nH]c2ncnc(N[C@@H]3CC[C@@H](O)[C@H]3O)c12)N1C[C@@H](F)C[C@@H]1c1cc(F)cc(F)c1F]

or a pharmaceutically acceptable salt thereof.

8. The method of claim 3, wherein the compound is

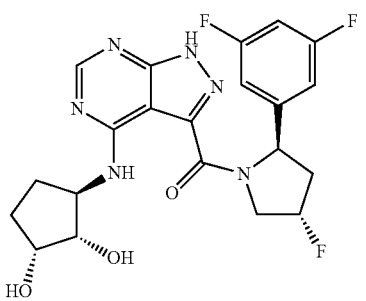 [SMILES: O=C(c1n[nH]c2ncnc(N[C@@H]3CC[C@@H](O)[C@H]3O)c12)N1C[C@@H](F)C[C@@H]1c1cc(F)cc(F)c1]

or a pharmaceutically acceptable salt thereof.

9. The method of claim 1, wherein the cancer tumor is characterized by an NTRK fusion.

10. The method of claim 9, wherein the kinase domain of the NTRK fusion has a mutation.

11. The method of claim 10, wherein the mutation is G595R.

12. The method of claim 3, wherein the tumor is from a cancer wherein the cancer is selected from non-small cell lung cancer, breast cancer, melanoma, low and high grade glioma, glioblastoma, pediatric astrocytoma, colorectal cancer, papillary thyroid carcinoma, pancreatic adenocarcinoma, head and neck cancer, cholangiocarcinoma, secretory breast cancer, salivary cancer and spitzoid neoplasms.

13. The method of claim 12, wherein the cancer is non-small cell lung cancer.

14. The method of claim 12, wherein the cancer is papillary thyroid cancer.

15. The method of claim 12, wherein the cancer is pancreatic adenocarcinoma.

16. The method of claim 12, wherein the cancer is colorectal cancer.

17. The method of claim 12, wherein the cancer is characterized by an NTRK fusion protein.

18. The method of claim 17, wherein the kinase domain of the NTRK fusion has a mutation.

19. The method of claim 18, wherein the mutation is G595R.

20. The method of claim 1, wherein the tumor is from a cancer, wherein the cancer is selected from non-small cell lung cancer, breast cancer, melanoma, low and high grade glioma, glioblastoma, pediatric astrocytoma, colorectal cancer, papillary thyroid carcinoma, pancreatic adenocarcinoma, head and neck cancer, cholangiocarcinoma, secretory breast cancer, salivary cancer and spitzoid neoplasms.

* * * * *